US011583548B2

(12) United States Patent
Freier

(10) Patent No.: US 11,583,548 B2
(45) Date of Patent: Feb. 21, 2023

(54) COMPOUNDS AND METHODS FOR REDUCING ATXN3 EXPRESSION

(71) Applicant: Ionis Pharmaceuticals, Inc., Carlsbad, CA (US)

(72) Inventor: Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 346 days.

(21) Appl. No.: 16/344,254

(22) PCT Filed: Nov. 10, 2017

(86) PCT No.: PCT/US2017/061121
§ 371 (c)(1),
(2) Date: Apr. 23, 2019

(87) PCT Pub. No.: WO2018/089805
PCT Pub. Date: May 17, 2018

(65) Prior Publication Data
US 2019/0247420 A1 Aug. 15, 2019

Related U.S. Application Data

(60) Provisional application No. 62/420,294, filed on Nov. 10, 2016.

(51) Int. Cl.
| | | |
|---|---|---|
| *C07H 21/02* | (2006.01) | |
| *A61K 31/7115* | (2006.01) | |
| *C12N 15/113* | (2010.01) | |
| *A61P 25/28* | (2006.01) | |
| *A61K 31/7125* | (2006.01) | |

(52) U.S. Cl.
CPC ...... *A61K 31/7115* (2013.01); *A61K 31/7125* (2013.01); *A61P 25/28* (2018.01); *C12N 15/113* (2013.01); *C12N 15/1137* (2013.01); *C12N 2310/11* (2013.01); *C12N 2310/315* (2013.01); *C12N 2310/3181* (2013.01); *C12N 2310/321* (2013.01); *C12N 2310/3341* (2013.01); *C12N 2310/341* (2013.01); *C12N 2310/346* (2013.01); *C12N 2310/3525* (2013.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |

(Continued)

FOREIGN PATENT DOCUMENTS

| | | |
|---|---|---|
| JP | 2011125219 A | 6/2011 |
| WO | WO 2002/058626 | 8/2002 |
| WO | WO 2004/013280 | 2/2004 |
| WO | 2004058940 A2 | 7/2004 |
| WO | 2006006948 A2 | 1/2006 |

(Continued)

OTHER PUBLICATIONS

Partial Search Report for 17869883.3 dated Apr. 24, 2020.
Alves et al., "Allele-Specific RNA Silencing of Mutant Ataxin-3 Mediates Neuroprotection in a Rat Model of Machado-Joseph Disease" PLoS ONE (2008) 3(10):e3341.
Alves et al., "Silencing ataxin-3 mitigates degeneration in a rat model of Machado-Joseph disease: no role for wild-type ataxin-3?" Hum. Mol. Gen. (2010) 19(12): 2380-2394.

(Continued)

*Primary Examiner* — Amy H Bowman
(74) *Attorney, Agent, or Firm* — McNeill Baur LLC

(57) ABSTRACT

Provided are compounds, methods, and pharmaceutical compositions for reducing the amount or activity of ATXN3 mRNA in a cell or animal, and in certain instances reducing the amount of Ataxin-3 protein in a cell or animal. Such compounds, methods, and pharmaceutical compositions are useful to prevent or ameliorate at least one symptom or hallmark of a neurodegenerative disease. Such symptoms and hallmarks include ataxia, neuropathy, and aggregate formation. Such neurodegenerative diseases include SCA3.

25 Claims, No Drawings

Specification includes a Sequence Listing.

(56) References Cited

U.S. PATENT DOCUMENTS

| | | |
|---|---|---|
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,840,491 A | 11/1998 | Kakizuka |
| 5,859,221 A | 1/1999 | Cook et al. |
| 5,945,290 A | 8/1999 | Cowsert et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,255,051 B1 * | 7/2001 | Hammond ............ C12Q 1/6813 435/6.12 |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,250,289 B2 * | 7/2007 | Zhou .................... C12Q 1/6837 435/287.2 |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,834,170 B2 | 11/2010 | Khvorova et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,263,760 B2 | 9/2012 | De Kimpe et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,329,890 B2 | 12/2012 | Davidson et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,779,116 B2 | 7/2014 | Davidson et al. |
| 8,828,956 B2 | 9/2014 | Manoharan et al. |
| 8,901,095 B2 | 12/2014 | Corey et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,340,785 B2 | 5/2016 | Corey et al. |
| 9,487,779 B2 | 11/2016 | Davidson et al. |
| 9,574,191 B2 | 2/2017 | Corey et al. |
| 9,976,138 B2 | 5/2018 | Prakash et al. |
| 10,041,074 B2 * | 8/2018 | Ozsolak ............ A61K 31/7088 |
| 10,364,432 B2 | 7/2019 | Van Roon-Mom et al. |
| 10,533,175 B2 | 1/2020 | Rigo et al. |

(56) References Cited

U.S. PATENT DOCUMENTS

| | | |
|---|---|---|
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2005/0244851 A1 | 11/2005 | Blume et al. |
| 2005/0272080 A1 | 12/2005 | Palma et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2011/0190222 A1 | 8/2011 | Corey et al. |
| 2013/0130378 A1 | 5/2013 | Manoharan et al. |
| 2013/0198877 A1 | 8/2013 | Van Roon-Mom et al. |
| 2013/0225659 A1 | 8/2013 | Bennett |
| 2014/0039037 A1 | 2/2014 | Van Roon-Mom et al. |
| 2014/0107330 A1 | 4/2014 | Freier et al. |
| 2015/0018540 A1 | 1/2015 | Prakash et al. |
| 2015/0141320 A1* | 5/2015 | Krieg ............... C12N 15/113 514/1.1 |
| 2015/0184153 A1 | 7/2015 | Freier et al. |
| 2015/0191727 A1 | 7/2015 | Migawa et al. |
| 2015/0211006 A1 | 7/2015 | Butler et al. |
| 2015/0267195 A1 | 9/2015 | Seth et al. |
| 2015/0267197 A1 | 9/2015 | Bennett et al. |
| 2015/0275212 A1 | 10/2015 | Albaek et al. |
| 2015/0315595 A1 | 11/2015 | Uzcategui et al. |
| 2016/0159846 A1 | 6/2016 | Prakash et al. |
| 2018/0258425 A1 | 9/2018 | Rigo et al. |
| 2022/0064637 A1 | 3/2022 | Freier |

FOREIGN PATENT DOCUMENTS

| | | |
|---|---|---|
| WO | WO 2010/014592 | 2/2010 |
| WO | 2011097643 A1 | 8/2011 |
| WO | WO 2011/097388 | 8/2011 |
| WO | 2012012467 A2 | 1/2012 |
| WO | WO 2012/018257 | 2/2012 |
| WO | WO 2013/033223 | 5/2013 |
| WO | WO 2013/138353 | 9/2013 |
| WO | 2013173635 A1 | 11/2013 |
| WO | WO 2013/173637 | 11/2013 |
| WO | WO 2015/017675 | 2/2015 |
| WO | WO 2015/053624 | 4/2015 |
| WO | 2015143246 A1 | 9/2015 |
| WO | WO 2017/053781 | 3/2017 |
| WO | WO 2018/002886 | 1/2018 |
| WO | WO 2018/089805 | 5/2018 |
| WO | WO 2019/217708 | 11/2019 |
| WO | 2020172559 A1 | 8/2020 |
| WO | 2020245233 A1 | 12/2020 |

OTHER PUBLICATIONS

Crooke, ST., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Evers et al., "Ataxin-3 Protein and RNA Toxicity in Spinocerebellar Ataxia Type 3: Current Insights and Emerging Therapeutic Strategies." Mol Neurobiol (2014) 49:1513-1531.

Evers et al., "Ataxin-3 protein modification as a treatment strategy for spinocerebellar ataxia type 3: Removal of the CAG containing exon" Neurobiloby of Disease (2013) 58: 49-56.

Gautschi et al., "Activity of a novel bcl-2/bcl-xLbispecific antisense oligonucleotide against tumors of diverse histologic origins" J. Natl. Cancer Inst. (2001) 93:463-471.

Hu et al., "Allele-specific silencing of mutant huntingtin and ataxin-3 genes by targeting expanded CAG repeats in mRNAs." Nat. Biotech. (2009) 27(5): 478-484.

Hu et al., "Allele-selective inhibition of huntingtin expression by switching to an miRNA-like RNAi mechanism" Chem Biol (2010) 17(11): 1183-1188.

Hu et al., Allele-selective inhibition of ataxin-3 (ATX3) expression by antisense oligomers and duplex RNAs. Biol. Chem. (2011) 392(4): 315-325.

Kawaguchi et al., "CAG expansions in a novel gene for Machado-Joseph disease at chromosome 14q32.1." Nat. Genet. (1994) 8(3): 221-228.

Kenski et al., "siRNA-optimized Modifications for Enhanced In Vivo Activity" Mol Ther Nucleic Acids (2012) 1-8.

Liu et al., "ss-siRNAs allele selectively inhibit ataxin-3 expression: multiple mechanisms for an alternative gene silencing strategy." Nucleic Acids Res. (2013) 41(20): 9570-9583.

Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.

McLoughlin et al., "Oligonucleotide therapy mitigates disease in Spinocerebellar Ataxia Type 3 mice." Annals of Neurology (2018) Accepted Article online Jun. 16, 2018, pp. 1-25.

Miller et al., "Allele-specific silencing of dominant disease genes." PNAS (2003) 100(12): 7195-7200.

Moore et al., "Evaluation of Antisense Oligonucleotides Targeting ATXN3 in SCA3 Mouse Models" Molecual Therapy:Nucliec Acids (2017) 7:200-210.

Moore et al., "Widespread In vivo suppression of mutant ATXN3 by anti sense oligonucleotides in transgenic mouse models of SCA3" Society for Neuroscience 2016 Neuroscience meeting, SanDiego, CA, Retreievd from the internet on Aug. 2, 2018, http://www.abstractsonline.com/pp8/#!/4071/presentation/6726.

Moore et al., "Widespread In vivo suppression of mutant ATXN3 by antisense oligonucleotides in transgenic mouse models of SCA3" Society for Neuroscience 2016 Neuroscience meeting, SanDiego, CA, Poster Presentation Nov. 12, 2016.

Riess, et al., "SCA:3 Neurological features, patholgenesis and animal models." The Cerebellum (2008) 7:125-137.

Rodriguez-Lebron et al., "Silencing mutant ATXN3 expression resolves molecular phenotypes in SCA3 transgenic mice." Mol. Ther. (2013) 21(10): 1909-1918.

Seidel et al., "Axonal inclusions in spinocerebellar ataxia type 3," Acta Neuropathol (2010) 120:449-460.

Seth et al., "Short Antisense Oligonucleotides with Novel 2'-4' Conformationaly Restricted Nucleoside Analogues Show Improved Potency Without Increased Toxicity in Animals." J Med Chern (2009) 52:10-13.

Toonen et al., "Antisense Oligonucleotide-Mediated Removal of the Polyglutamine Repeat in Spinocerebellar Ataxia Type 3 Mice" Mol Ther Nucleic Acids (2017) 8:232-242.

Toonen et al., "Ataxin-3 exon skipping as a treatment strategy for Spinocerebellar Ataxia type 3" Oligonucleotide Therapeutics Society 2015 Annual Meeting, Leiden, The Netherlands, Poster Presentaiton, Oct. 11, 2015.

Ward et al., "Ataxin-3, DAN damage repair, and SCA3 cerebellar degeneration: on the path to parsimony?" PLoS Genet (2015) 11(1):e1004937(1-4).

Woolf et al., "Specificity of antisense oligonucleotides in vivo" PNAS (1992) 89: 7305-7309.

Yu et al., "Single-stranded RNAs use RNAi to potently and allele-selectively inhibit mutant huntingtin expression" Cell (2012) 150(5): 895-908.

Partial Search Report for 16849742.8 dated Mar. 14, 2019.

International Search Report for PCT/US 17/61121 dated Apr. 26, 2018.

International Search Report for PCT/US19/031562 dated Sep. 17, 2019.

Branch et al., "A good antisense molecule is hard to find," TIBS (1998) 23:45-50.

(56) References Cited

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002, 1 page.
Costa et al., "Toward RNAi therapy for the polyglutamine disease Machado-Joseph disease" Mol Ther (2013) 21: 1898-1908.
Crooke et al., "Basic Principles of Antisense Therapeutics" Antisense Research and Application (1998) Chapter 1:1-50.
Extended EP Search report for 17869883.3 dated Jul. 16, 2020, 16 pages.
International Search Report for PCT/US20/019272 dated Jul. 1, 2020, 13 pages.
New England Biolabs 1998/99 Catalog (cover page and pp. 121 and 284).
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Extended EP Search report for 19799466.8 dated Jan. 14, 2022, 6 pages.
Fiszer et al., "Oligonucleotide-based strategies to combat polyglutamine diseases" Nucleic Acids Res (2014) 42: 6787-6810.
GenBank Accession No. NM_004993.5 (downloaded Sep. 18, 2019), 11 pages.

\* cited by examiner

COMPOUNDS AND METHODS FOR REDUCING ATXN3 EXPRESSION

SEQUENCE LISTING

The present application is being filed along with a Sequence Listing in electronic format. The Sequence Listing is provided as a file entitled BIOL0312USASEQ_ST25.txt, created on Apr. 23, 2019, which is 280 KB in size. The information in the electronic format of the sequence listing is incorporated herein by reference in its entirety.

FIELD

Provided are compounds, methods, and pharmaceutical compositions for reducing the amount or activity of ATXN3 mRNA in a cell or animal, and in certain instances reducing the amount of Ataxin-3 protein in a cell or animal. Such compounds, methods, and pharmaceutical compositions are useful to prevent or ameliorate at least one symptom or hallmark of a neurodegenerative disease. Such symptoms and hallmarks include ataxia, neuropathy, and aggregate formation. Such neurodegenerative diseases include spinocerebellar ataxia type 3 (SCA3).

BACKGROUND

Spinocerebellar ataxia type 3 (SCA3), also known as Machado-Joseph disease (MJD), is caused by a mutation in the ATXN3 gene and is characterized by progressive cerebellar ataxia and variable findings including a dystonic-rigid syndrome, a parkinsonian syndrome, or a combined syndrome of dystonia and peripheral neuropathy. SCA3 is inherited in an autosomal dominant manner. Offspring of affected individuals have a 50% chance of inheriting the mutation. The diagnosis of SCA3 rests on the use of molecular genetic testing to detect an abnormal CAG trinucleotide repeat expansion in ATXN3. Affected individuals have alleles with 52 to 86 CAG trinucleotide repeats. Such testing detects 100% of affected individuals. Expanded CAG repeats in the ATXN3 gene are translated into expanded polyglutamine repeats (polyQ) in the ataxin-3 protein and this toxic ataxin-3 protein is associated with aggregates. The polyglutamine expanded ataxin-3 protein in these aggregates is ubiquinated and the aggregates contain other proteins, including heat shock proteins and transcription factors. Aggregates are frequently observed in the brain tissue of SCA3 patients. Management of SCA3 is supportive as no medication slows the course of disease; restless legs syndrome and extrapyramidal syndromes resembling parkinsonism may respond to levodopa or dopamine agonists; spasticity, drooling, and sleep problems respond variably to lioresal, atropine-like drugs, and hypnotic agents; botulinum toxin has been used for dystonia and spasticity; daytime fatigue may respond to psychostimulants such as modafinil; accompanying depression should be treated. Riess, O., Rüb, U., Pastore, A. et al. Cerebellum (2008) 7: 125.

Currently there is a lack of acceptable options for treating neurodegenerative diseases such as SCA3. It is therefore an object herein to provide compounds, methods, and pharmaceutical compositions for the treatment of such diseases.

SUMMARY OF THE INVENTION

Provided herein are compounds, methods, and pharmaceutical compositions for reducing the amount or activity of ATXN3 mRNA, and in certain embodiments reducing the amount of Ataxin-3 protein in a cell or animal. In certain embodiments, the animal has a neurodegenerative disease. In certain embodiments, the animal has SCA3. In certain embodiments, compounds useful for reducing expression of ATXN3 mRNA are oligomeric compounds or modified oligonucleotides. In certain embodiments, the oligomeric compound comprises a modified oligonucleotide.

Also provided are methods useful for ameliorating at least one symptom or hallmark of a neurodegenerative disease. In certain embodiments, the neurodegenerative disease is SCA3. In certain embodiments symptoms and hallmarks include ataxia, neuropathy, and aggregate formation. In certain embodiments, amelioration of these symptoms results in improved motor function, reduced neuropathy, and reduction in number of aggregates.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "administering" means providing a pharmaceutical agent to an animal.

As used herein, "animal" means a human or non-human animal.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound or oligomeric duplex capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom or hallmark is ataxia, neuropathy, and aggregate formation. In certain embodiments, amelioration of these symptoms results in improved motor function, reduced neuropathy, or reduction in number of aggregates.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "cleavable moiety" means a bond or group of atoms that is cleaved under physiological conditions, for example, inside a cell, an animal, or a human.

As used herein, "complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine (mC) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." Unless otherwise indicated, "gapmer" refers to a sugar motif. Unless otherwise indicated, the sugar moieties of the nucleosides of the gap of a gapmer are unmodified 2'-deoxyfuranosyl. Thus, the term "MOE gapmer" indicates a gapmer having a sugar motif of 2'-MOE nucleosides in both wings and a gap of 2'-deoxynucleosides. Unless otherwise indicated, a MOE gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid amenable to oligomeric compounds for reducing the amount or activity of the target nucleic acid as demonstrated in the examples hereinbelow.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, the term "internucleoside linkage" is the covalent linkage between adjacent nucleosides in an oligonucleotide. As used herein "modified internucleoside linkage" means any internucleoside linkage other than a phosphodiester internucleoside linkage. "Phosphorothioate linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substitutent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "MOE" means methoxyethyl. "2'-MOE" means a —OCH$_2$CH$_2$OCH$_3$ group at the 2' position of a furanosyl ring.

As used herein, "motif" means the pattern of unmodified and/or modified sugar moieties, nucleobases, and/or internucleoside linkages, in an oligonucleotide.

As used herein, "mRNA" means an RNA transcript that encodes a protein and includes pre-mRNA and mature mRNA unless otherwise specified.

As used herein, "neurodegenerative disease" means a condition marked by progressive loss of structure or function of neurons, including death of neurons. In certain embodiments, neurodegenerative disease is spinocerebellar ataxia type 3 (SCA3).

As used herein, "nucleobase" means an unmodified nucleobase or a modified nucleobase. As used herein an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methylcytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein "prodrug" means a therapeutic agent in a form outside the body that is converted to a different form within an animal or cells thereof. Typically conversion of a prodrug within the animal is facilitated by the action of an enzymes (e.g., endogenous or viral enzyme) or chemicals present in cells or tissues and/or by physiologic conditions.

As used herein, "reducing or inhibiting the amount or activity" refers to a reduction or blockade of the transcriptional expression or activity relative to the transcriptional expression or activity in an untreated or control sample and does not necessarily indicate a total elimination of transcriptional expression or activity.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard cell assay" means the assay described in Example 1 and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1

An oligomeric compound comprising a modified oligonucleotide consisting of 10-30 linked nucleosides and having a nucleobase sequence comprising at least 12, at least 13, at least 14, at least 15, or at least 16 contiguous nucleobases of any of SEQ ID NO: 23-334.

Embodiment 2

The oligomeric compound of embodiment 1, wherein the modified oligonucleotide has a nucleobase sequence that is at least 80%, 85%, 90%, 95%, or 100% complementary to the nucleobase sequence of SEQ ID NO: 1, when measured across the entire nucleobase sequence of the modified oligonucleotide.

Embodiment 3

The oligomeric compound of embodiments 1 or 2, wherein the modified oligonucleotide comprises at least one modified nucleoside.

Embodiment 4

The oligomeric compound of embodiments 3, wherein the modified oligonucleotide comprises at least one modified nucleoside comprising a modified sugar moiety.

Embodiment 5

The oligomeric compound of embodiment 4, wherein the modified oligonucleotide comprises at least one modified nucleoside comprising a bicyclic sugar moiety.

Embodiment 6

The oligomeric compound of embodiment 5, wherein the modified oligonucleotide comprises at least one modified nucleoside comprising a bicyclic sugar moiety having a 2'-4' bridge, wherein the 2'-4' bridge is selected from —O—CH2-; and —O—CH(CH3)-.

Embodiment 7

The oligomeric compound of any of embodiments 3-6, wherein the modified oligonucleotide comprises at least one modified nucleoside comprising a modified non-bicyclic sugar moiety.

Embodiment 8

The oligomeric compound of embodiment 7, wherein the modified oligonucleotide comprises at least one modified nucleoside comprising a non-bicylic sugar moiety comprising a 2'-MOE or 2'-OMe.

Embodiment 9

The oligomeric compound of any of embodiments 4-8, wherein the modified oligonucleotide comprises at least one modified nucleoside comprising a sugar surrogate.

Embodiment 10

The oligomeric compound of embodiment 7, wherein the modified oligonucleotide comprises at least one modified nucleoside comprising a sugar surrogate selected from morpholino and PNA.

Embodiment 11

The oligomeric compound of any of embodiments 1-10, wherein the modified oligonucleotide has a sugar motif comprising:
a 5'-region consisting of 1-5 linked 5'-nucleosides;
a central region consisting of 6-10 linked central region nucleosides; and
a 3'-region consisting of 1-5 linked 3'-region nucleosides;
wherein each of the 5'-region nucleosides and each of the 3'-region nucleosides comprises a modified sugar moiety and each of the central region nucleosides comprises an unmodified DNA sugar moiety.

Embodiment 12

The oligomeric compound of any of embodiments 1-11, wherein the modified oligonucleotide comprises at least one modified internucleoside linkage.

Embodiment 13

The oligomeric compound of embodiment 12, wherein each internucleoside linkage of the modified oligonucleotide is a modified internucleoside linkage.

Embodiment 14

The oligomeric compound of embodiment 12 or 13 wherein at least one internucleoside linkage is a phosphorothioate internucleoside linkage.

Embodiment 15

The oligomeric compound of embodiment 12 or 13 wherein the modified oligonucleotide comprises at least one phosphodiester internucleoside linkage.

Embodiment 16

The oligomeric compound of any of embodiments 12-15, wherein each internucleoside linkage is either a phosphodiester internucleoside linkage or a phosphorothioate internucleoside linkage.

Embodiment 17

The oligomeric compound of any of embodiments 1-16, wherein the modified oligonucleotide comprises at least one modified nucleobase.

Embodiment 18

The oligomeric compound of embodiment 17, wherein the modified nucleobase is a 5-methylcytosine.

Embodiment 19

The oligomeric compound of any of embodiments 1-18, wherein the modified oligonucleotide consists of 12-22, 12-20, 14-20, 16-20, or 18-20 linked nucleosides.

Embodiment 20

The oligomeric compound of any of embodiments 1-14, wherein the modified oligonucleotide consists of 16, 17, 18, 19 or 20 linked nucleosides.

Embodiment 21

The oligomeric compound of any of embodiments 1-20 consisting of the modified oligonucleotide.

Embodiment 22

The oligomeric compound of any of embodiments 1-20 comprising a conjugate group comprising a conjugate moiety and a conjugate linker.

Embodiment 23

The oligomeric compound of embodiment 22, wherein the conjugate group comprises a GalNAc cluster comprising 1-3 GalNAc ligands.

Embodiment 24

The oligomeric compound of embodiment 22 or 23, wherein the conjugate linker consists of a single bond.

Embodiment 25

The oligomeric compound of embodiment 23, wherein the conjugate linker is cleavable.

Embodiment 26

The oligomeric compound of embodiment 25, wherein the conjugate linker comprises 1-3 linker-nucleosides.

Embodiment 27

The oligomeric compound of any of embodiments 22-26, wherein the conjugate group is attached to the modified oligonucleotide at the 5'-end of the modified oligonucleotide.

Embodiment 28

The oligomeric compound of any of embodiments 22-26, wherein the conjugate group is attached to the modified oligonucleotide at the 3'-end of the modified oligonucleotide.

Embodiment 29

The oligomeric compound of any of embodiments 1-28 comprising a terminal group.

Embodiment 30

The oligomeric compound of any of embodiments 1-29 wherein the oligomeric compound is a singled-stranded oligomeric compound.

Embodiment 31

The oligomeric compound of any of embodiments 1-25 or 27-30, wherein the oligomeric compound does not comprise linker-nucleosides.

Embodiment 32

An oligomeric duplex comprising an oligomeric compound of any of embodiments 1-29 and 31.

Embodiment 33

An antisense compound comprising or consisting of an oligomeric compound of any of embodiments 1-31 or an oligomeric duplex of embodiment 32.

Embodiment 34

A modified oligonucleotide consisting of 10-30 linked nucleosides and having a nucleobase sequence comprising at least 12, at least 13, at least 14, at least 15, or at least 16 contiguous nucleobases of any of SEQ ID NO: 23-334.

Embodiment 35

An oligomeric compound comprising a modified oligonucleotide consisting of 10-30 linked nucleosides and having a nucleobase sequence comprising a portion of at least 8, at least 9, at least 10, at least 11, at least 12, at least 13, or at least 14 contiguous nucleobases 100% complementary to an equal length portion of nucleobases 614-637 of SEQ ID NO: 1, nucleobases 833-852 of SEQ ID NO: 1, or nucleobases 1091-1131 of SEQ ID NO: 1, wherein the nucleobase sequence of the modified oligonucleotide is at least 90% complementary to SEQ ID NO: 1 as measured over the entirety of the modified oligonucleotide.

Embodiment 36

A pharmaceutical composition comprising an oligomeric compound of any of embodiments 1-31 and 35, an oligomeric duplex of embodiment 32, or a modified oligonucleotide of embodiment 34 and a pharmaceutically acceptable carrier or diluent.

Embodiment 37

A method comprising administering to an animal a pharmaceutical composition of embodiments 36.

Embodiment 38

A method of treating a disease associated with ATXN3 comprising administering to an individual having or at risk for developing a disease associated with ATXN3 a therapeutically effective amount of a pharmaceutical composition according to embodiment 36; and thereby treating the disease associated with ATXN3.

Embodiment 39

The method of embodiment 38, wherein the disease associated with ATXN3 is a neurodegenerative disease.

Embodiment 40

The method of embodiment 39, wherein the neurodegenerative disease is SCA3.

Embodiment 41

The method of embodiment 39, wherein at least one symptom or hallmark of the neurodegenerative disease is ameliorated.

Embodiment 42

The method of embodiment 41, wherein the symptom or hallmark is ataxia, neuropathy, and aggregate formation.

Embodiment 43

A chirally enriched population of oligomeric compounds of any of embodiments 1-32 or 35 wherein the population is enriched for modified oligonucleotides comprising at least one particular phosphorothioate internucleoside linkage having a particular stereochemical configuration.

Embodiment 44

The chirally enriched population of embodiment 43, wherein the population is enriched for modified oligonucleotides comprising at least one particular phosphorothioate internucleoside linkage having the (Sp) configuration.

Embodiment 45

The chirally enriched population of embodiment 43, wherein the population is enriched for modified oligonucleotides comprising at least one particular phosphorothioate internucleoside linkage having the (Rp) configuration.

Embodiment 46

The chirally enriched population of embodiment 43, wherein the population is enriched for modified oligonucleotides having a particular, independently selected stereochemical configuration at each phosphorothioate internucleoside linkage

Embodiment 47

The chirally enriched population of embodiment 46, wherein the population is enriched for modified oligonucleotides having the (Sp) configuration at each phosphorothioate internucleoside linkage.

Embodiment 48

The chirally enriched population of embodiment 46, wherein the population is enriched for modified oligonucleotides having the (Rp) configuration at each phosphorothioate internucleoside linkage.

Embodiment 49

The chirally enriched population of embodiment 46, wherein the population is enriched for modified oligonucleotides having the (Rp) configuration at one particular phosphorothioate internucleoside linkage and the (Sp) configuration at each of the remaining phosphorothioate internucleoside linkages.

Embodiment 50

The chirally enriched population of embodiment 43 or embodiment 46 wherein the population is enriched for modified oligonucleotides having at least 3 contiguous phosphorothioate internucleoside linkages in the Sp, Sp, and Rp configurations, in the 5' to 3' direction.

Embodiment 51

A chirally enriched population of oligomeric compounds of any of embodiments 1-32 or 35, wherein all of the phosphorothioate internucleoside linkages of the modified oligonucleotide are stereorandom.

Embodiment 52

A chirally enriched population of modified oligonucleotides of embodiment 34 wherein the population is enriched for modified oligonucleotides comprising at least one particular phosphorothioate internucleoside linkage having a particular stereochemical configuration.

Embodiment 53

The chirally enriched population of embodiment 52, wherein the population is enriched for modified oligonucleotides comprising at least one particular phosphorothioate internucleoside linkage having the (Sp) configuration.

Embodiment 54

The chirally enriched population of embodiment 52, wherein the population is enriched for modified oligonucleotides comprising at least one particular phosphorothioate internucleoside linkage having the (Rp) configuration.

Embodiment 55

The chirally enriched population of embodiment 52, wherein the population is enriched for modified oligonucleotides having a particular, independently selected stereochemical configuration at each phosphorothioate internucleoside linkage Embodiment 56

The chirally enriched population of embodiment 55, wherein the population is enriched for modified oligonucleotides having the (Sp) configuration at each phosphorothioate internucleoside linkage.

Embodiment 57

The chirally enriched population of embodiment 55, wherein the population is enriched for modified oligonucleotides having the (Rp) configuration at each phosphorothioate internucleoside linkage.

Embodiment 58

The chirally enriched population of embodiment 55, wherein the population is enriched for modified oligonucleotides having the (Rp) configuration at one particular phosphorothioate internucleoside linkage and the (Sp) configuration at each of the remaining phosphorothioate internucleoside linkages.

Embodiment 59

The chirally enriched population of embodiment 52 or embodiment 55 wherein the population is enriched for modified oligonucleotides having at least 3 contiguous phosphorothioate internucleoside linkages in the Sp, Sp, and Rp configurations, in the 5' to 3' direction.

Embodiment 60

A chirally enriched population of modified oligonucleotides of embodiment 34, wherein all of the phosphorothioate internucleoside linkages of the modified oligonucleotide are stereorandom.

I. Certain Oligonucleotides

In certain embodiments, provided herein are oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_a$), where each R$_m$ and R$_a$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', 4'-(CH$_2$)$_2$—O-2' ("ENA"), 4'-CH(CH$_3$)—O-2' (referred to as "constrained ethyl" or "cEt"), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O- 2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J Org. Chem.*, 1998, 63, 10035-10039; Srivastava et al., *J Am. Chem. Soc.*, 20017, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

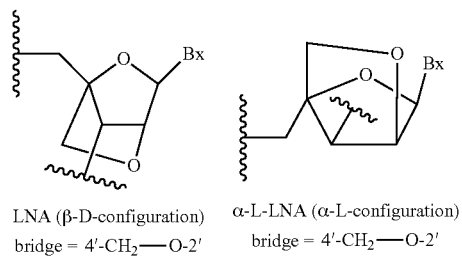

LNA (β-D-configuration)  α-L-LNA (α-L-configuration)
bridge = 4'-CH$_2$—O-2'  bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

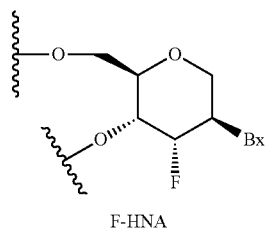

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

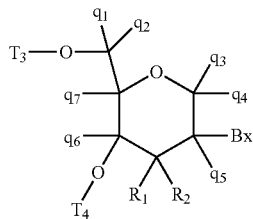

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

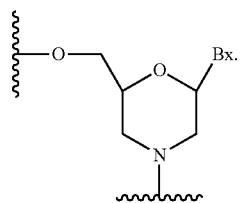

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($—C\equiv C—CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908;

Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

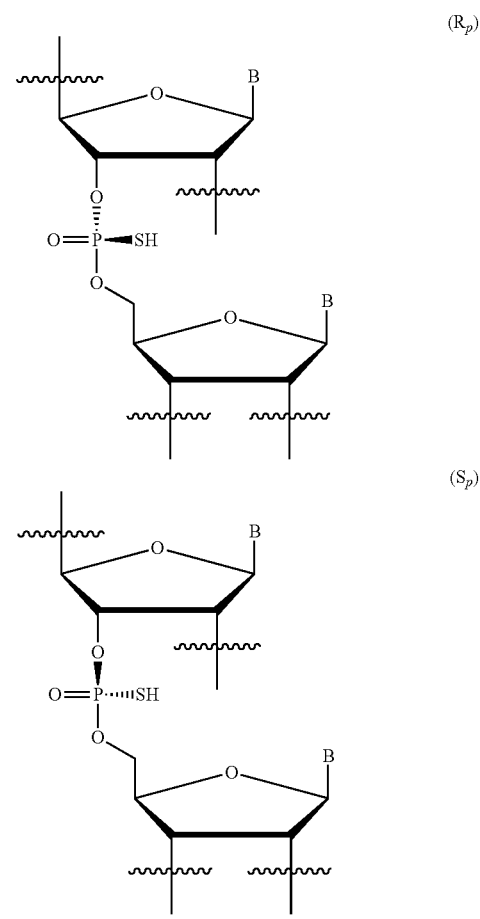

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside.

In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

Herein, the lengths (number of nucleosides) of the three regions of a gapmer may be provided using the notation [#of nucleosides in the 5'-wing]-[#of nucleosides in the gap]-[#of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in the wings and the gap nucleosides comprise unmodified deoxynucleosides sugars. Thus, a 5-10-5 MOE gapmer consists of 5 linked MOE modified nucleosides in the 5'-wing, 10 linked deoxynucleosides in the gap, and 5 linked MOE nucleosides in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines. In certain embodiments, all of the cytosine nucleobases are 5-methylcytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphodiester internucleoside linkage (P=O). In certain embodiments, each internucleoside linking group of a modified oligonucleotide is a phosphorothioate internucleoside linkage (P=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

C. Certain Lengths

It is possible to increase or decrease the length of an oligonucleotide without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphanates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a region complementary to a target nucleic acid and a second oligomeric compound having a region complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce or inhibit the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a premRNA, including intronic, exonic and untranslated regions. In certain embodiments, the target RNA is a mature mRNA. In certain embodiments, the target nucleic acid is a premRNA. In certain such embodiments, the target region is entirely within an intron. In certain embodiments, the target region spans an intron/exon junction. In certain embodiments, the target region is at least 50% within an intron. In certain embodiments, the target nucleic acid is the RNA transcriptional product of a retrogene. In certain embodiments, the target nucleic acid is a non-coding RNA. In certain such embodiments, the target non-coding RNA is selected from: a long non-coding RNA, a short non-coding RNA, an intronic RNA molecule.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligomeric compounds comprise oligonucleotides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligomeric compound comprising an oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. ATXN3

In certain embodiments, oligomeric compounds comprise or consist of an oligonucleotide comprising a region that is complementary to a target nucleic acid, wherein the target nucleic acid is ATXN3. In certain embodiments, ATXN3 nucleic acid has the sequence set forth in SEQ ID NO: 1 (GENBANK Accession No: NM_004993.5); SEQ ID NO: 2 (GENBANK Accession No: GENBANK Accession No. NT_026437.12 truncated from nucleotides 73,524,000 to 73,574,000); SEQ ID NO: 3 (GENBANK Accession No: NM_001164778.1); SEQ ID NO: 4 (GENBANK Accession No: NM_001127696.1); SEQ ID NO: 5 (GENBANK Accession No: NM_001164781.1); SEQ ID NO: 6 (GENBANK Accession No: NR_028454.1); SEQ ID NO: 7 (GENBANK Accession No: NM_001164780.1); SEQ ID NO: 8 (GENBANK Accession No: NR_028469.1); SEQ ID NO: 9 (GENBANK Accession No: NM_001164779.1); SEQ ID NO: 10 (GENBANK Accession No: NR_028461.1); SEQ ID NO: 11 (GENBANK Accession No: NR_028466.1); SEQ ID NO: 12 (GENBANK Accession No: NR_028462.1); SEQ ID NO: 13 (GENBANK Accession No: NR_028467.1); SEQ ID NO: 14 (GENBANK Accession No: NR_031765.1); SEQ ID NO: 15 (GENBANK Accession No: NM_001164782.1): SEQ ID NO: 16 (GENBANK Accession No: NR_028465.1); SEQ ID NO: 17 (GENBANK Accession No: NR_028457.1); SEQ ID NO: 18 (GENBANK Accession No: NM_001164777.1); and SEQ ID NO: 19 (GENBANK Accession No: NM_001164774.1).

In certain embodiments, contacting a cell with an oligomeric compound complementary to SEQ ID NO: 1-19 reduces the amount of ATXN3 mRNA, and in certain embodiments reduces the amount of Ataxin-3 protein. In certain embodiments, contacting a cell in an animal with an oligomeric compound complementary to SEQ ID NO: 1-19 ameliorate one or more symptoms or hallmarks of neurodegenerative disease. In certain embodiments, such symptoms and hallmarks include ataxia, neuropathy, and aggregate formation. In certain embodiments, the neurodegenerative disease is spinocerebellar ataxia type 3 (SCA3).

VI. Certain Hotspot Regions

1. Nucleobases 614-637 of SEQ ID NO: 1

In certain embodiments, modified oligonucleotides are complementary to nucleobases 614-637 of SEQ ID NO: 1. In certain embodiments, nucleobases 614-637 of SEQ ID NO: 1 is a hotspot region. In certain embodiments, such modified oligonucleotides are 18 nucleobases in length. In certain embodiments, such modified oligonucleotides are gapmers. In certain such embodiments, the gapmers are 5-8-5 MOE gapmers. In certain embodiments, the nucleosides of the modified oligonucleotides are linked by mixed phosphodiester ("o") and phosphorothioate ("s") internucleoside linkages. In certain embodiments, the mixed phosphodiester ("o") and phosphorothioate ("s") internucleoside linkages arranged in order from 5' to 3': sooosssssssssooss.

The nucleobase sequences of SEQ ID Nos: 73, 74, and 75 are complementary to nucleobases 614-637 of SEQ ID NO: 1.

In certain embodiments, modified oligonucleotides complementary to nucleobases 614-637 of SEQ ID NO: 1 achieve at least 40% reduction of ATXN3 mRNA in vitro in the standard cell assay.

2. Nucleobases 833-852 of SEQ ID NO: 1

In certain embodiments, modified oligonucleotides are complementary to nucleobases 833-852 of SEQ ID NO: 1. In certain embodiments, nucleobases 833-852 of SEQ ID NO: 1 is a hotspot region. In certain embodiments, such modified oligonucleotides are 18 nucleobases in length. In certain embodiments, such modified oligonucleotides are gapmers. In certain such embodiments, the gapmers are 5-8-5 MOE gapmers. In certain embodiments, the nucleosides of the modified oligonucleotides are linked by mixed phosphodiester ("o") and phosphorothioate ("s") internucleoside linkages. In certain embodiments, the mixed phosphodiester ("o") and phosphorothioate ("s") internucleoside linkages arranged in order from 5' to 3': sooosssssssssooss.

The nucleobase sequences of SEQ ID Nos: 86 and 87 are complementary to nucleobases 833-852 of SEQ ID NO: 1.

In certain embodiments, modified oligonucleotides complementary to nucleobases 833-852 of SEQ ID NO: 1 achieve at least 30% reduction of ATXN3 mRNA in vitro in the standard cell assay.

3. Nucleobases 1091-1131 of SEQ ID NO: 1

In certain embodiments, modified oligonucleotides are complementary to nucleobases 1091-1131 of SEQ ID NO: 1. In certain embodiments, nucleobases 1091-1131 of SEQ ID NO: 1 is a hotspot region. In certain embodiments, such modified oligonucleotides are 18 nucleobases in length. In certain embodiments, such modified oligonucleotides are gapmers. In certain such embodiments, the gapmers are 5-8-5 MOE gapmers. In certain embodiments, the nucleosides of the modified oligonucleotides are linked by mixed phosphodiester ("o") and phosphorothioate ("s") internucleoside linkages. In certain embodiments, the mixed phosphodiester ("o") and phosphorothioate ("s") internucleoside linkages arranged in order from 5' to 3': sooosssssssssooss.

The nucleobase sequences of SEQ ID Nos: 98, 99, 100, 101, and 102 are complementary to nucleobases 1091-1131 of SEQ ID NO: 1.

In certain embodiments, modified oligonucleotides complementary to nucleobases 1091-1131 of SEQ ID NO: 1 achieve at least 30% reduction of ATXN3 mRNA in vitro in the standard cell assay.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in a pharmacologically relevant tissue.

VII. Certain Pharmaceutical Compositions

In certain embodiments, described herein are pharmaceutical compositions comprising one or more oligomeric compounds or a salt thereof. In certain embodiments, the pharmaceutical composition comprises a pharmaceutically acceptable diluent or carrier. In certain embodiments, a pharmaceutical composition comprises a sterile saline solution and one or more oligomeric compound. In certain embodiments, a pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 1 such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, all tautomeric forms of the compounds herein are also included unless otherwise indicated. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1H$ hydrogen atoms. Isotopic substitutions encompassed by the compounds herein include but are not limited to: $^2H$ or $^3H$ in place of $^1H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: Effect of Modified Oligonucleotides on Human ATXN3 In Vitro, Single Dose Modified oligonucleotides complementary to an ATXN3 nucleic acid were designed and tested for their effect on ATXN3 mRNA in vitro. The modified oligonucleotides were tested in a series of experiments that had similar culture conditions.

Cultured HepG2 cells at a density of 20,000 cells per well were transfected using electroporation with a 2,000 nM concentration of modified oligonucleotide. After a treatment period of approximately 24 hours, RNA was isolated from the cells and ATXN3 mRNA levels were measured by quantitative real-time PCR. Human primer probe set RTS4392 (forward primer sequence TCAGGACAGAGTT-CACATCCATGT, designated herein as SEQ ID NO: 20; reverse primer sequence TTCACTCATAGCATCACCTA-GATCACT, designated herein as SEQ ID NO: 21; probe sequence AAGGCCAGCCACCAGTTCAGGAGC, designated herein as SEQ ID NO: 22) was used to measure mRNA levels. ATXN3 mRNA levels were adjusted according to total RNA content, as measured by RIBOGREEN®. Results are presented as percent reduction of the amount of ATXN3 mRNA, relative to untreated control cells (these conditions describe a "standard cell assay"). The oligonucleotides marked with an asterisk (*) target the amplicon region of the primer probe set. Additional assays may be used to measure the potency and efficacy of these oligonucleotides.

The modified oligonucleotides in the table below were designed as 5-8-5 MOE gapmers. The gapmers are 18 nucleosides in length, wherein the central gap segment comprises eight 2'-deoxynucleosides and is flanked by wing segments on both the 5' end and on the 3' end comprising five nucleosides each. Each nucleoside in the 5' wing segment and each nucleoside in the 3' wing segment comprises a MOE modification. All cytosine residues throughout each gapmer are 5-methylcytosines. The internucleoside linkages are mixed phosphodiester and phosphorothioate linkages. The internucleoside linkages are arranged in order from 5' to 3': sooossssssssssooss; wherein ("o") is phosphodiester and ("s") is phosphorothioate. "Start site" indicates the 5'-most nucleoside to which the gapmer is targeted in the human gene sequence. "Stop site" indicates the 3'-most nucleoside to which the gapmer is targeted human gene sequence.

Each modified oligonucleotide listed in Table 1 is targeted to either human ATXN3 mRNA sequence (isoform 1), designated herein as SEQ ID NO: 1 (GENBANK Accession No. NM_004993.5) or the human ATXN3 genomic sequence, designated herein as SEQ ID NO: 2 (GENBANK Accession No. NT_026437.12 truncated from nucleotides 73,524,000 to 73,574,000), or both. 'N/A' indicates that the antisense oligonucleotide does not target that particular gene sequence with 100% complementarity.

TABLE 1

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650362 | 14 | 31 | 1049 | 1066 | $A_{es}{}^mC_{eo}{}^mC_{eo}{}^mC_{eo}{}^mC_{es}{}^mC_{ds}T_{ds}{}^mC_{ds}{}^mC_{ds}A_{ds}G_{ds}{}^mC_{ds}T_{ds}{}^mC_{eo}{}^mC_{eo}G_{es}{}^mC_{es}{}^mC_e$ | 0 | 23 |
| 650363 | 37 | 54 | 1072 | 1089 | $G_{es}{}^mC_{eo}{}^mC_{eo}A_{eo}A_{es}{}^mC_{ds}G_{ds}{}^mG_{ds}{}^mC_{ds}{}^mC_{ds}{}^mC_{ds}{}^mC_{ds}A_{eo}{}^mC_{eo}G_{es}{}^mC_{es}{}^mC_e$ | 10 | 24 |
| 650364 | 43 | 60 | 1078 | 1095 | $T_{es}{}^mC_{eo}T_{eo}G_{eo}G_{es}A_{ds}G_{ds}{}^mC_{ds}{}^mC_{ds}A_{ds}A_{ds}{}^mC_{ds}G_{ds}G_{eo}{}^mC_{eo}{}^mC_{es}{}^mC_{es}{}^mC_e$ | 0 | 25 |
| 650365 | 48 | 65 | 1083 | 1100 | $A_{es}T_{eo}T_{eo}G_{es}T_{ds}{}^mC_{ds}T_{ds}G_{ds}G_{ds}A_{ds}G_{ds}{}^mC_{ds}{}^mC_{eo}A_{eo}A_{es}{}^mC_{es}G_e$ | 2 | 26 |
| 650366 | 53 | 70 | 1088 | 1105 | $T_{es}G_{eo}T_{eo}T_{eo}T_{es}A_{ds}T_{ds}T_{ds}T_{ds}G_{ds}T_{ds}{}^mC_{ds}T_{ds}G_{eo}G_{eo}A_{es}G_{es}{}^mC_e$ | 25 | 27 |
| 650367 | 59 | 76 | 1094 | 1111 | $A_{es}{}^mC_{eo}T_{eo}{}^mC_{eo}{}^mC_{es}A_{ds}T_{ds}G_{ds}T_{ds}T_{ds}A_{ds}T_{ds}T_{eo}T_{eo}G_{es}T_{es}{}^mC_e$ | 8 | 28 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650368 | 64 | 81 | 1099 | 1116 | $G_{es}A_{eo}T_{eo}G_{eo}G_{es}A_{ds}{}^mC_{ds}T_{ds}{}^mC_{ds}{}^mC_{ds}A_{ds}T_{ds}G_{ds}T_{eo}T_{eo}T_{es}A_{es}T_e$ | 0 | 29 |
| 650369 | 69 | 86 | 1104 | 1121 | $T_{es}G_{eo}T_{eo}A_{eo}A_{es}G_{ds}A_{ds}T_{ds}G_{ds}G_{ds}A_{ds}{}^mC_{ds}T_{ds}{}^mC_{eo}{}^mC_{eo}A_{es}T_{es}G_e$ | 13 | 30 |
| 650370 | 87 | 104 | N/A | N/A | $G_{es}A_{eo}G_{eo}{}^mC_{eo}{}^mC_{es}T_{ds}T_{ds}{}^mC_{ds}T_{ds}T_{ds}G_{ds}T_{ds}T_{ds}T_{eo}{}^mC_{eo}T_{es}{}^mC_{es}G_e$ | 33 | 31 |
| 650371 | 92 | 109 | N/A | N/A | $A_{es}A_{eo}A_{eo}G_{eo}T_{es}G_{ds}A_{ds}G_{ds}{}^mC_{ds}{}^mC_{ds}T_{ds}T_{ds}{}^mC_{ds}T_{eo}T_{eo}G_{es}T_{es}T_e$ | 20 | 32 |
| 650372 | 97 | 114 | 10822 | 10839 | $A_{es}G_{eo}{}^mC_{eo}A_{eo}{}^mC_{es}A_{ds}A_{ds}A_{ds}G_{ds}T_{ds}G_{ds}A_{ds}G_{ds}{}^mC_{eo}{}^mC_{eo}T_{es}T_{es}{}^mC_e$ | 57 | 33 |
| 650373 | 100 | 117 | 10825 | 10842 | $T_{es}T_{eo}G_{eo}A_{eo}G_{es}{}^mC_{ds}A_{ds}{}^mC_{ds}A_{ds}A_{ds}A_{ds}G_{ds}T_{ds}G_{eo}A_{eo}G_{es}{}^mC_{es}{}^mC_e$ | 19 | 34 |
| 650374 | 123 | 140 | 10848 | 10865 | $T_{es}G_{eo}{}^mC_{eo}A_{eo}A_{es}T_{ds}A_{ds}A_{ds}G_{ds}T_{ds}T_{ds}A_{ds}T_{ds}T_{eo}{}^mC_{eo}A_{es}G_{es}G_e$ | 39 | 35 |
| 650375 | 147 | 164 | 10872 | 10889 | $T_{es}{}^mC_{eo}{}^mC_{eo}A_{eo}{}^mC_{es}A_{ds}G_{ds}G_{ds}G_{ds}{}^mC_{ds}T_{ds}A_{ds}A_{ds}A_{eo}A_{eo}T_{es}A_{es}T_e$ | 0 | 36 |
| 650376 | 170 | 187 | 10895 | 10912 | $G_{es}{}^mC_{eo}T_{eo}G_{eo}A_{es}T_{ds}G_{ds}T_{ds}G_{ds}{}^mC_{ds}A_{ds}A_{ds}T_{ds}T_{eo}G_{eo}A_{es}G_{es}G_e$ | 36 | 37 |
| 650377 | 195 | 212 | 10920 | 10937 | $A_{es}T_{eo}T_{eo}{}^mC_{eo}T_{es}{}^mC_{ds}A_{ds}T_{ds}{}^mC_{ds}{}^mC_{ds}T_{ds}{}^mC_{ds}T_{ds}{}^mC_{eo}{}^mC_{eo}T_{es}{}^mC_{es}{}^mC_e$ | 29 | 38 |
| 650378 | 218 | 235 | 10943 | 10960 | ${}^mC_{es}A_{eo}{}^mC_{eo}T_{eo}A_{es}G_{ds}T_{ds}A_{ds}A_{ds}{}^mC_{ds}T_{ds}T_{ds}{}^mC_{ds}{}^mC_{ds}T_{eo}{}^mC_{eo}{}^mC_{es}T_{es}T_e$ | 39 | 39 |
| 650379 | 248 | 265 | N/A | N/A | $A_{es}A_{eo}G_{eo}G_{eo}{}^mC_{es}T_{ds}G_{ds}{}^mC_{ds}T_{ds}G_{ds}T_{ds}A_{ds}A_{ds}A_{eo}A_{eo}A_{es}{}^mC_{es}G_e$ | 55 | 40 |
| 650380 | 251 | 268 | N/A | N/A | ${}^mC_{es}A_{eo}G_{eo}A_{eo}A_{es}G_{ds}G_{ds}{}^mC_{ds}T_{ds}G_{ds}{}^mC_{ds}T_{ds}G_{ds}T_{eo}A_{eo}A_{es}A_{es}A_e$ | 17 | 41 |
| 650381 | 256 | 273 | 11517 | 11534 | $A_{es}T_{eo}T_{eo}T_{eo}{}^mC_{es}{}^mC_{ds}A_{ds}G_{ds}A_{ds}A_{ds}G_{ds}G_{ds}{}^mC_{ds}T_{eo}G_{eo}{}^mC_{es}T_{es}G_e$ | 21 | 42 |
| 650382 | 261 | 278 | 11522 | 11539 | $T_{es}{}^mC_{eo}{}^mC_{eo}A_{eo}T_{es}T_{ds}T_{ds}T_{ds}{}^mC_{ds}{}^mC_{ds}A_{ds}G_{ds}A_{ds}A_{eo}G_{eo}G_{es}{}^mC_e$ | 43 | 43 |
| 650383 | 266 | 283 | 11527 | 11544 | $T_{es}G_{eo}T_{eo}{}^mC_{eo}A_{es}T_{ds}{}^mC_{ds}{}^mC_{ds}A_{ds}T_{ds}T_{ds}T_{ds}T_{ds}T_{eo}{}^mC_{eo}{}^mC_{es}A_{es}G_e$ | 14 | 44 |
| 650384 | 271 | 288 | 11532 | 11549 | $A_{es}{}^mC_{eo}{}^mC_{eo}A_{eo}{}^mC_{es}T_{ds}G_{ds}T_{ds}{}^mC_{ds}A_{ds}T_{ds}{}^mC_{ds}{}^mC_{ds}A_{eo}T_{eo}A_{es}T_{es}T_e$ | 29 | 45 |
| 650385 | 294 | 311 | N/A | N/A | ${}^mC_{es}T_{eo}T_{eo}A_{eo}T_{es}A_{ds}A_{ds}{}^mC_{ds}A_{ds}{}^mC_{ds}T_{ds}G_{ds}A_{ds}A_{ds}T_{eo}A_{eo}G_{es}A_{es}G_e$ | 9 | 46 |
| 650386 | 320 | 337 | 13842 | 13859 | ${}^mC_{es}T_{eo}A_{eo}A_{eo}A_{es}{}^mC_{ds}{}^mC_{ds}{}^mC_{ds}{}^mC_{ds}A_{ds}A_{ds}A_{ds}{}^mC_{ds}T_{eo}T_{eo}T_{es}{}^mC_{es}A_e$ | 30 | 47 |
| 650387 | 325 | 342 | 13847 | 13864 | $T_{es}A_{eo}G_{eo}T_{eo}T_{es}{}^mC_{ds}T_{ds}A_{ds}A_{ds}A_{ds}{}^mC_{ds}{}^mC_{ds}{}^mC_{ds}{}^mC_{eo}A_{eo}A_{es}A_{es}{}^mC_e$ | 0 | 48 |
| 650388 | 330 | 347 | 13852 | 13869 | $A_{es}G_{eo}G_{eo}A_{eo}T_{es}T_{ds}A_{ds}G_{ds}T_{ds}T_{ds}{}^mC_{ds}T_{ds}A_{ds}A_{eo}A_{eo}{}^mC_{es}{}^mC_{es}{}^mC_e$ | 15 | 49 |
| 650389 | 335 | 352 | 13857 | 13874 | $T_{es}G_{eo}A_{eo}A_{eo}{}^mC_{es}A_{ds}G_{ds}G_{ds}A_{ds}T_{ds}T_{ds}A_{ds}G_{ds}T_{eo}{}^mC_{es}T_{es}A_e$ | 2 | 50 |
| 650390 | 340 | 357 | 13862 | 13879 | $A_{es}{}^mC_{eo}T_{eo}G_{eo}T_{es}G_{ds}A_{ds}A_{ds}{}^mC_{ds}A_{ds}G_{ds}G_{ds}A_{eo}T_{eo}T_{es}A_{es}G_e$ | 33 | 51 |
| 650391 | 345 | 362 | 13867 | 13884 | $T_{es}{}^mC_{eo}T_{eo}G_{eo}G_{es}A_{ds}{}^mC_{ds}T_{ds}G_{ds}T_{ds}G_{ds}A_{ds}A_{ds}{}^mC_{eo}A_{es}G_{es}G_e$ | 11 | 52 |
| 650392 | 349 | 366 | 13871 | 13888 | $A_{es}T_{eo}A_{eo}{}^mC_{eo}T_{es}{}^mC_{ds}T_{ds}G_{ds}G_{ds}A_{ds}{}^mC_{ds}T_{ds}G_{ds}T_{eo}T_{eo}G_{es}A_{es}A_e$ | 23 | 53 |
| 650393 | 372 | 389 | 13894 | 13911 | $A_{es}T_{eo}A_{eo}G_{eo}G_{es}A_{ds}T_{ds}{}^mC_{ds}G_{ds}G_{ds}A_{ds}T_{ds}{}^mC_{ds}{}^mC_{ds}T_{eo}G_{eo}A_{es}G_{es}{}^mC_e$ | 39 | 54 |
| 650394 | 404 | 421 | 14353 | 14370 | ${}^mC_{es}{}^mC_{eo}T_{eo}T_{eo}A_{es}T_{ds}A_{ds}A_{ds}T_{ds}T_{ds}G_{ds}{}^mC_{ds}A_{ds}T_{eo}A_{eo}T_{es}A_{es}A_e$ | 24 | 55 |
| 650395 | 422 | 439 | 14371 | 14388 | $T_{es}A_{eo}A_{eo}{}^mC_{eo}T_{es}G_{ds}T_{ds}A_{ds}A_{ds}A_{ds}{}^mC_{ds}{}^mC_{ds}A_{ds}G_{eo}T_{eo}G_{es}T_{es}T_e$ | 8 | 56 |
| 650396 | 432 | 449 | 14381 | 14398 | ${}^mC_{es}{}^mC_{eo}T_{eo}A_{eo}A_{es}T_{ds}T_{ds}T_{ds}T_{ds}{}^mC_{ds}T_{ds}A_{ds}A_{ds}{}^mC_{eo}T_{eo}G_{es}T_{es}A_e$ | 0 | 57 |
| 650397 | 433 | 450 | 14382 | 14399 | $T_{es}{}^mC_{eo}{}^mC_{eo}T_{eo}A_{es}A_{ds}T_{ds}T_{ds}T_{ds}T_{ds}{}^mC_{ds}T_{ds}A_{ds}A_{eo}{}^mC_{eo}T_{es}G_{es}T_e$ | 13 | 58 |
| 650398 | 454 | 471 | 18837 | 18854 | $A_{es}T_{eo}T_{eo}{}^mC_{eo}A_{es}A_{ds}G_{ds}T_{ds}A_{ds}A_{ds}A_{ds}A_{ds}{}^mC_{ds}{}^mC_{eo}A_{eo}{}^mC_{es}T_{es}G_e$ | 34 | 59 |
| 650399 | 459 | 476 | 18842 | 18859 | $A_{es}G_{eo}A_{eo}G_{eo}A_{es}A_{ds}T_{ds}T_{ds}{}^mC_{ds}A_{ds}A_{ds}G_{ds}T_{ds}T_{eo}A_{eo}A_{es}A_{es}{}^mC_e$ | 5 | 60 |
| 650400 | 462 | 479 | 18845 | 18862 | $A_{es}A_{eo}G_{eo}A_{eo}G_{es}A_{ds}G_{ds}A_{ds}A_{ds}T_{ds}T_{ds}{}^mC_{ds}A_{ds}A_{eo}G_{eo}T_{es}T_{es}A_e$ | 17 | 61 |
| 650401 | 478 | 495 | 18861 | 18878 | $T_{es}A_{eo}A_{eo}T_{eo}T_{es}{}^mC_{ds}A_{ds}G_{ds}G_{ds}A_{ds}A_{ds}{}^mC_{ds}{}^mC_{ds}{}^mC_{ds}G_{eo}T_{eo}{}^mC_{es}A_{es}A_e$ | 25 | 62 |
| 650402 | 483 | 500 | 18866 | 18883 | $G_{es}A_{eo}T_{eo}A_{eo}A_{es}T_{ds}T_{ds}A_{ds}A_{ds}T_{ds}T_{ds}{}^mC_{ds}T_{ds}G_{ds}G_{eo}A_{eo}{}^mC_{es}{}^mC_{es}{}^mC_e$ | 47 | 63 |
| 650403 | 489 | 506 | 18872 | 18889 | $G_{es}T_{eo}A_{eo}T_{eo}{}^mC_{es}T_{ds}G_{ds}A_{ds}T_{ds}A_{ds}A_{ds}T_{ds}T_{ds}A_{ds}A_{eo}T_{eo}T_{es}{}^mC_{es}T_e$ | 6 | 64 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650404 | 494 | 511 | 18877 | 18894 | $G_{es}A_{eo}T_{eo}A_{eo}T_{es}G_{ds}T_{ds}A_{ds}T_{ds}{}^mC_{ds}T_{ds}G_{ds}A_{ds}T_{eo}A_{eo}T_{es}T_{es}A_{e}$ | 19 | 65 |
| 650405 | 517 | 534 | 18900 | 18917 | $T_{es}A_{eo}T_{eo}T_{es}G_{ds}A_{ds}G_{ds}{}^mC_{ds}{}^mC_{ds}A_{ds}A_{ds}G_{ds}A_{eo}A_{eo}A_{es}G_{e}$ | 0 | 66 |
| 650406 | 540 | 557 | N/A | N/A | $A_{es}A_{eo}T_{eo}A_{eo}T_{es}A_{ds}G_{ds}A_{ds}A_{ds}T_{ds}A_{ds}A_{ds}{}^mC_{ds}{}^mC_{eo}T_{eo}T_{es}{}^mC_{es}{}^mC_{e}$ | 17 | 67 |
| 650407 | 542 | 559 | N/A | N/A | ${}^mC_{es}A_{eo}A_{eo}A_{eo}T_{es}A_{ds}T_{ds}A_{ds}G_{ds}A_{ds}A_{ds}T_{ds}A_{ds}A_{ds}{}^mC_{eo}{}^mC_{eo}{}^mC_{es}T_{es}T_{e}$ | 2 | 68 |
| 650408 | 562 | 579 | 24416 | 24433 | $T_{es}G_{eo}G_{eo}{}^mC_{eo}A_{es}G_{ds}A_{ds}T_{ds}{}^mC_{ds}A_{ds}{}^mC_{ds}{}^mC_{ds}{}^mC_{ds}T_{eo}T_{eo}A_{es}A_{es}{}^mC_{e}$ | 19 | 69 |
| 650409 | 567 | 584 | 24421 | 24438 | ${}^mC_{es}A_{eo}A_{eo}T_{eo}{}^mC_{es}T_{ds}G_{ds}G_{ds}{}^mC_{ds}A_{ds}G_{ds}A_{ds}T_{ds}{}^mC_{eo}A_{eo}{}^mC_{es}{}^mC_{es}{}^mC_{e}$ | 30 | 70 |
| 650410 | 568 | 585 | 24422 | 24439 | $G_{es}{}^mC_{eo}A_{eo}A_{eo}T_{es}{}^mC_{ds}T_{ds}G_{ds}G_{ds}{}^mC_{ds}A_{ds}G_{ds}A_{ds}T_{eo}{}^mC_{eo}A_{eo}{}^mC_{es}{}^mC_{e}$ | 57 | 71 |
| 650411 | 591 | 608 | 24445 | 24462 | $A_{es}T_{eo}{}^mC_{eo}T_{eo}G_{es}{}^mC_{ds}A_{ds}G_{ds}G_{ds}A_{ds}G_{ds}T_{ds}T_{ds}G_{eo}G_{eo}T_{es}{}^mC_{es}A_{e}$ | 12 | 72 |
| 650412 | 614 | 631 | 24468 | 24485 | $G_{es}A_{eo}T_{eo}G_{eo}{}^mC_{es}A_{ds}T_{ds}{}^mC_{ds}T_{ds}G_{ds}T_{ds}T_{ds}G_{ds}G_{eo}A_{eo}{}^mC_{es}{}^mC_{es}{}^mC_{e}$ | 45 | 73 |
| 650413 | 615 | 632 | 24469 | 24486 | ${}^mC_{es}G_{eo}A_{eo}T_{eo}G_{eo}{}^mC_{es}{}^mC_{ds}A_{ds}T_{ds}{}^mC_{ds}T_{ds}G_{ds}T_{ds}T_{ds}G_{eo}G_{eo}A_{es}{}^mC_{es}{}^mC_{e}$ | 41 | 74 |
| 650414 | 620 | 637 | 24474 | 24491 | $T_{es}T_{eo}G_{eo}G_{eo}T_{es}{}^mC_{ds}G_{ds}A_{ds}T_{ds}G_{ds}{}^mC_{ds}{}^mC_{ds}A_{ds}T_{ds}{}^mC_{eo}T_{eo}G_{es}T_{es}T_{e}$ | 41 | 75 |
| 650415 | 625 | 642 | 24479 | 24496 | $A_{es}A_{eo}G_{eo}A_{eo}T_{es}T_{ds}T_{ds}G_{ds}G_{ds}T_{ds}{}^mC_{ds}G_{ds}A_{ds}T_{eo}G_{eo}{}^mC_{es}{}^mC_{es}A_{e}$ | 0 | 76 |
| 650416 | 630 | 647 | 24484 | 24501 | ${}^mC_{es}{}^mC_{eo}A_{eo}A_{eo}T_{es}A_{ds}A_{ds}G_{ds}A_{ds}T_{ds}T_{ds}T_{ds}G_{ds}G_{eo}T_{eo}{}^mC_{es}G_{es}A_{e}$ | 23 | 77 |
| 650417 | 638 | 655 | 24492 | 24509 | $A_{es}T_{eo}T_{eo}{}^mC_{eo}T_{es}T_{ds}{}^mC_{ds}T_{ds}{}^mC_{ds}{}^mC_{ds}A_{ds}A_{ds}T_{ds}A_{eo}A_{eo}G_{es}T_{es}T_{e}$ | 0 | 78 |
| 650418 | 661 | 678 | N/A | N/A | $T_{es}{}^mC_{eo}T_{eo}T_{eo}T_{es}G_{ds}{}^mC_{ds}T_{ds}{}^mC_{ds}T_{ds}T_{ds}T_{ds}T_{ds}A_{eo}G_{eo}T_{es}T_{es}G_{e}$ | 26 | 79 |
| 650419 | 684 | 701 | 25197 | 25214 | ${}^mC_{es}G_{eo}T_{eo}T_{eo}{}^mC_{es}{}^mC_{ds}A_{ds}G_{ds}G_{ds}T_{ds}{}^mC_{ds}T_{ds}G_{ds}T_{eo}T_{eo}T_{es}T_{es}A_{e}$ | 47 | 80 |
| 650420 | 708 | 725 | 25221 | 25238 | $G_{es}A_{eo}G_{eo}{}^mC_{eo}{}^mC_{es}A_{ds}T_{ds}{}^mC_{ds}A_{ds}T_{ds}T_{ds}T_{ds}T_{ds}G_{ds}{}^mC_{eo}T_{eo}T_{es}{}^mC_{es}T_{e}$ | 37 | 81 |
| 650421 | 738 | 755 | 25251 | 25268 | $A_{es}A_{eo}A_{eo}T_{eo}{}^mC_{es}{}^mC_{ds}T_{ds}{}^mC_{ds}T_{ds}{}^mC_{ds}T_{ds}{}^mC_{ds}A_{ds}T_{ds}{}^mC_{eo}T_{eo}T_{es}{}^mC_{es}G_{e}$ | 7 | 82 |
| 650422 | 761 | 778 | 25274 | 25291 | $G_{es}A_{eo}{}^mC_{eo}T_{eo}T_{es}A_{ds}G_{ds}T_{ds}G_{ds}{}^mC_{ds}{}^mC_{ds}A_{ds}G_{ds}A_{eo}G_{eo}{}^mC_{es}{}^mC_{es}{}^mC_{e}$ | 47 | 83 |
| 650423 | 787 | 804 | 25300 | 25317 | ${}^mC_{es}T_{eo}{}^mC_{eo}A_{eo}T_{es}{}^mC_{ds}T_{ds}T_{ds}{}^mC_{ds}{}^mC_{ds}A_{ds}T_{ds}G_{ds}T_{eo}{}^mC_{eo}A_{es}A_{es}T_{e}$ | 0 | 84 |
| 650424 | 810 | 827 | 25323 | 25340 | $A_{es}T_{eo}A_{eo}G_{eo}{}^mC_{es}T_{ds}{}^mC_{ds}T_{ds}G_{ds}{}^mC_{ds}G_{ds}G_{ds}A_{ds}G_{eo}A_{eo}T_{es}{}^mC_{es}T_{e}$ | 12 | 85 |
| 650425 | 833 | 850 | N/A | N/A | $A_{es}A_{eo}{}^mC_{eo}T_{eo}A_{es}{}^mC_{ds}{}^mC_{ds}T_{ds}T_{ds}G_{ds}{}^mC_{ds}A_{ds}T_{ds}A_{eo}{}^mC_{eo}T_{es}T_{es}A_{e}$ | 31 | 86 |
| 650426 | 835 | 852 | N/A | N/A | $G_{es}G_{eo}A_{eo}A_{eo}{}^mC_{es}T_{ds}A_{ds}{}^mC_{ds}{}^mC_{ds}T_{ds}T_{ds}G_{ds}{}^mC_{ds}A_{ds}T_{eo}A_{eo}{}^mC_{es}T_{e}$ | 33 | 87 |
| 650427 | 856 | 873 | 26607 | 26624 | ${}^mC_{es}A_{eo}A_{eo}A_{eo}T_{es}{}^mC_{ds}T_{ds}T_{ds}G_{ds}A_{ds}G_{ds}A_{ds}T_{ds}A_{eo}T_{eo}G_{es}T_{es}T_{e}$ | 48 | 88 |
| 650428 | 879 | 896 | 26630 | 26647 | $A_{es}G_{eo}A_{eo}A_{eo}T_{es}T_{ds}G_{ds}T_{ds}A_{ds}{}^mC_{ds}{}^mC_{ds}T_{ds}G_{ds}A_{eo}T_{eo}G_{es}T_{es}{}^mC_{e}$ | 20 | 89 |
| 650429 | 902 | 919 | 26653 | 26670 | $T_{es}{}^mC_{eo}T_{eo}T_{eo}{}^mC_{es}{}^mC_{ds}G_{ds}A_{ds}A_{ds}G_{ds}{}^mC_{ds}T_{ds}{}^mC_{ds}T_{eo}T_{eo}{}^mC_{es}T_{es}G_{e}$ | 3 | 90 |
| 650430 | 922 | 939 | 26673 | 26690 | $T_{es}T_{eo}{}^mC_{eo}A_{eo}A_{es}A_{ds}G_{ds}T_{ds}A_{ds}G_{ds}G_{ds}{}^mC_{ds}T_{ds}T_{eo}{}^mC_{eo}T_{es}{}^mC_{es}G_{e}$ | 47 | 91 |
| 650431 | 925 | 942 | N/A | N/A | $T_{es}T_{eo}T_{eo}T_{eo}T_{es}{}^mC_{ds}A_{ds}A_{ds}A_{ds}G_{ds}T_{ds}A_{ds}G_{ds}G_{eo}{}^mC_{eo}T_{es}T_{es}{}^mC_{e}$ | 0 | 92 |
| 650432* | 976 | 993 | 36638 | 36655 | $T_{es}A_{eo}G_{eo}G_{eo}T_{es}{}^mC_{ds}{}^mC_{ds}{}^mC_{ds}{}^mC_{ds}{}^mC_{ds}T_{ds}G_{ds}{}^mC_{ds}T_{eo}G_{eo}{}^mC_{es}T_{es}G_{e}$ | 68 | 93 |
| 650433* | 999 | 1016 | 36661 | 36678 | ${}^mC_{es}A_{eo}T_{eo}G_{eo}G_{es}A_{ds}T_{ds}G_{ds}T_{ds}G_{ds}A_{ds}A_{ds}{}^mC_{ds}T_{eo}{}^mC_{eo}T_{es}G_{es}T_{e}$ | 21 | 94 |
| 650434* | 1022 | 1039 | 36684 | 36701 | ${}^mC_{es}T_{eo}G_{eo}A_{eo}A_{es}{}^mC_{ds}T_{ds}G_{ds}G_{ds}T_{ds}G_{ds}G_{ds}{}^mC_{ds}T_{eo}G_{eo}G_{es}{}^mC_{es}{}^mC_{e}$ | 49 | 95 |
| 650435* | 1045 | 1062 | 36707 | 36724 | $A_{es}{}^mC_{eo}{}^mC_{eo}T_{eo}A_{es}G_{ds}A_{ds}T_{ds}{}^mC_{ds}A_{ds}{}^mC_{ds}T_{ds}{}^mC_{ds}{}^mC_{eo}{}^mC_{eo}A_{es}A_{es}G_{e}$ | 12 | 96 |
| 650436* | 1068 | 1085 | 43250 | 43267 | $A_{es}T_{eo}G_{eo}T_{eo}{}^mC_{es}T_{ds}T_{ds}{}^mC_{ds}T_{ds}T_{ds}{}^mC_{ds}A_{ds}{}^mC_{ds}T_{eo}{}^mC_{eo}A_{es}T_{es}A_{e}$ | 32 | 97 |
| 650437 | 1091 | 1108 | 43273 | 43290 | $A_{es}{}^mC_{eo}A_{eo}T_{eo}G_{es}T_{ds}{}^mC_{ds}T_{ds}{}^mC_{ds}A_{ds}{}^mC_{ds}G_{ds}G_{ds}{}^mC_{ds}T_{eo}G_{eo}{}^mC_{es}{}^mC_{es}T_{e}$ | 67 | 98 |
| 650438 | 1092 | 1109 | 43274 | 43291 | $G_{es}A_{eo}{}^mC_{eo}A_{eo}T_{es}G_{ds}G_{ds}T_{ds}{}^mC_{ds}A_{ds}{}^mC_{ds}A_{ds}G_{ds}{}^mC_{eo}T_{eo}G_{es}{}^mC_{es}{}^mC_{e}$ | 69 | 99 |
| 650439 | 1097 | 1114 | 43279 | 43296 | ${}^mC_{es}T_{eo}A_{eo}A_{eo}A_{es}G_{ds}A_{ds}{}^mC_{ds}A_{ds}T_{ds}G_{ds}G_{ds}T_{ds}{}^mC_{eo}A_{eo}{}^mC_{es}A_{es}G_{e}$ | 36 | 100 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650440 | 1102 | 1119 | 43284 | 43301 | $A_{es}G_{eo}T_{eo}T_{eo}T_{es}{}^mC_{ds}T_{ds}A_{ds}A_{ds}A_{ds}G_{ds}A_{ds}{}^mC_{ds}A_{eo}T_{eo}G_{es}G_{es}T_e$ | 40 | 101 |
| 650441 | 1114 | 1131 | 43296 | 43313 | $A_{es}T_{eo}{}^mC_{eo}A_{eo}T_{es}T_{ds}T_{ds}{}^mC_{ds}T_{ds}G_{ds}A_{ds}{}^mC_{ds}A_{ds}G_{eo}T_{eo}T_{es}T_{es}{}^mC_e$ | 31 | 102 |
| 650442 | 1173 | 1190 | 43355 | 43372 | $G_{es}A_{eo}A_{eo}A_{eo}G_{es}T_{ds}A_{ds}T_{ds}G_{ds}A_{ds}A_{ds}T_{ds}A_{ds}T_{eo}{}^mC_{eo}T_{es}A_{es}A_e$ | 27 | 103 |
| 650443 | 1196 | 1213 | 43378 | 43395 | $T_{es}G_{eo}T_{eo}A_{eo}A_{es}T_{ds}{}^mC_{ds}A_{ds}{}^mC_{ds}A_{ds}{}^mC_{ds}A_{ds}G_{ds}G_{eo}A_{eo}T_{es}A_{es}A_e$ | 35 | 104 |
| 650444 | 1219 | 1236 | 43401 | 43418 | ${}^mC_{es}A_{eo}T_{eo}T_{eo}{}^mC_{es}{}^mC_{ds}A_{ds}A_{ds}A_{ds}G_{ds}T_{ds}G_{ds}G_{eo}A_{eo}{}^mC_{es}{}^mC_{es}{}^mC_e$ | 18 | 105 |
| 650445 | 1250 | 1267 | 43432 | 43449 | ${}^mC_{es}T_{eo}A_{eo}A_{es}A_{ds}G_{ds}T_{ds}{}^mC_{ds}T_{ds}T_{ds}A_{ds}T_{ds}T_{eo}T_{eo}{}^mC_{es}{}^mC_{es}T_e$ | 17 | 106 |
| 650446 | 1279 | 1296 | 43461 | 43478 | ${}^mC_{es}A_{eo}{}^mC_{eo}T_{eo}T_{es}T_{ds}{}^mC_{ds}{}^mC_{ds}{}^mC_{ds}A_{ds}T_{ds}{}^mC_{ds}A_{ds}T_{eo}T_{eo}T_{es}T_{es}G_e$ | 17 | 107 |
| 650447 | 1302 | 1319 | 43484 | 43501 | $G_{es}T_{eo}{}^mC_{eo}{}^mC_{eo}T_{es}A_{ds}{}^mC_{ds}A_{ds}A_{ds}{}^mC_{ds}{}^mC_{ds}G_{ds}A_{ds}{}^mC_{eo}G_{eo}{}^mC_{es}A_{es}T_e$ | 21 | 108 |
| 650448 | 1327 | 1344 | 43509 | 43526 | ${}^mC_{es}T_{eo}A_{eo}A_{eo}T_{es}A_{ds}T_{ds}T_{ds}T_{ds}G_{ds}G_{ds}A_{ds}A_{ds}G_{eo}A_{eo}T_{es}{}^mC_{es}A_e$ | 39 | 109 |
| 650449 | 1350 | 1367 | 43532 | 43549 | $T_{es}T_{eo}A_{eo}A_{eo}T_{es}T_{ds}G_{ds}{}^mC_{ds}T_{ds}G_{ds}A_{ds}A_{ds}T_{ds}G_{eo}{}^mC_{eo}{}^mC_{es}T_{es}{}^mC_e$ | 51 | 110 |
| 650450 | 1402 | 1419 | 43584 | 43601 | $T_{es}T_{eo}G_{eo}{}^mC_{eo}A_{es}{}^mC_{ds}A_{ds}{}^mC_{ds}T_{ds}{}^mC_{ds}A_{ds}A_{ds}A_{ds}A_{eo}A_{eo}A_{es}G_{es}A_e$ | 21 | 111 |
| 650451 | 1425 | 1442 | 43607 | 43624 | ${}^mC_{es}{}^mC_{eo}T_{eo}A_{eo}A_{es}{}^mC_{ds}T_{ds}T_{ds}T_{ds}A_{ds}G_{ds}A_{ds}{}^mC_{ds}A_{eo}T_{eo}G_{es}T_{es}T_e$ | 15 | 112 |
| 650452 | 1450 | 1467 | 43632 | 43649 | ${}^mC_{es}T_{eo}G_{eo}{}^mC_{eo}A_{es}A_{ds}A_{ds}A_{ds}A_{ds}A_{ds}G_{ds}A_{ds}T_{ds}{}^mC_{ds}{}^mC_{eo}A_{eo}A_{es}G_{es}A_e$ | 20 | 113 |
| 650453 | 1473 | 1490 | 43655 | 43672 | $G_{es}A_{eo}G_{eo}G_{eo}{}^mC_{es}G_{ds}A_{ds}G_{ds}A_{ds}G_{ds}{}^mC_{ds}T_{ds}A_{ds}A_{eo}T_{eo}T_{es}A_{es}G_e$ | 17 | 114 |
| 650454 | 1518 | 1535 | 43700 | 43717 | $T_{es}A_{eo}{}^mC_{eo}{}^mC_{eo}T_{es}A_{ds}{}^mC_{ds}A_{ds}A_{ds}G_{ds}A_{ds}{}^mC_{ds}A_{ds}G_{eo}A_{eo}A_{es}A_{es}A_e$ | 12 | 115 |
| 650455 | 1541 | 1558 | 43723 | 43740 | ${}^mC_{es}T_{eo}A_{eo}T_{eo}T_{es}A_{ds}{}^mC_{ds}A_{ds}A_{ds}T_{ds}G_{ds}A_{ds}T_{ds}G_{ds}T_{eo}G_{eo}A_{es}G_{es}{}^mC_e$ | 13 | 116 |
| 650456 | 1564 | 1581 | 43746 | 43763 | $T_{es}G_{eo}G_{eo}T_{eo}T_{es}A_{ds}A_{ds}T_{ds}A_{ds}A_{ds}G_{ds}A_{ds}A_{ds}A_{eo}T_{eo}G_{es}A_{es}A_e$ | 0 | 117 |
| 650457 | 1588 | 1605 | 43770 | 43787 | $A_{es}G_{eo}A_{eo}T_{eo}A_{es}{}^mC_{ds}T_{ds}T_{ds}T_{ds}{}^mC_{ds}{}^mC_{ds}T_{ds}G_{ds}A_{eo}A_{eo}A_{es}G_{es}G_e$ | 0 | 118 |
| 650458 | 1613 | 1630 | 43795 | 43812 | $A_{es}{}^mC_{eo}T_{eo}A_{eo}T_{es}T_{ds}A_{ds}A_{ds}T_{ds}{}^mC_{ds}A_{ds}A_{ds}{}^mC_{ds}A_{ds}T_{eo}{}^mC_{eo}A_{es}G_{es}G_e$ | 6 | 119 |
| 650459 | 1636 | 1653 | 43818 | 43835 | ${}^mC_{es}T_{eo}G_{eo}T_{eo}T_{es}{}^mC_{ds}A_{ds}T_{ds}{}^mC_{ds}{}^mC_{ds}T_{ds}T_{ds}{}^mC_{ds}T_{eo}A_{eo}G_{es}A_{es}A_e$ | 15 | 120 |
| 650460 | 1659 | 1676 | 43841 | 43858 | $A_{es}{}^mC_{eo}G_{eo}G_{eo}T_{es}A_{ds}T_{ds}A_{ds}{}^mC_{ds}A_{ds}A_{ds}G_{ds}T_{ds}T_{ds}G_{eo}A_{eo}A_{es}G_{es}G_e$ | 8 | 121 |
| 650461 | 1695 | 1712 | 43877 | 43894 | $G_{es}A_{eo}T_{eo}{}^mC_{eo}A_{es}G_{ds}A_{ds}G_{ds}A_{ds}A_{ds}A_{ds}A_{ds}{}^mC_{ds}A_{eo}A_{eo}{}^mC_{es}A_{es}{}^mC_e$ | 18 | 122 |
| 650462 | 1720 | 1737 | 43902 | 43919 | $G_{es}A_{eo}A_{eo}A_{eo}A_{es}{}^mC_{ds}{}^mC_{ds}A_{ds}G_{ds}G_{ds}T_{ds}A_{ds}G_{ds}{}^mC_{eo}A_{eo}G_{es}A_{es}A_e$ | 15 | 123 |
| 650463 | 1743 | 1760 | 43925 | 43942 | ${}^mC_{es}A_{eo}A_{eo}A_{eo}A_{es}G_{ds}A_{ds}A_{ds}T_{ds}T_{ds}G_{ds}T_{ds}G_{ds}G_{eo}G_{eo}A_{es}A_{es}A_e$ | 11 | 124 |
| 650464 | 1766 | 1783 | 43948 | 43965 | ${}^mC_{es}{}^mC_{eo}T_{eo}{}^mC_{eo}A_{es}G_{ds}A_{ds}A_{ds}A_{ds}A_{ds}G_{ds}A_{ds}T_{ds}T_{eo}A_{eo}{}^mC_{es}{}^mC_{es}A_e$ | 29 | 125 |
| 650465 | 1803 | 1820 | 43985 | 44002 | $G_{es}A_{eo}A_{eo}A_{eo}T_{es}A_{ds}A_{ds}T_{ds}G_{ds}A_{ds}T_{ds}{}^mC_{ds}{}^mC_{ds}{}^mC_{eo}A_{eo}T_{es}{}^mC_{es}G_e$ | 2 | 126 |
| 650466 | 1826 | 1843 | 44008 | 44025 | $G_{es}A_{eo}G_{eo}T_{eo}T_{es}T_{ds}A_{ds}G_{ds}G_{ds}A_{ds}{}^mC_{ds}G_{ds}{}^mC_{eo}A_{eo}{}^mC_{es}{}^mC_{es}A_e$ | 57 | 127 |
| 650467 | 1849 | 1866 | 44031 | 44048 | $G_{es}T_{eo}A_{eo}{}^mC_{eo}T_{es}T_{ds}G_{ds}T_{ds}G_{ds}{}^mC_{ds}A_{ds}A_{ds}A_{ds}G_{ds}G_{eo}{}^mC_{eo}T_{es}G_{es}A_e$ | 33 | 128 |
| 650468 | 1891 | 1908 | 44073 | 44090 | $G_{es}{}^mC_{eo}A_{eo}{}^mC_{eo}A_{es}T_{ds}G_{ds}{}^mC_{ds}T_{ds}{}^mC_{ds}A_{ds}{}^mC_{ds}A_{ds}{}^mC_{eo}A_{eo}T_{es}T_{es}T_e$ | 34 | 129 |
| 650469 | 1915 | 1932 | 44097 | 44114 | $G_{es}A_{eo}{}^mC_{eo}A_{eo}T_{es}{}^mC_{ds}A_{ds}T_{ds}A_{ds}A_{ds}A_{ds}A_{ds}G_{ds}{}^mC_{eo}A_{eo}T_{es}{}^mC_{es}T_e$ | 14 | 130 |
| 650470 | 1938 | 1955 | 44120 | 44137 | $T_{es}A_{eo}A_{eo}G_{eo}G_{es}T_{ds}T_{ds}T_{ds}T_{ds}G_{ds}A_{ds}T_{ds}A_{ds}T_{eo}A_{eo}A_{es}G_{es}T_e$ | 0 | 131 |
| 650471 | 1971 | 1988 | 44153 | 44170 | $A_{es}A_{eo}G_{eo}G_{eo}{}^mC_{es}G_{ds}{}^mC_{ds}A_{ds}G_{ds}A_{ds}G_{ds}A_{ds}G_{ds}A_{eo}A_{eo}G_{es}G_{es}G_e$ | 19 | 132 |
| 650472 | 1996 | 2013 | 44178 | 44195 | $T_{es}{}^mC_{eo}A_{eo}A_{eo}T_{es}T_{ds}G_{ds}G_{ds}A_{ds}G_{ds}A_{ds}A_{ds}G_{ds}A_{eo}A_{eo}A_{es}G_{es}G_e$ | 2 | 133 |
| 650473 | 2019 | 2036 | 44201 | 44218 | $A_{es}T_{eo}A_{eo}{}^mC_{eo}T_{es}A_{ds}T_{ds}G_{ds}{}^mC_{ds}T_{ds}T_{ds}{}^mC_{ds}T_{ds}{}^mC_{eo}{}^mC_{eo}T_{es}A_{es}G_e$ | 6 | 134 |
| 650474 | 2042 | 2059 | 44224 | 44241 | ${}^mC_{es}T_{eo}A_{eo}A_{eo}{}^mC_{es}A_{ds}G_{ds}A_{ds}A_{ds}G_{ds}G_{ds}A_{ds}G_{ds}A_{eo}{}^mC_{eo}T_{es}T_{es}G_e$ | 18 | 135 |
| 650475 | 2073 | 2090 | 44255 | 44272 | $A_{es}{}^mC_{eo}A_{eo}A_{eo}T_{es}{}^mC_{ds}A_{ds}T_{ds}G_{ds}G_{ds}T_{ds}G_{ds}G_{ds}G_{eo}T_{eo}A_{es}{}^mC_{es}G_e$ | 19 | 136 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650476 | 2096 | 2113 | 44278 | 44295 | $G_{es}A_{eo}A_{eo}G_{eo}G_{es}{}^mC_{ds}{}^mC_{ds}A_{ds}A_{ds}A_{ds}T_{ds}T_{ds}T_{ds}{}^mC_{eo}A_{eo}T_{es}G_{es}T_e$ | 29 | 137 |
| 650477 | 2141 | 2158 | 44323 | 44340 | ${}^mC_{es}T_{eo}{}^mC_{eo}{}^mC_{eo}A_{es}G_{ds}T_{ds}{}^mC_{ds}A_{ds}T_{ds}A_{ds}G_{ds}G_{ds}A_{eo}G_{eo}A_{es}A_{es}A_e$ | 32 | 138 |
| 650478 | 2166 | 2183 | 44348 | 44365 | $A_{es}{}^mC_{eo}T_{eo}{}^mC_{eo}A_{es}A_{ds}{}^mC_{ds}T_{ds}T_{ds}G_{ds}T_{ds}A_{ds}A_{ds}A_{ds}G_{eo}A_{eo}G_{es}A_{es}A_e$ | 36 | 139 |
| 650479 | 2189 | 2206 | 44371 | 44388 | $G_{es}A_{eo}A_{eo}G_{eo}{}^mC_{es}A_{ds}G_{ds}A_{ds}{}^mC_{ds}A_{ds}{}^mC_{ds}{}^mC_{ds}T_{ds}A_{ds}{}^mC_{eo}A_{eo}T_{es}T_{es}T_e$ | 0 | 140 |
| 650480 | 2213 | 2230 | 44395 | 44412 | ${}^mC_{es}A_{eo}A_{eo}G_{eo}{}^mC_{es}T_{ds}A_{ds}T_{ds}A_{ds}{}^mC_{ds}{}^mC_{ds}T_{ds}A_{ds}{}^mC_{eo}T_{eo}A_{es}A_{es}A_e$ | 0 | 141 |
| 650481 | 2236 | 2253 | 44418 | 44435 | $A_{es}T_{eo}G_{eo}T_{es}T_{es}{}^mC_{ds}{}^mC_{ds}A_{ds}G_{ds}A_{ds}T_{ds}{}^mC_{ds}A_{ds}{}^mC_{eo}{}^mC_{eo}A_{es}T_{es}{}^mC_e$ | 34 | 142 |
| 650482 | 2279 | 2296 | 44461 | 44478 | ${}^mC_{es}A_{eo}{}^mC_{eo}A_{eo}G_{es}T_{ds}A_{ds}T_{ds}A_{ds}A_{ds}A_{ds}T_{ds}T_{ds}T_{eo}A_{eo}A_{es}A_{es}{}^mC_e$ | 4 | 143 |
| 650483 | 2302 | 2319 | 44484 | 44501 | $T_{es}A_{eo}A_{eo}A_{eo}{}^mC_{es}A_{ds}T_{ds}G_{ds}A_{ds}T_{ds}G_{ds}{}^mC_{ds}A_{ds}A_{eo}G_{eo}T_{es}G_{es}T_e$ | 3 | 144 |
| 650484 | 2325 | 2342 | 44507 | 44524 | $A_{es}{}^mC_{eo}T_{eo}T_{eo}{}^mC_{es}{}^mC_{ds}A_{ds}A_{ds}T_{ds}T_{ds}G_{ds}T_{ds}T_{ds}{}^mC_{ds}T_{eo}T_{eo}A_{es}A_{es}G_e$ | 31 | 145 |
| 650485 | 2348 | 2365 | 44530 | 44547 | $T_{es}T_{eo}A_{eo}T_{eo}A_{es}G_{ds}A_{ds}T_{ds}{}^mC_{ds}{}^mC_{ds}A_{ds}{}^mC_{ds}T_{ds}A_{eo}A_{eo}G_{es}T_{es}A_e$ | 3 | 146 |
| 650486 | 2371 | 2388 | 44553 | 44570 | $A_{es}T_{eo}{}^mC_{eo}A_{eo}A_{es}A_{ds}A_{ds}{}^mC_{ds}T_{ds}A_{ds}T_{ds}G_{ds}G_{ds}A_{ds}{}^mC_{eo}T_{es}T_{es}T_e$ | 32 | 147 |
| 650487 | 2396 | 2413 | 44578 | 44595 | $T_{es}A_{eo}{}^mC_{eo}A_{eo}T_{es}{}^mC_{ds}T_{ds}{}^mC_{ds}A_{ds}A_{ds}T_{ds}T_{ds}A_{ds}A_{eo}A_{eo}G_{es}A_{es}G_e$ | 9 | 148 |
| 650488 | 2419 | 2436 | 44601 | 44618 | $T_{es}T_{eo}G_{eo}A_{eo}{}^mC_{es}{}^mC_{ds}{}^mC_{ds}A_{ds}G_{ds}{}^mC_{ds}A_{ds}A_{ds}G_{ds}A_{eo}A_{eo}A_{es}{}^mC_{es}T_e$ | 14 | 149 |
| 650489 | 2442 | 2459 | 44624 | 44641 | $T_{es}T_{eo}{}^mC_{eo}A_{eo}{}^mC_{es}{}^mC_{ds}A_{ds}A_{ds}A_{ds}A_{ds}T_{ds}G_{ds}A_{ds}T_{eo}A_{eo}{}^mC_{es}T_{es}A_e$ | 19 | 150 |
| 650490 | 2466 | 2483 | 44648 | 44665 | $A_{es}A_{eo}{}^mC_{eo}A_{eo}T_{es}{}^mC_{ds}A_{ds}A_{ds}T_{ds}T_{ds}T_{ds}{}^mC_{ds}A_{ds}G_{eo}A_{eo}G_{es}A_{es}{}^mC_e$ | 28 | 151 |
| 650491 | 2501 | 2518 | 44683 | 44700 | $G_{es}A_{eo}T_{eo}G_{eo}G_{es}A_{ds}G_{ds}A_{ds}A_{ds}T_{ds}G_{ds}A_{ds}G_{ds}G_{eo}G_{eo}A_{es}T_{es}A_e$ | 0 | 152 |
| 650492 | 2527 | 2544 | 44709 | 44726 | ${}^mC_{es}A_{eo}A_{eo}{}^mC_{eo}A_{es}T_{ds}T_{ds}{}^mC_{ds}A_{ds}A_{ds}A_{ds}A_{ds}G_{ds}A_{eo}G_{eo}{}^mC_{es}T_{es}T_e$ | 28 | 153 |
| 650493 | 2550 | 2567 | 44732 | 44749 | $T_{es}G_{eo}G_{eo}A_{eo}T_{es}T_{ds}T_{ds}T_{ds}A_{ds}G_{ds}{}^mC_{ds}T_{ds}A_{ds}A_{eo}T_{eo}G_{es}A_{es}A_e$ | 23 | 154 |
| 650494 | 2573 | 2590 | 44755 | 44772 | ${}^mC_{es}G_{eo}A_{eo}A_{eo}G_{es}T_{ds}T_{ds}G_{ds}T_{ds}{}^mC_{ds}A_{ds}G_{ds}{}^mC_{ds}T_{eo}G_{eo}A_{es}A_{es}A_e$ | 59 | 155 |
| 650495 | 2596 | 2613 | 44778 | 44795 | $G_{es}{}^mC_{eo}A_{eo}A_{eo}T_{es}A_{ds}T_{ds}A_{ds}{}^mC_{ds}{}^mC_{ds}A_{ds}T_{ds}A_{ds}T_{eo}T_{eo}A_{es}T_{es}A_e$ | 4 | 156 |
| 650496 | 2619 | 2636 | 44801 | 44818 | $G_{es}T_{eo}G_{eo}T_{eo}G_{es}{}^mC_{ds}A_{ds}G_{ds}{}^mC_{ds}{}^mC_{ds}A_{ds}{}^mC_{ds}A_{ds}{}^mC_{eo}A_{eo}{}^mC_{es}{}^mC_{es}A_e$ | 0 | 157 |
| 650497 | 2639 | 2656 | 44821 | 44838 | $A_{es}A_{eo}A_{eo}A_{eo}{}^mC_{es}T_{ds}T_{ds}T_{ds}{}^mC_{ds}{}^mC_{ds}{}^mC_{ds}T_{ds}G_{ds}A_{eo}T_{eo}A_{es}A_{es}A_e$ | 1 | 158 |
| 650498 | 2642 | 2659 | 44824 | 44841 | ${}^mC_{es}A_{eo}A_{eo}A_{eo}A_{es}A_{ds}A_{ds}{}^mC_{ds}T_{ds}T_{ds}T_{ds}{}^mC_{ds}{}^mC_{ds}{}^mC_{eo}T_{eo}G_{es}A_{es}T_e$ | 22 | 159 |
| 650499 | 2665 | 2682 | 44847 | 44864 | $T_{es}T_{eo}A_{eo}G_{eo}T_{es}T_{ds}A_{ds}G_{ds}{}^mC_{ds}A_{ds}A_{ds}T_{ds}A_{ds}A_{eo}A_{eo}T_{es}{}^mC_{es}{}^mC_e$ | 38 | 160 |
| 650500 | 2713 | 2730 | 44895 | 44912 | $A_{es}G_{eo}{}^mC_{eo}T_{eo}A_{es}T_{ds}T_{ds}T_{ds}T_{ds}A_{ds}T_{ds}A_{ds}A_{ds}T_{eo}{}^mC_{eo}A_{es}T_{es}A_e$ | 0 | 161 |
| 650501 | 2736 | 2753 | 44918 | 44935 | $A_{es}A_{eo}A_{eo}A_{eo}T_{es}{}^mC_{ds}T_{ds}G_{ds}T_{ds}{}^mC_{ds}T_{ds}A_{ds}T_{ds}A_{ds}T_{eo}{}^mC_{eo}G_{es}A_{es}A_e$ | 0 | 162 |
| 650502 | 2759 | 2776 | 44941 | 44958 | $A_{es}T_{eo}G_{eo}G_{es}{}^mC_{ds}A_{ds}{}^mC_{ds}A_{ds}A_{ds}A_{ds}A_{ds}T_{ds}A_{eo}A_{eo}T_{es}G_{es}A_e$ | 3 | 163 |
| 650503 | 2782 | 2799 | 44964 | 44981 | $G_{es}T_{eo}A_{eo}A_{eo}G_{es}G_{ds}G_{ds}A_{ds}A_{ds}A_{ds}{}^mC_{ds}T_{ds}T_{ds}{}^mC_{eo}A_{eo}G_{es}A_{es}A_e$ | 6 | 164 |
| 650504 | 2853 | 2870 | 45035 | 45052 | $T_{es}T_{eo}A_{eo}T_{eo}A_{es}A_{ds}T_{ds}T_{ds}{}^mC_{ds}T_{ds}T_{ds}{}^mC_{ds}T_{ds}G_{eo}A_{eo}A_{es}A_{es}{}^mC_e$ | 0 | 165 |
| 650505 | 2876 | 2893 | 45058 | 45075 | $A_{es}{}^mC_{eo}A_{eo}T_{eo}{}^mC_{es}{}^mC_{ds}{}^mC_{ds}T_{ds}T_{ds}G_{ds}{}^mC_{ds}A_{ds}G_{ds}T_{eo}T_{eo}T_{es}T_{es}A_e$ | 35 | 166 |
| 650506 | 2899 | 2916 | 45081 | 45098 | $T_{es}G_{eo}A_{eo}G_{eo}G_{es}{}^mC_{ds}G_{ds}A_{ds}G_{ds}T_{ds}A_{ds}G_{ds}T_{ds}A_{ds}{}^mC_{eo}T_{eo}A_{es}A_{es}A_e$ | 32 | 167 |
| 650507 | 2927 | 2944 | 45109 | 45126 | $G_{es}T_{eo}{}^mC_{eo}T_{eo}T_{es}A_{ds}A_{ds}A_{ds}A_{ds}T_{ds}A_{ds}T_{ds}T_{ds}T_{eo}A_{eo}G_{es}{}^mC_{es}T_e$ | 55 | 168 |
| 650508 | 2951 | 2968 | 45133 | 45150 | $G_{es}G_{eo}T_{eo}A_{eo}A_{es}T_{ds}A_{ds}A_{ds}T_{ds}T_{ds}A_{ds}A_{ds}{}^mC_{ds}A_{eo}T_{eo}A_{es}A_{es}A_e$ | 0 | 169 |
| 650509 | 2977 | 2994 | 45159 | 45176 | $T_{es}{}^mC_{eo}{}^mC_{eo}A_{eo}T_{es}G_{ds}G_{ds}A_{ds}A_{ds}A_{ds}A_{ds}T_{ds}A_{ds}T_{eo}G_{eo}A_{es}{}^mC_{es}A_e$ | 31 | 170 |
| 650510 | 3000 | 3017 | 45182 | 45199 | $T_{es}G_{eo}A_{eo}A_{eo}A_{es}A_{ds}A_{ds}G_{ds}G_{ds}G_{ds}T_{ds}A_{ds}A_{ds}T_{eo}G_{eo}A_{es}A_{es}{}^mC_e$ | 13 | 171 |
| 650511 | 3025 | 3042 | 45207 | 45224 | $T_{es}G_{eo}A_{eo}A_{eo}A_{es}T_{ds}G_{ds}T_{ds}T_{ds}T_{ds}A_{ds}A_{ds}T_{ds}G_{eo}T_{eo}A_{es}A_{es}{}^mC_e$ | 0 | 172 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650512 | 3048 | 3065 | 45230 | 45247 | $G_{es}G_{eo}T_{eo}A_{eo}G_{es}{}^mC_{ds}T_{ds}{}^mC_{ds}A_{ds}T_{ds}{}^mC_{ds}A_{ds}A_{ds}T_{eo}T_{eo}{}^mC_{es}A_{es}A_e$ | 64 | 173 |
| 650513 | 3076 | 3093 | 45258 | 45275 | $G_{es}{}^mC_{eo}A_{eo}T_{eo}A_{es}T_{ds}T_{ds}G_{ds}G_{ds}T_{ds}T_{ds}T_{ds}{}^mC_{eo}T_{eo}{}^mC_{es}A_{es}T_e$ | 60 | 174 |
| 650514 | 3100 | 3117 | 45282 | 45299 | $A_{es}{}^mC_{eo}T_{eo}{}^mC_{eo}T_{es}A_{ds}A_{ds}A_{ds}G_{ds}T_{ds}T_{ds}A_{ds}A_{ds}A_{eo}A_{eo}{}^mC_{es}T_{es}T_e$ | 8 | 175 |
| 650515 | 3105 | 3122 | 45287 | 45304 | $T_{es}A_{eo}T_{eo}A_{es}A_{ds}{}^mC_{ds}T_{ds}{}^mC_{ds}A_{ds}A_{ds}A_{ds}G_{eo}T_{eo}T_{es}A_{es}A_e$ | 0 | 176 |
| 650516 | 3123 | 3140 | 45305 | 45322 | $T_{es}A_{eo}G_{eo}G_{es}T_{ds}A_{ds}A_{ds}T_{ds}A_{ds}T_{ds}G_{ds}A_{eo}A_{eo}{}^mC_{es}T_{es}T_e$ | 5 | 177 |
| 650517 | 3146 | 3163 | 45328 | 45345 | ${}^mC_{es}A_{eo}T_{eo}A_{eo}T_{es}T_{ds}T_{ds}T_{ds}{}^mC_{ds}T_{ds}T_{ds}A_{ds}A_{ds}G_{eo}T_{eo}G_{es}{}^mC_{es}T_e$ | 35 | 178 |
| 650518 | 3169 | 3186 | 45351 | 45368 | $T_{es}A_{eo}G_{eo}G_{eo}A_{es}A_{ds}{}^mC_{ds}T_{ds}A_{ds}A_{ds}A_{ds}A_{ds}G_{ds}T_{eo}{}^mC_{eo}A_{es}A_{es}A_e$ | 21 | 179 |
| 650519 | 3391 | 3408 | 45573 | 45590 | ${}^mC_{es}{}^mC_{eo}A_{eo}A_{eo}A_{es}{}^mC_{ds}A_{ds}T_{ds}G_{ds}T_{ds}G_{ds}A_{ds}A_{eo}A_{eo}{}^mC_{es}{}^mC_{es}G_e$ | 28 | 180 |
| 650520 | 3491 | 3508 | 45673 | 45690 | $T_{es}{}^mC_{eo}T_{eo}A_{eo}G_{es}{}^mC_{ds}T_{ds}G_{ds}G_{ds}{}^mC_{ds}{}^mC_{ds}A_{ds}G_{ds}G_{eo}{}^mC_{eo}G_{es}{}^mC_{es}A_e$ | 0 | 181 |
| 650521 | 3514 | 3531 | 45696 | 45713 | $G_{es}{}^mC_{eo}T_{eo}{}^mC_{eo}A_{es}G_{ds}{}^mC_{ds}T_{ds}{}^mC_{ds}T_{ds}G_{ds}{}^mC_{ds}T_{ds}T_{eo}T_{eo}A_{es}A_{es}A_e$ | 43 | 182 |
| 650522 | 3537 | 3554 | 45719 | 45736 | $A_{es}{}^mC_{eo}A_{eo}T_{eo}T_{es}{}^mC_{ds}A_{ds}A_{ds}A_{ds}{}^mC_{ds}G_{ds}{}^mC_{ds}A_{ds}T_{eo}{}^mC_{eo}{}^mC_{es}A_{es}G_e$ | 41 | 183 |
| 650523 | 3560 | 3577 | 45742 | 45759 | $A_{es}T_{eo}T_{eo}T_{eo}{}^mC_{es}A_{ds}{}^mC_{ds}A_{ds}A_{ds}{}^mC_{ds}A_{ds}A_{ds}A_{ds}{}^mC_{eo}T_{eo}A_{es}{}^mC_{es}A_e$ | 26 | 184 |
| 650524 | 3583 | 3600 | 45765 | 45782 | $G_{es}G_{eo}A_{eo}T_{eo}{}^mC_{es}T_{ds}G_{ds}{}^mC_{ds}{}^mC_{ds}T_{ds}G_{ds}{}^mC_{ds}T_{ds}A_{eo}A_{eo}A_{es}T_{es}G_e$ | 18 | 185 |
| 650525 | 3606 | 3623 | 45788 | 45805 | $G_{es}A_{eo}T_{eo}G_{eo}A_{es}{}^mC_{ds}A_{ds}G_{ds}T_{ds}T_{ds}{}^mC_{ds}A_{ds}{}^mC_{ds}T_{eo}A_{eo}G_{es}T_{es}G_e$ | 17 | 186 |
| 650526 | 3629 | 3646 | 45811 | 45828 | $T_{es}A_{eo}A_{eo}A_{eo}T_{es}T_{ds}T_{ds}A_{ds}A_{ds}G_{ds}{}^mC_{ds}{}^mC_{ds}A_{ds}A_{eo}{}^mC_{eo}{}^mC_{es}{}^mC_{es}{}^mC_e$ | 17 | 187 |
| 650527 | 3659 | 3676 | 45841 | 45858 | ${}^mC_{es}A_{eo}A_{eo}T_{eo}T_{es}A_{ds}A_{ds}G_{ds}A_{ds}A_{ds}A_{ds}T_{ds}G_{ds}G_{eo}A_{eo}A_{es}T_{es}{}^mC_e$ | 9 | 188 |
| 650528 | 3681 | 3698 | 45863 | 45880 | $G_{es}{}^mC_{eo}A_{eo}T_{eo}{}^mC_{es}T_{ds}T_{ds}T_{ds}T_{ds}{}^mC_{ds}A_{ds}T_{ds}A_{ds}{}^mC_{eo}T_{eo}G_{es}G_{es}{}^mC_e$ | 63 | 189 |
| 650529 | 3684 | 3701 | 45866 | 45883 | ${}^mC_{es}T_{eo}G_{eo}G_{eo}{}^mC_{es}A_{ds}T_{ds}{}^mC_{ds}T_{ds}T_{ds}T_{ds}T_{ds}{}^mC_{ds}A_{eo}T_{eo}A_{es}{}^mC_{es}T_e$ | 33 | 190 |
| 650530 | 3707 | 3724 | 45889 | 45906 | $T_{es}T_{eo}T_{eo}T_{eo}G_{es}A_{ds}T_{ds}A_{ds}{}^mC_{ds}T_{ds}A_{ds}T_{ds}G_{ds}G_{eo}T_{eo}T_{es}A_{es}{}^mC_e$ | 33 | 191 |
| 650531 | 3731 | 3748 | 45913 | 45930 | $A_{es}T_{eo}A_{eo}G_{eo}{}^mC_{es}T_{ds}T_{ds}T_{ds}G_{ds}A_{ds}A_{ds}T_{ds}A_{ds}A_{eo}T_{eo}T_{es}T_{es}T_e$ | 7 | 192 |
| 650532 | 3754 | 3771 | 45936 | 45953 | $T_{es}G_{eo}G_{eo}{}^mC_{eo}A_{es}G_{ds}T_{ds}A_{ds}{}^mC_{ds}{}^mC_{ds}T_{ds}G_{ds}A_{ds}T_{eo}G_{eo}T_{es}A_{es}T_e$ | 50 | 193 |
| 650533 | 3777 | 3794 | 45959 | 45976 | $T_{es}{}^mC_{eo}T_{eo}T_{eo}G_{es}{}^mC_{ds}A_{ds}G_{ds}G_{ds}T_{ds}G_{ds}G_{ds}T_{ds}T_{eo}T_{eo}A_{es}{}^mC_{es}A_e$ | 24 | 194 |
| 650534 | 3800 | 3817 | 45982 | 45999 | $G_{es}T_{eo}G_{eo}A_{eo}A_{es}T_{ds}T_{ds}T_{ds}A_{ds}G_{ds}T_{ds}T_{ds}G_{ds}T_{eo}T_{eo}{}^mC_{es}{}^mC_{es}T_e$ | 42 | 195 |
| 650535 | 3823 | 3840 | 46005 | 46022 | ${}^mC_{es}A_{eo}{}^mC_{eo}T_{eo}T_{es}{}^mC_{ds}T_{ds}T_{ds}T_{ds}A_{ds}G_{ds}{}^mC_{ds}A_{ds}G_{ds}G_{eo}A_{eo}{}^mC_{es}A_{es}G_e$ | 0 | 196 |
| 650536 | 3859 | 3876 | 46041 | 46058 | $T_{es}T_{eo}{}^mC_{eo}{}^mC_{eo}{}^mC_{es}A_{ds}A_{ds}T_{ds}T_{ds}A_{ds}G_{ds}T_{ds}A_{ds}A_{eo}A_{eo}A_{es}{}^mC_{es}A_e$ | 0 | 197 |
| 650537 | 3889 | 3906 | 46071 | 46088 | ${}^mC_{es}{}^mC_{eo}A_{eo}A_{eo}T_{es}A_{ds}G_{ds}T_{ds}T_{ds}A_{ds}A_{ds}A_{ds}T_{eo}A_{eo}T_{es}T_{es}A_e$ | 0 | 198 |
| 650538 | 3916 | 3933 | 46098 | 46115 | $T_{es}A_{eo}{}^mC_{eo}A_{eo}A_{es}A_{ds}T_{ds}A_{ds}T_{ds}A_{ds}T_{ds}{}^mC_{ds}A_{ds}T_{eo}T_{eo}A_{eo}G_{es}A_e$ | 0 | 199 |
| 650539 | 3939 | 3956 | 46121 | 46138 | ${}^mC_{es}T_{eo}G_{eo}T_{eo}A_{es}{}^mC_{ds}A_{ds}T_{ds}A_{ds}{}^mC_{ds}T_{ds}T_{ds}G_{ds}A_{eo}T_{eo}{}^mC_{es}{}^mC_{es}{}^mC_e$ | 32 | 200 |
| 650540 | 3962 | 3979 | 46144 | 46161 | $T_{es}T_{eo}A_{eo}A_{eo}A_{es}{}^mC_{ds}T_{ds}T_{ds}{}^mC_{ds}T_{ds}A_{ds}{}^mC_{ds}T_{ds}A_{eo}G_{eo}{}^mC_{es}A_{es}T_e$ | 0 | 201 |
| 650541 | 3985 | 4002 | 46167 | 46184 | $T_{es}A_{eo}T_{eo}G_{eo}A_{es}A_{ds}A_{ds}G_{ds}T_{ds}G_{ds}G_{ds}T_{ds}A_{ds}T_{eo}T_{eo}T_{es}{}^mC_{es}{}^mC_e$ | 26 | 202 |
| 650542 | 4008 | 4025 | 46190 | 46207 | $A_{es}T_{eo}T_{eo}A_{eo}A_{es}A_{ds}T_{ds}{}^mC_{ds}{}^mC_{ds}A_{ds}T_{ds}G_{ds}A_{ds}{}^mC_{eo}A_{eo}T_{es}{}^mC_{es}T_e$ | 31 | 203 |
| 650543 | 4045 | 4062 | 46227 | 46244 | $G_{es}A_{eo}T_{eo}G_{eo}A_{es}A_{ds}{}^mC_{ds}T_{ds}A_{ds}T_{ds}T_{ds}{}^mC_{ds}T_{ds}G_{eo}A_{eo}A_{es}T_{es}T_e$ | 28 | 204 |
| 650544 | 4068 | 4085 | 46250 | 46267 | $T_{es}A_{eo}G_{eo}A_{eo}T_{es}G_{ds}A_{ds}T_{ds}G_{ds}G_{ds}G_{ds}T_{ds}T_{ds}T_{eo}T_{eo}A_{es}G_{es}A_e$ | 23 | 205 |
| 650545 | 4091 | 4108 | 46273 | 46290 | $T_{es}T_{eo}A_{eo}{}^mC_{eo}A_{es}T_{ds}G_{ds}A_{ds}T_{ds}T_{ds}A_{ds}{}^mC_{ds}{}^mC_{ds}G_{eo}T_{eo}A_{es}A_{es}A_e$ | 26 | 206 |
| 650546 | 4114 | 4131 | 46296 | 46313 | $A_{es}A_{eo}{}^mC_{eo}A_{eo}G_{es}T_{ds}T_{ds}T_{ds}A_{ds}T_{ds}A_{ds}T_{ds}T_{ds}A_{eo}{}^mC_{eo}T_{es}G_{es}A_e$ | 10 | 207 |
| 650547 | 4137 | 4154 | 46319 | 46336 | $G_{es}T_{eo}T_{eo}T_{eo}A_{es}{}^mC_{ds}{}^mC_{ds}T_{ds}G_{ds}{}^mC_{ds}A_{ds}G_{ds}{}^mC_{ds}A_{eo}G_{eo}{}^mC_{es}{}^mC_{es}T_e$ | 12 | 208 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650548 | 4160 | 4177 | 46342 | 46359 | $T_{es}T_{eo}T_{eo}G_{eo}G_{es}{}^mC_{ds}{}^mC_{ds}A_{ds}A_{ds}G_{ds}A_{ds}T_{ds}{}^mC_{ds}{}^mC_{eo}T_{eo}A_{es}G_{es}T_e$ | 19 | 209 |
| 650549 | 4183 | 4200 | 46365 | 46382 | $A_{es}A_{eo}T_{eo}A_{eo}T_{es}T_{ds}{}^mC_{ds}T_{ds}G_{ds}T_{ds}G_{ds}A_{ds}A_{ds}T_{eo}T_{eo}G_{es}T_{es}A_e$ | 23 | 210 |
| 650550 | 4206 | 4223 | 46388 | 46405 | $A_{es}A_{eo}A_{eo}A_{eo}A_{es}A_{ds}A_{ds}G_{ds}{}^mC_{ds}A_{ds}{}^mC_{ds}{}^mC_{ds}A_{ds}{}^mC_{eo}{}^mC_{eo}T_{es}T_{es}A_e$ | 12 | 211 |
| 650551 | 4247 | 4264 | 46429 | 46446 | $T_{es}{}^mC_{eo}A_{eo}T_{eo}G_{es}A_{ds}T_{ds}A_{ds}A_{ds}A_{ds}G_{ds}T_{ds}T_{eo}A_{eo}A_{es}G_{es}A_e$ | 34 | 212 |
| 650552 | 4272 | 4289 | 46454 | 46471 | $G_{es}T_{eo}T_{eo}T_{eo}T_{es}T_{ds}T_{ds}T_{ds}{}^mC_{ds}{}^mC_{ds}T_{ds}{}^mC_{ds}A_{ds}T_{eo}T_{eo}T_{es}A_{es}{}^mC_e$ | 10 | 213 |
| 650553 | 4295 | 4312 | 46477 | 46494 | ${}^mC_{es}A_{eo}A_{eo}T_{eo}G_{es}A_{ds}T_{ds}A_{ds}{}^mC_{ds}T_{ds}{}^mC_{ds}A_{ds}A_{ds}{}^mC_{eo}T_{eo}G_{es}G_{es}T_e$ | 34 | 214 |
| 650554 | 4318 | 4335 | 46500 | 46517 | $T_{es}G_{eo}G_{eo}A_{eo}{}^mC_{es}T_{ds}A_{ds}{}^mC_{ds}T_{ds}G_{ds}G_{ds}T_{ds}A_{ds}G_{eo}T_{eo}T_{es}T_{es}T_e$ | 44 | 215 |
| 650555 | 4365 | 4382 | 46547 | 46564 | $T_{es}{}^mC_{eo}T_{eo}G_{eo}A_{es}{}^mC_{ds}T_{ds}G_{ds}G_{ds}A_{ds}A_{ds}T_{ds}A_{ds}A_{eo}A_{eo}A_{es}T_{es}T_e$ | 10 | 216 |
| 650556 | 4388 | 4405 | 46570 | 46587 | $G_{es}A_{eo}{}^mC_{eo}A_{eo}A_{es}T_{ds}{}^mC_{ds}A_{ds}A_{ds}A_{ds}A_{ds}T_{ds}G_{ds}T_{eo}G_{eo}A_{es}T_{es}T_e$ | 12 | 217 |
| 650557 | 4424 | 4441 | 46606 | 46623 | ${}^mC_{es}A_{eo}{}^mC_{eo}T_{eo}A_{es}G_{ds}{}^mC_{ds}A_{ds}T_{ds}G_{ds}A_{ds}T_{ds}T_{ds}T_{eo}T_{eo}A_{es}A_{es}A_e$ | 9 | 218 |
| 650558 | 4645 | 4662 | 46827 | 46844 | $T_{es}{}^mC_{eo}{}^mC_{eo}T_{eo}{}^mC_{es}T_{ds}G_{ds}T_{ds}{}^mC_{ds}G_{ds}{}^mC_{ds}{}^mC_{ds}A_{ds}G_{eo}G_{eo}G_{es}T_{es}T_e$ | 29 | 219 |
| 650559 | 4734 | 4751 | 46916 | 46933 | ${}^mC_{es}A_{eo}{}^mC_{eo}T_{eo}A_{es}G_{ds}{}^mC_{ds}A_{ds}T_{ds}G_{ds}A_{ds}T_{ds}T_{ds}T_{eo}T_{eo}T_{es}T_{es}T_e$ | 0 | 220 |
| 650560 | 4758 | 4775 | 46940 | 46957 | $T_{es}T_{eo}T_{eo}T_{eo}A_{es}A_{ds}G_{ds}A_{ds}T_{ds}T_{ds}T_{ds}A_{ds}G_{eo}T_{eo}A_{es}G_{es}{}^mC_e$ | 8 | 221 |
| 650561 | 4781 | 4798 | 46963 | 46980 | $T_{es}{}^mC_{eo}T_{eo}G_{eo}T_{es}A_{ds}{}^mC_{ds}A_{ds}G_{ds}G_{ds}G_{ds}T_{ds}{}^mC_{ds}{}^mC_{ds}A_{eo}A_{eo}T_{es}G_{es}G_e$ | 6 | 222 |
| 650562 | 4804 | 4821 | 46986 | 47003 | $T_{es}T_{eo}A_{eo}T_{eo}G_{es}{}^mC_{ds}A_{ds}{}^mC_{ds}T_{ds}G_{ds}A_{ds}A_{ds}T_{ds}{}^mC_{eo}T_{eo}A_{es}T_{es}T_e$ | 16 | 223 |
| 650563 | 4868 | 4885 | 47050 | 47067 | ${}^mC_{es}G_{eo}T_{eo}A_{eo}A_{es}G_{ds}A_{ds}A_{ds}T_{ds}T_{ds}T_{ds}A_{ds}A_{ds}A_{eo}{}^mC_{es}A_{es}T_e$ | 0 | 224 |
| 650564 | 4892 | 4909 | 47074 | 47091 | ${}^mC_{es}A_{eo}A_{eo}T_{eo}{}^mC_{es}A_{ds}T_{ds}A_{ds}T_{ds}T_{ds}A_{ds}A_{ds}{}^mC_{ds}T_{eo}A_{eo}T_{es}G_e$ | 0 | 225 |
| 650565 | 5092 | 5109 | 47274 | 47291 | $T_{es}G_{eo}{}^mC_{eo}G_{eo}A_{es}T_{ds}T_{ds}{}^mC_{ds}T_{ds}T_{ds}A_{ds}G_{ds}{}^mC_{ds}{}^mC_{eo}T_{eo}{}^mC_{es}{}^mC_{es}T_e$ | 45 | 226 |
| 650566 | 5128 | 5145 | 47310 | 47327 | ${}^mC_{es}{}^mC_{eo}{}^mC_{eo}{}^mC_{eo}T_{eo}T_{es}G_{ds}G_{ds}T_{ds}{}^mC_{ds}A_{ds}{}^mC_{ds}T_{ds}{}^mC_{ds}T_{ds}G_{eo}{}^mC_{eo}A_{es}A_{es}{}^mC_e$ | 14 | 227 |
| 650567 | 5167 | 5184 | 47349 | 47366 | $T_{es}G_{eo}T_{eo}{}^mC_{eo}T_{es}{}^mC_{ds}A_{ds}{}^mC_{ds}A_{ds}{}^mC_{ds}T_{ds}G_{ds}T_{ds}T_{eo}G_{eo}G_{es}G_{es}{}^mC_e$ | 34 | 228 |
| 650568 | 5245 | 5262 | 47427 | 47444 | $T_{es}A_{eo}G_{eo}G_{eo}A_{es}A_{ds}G_{ds}T_{ds}{}^mC_{ds}A_{ds}A_{ds}T_{ds}A_{ds}T_{ds}A_{eo}T_{eo}A_{es}T_{es}A_e$ | 0 | 229 |
| 650569 | 5268 | 5285 | 47450 | 47467 | ${}^mC_{es}{}^mC_{eo}{}^mC_{eo}G_{eo}A_{es}{}^mC_{ds}T_{ds}G_{ds}G_{ds}G_{ds}A_{ds}T_{ds}A_{ds}A_{eo}A_{eo}{}^mC_{es}T_{es}T_e$ | 1 | 230 |
| 650570 | 5406 | 5423 | 47588 | 47605 | $T_{es}A_{eo}{}^mC_{eo}{}^mC_{eo}T_{es}G_{ds}G_{ds}{}^mC_{ds}T_{ds}T_{ds}A_{ds}A_{ds}G_{ds}T_{eo}T_{eo}T_{es}G_{es}G_e$ | 15 | 231 |
| 650571 | 5551 | 5568 | 47733 | 47750 | $A_{es}{}^mC_{eo}{}^mC_{eo}T_{eo}T_{es}T_{ds}A_{ds}A_{ds}G_{ds}A_{ds}T_{ds}G_{ds}G_{ds}A_{eo}G_{eo}T_{es}T_{es}T_e$ | 49 | 232 |
| 650572 | 5575 | 5592 | 47757 | 47774 | $T_{es}{}^mC_{eo}{}^mC_{eo}G_{eo}G_{es}A_{ds}T_{ds}A_{ds}A_{ds}A_{ds}A_{ds}A_{ds}A_{eo}A_{eo}A_{es}A_{es}{}^mC_e$ | 0 | 233 |
| 650573 | 5602 | 5619 | 47784 | 47801 | $A_{es}A_{eo}A_{eo}A_{eo}T_{es}A_{ds}G_{ds}{}^mC_{ds}G_{ds}G_{ds}G_{ds}{}^mC_{ds}{}^mC_{ds}{}^mC_{ds}A_{eo}A_{eo}{}^mC_{es}G_{es}{}^mC_e$ | 11 | 234 |
| 650574 | 5797 | 5814 | 47979 | 47996 | $A_{es}A_{eo}{}^mC_{eo}A_{eo}A_{es}A_{ds}T_{ds}A_{ds}T_{ds}T_{ds}{}^mC_{ds}G_{ds}{}^mC_{ds}{}^mC_{eo}A_{eo}G_{es}G_{es}T_e$ | 8 | 235 |
| 650575 | 5927 | 5944 | 48109 | 48126 | $T_{es}G_{eo}G_{eo}{}^mC_{eo}{}^mC_{es}{}^mC_{ds}A_{ds}A_{ds}G_{ds}G_{ds}{}^mC_{ds}{}^mC_{ds}G_{ds}G_{eo}T_{es}G_{es}T_e$ | 7 | 236 |
| 650576 | 5953 | 5970 | 48135 | 48152 | ${}^mC_{es}A_{eo}A_{eo}{}^mC_{eo}A_{es}A_{ds}A_{ds}{}^mC_{ds}A_{ds}A_{ds}T_{ds}T_{ds}{}^mC_{ds}A_{eo}{}^mC_{eo}T_{es}T_{es}T_e$ | 8 | 237 |
| 650577 | 5976 | 5993 | 48158 | 48175 | $T_{es}A_{eo}T_{eo}{}^mC_{eo}{}^mC_{es}A_{ds}T_{ds}A_{ds}{}^mC_{ds}T_{ds}T_{ds}A_{ds}A_{ds}G_{eo}G_{eo}A_{es}{}^mC_{es}T_e$ | 8 | 238 |
| 650578 | 5999 | 6016 | 48181 | 48198 | $G_{es}T_{eo}T_{eo}{}^mC_{eo}T_{es}T_{ds}A_{ds}A_{ds}T_{ds}T_{ds}A_{ds}G_{ds}G_{ds}G_{eo}T_{eo}{}^mC_{es}A_{es}{}^mC_e$ | 57 | 239 |
| 650579 | 6022 | 6039 | 48204 | 48221 | $T_{es}G_{eo}A_{eo}T_{eo}T_{es}A_{ds}G_{ds}T_{ds}T_{ds}G_{ds}A_{ds}T_{ds}{}^mC_{ds}{}^mC_{eo}A_{eo}A_{es}T_{es}{}^mC_e$ | 32 | 240 |
| 650580 | 6045 | 6062 | 48227 | 48244 | $T_{es}A_{eo}A_{eo}A_{eo}G_{es}T_{ds}T_{ds}A_{ds}T_{ds}T_{ds}T_{ds}A_{ds}{}^mC_{ds}A_{eo}T_{eo}T_{es}G_{es}{}^mC_e$ | 0 | 241 |
| 650581 | 6103 | 6120 | 48285 | 48302 | $G_{es}A_{eo}A_{eo}G_{eo}{}^mC_{es}T_{ds}G_{ds}G_{ds}T_{ds}T_{ds}A_{ds}T_{ds}A_{ds}A_{eo}A_{eo}G_{es}G_{es}G_e$ | 0 | 242 |
| 650582 | 6128 | 6145 | 48310 | 48327 | $G_{es}{}^mC_{eo}{}^mC_{eo}A_{eo}G_{es}G_{ds}T_{ds}{}^mC_{ds}A_{ds}T_{ds}T_{ds}T_{ds}T_{ds}T_{eo}T_{eo}A_{es}A_{es}A_e$ | 20 | 243 |
| 650583 | 6158 | 6175 | 48340 | 48357 | $T_{es}T_{eo}A_{eo}T_{eo}T_{es}A_{ds}T_{ds}G_{ds}T_{ds}T_{ds}T_{ds}A_{ds}A_{ds}G_{eo}A_{eo}{}^mC_{es}T_{es}A_e$ | 35 | 244 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650584 | 6188 | 6205 | 48370 | 48387 | $T_{es}{}^mC_{eo}A_{eo}T_{eo}G_{es}A_{ds}A_{ds}A_{ds}G_{ds}{}^mC_{ds}A_{ds}A_{ds}A_{ds}T_{eo}T_{eo}A_{es}G_{es}A_e$ | 0 | 245 |
| 650585 | 6211 | 6228 | 48393 | 48410 | ${}^mC_{es}{}^mC_{eo}A_{eo}A_{eo}{}^mC_{es}G_{ds}A_{ds}T_{ds}G_{ds}T_{ds}{}^mC_{ds}A_{ds}A_{ds}T_{eo}A_{eo}A_{es}T_{es}{}^mC_e$ | 30 | 246 |
| 650586 | 6285 | 6302 | 48467 | 48484 | $A_{es}G_{eo}A_{eo}{}^mC_{eo}{}^mC_{es}A_{ds}{}^mC_{ds}T_{ds}T_{ds}G_{ds}G_{ds}A_{ds}A_{ds}A_{eo}A_{eo}A_{es}A_{es}T_e$ | 13 | 247 |
| 650587 | 6308 | 6325 | 48490 | 48507 | $T_{es}T_{eo}A_{eo}G_{eo}{}^mC_{es}{}^mC_{ds}T_{ds}A_{ds}A_{ds}T_{ds}T_{ds}{}^mC_{ds}T_{eo}T_{eo}A_{es}A_{es}A_e$ | 17 | 248 |
| 650588 | 6331 | 6348 | 48513 | 48530 | ${}^mC_{es}G_{eo}A_{eo}{}^mC_{eo}A_{es}A_{ds}A_{ds}T_{ds}T_{ds}T_{ds}A_{ds}G_{ds}A_{ds}A_{eo}G_{eo}T_{es}T_{es}A_e$ | 0 | 249 |
| 650589 | 6354 | 6371 | 48536 | 48553 | $T_{es}A_{eo}T_{eo}G_{eo}{}^mC_{es}T_{ds}A_{ds}T_{ds}T_{ds}A_{ds}A_{ds}{}^mC_{ds}A_{eo}T_{eo}G_{es}{}^mC_{es}{}^mC_e$ | 11 | 250 |
| 650590 | 6378 | 6395 | 48560 | 48577 | ${}^mC_{es}{}^mC_{eo}A_{eo}{}^mC_{eo}A_{es}G_{ds}G_{ds}{}^mC_{ds}T_{ds}T_{ds}A_{ds}A_{ds}A_{eo}T_{eo}G_{es}T_{es}T_e$ | 24 | 251 |
| 650591 | 6401 | 6418 | 48583 | 48600 | $T_{es}T_{eo}{}^mC_{eo}T_{eo}{}^mC_{es}A_{ds}T_{ds}T_{ds}G_{ds}{}^mC_{ds}T_{ds}T_{ds}G_{eo}T_{eo}{}^mC_{es}T_{es}A_e$ | 15 | 252 |
| 650592 | 6430 | 6447 | 48612 | 48629 | $A_{es}G_{eo}G_{eo}A_{eo}A_{es}T_{ds}A_{ds}T_{ds}{}^mC_{ds}{}^mC_{ds}A_{ds}T_{ds}T_{ds}T_{eo}A_{eo}T_{es}A_{es}T_e$ | 4 | 253 |
| 650593 | 6453 | 6470 | 48635 | 48652 | $A_{es}T_{eo}G_{eo}A_{es}G_{ds}A_{ds}G_{ds}{}^mC_{ds}T_{ds}T_{ds}{}^mC_{ds}{}^mC_{ds}T_{eo}A_{eo}A_{es}A_{es}T_e$ | 33 | 254 |
| 650594 | 6476 | 6493 | 48658 | 48675 | $T_{es}T_{eo}{}^mC_{eo}{}^mC_{eo}T_{es}G_{ds}A_{ds}A_{ds}A_{ds}{}^mC_{ds}T_{ds}A_{ds}T_{ds}G_{eo}{}^mC_{eo}A_{es}A_{es}G_e$ | 9 | 255 |
| 650595 | 6552 | 6569 | 48734 | 48751 | $A_{es}T_{eo}A_{eo}G_{es}A_{ds}T_{ds}A_{ds}A_{ds}T_{ds}{}^mC_{ds}A_{ds}{}^mC_{ds}A_{eo}T_{eo}T_{es}A_{es}A_e$ | 29 | 256 |
| 650596 | 6575 | 6592 | 48757 | 48774 | ${}^mC_{es}{}^mC_{eo}T_{eo}A_{eo}A_{es}T_{ds}A_{ds}G_{ds}{}^mC_{ds}{}^mC_{ds}A_{ds}G_{ds}T_{eo}G_{eo}T_{es}T_{es}G_e$ | 16 | 257 |
| 650597 | 6606 | 6623 | 48788 | 48805 | $T_{es}A_{eo}T_{eo}A_{eo}{}^mC_{es}A_{ds}G_{ds}A_{ds}A_{ds}{}^mC_{ds}A_{ds}G_{ds}T_{ds}A_{eo}A_{eo}T_{es}T_{es}T_e$ | 0 | 258 |
| 650598 | 6629 | 6646 | 48811 | 48828 | $T_{es}{}^mC_{eo}T_{eo}G_{eo}T_{es}A_{ds}{}^mC_{ds}T_{ds}T_{ds}G_{ds}A_{ds}A_{ds}T_{ds}T_{eo}T_{eo}{}^mC_{es}A_{es}A_e$ | 43 | 259 |
| 650599 | 6659 | 6676 | 48841 | 48858 | $A_{es}A_{eo}A_{eo}{}^mC_{eo}A_{es}A_{ds}{}^mC_{ds}A_{ds}A_{ds}A_{ds}T_{ds}G_{ds}{}^mC_{ds}T_{ds}T_{eo}T_{eo}T_{es}T_{es}G_e$ | 0 | 260 |
| 650600 | 6682 | 6699 | 48864 | 48881 | ${}^mC_{es}A_{eo}{}^mC_{eo}A_{eo}G_{es}T_{ds}G_{ds}{}^mC_{ds}A_{ds}{}^mC_{ds}T_{ds}G_{ds}G_{ds}T_{eo}A_{eo}T_{es}{}^mC_{es}A_e$ | 0 | 261 |
| 650601 | 6705 | 6722 | 48887 | 48904 | $G_{es}G_{eo}G_{eo}T_{eo}{}^mC_{es}{}^mC_{ds}T_{ds}G_{ds}A_{ds}G_{ds}{}^mC_{ds}A_{ds}A_{ds}A_{ds}G_{eo}{}^mC_{eo}G_{es}G_{es}{}^mC_e$ | 2 | 262 |
| 650602 | 6728 | 6745 | 48910 | 48927 | $A_{es}{}^mC_{eo}A_{eo}{}^mC_{eo}A_{es}{}^mC_{ds}A_{ds}G_{ds}A_{ds}G_{ds}G_{ds}G_{ds}{}^mC_{eo}T_{eo}G_{es}{}^mC_{es}A_e$ | 16 | 263 |
| 650603 | 6751 | 6768 | 48933 | 48950 | $G_{es}{}^mC_{eo}A_{eo}A_{eo}A_{es}T_{ds}A_{ds}A_{ds}A_{ds}{}^mC_{ds}T_{ds}T_{ds}A_{ds}A_{eo}{}^mC_{eo}G_{es}A_{es}G_e$ | 27 | 264 |
| 650604 | 6774 | 6791 | 48956 | 48973 | $G_{es}A_{eo}A_{eo}G_{eo}G_{es}{}^mC_{ds}{}^mC_{ds}T_{ds}G_{ds}T_{ds}G_{ds}T_{ds}G_{ds}T_{eo}G_{eo}T_{es}A_{es}A_e$ | 6 | 265 |
| 650605 | 6797 | 6814 | 48979 | 48996 | ${}^mC_{es}G_{eo}G_{eo}{}^mC_{eo}T_{es}T_{ds}T_{ds}T_{ds}{}^mC_{ds}T_{ds}A_{ds}A_{ds}{}^mC_{ds}G_{eo}A_{eo}{}^mC_{es}{}^mC_{es}A_e$ | 27 | 266 |
| 650606 | 6808 | 6825 | 48990 | 49007 | ${}^mC_{es}T_{eo}T_{eo}T_{eo}G_{es}G_{ds}A_{ds}A_{ds}G_{ds}{}^mC_{ds}{}^mC_{ds}{}^mC_{ds}G_{ds}G_{eo}{}^mC_{eo}T_{es}T_{es}T_e$ | 15 | 267 |
| 650607 | 6820 | 6837 | 49002 | 49019 | $T_{es}G_{eo}T_{eo}T_{eo}{}^mC_{es}A_{ds}T_{ds}{}^mC_{ds}A_{ds}A_{ds}G_{ds}T_{ds}G_{ds}{}^mC_{ds}T_{eo}T_{eo}T_{es}G_{es}G_e$ | 0 | 268 |
| 650608 | 6843 | 6860 | 49025 | 49042 | $T_{es}{}^mC_{eo}{}^mC_{eo}A_{eo}{}^mC_{es}A_{ds}{}^mC_{ds}T_{ds}A_{ds}A_{ds}A_{ds}{}^mC_{ds}A_{ds}A_{ds}{}^mC_{eo}A_{eo}G_{es}A_{es}A_e$ | 25 | 269 |
| 650609 | 6880 | 6897 | 49062 | 49079 | $A_{es}A_{eo}T_{eo}A_{eo}A_{es}T_{ds}{}^mC_{ds}T_{ds}T_{ds}T_{ds}T_{ds}G_{ds}A_{ds}T_{ds}A_{eo}T_{eo}T_{es}T_{es}A_e$ | 0 | 270 |
| 650612 | N/A | N/A | 13822 | 13839 | $G_{es}{}^mC_{eo}A_{eo}T_{eo}T_{es}G_{ds}{}^mC_{ds}T_{ds}T_{ds}A_{ds}T_{ds}A_{ds}A_{ds}{}^mC_{eo}{}^mC_{eo}T_{es}G_{es}T_e$ | 50 | 271 |
| 650616 | N/A | N/A | 26677 | 26694 | $A_{es}{}^mC_{eo}T_{eo}T_{eo}T_{es}T_{ds}{}^mC_{ds}A_{ds}A_{ds}A_{ds}G_{ds}T_{ds}A_{ds}G_{eo}G_{eo}{}^mC_{es}T_{es}T_e$ | 4 | 272 |
| 650617 | N/A | N/A | 26686 | 26703 | $A_{es}A_{eo}{}^mC_{eo}T_{eo}A_{eo}{}^mC_{es}T_{ds}T_{ds}T_{ds}T_{ds}A_{ds}{}^mC_{ds}T_{ds}T_{ds}T_{eo}T_{eo}{}^mC_{es}A_{es}A_e$ | 0 | 273 |
| 650625 | N/A | N/A | 24160 | 24177 | $T_{es}G_{eo}A_{eo}A_{es}G_{ds}A_{ds}A_{ds}G_{ds}{}^mC_{ds}{}^mC_{ds}G_{ds}T_{ds}{}^mC_{ds}T_{eo}{}^mC_{eo}A_{es}A_{es}T_e$ | 15 | 274 |
| 650626 | N/A | N/A | 24210 | 24227 | $T_{es}A_{eo}A_{eo}G_{eo}{}^{es}T_{ds}A_{ds}A_{ds}G_{ds}T_{ds}T_{ds}A_{ds}{}^mC_{ds}T_{eo}T_{eo}A_{es}A_{es}A_e$ | 0 | 275 |
| 650629 | N/A | N/A | 24515 | 24532 | ${}^mC_{es}{}^mC_{eo}T_{eo}T_{eo}T_{es}G_{ds}{}^mC_{ds}T_{ds}{}^mC_{ds}T_{ds}T_{ds}T_{ds}T_{ds}A_{eo}G_{eo}T_{es}T_{es}G_e$ | 9 | 276 |
| 650633 | N/A | N/A | 28195 | 28212 | ${}^mC_{es}{}^mC_{eo}T_{eo}T_{eo}{}^mC_{es}A_{ds}T_{ds}A_{ds}T_{ds}A_{ds}{}^mC_{ds}T_{ds}T_{ds}{}^mC_{eo}T_{eo}G_{es}A_{es}G_e$ | 38 | 277 |
| 650634 | N/A | N/A | 28217 | 28234 | $G_{es}A_{eo}T_{eo}G_{eo}T_{es}{}^mC_{ds}A_{ds}G_{ds}{}^mC_{ds}A_{ds}G_{ds}A_{ds}T_{ds}{}^mC_{eo}A_{eo}G_{es}A_{es}A_e$ | 25 | 278 |
| 650635 | N/A | N/A | 28222 | 28239 | $A_{es}A_{eo}G_{eo}A_{eo}G_{es}G_{ds}A_{ds}T_{ds}G_{ds}T_{ds}{}^mC_{ds}A_{ds}G_{ds}{}^mC_{eo}T_{eo}G_{es}A_{es}T_e$ | 12 | 279 |
| 650640 | N/A | N/A | 1233 | 1250 | ${}^mC_{es}G_{eo}{}^mC_{eo}{}^mC_{eo}G_{es}G_{ds}G_{ds}{}^mC_{ds}G_{ds}A_{ds}G_{ds}A_{ds}T_{ds}{}^mC_{eo}G_{eo}G_{es}{}^mC_{es}A_e$ | 0 | 280 |

TABLE 1-continued

Percent reduction of human ATXN3 mRNA by modified oligonucleotides relative to control

| IONIS No | SEQ ID No: 1 Start Site | SEQ ID No: 1 Stop Site | SEQ ID No: 2 Start Site | SEQ ID No: 2 Stop Site | Sequence (5' to 3') | % Inhib. | SEQ ID No |
|---|---|---|---|---|---|---|---|
| 650641 | N/A | N/A | 1754 | 1771 | $^{m}C_{es}{}^{m}C_{eo}{}^{m}C_{eo}G_{eo}T_{es}A_{ds}A_{ds}T_{ds}A_{ds}A_{ds}A_{ds}A_{ds}A_{ds}{}^{m}C_{eo}T_{eo}{}^{m}C_{es}T_{es}T_{e}$ | 8 | 281 |
| 650642 | N/A | N/A | 1820 | 1837 | $^{m}C_{es}T_{eo}A_{eo}A_{eo}A_{es}A_{ds}T_{ds}{}^{m}C_{ds}T_{ds}A_{ds}A_{ds}G_{ds}{}^{m}C_{ds}T_{eo}G_{eo}G_{es}{}^{m}C_{es}{}^{m}C_{e}$ | 17 | 282 |
| 650643 | N/A | N/A | 7243<br>7283 | 7260<br>7300 | $A_{es}T_{eo}A_{eo}G_{eo}{}^{m}C_{es}A_{ds}T_{ds}T_{ds}A_{ds}{}^{m}C_{ds}T_{ds}A_{ds}T_{ds}T_{eo}T_{eo}G_{es}T_{es}A_{e}$ | 0 | 283 |
| 650644 | N/A | N/A | 8090 | 8107 | $^{m}C_{es}A_{eo}G_{eo}A_{eo}T_{es}G_{ds}T_{ds}T_{ds}{}^{m}C_{ds}T_{ds}A_{ds}{}^{m}C_{ds}T_{ds}T_{eo}A_{eo}T_{es}A_{es}T_{e}$ | 8 | 284 |
| 650645 | N/A | N/A | 9762 | 9779 | $T_{es}T_{eo}A_{eo}A_{eo}{}^{m}C_{es}A_{ds}T_{ds}A_{ds}G_{ds}G_{ds}T_{ds}A_{ds}{}^{m}C_{ds}A_{eo}T_{eo}G_{es}{}^{m}C_{es}A_{e}$ | 28 | 285 |
| 650646 | N/A | N/A | 10816 | 10833 | $A_{es}A_{eo}G_{eo}T_{eo}G_{es}A_{ds}G_{ds}{}^{m}C_{ds}{}^{m}C_{ds}T_{ds}T_{ds}{}^{m}C_{ds}T_{ds}T_{eo}G_{eo}{}^{m}C_{es}T_{es}A_{e}$ | 0 | 286 |
| 650647 | N/A | N/A | 10975 | 10992 | $A_{es}A_{eo}T_{eo}{}^{m}C_{eo}A_{es}G_{ds}T_{ds}A_{ds}{}^{m}C_{ds}{}^{m}C_{ds}T_{ds}G_{ds}T_{ds}A_{eo}A_{eo}A_{es}A_{es}A_{e}$ | 36 | 287 |
| 650648 | N/A | N/A | 11515 | 11532 | $T_{es}T_{eo}{}^{m}C_{eo}{}^{m}C_{eo}A_{es}G_{ds}A_{ds}A_{ds}G_{ds}G_{ds}{}^{m}C_{ds}T_{ds}G_{ds}{}^{m}C_{eo}T_{eo}G_{es}T_{es}T_{e}$ | 30 | 288 |
| 650649 | N/A | N/A | 11609 | 11626 | $A_{es}A_{eo}A_{eo}G_{eo}G_{es}{}^{m}C_{ds}T_{ds}G_{ds}T_{ds}G_{ds}A_{ds}A_{ds}A_{ds}{}^{m}C_{eo}G_{eo}G_{es}T_{es}G_{e}$ | 35 | 289 |
| 650650 | N/A | N/A | 11690<br>11984 | 11707<br>12001 | $A_{es}A_{eo}A_{eo}A_{eo}A_{es}T_{ds}{}^{m}C_{ds}T_{ds}A_{ds}G_{ds}T_{ds}A_{ds}{}^{m}C_{ds}T_{eo}{}^{m}C_{eo}T_{es}A_{es}G_{e}$ | 26 | 290 |
| 650651 | N/A | N/A | 15320 | 15337 | $A_{es}G_{eo}{}^{m}C_{eo}T_{eo}G_{es}G_{ds}T_{ds}T_{ds}T_{ds}T_{ds}{}^{m}C_{ds}A_{ds}A_{ds}T_{eo}A_{eo}A_{es}{}^{m}C_{es}{}^{m}C_{e}$ | 23 | 291 |
| 650652 | N/A | N/A | 16170<br>16488 | 16187<br>16505 | $A_{es}G_{eo}A_{eo}A_{eo}A_{es}G_{ds}A_{ds}A_{ds}{}^{m}C_{ds}{}^{m}C_{ds}A_{ds}A_{ds}{}^{m}C_{ds}T_{eo}T_{eo}A_{es}G_{es}G_{e}$ | 10 | 292 |
| 650653 | N/A | N/A | 17193 | 17210 | $A_{es}T_{eo}T_{eo}T_{eo}A_{es}A_{ds}{}^{m}C_{ds}{}^{m}C_{ds}{}^{m}C_{ds}A_{ds}{}^{m}C_{ds}A_{ds}A_{ds}G_{ds}A_{eo}A_{eo}T_{es}A_{es}{}^{m}C_{e}$ | 2 | 293 |
| 650654 | N/A | N/A | 17686 | 17703 | $^{m}C_{es}A_{eo}T_{eo}G_{eo}{}^{m}C_{es}A_{ds}G_{ds}{}^{m}C_{ds}T_{ds}{}^{m}C_{ds}A_{ds}T_{ds}G_{ds}{}^{m}C_{eo}{}^{m}C_{eo}T_{es}A_{es}T_{e}$ | 8 | 294 |
| 650655 | N/A | N/A | 17703 | 17720 | $T_{es}{}^{m}C_{eo}A_{eo}{}^{m}C_{eo}T_{es}A_{ds}A_{ds}A_{ds}T_{ds}T_{ds}A_{ds}G_{ds}{}^{m}C_{ds}T_{eo}G_{eo}G_{es}G_{es}{}^{m}C_{e}$ | 25 | 295 |
| 650656 | N/A | N/A | 18799 | 18816 | $A_{es}A_{eo}G_{eo}T_{eo}T_{es}A_{ds}G_{ds}T_{ds}G_{ds}T_{ds}A_{ds}T_{ds}A_{ds}A_{ds}T_{eo}A_{eo}A_{es}T_{es}A_{e}$ | 0 | 296 |
| 650657 | N/A | N/A | 20598 | 20615 | $T_{es}{}^{m}C_{eo}T_{eo}{}^{m}C_{eo}A_{es}G_{ds}{}^{m}C_{ds}A_{ds}G_{ds}A_{ds}A_{ds}T_{ds}G_{ds}T_{eo}A_{eo}A_{es}{}^{m}C_{es}G_{e}$ | 16 | 297 |
| 650658 | N/A | N/A | 23358 | 23375 | $A_{es}A_{eo}{}^{m}C_{eo}T_{eo}A_{es}G_{ds}T_{ds}A_{ds}A_{ds}{}^{m}C_{ds}A_{ds}T_{ds}G_{ds}G_{eo}{}^{m}C_{eo}T_{es}A_{es}A_{e}$ | 16 | 298 |
| 650659 | N/A | N/A | 24393 | 24410 | $A_{es}T_{eo}A_{eo}T_{eo}A_{es}G_{ds}A_{ds}A_{ds}A_{ds}T_{ds}A_{ds}A_{ds}A_{ds}{}^{m}C_{ds}{}^{m}C_{ds}T_{eo}A_{eo}A_{es}A_{es}A_{e}$ | 0 | 299 |
| 650660 | N/A | N/A | 25114 | 25131 | $A_{es}A_{eo}G_{eo}G_{eo}{}^{m}C_{es}A_{ds}T_{ds}T_{ds}T_{ds}G_{ds}T_{ds}A_{ds}A_{ds}T_{eo}G_{eo}T_{es}A_{es}A_{e}$ | 22 | 300 |
| 650661 | N/A | N/A | 26689 | 26706 | $A_{es}{}^{m}C_{eo}{}^{m}C_{eo}A_{eo}A_{es}{}^{m}C_{ds}T_{ds}T_{ds}A_{ds}{}^{m}C_{ds}T_{ds}T_{ds}T_{ds}A_{ds}{}^{m}C_{eo}T_{eo}T_{es}T_{es}T_{e}$ | 0 | 301 |
| 650662 | N/A | N/A | 26813 | 26830 | $T_{es}G_{eo}{}^{m}C_{eo}{}^{m}C_{eo}{}^{m}C_{es}G_{ds}T_{ds}{}^{m}C_{ds}{}^{m}C_{ds}T_{ds}A_{ds}T_{ds}T_{ds}T_{eo}G_{eo}{}^{m}C_{es}T_{es}G_{e}$ | 10 | 302 |
| 650663 | N/A | N/A | 27243 | 27260 | $G_{es}T_{eo}{}^{m}C_{eo}{}^{m}C_{eo}T_{es}A_{ds}A_{ds}T_{ds}T_{ds}T_{ds}{}^{m}C_{ds}A_{ds}T_{ds}T_{eo}T_{eo}T_{es}T_{es}{}^{m}C_{e}$ | 0 | 303 |
| 650664 | N/A | N/A | 28181 | 28198 | $T_{es}G_{eo}A_{eo}G_{eo}T_{es}T_{ds}G_{ds}T_{ds}G_{ds}A_{ds}{}^{m}C_{ds}T_{ds}T_{ds}A_{eo}A_{eo}A_{es}A_{es}A_{e}$ | 12 | 304 |
| 650665 | N/A | N/A | 28226 | 28243 | $mC_{es}A_{eo}T_{eo}T_{eo}A_{es}A_{ds}G_{ds}A_{ds}A_{ds}G_{ds}G_{ds}A_{ds}T_{ds}G_{ds}T_{eo}{}^{m}C_{eo}A_{es}G_{es}{}^{m}C_{e}$ | 16 | 305 |
| 650666 | N/A | N/A | 28231 | 28248 | $T_{es}{}^{m}C_{eo}T_{eo}{}^{m}C_{eo}A_{es}{}^{m}C_{ds}A_{ds}T_{ds}T_{ds}A_{ds}A_{ds}G_{ds}A_{ds}G_{eo}G_{eo}A_{es}T_{es}G_{e}$ | 26 | 306 |
| 650667 | N/A | N/A | 28236 | 28253 | $A_{es}A_{eo}A_{eo}T_{eo}A_{es}T_{ds}{}^{m}C_{ds}T_{ds}{}^{m}C_{ds}A_{ds}{}^{m}C_{ds}A_{ds}T_{ds}T_{eo}A_{eo}A_{es}G_{es}A_{e}$ | 12 | 307 |
| 650668 | N/A | N/A | 28266 | 28283 | $A_{es}G_{eo}{}^{m}C_{eo}A_{eo}{}^{m}C_{es}A_{ds}T_{ds}T_{ds}A_{ds}A_{ds}T_{ds}{}^{m}C_{ds}T_{ds}A_{ds}T_{eo}A_{eo}{}^{m}C_{es}T_{es}G_{e}$ | 57 | 308 |
| 650669 | N/A | N/A | 35157 | 35174 | $A_{es}G_{eo}A_{eo}T_{eo}T_{es}T_{ds}G_{ds}A_{ds}A_{ds}A_{ds}A_{ds}T_{ds}T_{ds}T_{eo}G_{eo}G_{es}A_{es}T_{e}$ | 0 | 309 |
| 650670 | N/A | N/A | 35981 | 35998 | $A_{es}A_{eo}A_{eo}G_{eo}A_{es}G_{ds}T_{ds}G_{ds}T_{ds}T_{ds}G_{ds}G_{ds}T_{ds}T_{eo}T_{eo}A_{es}T_{es}A_{e}$ | 38 | 310 |
| 650671 | N/A | N/A | 38694 | 38711 | $T_{es}A_{eo}G_{eo}A_{eo}A_{es}A_{ds}A_{ds}A_{ds}A_{ds}G_{ds}T_{ds}A_{ds}{}^{m}C_{ds}{}^{m}C_{eo}A_{eo}G_{es}T_{es}T_{e}$ | 11 | 311 |
| 650672 | N/A | N/A | 43232 | 43249 | $G_{es}{}^{m}C_{eo}A_{eo}T_{eo}{}^{m}C_{es}A_{ds}{}^{m}C_{ds}{}^{m}C_{ds}T_{ds}G_{ds}T_{ds}T_{ds}G_{ds}G_{eo}G_{eo}A_{es}A_{es}A_{e}$ | 14 | 312 |

Subscripts: 'e' represents a 2'-MOE-nucleoside; 'd' represents a 2'-deoxynucleoside; 's' represents a phosphorothioate internucleoside linkage; and 'o' represents a phosphodiester internucleoside linkage. Superscript 'm' preceding a 'C' indicates that the cytosine is a 5-methylcytosine.

Additional modified oligonucleotide were designed targeting the ATXN3 nucleic acid sequences listed in Table 2.

TABLE 2

ATXN3 nucleic acids

| GenBank Accession number | Human ATXN3 transcript variant name | SEQ ID No |
|---|---|---|
| NM_001164778.1 | transcript variant o, mRNA | 3 |
| NM_001127696.1 | transcript variant ad, mRNA | 4 |
| NM_001164781.1 | transcript variant y, mRNA | 5 |
| NR_028454.1 | transcript variant d, non-coding | 6 |
| NM_001164780.1 | transcript variant u, mRNA | 7 |
| NR_028469.1 | transcript variant af, non-coding | 8 |
| NM_001164779.1 | transcript variant r, mRNA | 9 |
| NR_028461.1 | transcript variant p, non-coding | 10 |
| NR_028466.1 | transcript variant x, non-coding | 11 |
| NR_028462.1 | transcript variant q, non-coding | 12 |
| NR_028467.1 | transcript variant z, non-coding | 13 |
| NR_031765.1 | transcript variant c, non-coding | 14 |
| NM_001164782.1 | transcript variant ae, mRNA | 15 |
| NR_028465.1 | transcript variant w, non-coding | 16 |
| NR_028457.1 | transcript variant k, non-coding | 17 |
| NM_001164777.1 | transcript variant j, mRNA | 18 |
| NM_001164774.1 | transcript variant b, mRNA | 19 |

Modified oligonucleotides complementary to the ATXN3 nucleic acids from Table 2 were tested for the effect on ATXN3 mRNA according to the protocol described above. The modified oligonucleotides in the table below were designed as 5-8-5 MOE gapmers. The gapmers are 18 nucleosides in length, wherein the central gap segment comprises eight 2′-deoxynucleosides and is flanked by wing segments on both the 5′ end and on the 3′ end comprising five nucleosides each. Each nucleoside in the 5′ wing segment and each nucleoside in the 3′ wing segment comprises a MOE modification. All cytosine residues throughout each gapmer are 5-methylcytosines. The internucleoside linkages are mixed phosphodiester and phosphorothioate linkages. The internucleoside linkages are arranged in order from 5′ to 3′: sooossssssssssooss; wherein ("o") is phosphodiester and ("s") is phosphorothioate. "Start site" indicates the 5′-most nucleoside to which the gapmer is targeted in the human gene sequence. "Stop site" indicates the 3′-most nucleoside to which the gapmer is targeted human gene sequence.

TABLE 3

Percent reduction of human ATXN3 mRNA by modified oligonucleotides relative to control

| IONIS No | Target SEQ ID No | Start Site | Stop Site | Sequence (5' to 3') | % Inhib. | SEQ ID No |
|---|---|---|---|---|---|---|
| 650361 | 3 | 443 | 460 | $^mC_{es}T_{eo}G_{eo}T_{eo}{}^mC_{es}T_{ds}G_{ds}T_{ds}T_{ds}T_{ds}T_{ds}{}^mC_{ds}{}^mC_{ds}T_{eo}A_{eo}A_{es}T_{es}T_e$ | 1 | 313 |
| 650611 | 4 | 248 | 265 | $T_{es}T_{eo}A_{eo}T_{eo}A_{es}A_{ds}{}^mC_{ds}{}^mC_{ds}T_{ds}G_{ds}T_{ds}A_{ds}A_{ds}A_{eo}A_{eo}A_{es}{}^mC_{es}G_e$ | 48 | 314 |
| 650613 | 5 | 87 | 104 | $T_{es}T_{eo}G_{eo}{}^mC_{eo}{}^mC_{es}T_{ds}A_{ds}T_{ds}A_{ds}A_{ds}{}^mC_{ds}T_{ds}T_{ds}T_{eo}{}^mC_{eo}T_{es}{}^mC_{es}G_e$ | 0 | 315 |
| 650614 | 6 | 128 | 145 | $T_{es}T_{eo}{}^mC_{eo}A_{eo}{}^mC_{es}T_{ds}T_{ds}{}^mC_{ds}T_{ds}G_{ds}A_{ds}A_{ds}T_{ds}A_{eo}G_{eo}A_{es}G_{es}A_e$ | 8 | 316 |
| 650615 | 7 | 87 | 104 | $A_{es}T_{eo}{}^mC_{eo}T_{eo}{}^mC_{es}T_{ds}{}^mC_{ds}A_{ds}T_{ds}T_{ds}T_{ds}T_{ds}T_{ds}T_{eo}{}^mC_{eo}T_{es}{}^mC_{es}G_e$ | 7 | 317 |
| 650618 | 8 | 687 | 704 | $G_{es}T_{eo}{}^mC_{eo}A_{eo}A_{es}{}^mC_{ds}T_{ds}A_{ds}{}^mC_{ds}T_{ds}T_{ds}T_{ds}A_{ds}{}^mC_{eo}T_{eo}T_{es}T_{es}T_e$ | 5 | 318 |
| 650620 | 9 | 87 | 104 | $A_{es}A_{eo}G_{eo}T_{eo}T_{es}A_{ds}A_{ds}A_{ds}{}^mC_{ds}{}^mC_{ds}A_{ds}T_{ds}T_{ds}T_{eo}{}^mC_{eo}T_{es}{}^mC_{es}G_e$ | 20 | 319 |
| 650621 | 10 | 443 | 460 | $T_{es}A_{eo}A_{eo}{}^mC_{eo}{}^mC_{es}T_{ds}G_{ds}T_{ds}T_{ds}T_{ds}T_{ds}{}^mC_{ds}{}^mC_{ds}T_{eo}A_{eo}A_{es}T_{es}T_e$ | 2 | 320 |
| 650622 | 11 | 87 | 104 | $T_{es}A_{eo}T_{eo}A_{eo}G_{es}A_{ds}A_{ds}T_{ds}A_{ds}A_{ds}{}^mC_{ds}T_{ds}T_{ds}T_{eo}{}^mC_{eo}T_{es}{}^mC_{es}G_e$ | 3 | 321 |
| 650623 | 12 | 443 | 460 | $^mC_{es}{}^mC_{eo}{}^mC_{eo}T_{eo}T_{es}{}^mC_{ds}{}^mC_{ds}T_{ds}G_{ds}T_{ds}T_{ds}G_{ds}T_{ds}A_{eo}A_{eo}T_{es}T_{es}G_e$ | 23 | 322 |
| 650619 | 13 | 290 | 307 | $A_{es}{}^mC_{eo}{}^mC_{eo}A_{eo}{}^mC_{es}T_{ds}G_{ds}A_{ds}A_{ds}T_{ds}A_{ds}G_{ds}A_{ds}G_{eo}A_{eo}A_{es}A_{es}A_e$ | 27 | 323 |
| 650624 | 13 | 375 | 392 | $A_{es}{}^mC_{eo}T_{eo}T_{eo}{}^mC_{es}{}^mC_{ds}T_{ds}G_{ds}T_{ds}T_{ds}G_{ds}T_{ds}A_{ds}A_{eo}T_{eo}T_{es}G_{es}A_e$ | 9 | 324 |
| 650627 | 13 | 471 | 488 | $A_{es}T_{eo}{}^mC_{eo}A_{eo}{}^mC_{es}{}^mC_{ds}T_{ds}T_{ds}A_{ds}{}^mC_{ds}T_{ds}T_{ds}A_{ds}G_{ds}T_{eo}A_{es}A_{es}G_e$ | 9 | 325 |
| 650628 | 14 | 87 | 104 | $T_{es}T_{eo}T_{eo}T_{eo}A_{es}T_{ds}G_{ds}G_{ds}A_{ds}{}^mC_{ds}T_{ds}T_{ds}T_{ds}T_{eo}{}^mC_{eo}T_{es}{}^mC_{es}G_e$ | 0 | 326 |
| 650630 | 15 | 87 | 104 | $T_{es}T_{eo}T_{eo}G_{eo}{}^mC_{es}T_{ds}G_{ds}{}^mC_{ds}T_{ds}G_{ds}T_{ds}T_{ds}T_{ds}T_{eo}{}^mC_{eo}T_{es}{}^mC_{es}G_e$ | 11 | 327 |
| 650631 | 16 | 248 | 265 | $T_{es}T_{eo}{}^mC_{eo}A_{eo}T_{es}T_{ds}T_{ds}{}^mC_{ds}T_{ds}G_{ds}G_{ds}T_{ds}A_{ds}A_{ds}A_{eo}A_{eo}A_{es}{}^mC_{es}G_e$ | 17 | 328 |
| 650632 | 16 | 794 | 811 | $A_{es}T_{eo}T_{eo}T_{eo}T_{es}{}^mC_{ds}A_{ds}A_{ds}A_{ds}G_{ds}T_{ds}A_{ds}G_{ds}G_{eo}{}^mC_{eo}T_{es}{}^mC_{es}{}^mC_e$ | 0 | 329 |
| 650636 | 16 | 848 | 865 | $T_{es}A_{eo}T_{eo}A_{eo}A_{es}A_{ds}G_{ds}A_{ds}G_{ds}G_{ds}G_{ds}A_{ds}T_{ds}G_{ds}T_{eo}{}^mC_{eo}A_{es}G_{es}{}^mC_e$ | 6 | 330 |
| 650637 | 17 | 535 | 552 | $A_{es}A_{eo}{}^mC_{eo}T_{eo}T_{es}A_{ds}{}^mC_{ds}T_{ds}A_{ds}G_{ds}T_{ds}A_{ds}A_{ds}A_{eo}G_{eo}T_{es}{}^mC_{es}G_e$ | 20 | 331 |
| 650610 | 18 | 87 | 104 | $^mC_{es}{}^mC_{eo}A_{eo}G_{eo}A_{es}A_{ds}G_{ds}G_{ds}{}^mC_{ds}G_{ds}T_{ds}G_{ds}T_{ds}T_{eo}{}^mC_{eo}T_{es}{}^mC_{es}G_e$ | 0 | 332 |
| 650638 | 18 | 125 | 142 | $^mC_{es}T_{eo}G_{eo}T_{eo}{}^mC_{es}T_{ds}G_{ds}A_{ds}A_{ds}T_{ds}A_{ds}G_{ds}A_{eo}G_{eo}A_{es}A_{es}A_e$ | 1 | 333 |
| 650639 | 19 | 248 | 265 | $^mC_{es}T_{eo}G_{eo}{}^mC_{eo}T_{es}G_{ds}T_{ds}{}^mC_{ds}T_{ds}G_{ds}G_{ds}T_{ds}A_{ds}A_{eo}A_{eo}A_{es}{}^mC_{es}G_e$ | 0 | 334 |

Subscripts: 'e' represents a 2′-MOE nucleoside; 'd' represents a 2′-deoxynucleoside; 's' represents a phosphorothioate internucleoside linkage; and 'o' represents a phosphodiester internucleoside linkage. Superscript 'm' preceding a 'C' indicates that the cytosine is a 5-methylcytosine.

Example 2: Effect of Modified Oligonucleotides on Human ATXN3 In Vitro, Multiple Doses Modified oligonucleotides selected from Example 1 were also tested at various doses in HepG2 cells in studies of in vitro reduction of human ATXN3 mRNA. The modified oligonucleotides were tested in a series of experiments that had similar culture conditions.

Cells were plated at a density of 20,000 cells per well and transfected using electroporation with 0.11 µM, 0.33 µM, 1.00 µM, 3.00 µM, and 9.00 µM concentrations of modified oligonucleotide, as specified in the table below. After a treatment period of approximately 16 hours, RNA was isolated from the cells and ATXN3 mRNA levels were measured by quantitative real-time PCR. Human ATXN3 primer probe set RTS4392 was used to measure mRNA levels. ATXN3 mRNA levels were adjusted according to total RNA content, as measured by RIBOGREEN®. Results are presented as percent reduction of ATXN3, relative to untreated control cells. "0" indicate that the antisense oligonucleotide did not reduce ATXN3 mRNA levels. The half maximal inhibitory concentration ($IC_{50}$) of each oligonucleotide is also presented in the table below.

TABLE 4

Percent reduction of human ATXN3 mRNA by modified oligonucleotides relative to control

| IONIS No | 0.11 µM | 0.33 µM | 1.00 µM | 3.00 µM | 9.00 µM | $IC_{50}$ (µM) |
|---|---|---|---|---|---|---|
| 650372 | 2 | 24 | 39 | 76 | 80 | 1.4 |
| 650379 | 6 | 13 | 29 | 52 | 66 | 3.2 |
| 650410 | 16 | 20 | 42 | 68 | 85 | 1.3 |
| 650437 | 0 | 32 | 59 | 77 | 90 | 1.0 |
| 650438 | 8 | 19 | 42 | 68 | 78 | 1.5 |
| 650466 | 15 | 15 | 45 | 53 | 76 | 1.9 |
| 650494 | 15 | 17 | 32 | 53 | 82 | 1.9 |
| 650507 | 9 | 8 | 37 | 59 | 81 | 1.9 |
| 650512 | 2 | 23 | 46 | 73 | 82 | 1.3 |
| 650513 | 25 | 42 | 63 | 72 | 84 | 0.6 |
| 650528 | 8 | 32 | 47 | 68 | 81 | 1.2 |
| 650532 | 1 | 20 | 31 | 60 | 76 | 2.0 |
| 650578 | 9 | 24 | 41 | 54 | 64 | 2.5 |
| 650668 | 1 | 19 | 41 | 65 | 77 | 1.7 |

Example 3: Acute Tolerability of Modified Oligonucleotides Complementary to Human ATXN3 in C57BL/6 Mice Modified oligonucleotides selected from the examples above were tested in mice to assess tolerability of the oligonucleotides in vivo. Female wild type C57BL/6 mice were divided into treatment groups consisting of four mice. The mice were administered a single intracerebroventricular (ICV) dose of 700 µg of a modified oligonucleotide listed in the table below. One group of four mice was administered a single ICV dose of PBS as a control to which the modified oligonucleotide treated groups was compared.

At 3 hours post injection, each mouse was evaluated according to 7 different criteria. The 7 criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 700 µg ICV dose, and met all other criteria, it would get a summed score of 0. If another mouse was not bright, alert, and responsive 3 hours after the 700 µg ICV dose but met all other criteria, it would receive a score of 1. The results are presented as the average score for each treatment group.

TABLE 5

Acute tolerability scores

| Treatment (IONIS No) | Score |
|---|---|
| PBS | 0.00 |
| 650372 | 5.25 |
| 650410 | 3.25 |
| 650438 | 6.50 |
| 650507 | 0.75 |
| 650512 | 1.25 |
| 650513 | 6.00 |
| 650528 | 2.50 |
| 650668 | 3.25 |

Example 4: Acute Tolerability of Modified Oligonucleotides Complementary to Human ATXN3 in Sprague Dawley Rats (3 mg)

Sprague Dawley rats were separated into groups of 4 rats for the experiment presented in the table below. Each rat in each group of rats was administered a single 3 mg intrathecal (IT) dose of an oligonucleotide described in example 1 or example 2 above. At 3 hours after injection, the movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group (the functional observational battery score or FOB). For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Saline treated rats generally receive a score of 0. A score of at the top end of the range would be suggestive of acute toxicity. Results are presented as the average score for each treatment group.

TABLE 6

Acute tolerability scores

| Compound ID | 3 hr FOB |
|---|---|
| PBS | 0.50 |
| 650410 | 3.25 |
| 650507 | 0.25 |
| 650512 | 0.75 |
| 650528 | 1.75 |
| 650668 | 1.75 |

The invention claimed is:

1. An oligomeric compound comprising a modified oligonucleotide consisting of 18-30 linked nucleosides and having a nucleobase sequence comprising at least 17 contiguous nucleobases of any of SEQ ID NOs: 98-102, wherein the modified oligonucleotide comprises at least one modification selected from a modified sugar moiety and a modified internucleoside linkage.

2. The oligomeric compound of claim 1, wherein the modified oligonucleotide has a nucleobase sequence that is at least 95%, or is 100% complementary to the nucleobase sequence of SEQ ID NO: 1, when measured across the entire nucleobase sequence of the modified oligonucleotide.

3. The oligomeric compound of claim 1, wherein the modified oligonucleotide comprises at least one modified nucleoside.

4. The oligomeric compound of claim 3, wherein the modified oligonucleotide comprises at least one modified nucleoside comprising a modified sugar moiety.

5. The oligomeric compound of claim 4, wherein the modified oligonucleotide comprises at least one modified nucleoside comprising a bicyclic sugar moiety.

6. The oligomeric compound of claim 5, wherein the bicyclic sugar moiety has a 2'-4' bridge, wherein the 2'-4' bridge is —O—CH$_2$— or —O—CH(CH$_3$)—.

7. The oligomeric compound of claim 3, wherein the modified oligonucleotide comprises at least one modified nucleoside comprising a modified non-bicyclic sugar moiety.

8. The oligomeric compound of claim 7, wherein the non-bicyclic sugar moiety comprises a 2'-MOE group or a 2'-OMe group.

9. The oligomeric compound of claim 3, wherein the modified oligonucleotide comprises at least one modified nucleoside comprising a sugar surrogate selected from morpholino and PNA.

10. The oligomeric compound of claim 1, wherein the modified oligonucleotide has a sugar motif comprising:
a 5'-region consisting of 1-5 linked 5'-region nucleosides;
a central region consisting of 6-10 linked central region nucleosides; and
a 3'-region consisting of 1-5 linked 3'-region nucleosides; wherein
each of the 5'-region nucleosides and each of the 3'-region nucleosides comprises a modified sugar moiety and each of the central region nucleosides comprises an unmodified DNA sugar moiety.

11. The oligomeric compound of claim 1, wherein the modified oligonucleotide comprises at least one modified internucleoside linkage.

12. The oligomeric compound of claim 11, wherein at least one internucleoside linkage is a phosphorothioate internucleoside linkage.

13. The oligomeric compound of claim 11, wherein the modified oligonucleotide comprises at least one phosphodiester internucleoside linkage.

14. The oligomeric compound of claim 11, wherein each internucleoside linkage is either a phosphodiester internucleoside linkage or a phosphorothioate internucleoside linkage.

15. The oligomeric compound of claim 1, wherein the modified oligonucleotide comprises at least one modified nucleobase.

16. The oligomeric compound of claim 15, wherein the modified nucleobase is a 5-methylcytosine.

17. The oligomeric compound of claim 1, wherein the modified oligonucleotide consists of 18-20 linked nucleosides.

18. The oligomeric compound of claim 1, comprising a conjugate group comprising a conjugate moiety and a conjugate linker.

19. The oligomeric compound of claim 1, wherein the oligomeric compound is a single-stranded oligomeric compound.

20. An oligomeric duplex comprising an oligomeric compound of claim 1.

21. A modified oligonucleotide consisting of 18-30 linked nucleosides and having a nucleobase sequence comprising at least 17 contiguous nucleobases of any of SEQ ID NOs: 98-102, wherein the modified oligonucleotide comprises at least one modification selected from a modified sugar moiety and a modified internucleoside linkage.

22. An oligomeric compound comprising a modified oligonucleotide consisting of 18-30 linked nucleosides and having a nucleobase sequence comprising a portion of at least 17 contiguous nucleobases 100% complementary to an equal length portion of nucleobases 1091-1131 of SEQ ID NO: 1,
wherein the nucleobase sequence of the modified oligonucleotide is at least 90% complementary to SEQ ID NO: 1 as measured over the entirety of the modified oligonucleotide, and wherein the modified oligonucleotide comprises at least one modification selected from a modified sugar moiety and a modified internucleoside linkage.

23. A pharmaceutical composition comprising an oligomeric compound of claim 1 and a pharmaceutically acceptable carrier or diluent.

24. A chirally enriched population of oligomeric compounds of claim 1, wherein the population is enriched for modified oligonucleotides comprising at least one particular phosphorothioate internucleoside linkage having a particular stereochemical configuration.

25. An oligomeric compound comprising a modified oligonucleotide consisting of 15-30 linked nucleosides and having a nucleobase sequence comprising at least 15 contiguous nucleobases 100% complementary to an equal length portion of nucleobases 1091-1131 of SEQ ID NO: 1, wherein the modified oligonucleotide has a nucleobase sequence that is 100% complementary to the nucleobase sequence of SEQ ID NO: 1 when measured across the entire nucleobase sequence of the modified oligonucleotide, and wherein the modified oligonucleotide comprises at least one modification selected from a modified sugar moiety and a modified internucleoside linkage.

* * * * *

SEQUENCE LISTING

<160> NUMBER OF SEQ ID NOS: 334

<210> SEQ ID NO 1
<211> LENGTH: 6923
<212> TYPE: DNA
<213> ORGANISM: Homo sapiens

<400> SEQUENCE: 1

| | | | | | | |
|---|---|---|---|---|---|---|
| gagaggggca | gggggcggag | ctggaggggg | tggttcggcg | tgggggccgt | tggctccaga | 60 |
| caaataaaca | tggagtccat | cttccacgag | aaacaagaag | gctcactttg | tgctcaacat | 120 |
| tgcctgaata | acttattgca | aggagaatat | tttagccctg | tggaattatc | ctcaattgca | 180 |
| catcagctgg | atgaggagga | gaggatgaga | atggcagaag | gaggagttac | tagtgaagat | 240 |
| tatcgcacgt | ttttacagca | gccttctgga | aatatggatg | acagtggttt | tttctctatt | 300 |
| caggttataa | gcaatgcctt | gaaagtttgg | ggtttagaac | taatcctgtt | caacagtcca | 360 |
| gagtatcaga | ggctcaggat | cgatcctata | aatgaaagat | catttatatg | caattataag | 420 |
| gaacactggt | ttacagttag | aaaattagga | aaacagtggt | ttaacttgaa | ttctctcttg | 480 |
| acgggtccag | aattaatatc | agatacatat | cttgcacttt | tcttggctca | attacaacag | 540 |
| gaaggttatt | ctatatttgt | cgttaagggt | gatctgccag | attgcgaagc | tgaccaactc | 600 |
| ctgcagatga | ttagggtcca | acagatgcat | cgaccaaaac | ttattggaga | agaattagca | 660 |
| caactaaaag | agcaaagagt | ccataaaaca | gacctggaac | gagtgttaga | agcaaatgat | 720 |
| ggctcaggaa | tgttagacga | agatgaggag | gatttgcaga | gggctctggc | actaagtcgc | 780 |
| caagaaattg | acatggaaga | tgaggaagca | gatctccgca | gggctattca | gctaagtatg | 840 |
| caaggtagtt | ccagaaacat | atctcaagat | atgacacaga | catcaggtac | aaatcttact | 900 |
| tcagaagagc | ttcggaagag | acgagaagcc | tactttgaaa | aacagcagca | aaagcagcaa | 960 |
| cagcagcagc | agcagcagca | gcaggggac | ctatcaggac | agagttcaca | tccatgtgaa | 1020 |
| aggccagcca | ccagttcagg | agcacttggg | agtgatctag | gtgatgctat | gagtgaagaa | 1080 |
| gacatgcttc | aggcagctgt | gaccatgtct | ttagaaactg | tcagaaatga | tttgaaaaca | 1140 |
| gaaggaaaaa | aataatacct | ttaaaaaata | atttagatat | tcatactttc | caacattatc | 1200 |
| ctgtgtgatt | acagcatagg | gtccactttg | gtaatgtgtc | aaagagatga | ggaaataaga | 1260 |
| cttttagcgg | tttgcaaaca | aaatgatggg | aaagtggaac | aatgcgtcgg | ttgtaggact | 1320 |
| aaataatgat | cttccaaata | ttagccaaag | aggcattcag | caattaaaga | catttaaaat | 1380 |
| agttttctaa | atgtttcttt | ttcttttttg | agtgtgcaat | atgtaacatg | tctaaagtta | 1440 |
| gggcatttttt | cttggatctt | tttgcagact | agctaattag | ctctcgcctc | aggcttttc | 1500 |
| catatagttt | gttttctttt | tctgtcttgt | aggtaagttg | gctcacatca | tgtaatagtg | 1560 |
| gctttcattt | cttattaacc | aaattaacct | ttcaggaaag | tatctctact | ttcctgatgt | 1620 |
| tgataatagt | aatggttcta | gaaggatgaa | cagttctccc | ttcaactgta | taccgtgtgc | 1680 |
| tccagtgttt | tcttgtgttg | ttttctctga | tcacaacttt | tctgctacct | ggttttcatt | 1740 |
| attttcccac | aattcttttg | aaagatggta | atctttctg | aggtttagcg | ttttaagccc | 1800 |
| tacgatggga | tcattattc | atgactggtg | cgttcctaaa | ctctgaaatc | agccttgcac | 1860 |
| aagtacttga | gaataaatga | gcatttttta | aaatgtgtga | gcatgtgctt | tcccagatgc | 1920 |
| tttatgaatg | tcttttcact | tatatcaaaa | ccttacagct | tgttgcaac | cccttcttcc | 1980 |
| tgcgccttat | tttttccttt | cttctccaat | tgagaaaact | aggagaagca | tagtatgcag | 2040 |
| gcaagtctcc | ttctgttaga | agactaaaca | tacgtaccca | ccatgaatgt | atgatacatg | 2100 |

```
aaatttggcc ttcaatttta atagcagttt tattttattt tttctcctat gactggagct    2160
ttgtgttctc tttacagttg agtcatggaa tgtaggtgtc tgcttcacat cttttagtag    2220
gtatagcttg tcaaagatgg tgatctggaa catgaaaata atttactaat gaaaatatgt    2280
ttaaatttat actgtgattt gacacttgca tcatgtttag atagcttaag aacaatggaa    2340
gtcacagtac ttagtggatc tataaataag aaagtccata gttttgataa atattctctt    2400
taattgagat gtacagagag tttcttgctg ggtcaatagg atagtatcat tttggtgaaa    2460
accatgtctc tgaaattgat gttttagttt cagtgttccc tatccctcat tctccatctc    2520
cttttgaagc tcttttgaat gttgaattgt tcataagcta aaatccaaga aatttcagct    2580
gacaacttcg aaaattataa tatggtatat tgccctcctg gtgtgtggct gcacacattt    2640
tatcagggaa agttttttga tctaggattt attgctaact aactgaaaag agaagaaaaa    2700
atatctttta tttatgatta taaaatagct ttttcttcga tataacagat ttttttaagtc   2760
attattttgt gccaatcagt tttctgaagt ttcccttaca caaaggata gctttatttt     2820
aaaatctaaa gtttctttta atagttaaaa atgtttcaga agaattataa aactttaaaa    2880
ctgcaaggga tgttggagtt tagtactact ccctcaagat ttaaaaagct aaatatttta    2940
agactgaaca tttatgttaa ttattaccag tgtgtttgtc atattttcca tggatatttg    3000
ttcattacct ttttccattg aaaagttaca ttaaactttt catacacttg aattgatgag    3060
ctacctaata taaaaatgag aaaaccaata tgcattttaa agttttaact ttagagttta    3120
taaagttcat atatacccta gttaaagcac ttaagaaaat atggcatgtt tgactttag    3180
ttcctagaga gttttttgttt tgttttttgt ttttttttga gacggagtct tgctatgtct   3240
cccaggctgg agggcagtgg catgatctcg gctcactaca acttccacct cccgggttca    3300
agcaattctc ctgcctcagc ctccagagta gctgggatta caggcgccca ccaccacacc    3360
cggcagattt ttgtattttt ggtagagacg cggtttcatc atgttggcc aggctggtct     3420
cgaactcctg acctcaggtg atccgcctgc cttggcctcc caaagtgttg ggattacagg    3480
catgagccac tgcgcctggc cagctagaga gttttttaaag cagagctgag cacacactgg   3540
atgcgtttga atgtgtttgt gtagtttgtt gtgaaattgt tacatttagc aggcagatcc    3600
agaagcacta gtgaactgtc atcttggtgg ggttggctta aatttaattg actgtttaga    3660
ttccatttct taattgattg gccagtatga aaagatgcca gtgcaagtaa ccatagtatc    3720
aaaaaagtta aaaattattc aaagctatag tttatacatc aggtactgcc atttactgta    3780
aaccacctgc aagaaagtca ggaacaacta aattcacaag aactgtcctg ctaagaagtg    3840
tattaaagat ttccattttg ttttactaat tgggaacatc ttaatgttta atatttaaac    3900
tattggtatc attttctaa tgtataattt gtattactgg gatcaagtat gtacagtggt     3960
gatgctagta gaagtttaag ccttggaaat accactttca tattttcaga tgtcatggat    4020
ttaatgagta atttatgttt ttaaaattca gaatagttaa tctctgatct aaaaccatca    4080
atctatgttt tttacggtaa tcatgtaaat atttcagtaa tataaactgt tgaaaaggc     4140
tgctgcaggt aaactctata ctaggatctt ggccaaataa tttacaattc acagaatatt    4200
ttatttaagg tggtgctttt tttttttgtc cttaaaactt gattttctt aactttattc     4260
atgatgccaa agtaaatgag gaaaaaaact caaaaccagt tgagtatcat tgcagacaaa    4320
actaccagta gtccatattg tttaatatta agttgaataa aataaatttt atttcagtca    4380
gagcctaaat cacattttga ttgtctgaat ttttgatact attttttaaaa tcatgctagt   4440
```

-continued

```
ggcggctggg cgtggtagct cacgcctgta atcccagcat tttgggaggc cgaagtgggt    4500
ggatcacgag gtcgggagtt cgagaccagc ttggccaaaa tggtgaaacc ccatctgtac    4560
taaaaactac aaaaattagc tgggcgcggt ggcaggtgcc tgtaatccca gctacctggg    4620
agtctgaggc aggagaattg cttgaaccct ggcgacagag gatgcagtga gccaagatgg    4680
tgccactgta ctccagactg ggcgacagag tgagactctg tctcaaaaaa aaaaaaaaaa    4740
tcatgctagt gccaagagct actaaattct taaaaccggc ccattggacc tgtacagata    4800
aaaaatagat tcagtgcata atcaaaatat gataatttta aaatcttaag tagaaaaata    4860
aatcttgatg tttttaaattc ttacgaggat tcaatagtta atattgatga tctcccggct    4920
gggtgcagtg gctcacgcct gtaatcccag cagttctgga ggctgaggtg ggcgaatcac    4980
ttcaggccag gagttcaaga ccagtctggg caacatggtg aaacctcgtt tctactaaaa    5040
atacaaaaat tagccgggcg tggttgcaca cacttgtaat cccagctact caggaggcta    5100
agaatcgcat gagcctagga ggcagaggtt gcagagtgcc aagggctcac cactgcattc    5160
cagcctgccc aacagagtga gacactgttt ctgaaaaaaa aaaatatata tatatatata    5220
tatatgtgtg tatatatata tgtatatata tatgacttcc tattaaaaac tttatcccag    5280
tcgggggcag tggctcacgc ctgtaatccc aacactttgg gaggctgagg caggtggatc    5340
acctgaagtc cggagtttga ccagcctg gccaacatgg tgaaacccca tctctactaa    5400
aaatacaaaa cttaagccag gtatggtggc gggcacctgt aatcccagtt acttgggagg    5460
ctgaggcagg agaatcgttt aaacccagga ggtggaggtt gcagtgagct gagatcgtgc    5520
cattgcactc tagcctgggc aacaagagta aaactccatc ttaaaggttt gtttgttttt    5580
ttttaatccg gaaacgaaga ggcgttgggc cgctattttc ttttctttc tttctttctt    5640 tctttttttt tttttctgag acggagtcta gctctgctgc ccaggctgga gtacaatgac    5700
acgatgttgg ctcactgcaa cctccacctc ctgggttcaa gcgattctcc tgcctcagcc    5760
tcccaagtac ctgggattac aggcacctgc cactacacct ggcgaatatt tgttttttt    5820 agtagagacg ggcttttacc atgttaggct ggtctcaaac tcctgacctc aggtgatctg    5880
cctgccttgg cctcccaaag tgctgggatt acaggtgcag gccaccacac ccggccttgg    5940
gccactgttt tcaaagtgaa ttgtttgttg tatcgagtcc ttaagtatgg atatatatgt    6000
gaccctaatt aagaactacc agattggatc aactaatcat gtcagcaatg taaataactt    6060
tatttttcat attcaaaata aaaactttct tttatttctg gccccttat aaccagcatc    6120 tttttgcttt aaaaaatgac ctggctttgt atttttttag tcttaaacat aataaaaata    6180
tttttgttct aatttgcttt catgagtgaa gattattgac atcgttggta aattctagaa    6240
ttttgatttt gttttttaat ttgaagaaaa tctttgctat tattattttt tccaagtggt    6300
ctggcatttt aagaattagt gctaataacg taacttctaa atttgtcgta attggcatgt    6360
ttaatagcat atcaaaaaac attttaagcc tgtggattca tagacaaagc aatgagaaac    6420
attagtaaaa tataaatgga tattcctgat gcatttagga agctctcaat tgtctcttgc    6480
atagttcaag gaatgttttc tgaatttttt taatgctttt tttttttttg aaagaggaaa    6540
acatacattt ttaaatgtga ttatctaatt tttacaacac tgggctatta ggaataactt    6600
tttaaaaatt actgttctgt ataaatattt gaaattcaag tacagaaaat atctgaaaca    6660
aaaagcattg ttgtttggcc atgatacaag tgcactgtgg cagtgccgct tgctcaggac    6720
ccagccctgc agcccttctg tgtgtgctcc ctcgttaagt tcatttgctg ttattacaca    6780
cacaggcctt cctgtctggt cgttagaaaa gccgggcttc caaagcactg ttgaacacag    6840
```

| | | | | | |
|---|---|---|---|---|---|
| gattctgttg | ttagtgtgga | tgttcaatga | gttgtatttt | aaatatcaaa | gattattaaa | 6900 |
| taaagataat | gtttgctttt | cta | | | 6923 |

<210> SEQ ID NO 2
<211> LENGTH: 50001
<212> TYPE: DNA
<213> ORGANISM: Homo sapiens

<400> SEQUENCE: 2

| | | | | | |
|---|---|---|---|---|---|
| gtttcatcaa | accgctgcta | cctccccgtc | tcccacacaa | tttatgggac | ttctaagttc | 60 |
| cctctaaagg | gtccgaacac | ctacactggt | aacaagccac | ctggatttga | atcctggcaa | 120 |
| gacaacttac | tatctgacct | tggacattgt | gctgttctta | acctctccgt | gcctcggttt | 180 |
| cctcatgtgt | atgaataaca | tcaacaccta | catcaaagtt | tgctgtatta | aatttgataa | 240 |
| tatatgcaaa | gcatttagaa | aagtgcctag | ctcatagaaa | gccttatgta | aatattaact | 300 |
| atcattttt | ttcttttttg | gggtggtggg | ggaggggttt | cgcttttgtt | gcccaggctg | 360 |
| gcgtgcaatg | gcacgatctc | ggctcaccac | aacctcggcc | tcccgggttc | aagcgattct | 420 |
| cctgcctcag | cctcccgagt | acctgggatt | acaggcatgc | accaccacgc | ccgggtaatt | 480 |
| ttgtatttt | agtggagacg | gggtttctcc | atgttggtca | ggctgatctc | aaactcccga | 540 |
| cctcaggtga | tccgcccgcc | tcggcctccc | aaagtgctgg | gattacaagc | gtgaagcacc | 600 |
| tcgcccggcc | tagctatcat | ttttatacaa | gtgctgggtt | ttgggagaat | gtaatgatgg | 660 |
| cttttttctt | actaaacttt | cagtgcagga | ggaggagaaa | gaaagtaaat | agttatatga | 720 |
| acacagtaga | aagtcaaagt | ggaaaacaaa | aagaacatag | aacccaggtg | agcggtccag | 780 |
| acctcccccc | agaaacctaa | gaatccatag | aaatgggtgg | gaagcggaga | agatcctcca | 840 |
| gacagcaggt | ggcgatgtag | catccccccag | aaggcccgct | aacagaagct | aggaggacgc | 900 |
| gctaccaagg | tcacgtgtcc | ccggcgttca | ctcgctcttc | gcttcacgac | actcgcatcc | 960 |
| tcacgggtga | ttggtctgcg | tgcggcacgt | gggcgggta | ccggggcggg | ccggggaggg | 1020 |
| gcggggtggg | cggaggagag | gggcagggggg | cggagctgga | gggggtggtt | cggcgtgggg | 1080 |
| gccgttggct | ccagacaaat | aaacatggag | tccatcttcc | acgagaaagt | gagtgtccgc | 1140 |
| gttcggtggg | gagctgtctg | ccgcgcggtg | gcgggcgtgg | agcgcggcat | caccgcctct | 1200 |
| cggagggctg | ggtggggccc | gagtcgcccc | catgccgatc | tcgcccggcg | aggggcgacg | 1260 |
| ccgcagcctc | ccgcctcctc | ggctcgagga | ggggagcatc | acctacgccc | ctacttcccc | 1320 |
| cgcggcccc | gccctgggag | ccgggaggga | gtatgggcgg | ggccggggc | gtctcgggac | 1380 |
| acgggagtgg | ggtggcgccc | agtgggtttg | cttctgcctt | tctccgtcac | tttccatcgc | 1440 |
| ttttcggagg | attccttcac | ccctccccaa | tccttccctc | tccctagggt | ctagctagag | 1500 |
| tcatctctgg | gacacctccc | tcaacccctc | ctaccctaat | cctggcagaa | ttaacttttc | 1560 |
| ctcctccgga | ctgctcaatt | ctatattgga | gtcttcccta | cacgtagatc | tttgggtct | 1620 |
| tgttcgtgtc | tttcccctgc | actaggtccg | cgagcctccc | gagggaggag | accttggctc | 1680 |
| gcccactgta | gggcctgaca | tttaggaagt | gaagtaggaa | acccggcgtg | ccctaaaca | 1740 |
| gggaagtcgt | cacaagagtt | tttattacgg | gatgtttggg | tttggtttct | tttggtactc | 1800 |
| ccatctttcc | ggagcaggcg | gccagctttg | tttttaggta | ttaggagtgg | actgggatga | 1860 |
| ttttgttgta | gtctgcctag | cctgctgtcc | ctttaactct | tccgtgacca | tgcacttgaa | 1920 |
| gatactgttt | gtgatatgta | aagaaactcc | tcgtttctct | catactatta | tccagccatt | 1980 |

```
tgtgtgtgag tgaagccttc cccaggacag ctttggcaca tggtatcatg tttcataata    2040
gtttcgtgtt tggaaagagt tgctggtaag gctgttattt aataggagga gcaaagggtt    2100
tttgttttat taaatactta taaatgatca tttatcccag acatttaaaa ttcacacaca    2160
cacaacaaat aaagcaaaga caaaagaata catttaccaa atgtaaatct gtagcataaa    2220
ttttttttaa ttttattttt aaagatgggg tctcattctg tcacccaggc aggtgtgcaa    2280
tggagagatc atggctcact gcagccttga tctcctaggc acaagcgatc ctcccgcctc    2340
tgcctccaga gtagctggga ctacaggtgc atatcgccag gccaggtaa tgttttttggg    2400 agagacgggg tctcgctgtg ttgcccaggc tggtctcgaa ctcctggact caggtgattc    2460
tcccacctcg gcctctcgaa gtgctgtgat tacaggcgtg agccactgtg cctggaacaa    2520
attgttaagt acaatgcttt tcattgtaga aaacatctcg gaaacttttg aaataggctg    2580
atgttcagtg ggggaggaag gactcagtcg tatagttgtc actaattttt tgacttgatt    2640
gacatgactc gtaaatcata gacaatagag atttggttgc ttggctgagt agagtgcgtg    2700
aaaaatacac acgtactttt ttttttttt tttgagatg gagtttggct cttgtcaccc    2760
aggctggagt gcaatggcgc catcatggct cactgcaacc tccgcctccc cgttcaagcg    2820
attctcctgc ctcagtctcc ccagtagctg agattacagg cgcccgccac cacgcccagc    2880 taattttgt atttttagta gagacagggt ttcaccatgt tggccaggct ggtctccaac    2940
tcctgacagg tggtccgccc gcctcggcct cccaaagtgc tgggattaca ggcgtgagcc    3000
accgcacccg gccatatttt tgttattaat tttcaaaggc tttggtgtgg gaccacattt    3060
caacatggaa ggccttaaac atgttccaca ctacttcctg agaattagac aagatttta    3120 acaatattgt tacctagttg ggacacattt gtactgaccc atgggatgaa aaaagctga    3180 gtgctagcct agtgaaaatc tacttacccg aaagaaatcc ctcttagtct gggtgcagtg    3240
gctcacacca gtgctttggg aggcccagac gggcggatca tgaggtcagt agtttgagac    3300
cagcctggcc aacatggtga aacccgtct ctactaaaaa tacaaaaaat tagccaggtg    3360
tggtggcagg cgcctgtaat cccaggtact ctggaggctg aggcaggaga attgcttgaa    3420
cccgagaggc agaggttgca gtgagccgag accgtgccac tgcacttcag cctgggcaac    3480
agagcgagac tccgtctcaa aaaaagaaaa aggaaaaaag agtccctctt aattatcagc    3540
atgtgtatag gcctacagat acttcaggaa tacctttacc attatcatca acttgtatct    3600
acatagcatg tgaagattca acaatttagt ttttttgggcg tcctcaagag tacgcaccta    3660
taaccatatg gcccaattgt taatctccta tacagtccat tctgggaatg tttgggctta    3720
ctgtgccatt tttccgttca ctgccttccc ctctgcaata tacctttaac ccttgctagg    3780
tcctgggttt ggagagccag agaaccaact ttggccctaa agaagctgtg taggtagcaa    3840
tatctgccta cgaagggcct tgcaaccatt tcctcttgga accttggttt cctctttctg    3900
agtagtcact ttgagtaccc tttattaagt tagaatgtaa aaacagtttc tcactgatat    3960
atctgcagtg cctgagagag ggcctggcac agagtaagta ctcaataaat atttgaatgg    4020
ggccgggcgt ggtgagacct gtctctacaa gaatgaacaa aattagctgg gcgtgttagc    4080
acatgcctgt agacttggga ggctgaggtg ggaggattgc atgagtctgg gaggtcgagg    4140
ctgtagtgag ccatgatcgc accactgcac tccagcctag gggacagagc aagatcctgt    4200
ctcaaaagaa aaaatgtat atatttgaat ggataaagag atggctttga gtttctgaga    4260
tatatatggt gctgtttatc taaagtaaac aagtttctg taaatatttt aaggctttgc    4320
aggccagctg tagtctctgt cacacattct tatttgtgca tgttttttccc aaccatgtaa    4380
```

```
aaatgtaaag tgcattctta gctactgggg caggttgaat ttggcccatg ggctagagtt    4440
tgccaacccc taacttaaac ctttgtacta actttatgac cactactgga tttttgttgt    4500
tgtttgtttt agttctggtg cctgctttgt tttttttttt tttttttaatc ctcttgctga   4560
tgtttcttgg tgcagttact gtgccatttg tattggtgct tttaatgtaa tgcaaactgg    4620
taataatatc taaacttgct ggggttgtac ataaaattat tgaaaagatt gaaaagatgc    4680
tgagcattga ctctgtggca ttcattatgc ccttttgtga ttgctggatt ttagccatct    4740
ttaggacatt tgagctttag gagaagccaa attctgtata aatgacttga agtgctaata    4800
gcacaggttt tgaaacctct gcctgggttt gagtctcagc tctgcctttt actacctgtg    4860
tgatcctgag caagttactt agtatccctg tcctctagtt tcctcctctg tagtgtgggg    4920
ataataacat agacataacc tgagagttag agtgtagaga aggctccctg gcagatagtg    4980
ctgtagaagt actggccatt gccattactc aggtgcttgt gtttgctgaa cctcatagta    5040
agggctcgga gagcactaag aggaggtgag aaatgctgct agattgacag cttgtcccca    5100
gatagcccat tcccgagagc accttaggtt tatacctgat ttgtgttgta gttagtagtg    5160
tctctggtaa tttgaactag tttcaggttg gtcttgaaaa cctggggagg ttgggggtaa    5220
atgatttggt agcagttctc ttttgtgatt ttatacatta tctttgtaga actgcagttt    5280
gctaattctc tgagcccaac acaatgaagt ctgggcctaa aatcatagaa tttcttttat    5340
tttttttttt gttttaatt tatttattcc ctccctccct cctttcttcc tttcttcctt    5400
ttctttcttt ctttccttcc ttccttcctt ctttcttttc tttctttctt ttctttcttt    5460
ggagtctcac tctgtcacca ggctggagtg cagtggcacg aactttcttc agagtctcac    5520
tttgtcacca ggctggagtg cagtggcgcg aactcagctc actgcaacct ccgtctcctg    5580
agttcaagag attctcctgc ctcagcctcc cgagtagctg ggactatagg catgtgccac    5640
catgcccagc taattttctt attttttagta gagacgaggt ttcaccatgt tggccaggat    5700
ggtcttgatc tcttgacctc gtgatccacc tgcctcagcc tcccaaagtg cggggattac    5760
aggcgtgagc taccacgccc agcctatttt ttatttttg aggcagagtc tcactctgtc    5820
acccaggctg gagtgcagtg gtgcaatctc agctcactgc aacctcgcc tcctgggttc    5880
aggtgattct cctgccttag cctcctgagc acctgggact acaggcgcct gccaccacac    5940
ctggctaatt cttatatttt tagtagaggc ggggtttcac catgttggcc aggctggtct    6000
cgaactcctg atctcaagtg atcaacctgc cttggcctcc caaagtgctg gaattacagc    6060
catgagccac catgcccagc caaatcatga gatttcaata ccgctgaact ttgattatgg    6120
caaagtgaac ttctgctttg attaaagctt gatgagagag gtggctgggg atagtttgag    6180
ataagggcaa ggcaggaaaa tgcataatct tacgtgggct cattgtcatt gtacaattct    6240
tttggtccat gtggaatttg atccgtccta tgacttaagt tatgtttatt tttgttttta    6300
tttttattta ttttgtgtct ttttgagaga catgatgttg ctctgtcacc tgggccagaa    6360
tacagtggca caatcttagc tccgtgtagc cttgaactcc tgggctcaag tgatcctccc    6420
acctcagccc ctcaaacagt tgagattata gtatgaacca ctgtgcctag ccttaagtga    6480
tttttaaatt tgtactgaac agtttgtcct ttccttccat taaatcatat tagaagtaca    6540
gaacttgata tttcctgtag caatacagtt tttctttgat gaagtttgat ttcaagtact    6600
tattttttcat aatttaaagc tattttttat agagagaatt ttaatcaaat atttggatgt    6660
cactattgct atatatggta ttaagtatgg tgaccatagt ttgtaaactc caaactgaca    6720
```

```
gcaagacagg aaatttgtgt tagcaaaggc ttttttctta ctgtttgaat ttttaaaaa       6780 ttagatacaa tacagagagg agcacacaaa tcattaagag tacagctcag cgaattttca       6840
cacagtgaac atgtgtaaac agcaagtaac aaaagattta cctgcatcct ataacctccc       6900
attattccct tttctaggta ctgtctctcc actgcattcc caccaaatat aaccactatg       6960
ctgaattctg acatcataaa tgagttttgc ctgattttga gcttttgtga ctggaagtgt       7020
acagtgtata tacccttcg attctgtcct ctttagttta ccattgtttg agaaatttat       7080
ccatactgtt ccagaattaa ctactgttaa ttattgttaa ttaactactg ttgtagttaa       7140
ttcatcctca ttgttatcta gtattctttt gtgagtaaac acaatttcca ttctactgtg       7200
atcccagcta tccatttggg tcgtttccag tttggggtcc attacaaata gtaatgctat       7260
ctgtaatgct attttgtatt actacaaata gtaatgctat ttgtggcaca aaaatactgc       7320
ttttgtgaac attcttatac atgtcttttg atgaatgtat gtttgcattg ctgttgttta       7380
cattatgtac ctagtaatgg aattgctaga tcataggaga tgtatatatt aagctttagt       7440
ggatgcatta cataattatt agttattatt ggttatacca atttatcctc tcatcagtag       7500
tatacaacag tttctgtatc tctaatctcc aacattttag ccatttaga gtttgtgtac       7560 taacacattg tggttttaat ttacatttcc ctgatgacta ataaagttga gtacctcttt       7620
tgtgttcttt atagccattt gactgtcttg tgaagtgctt gtttgtcttg cctattttc       7680 ttttcttct ttcttttct tccttccttc ctttcttct ttcttcttc tttccttcct       7740 tcttttcttt ctttctgtct ttctttcttg tcttttcttgt ctttctgtct ttcttggtct       7800
tgccctgtca cccatgctgg agtgcagtgg tgcagtctca gcttactgta gcctcgacct       7860
ttttggggct caagttatcc tcctttctca gcctcccaag aagctggact acaagcacgc       7920
accaccatgc tcagttaatt tttatttt tgtagaaatg gggtttcacc atgttgtcca       7980
ggctggtctc aaacttctgg gctcaagtaa tcctcctgcc ttggcctccc aaaatgctgg       8040
gattacaggc atgagccacc gcagccagcc ttggctattt tcaaaagga tataagtaga       8100 acatctgtat atcccttcaa tttgcatatt attcagtaag agttgcactc tggtagtaga       8160
aatatataag gaggagaaag aagtggaaac aaaaagtcta ttctcatgag aagacttggg       8220
ggatagtgtt ctctctagct ccaagctact tattccttac gaaaagttga agataaactt       8280
atctcagact gaggctgtct caatgttgtc ttcctattcc attatacaca tataacccat       8340
atttttttca ccagctgaat tttgctccta gaaaattgat tcatcaggaa aaatatccgt       8400
cttgcaaggt ggttctcttt agagtctgct gtgtgacata gctcaggaca aattgtgtga       8460
tgtcagatag gttgggttaa ggaatagacc ttattgggga aagagagaac ttggagggcc       8520
aaggttagca ggagaaggaa atgttctctc atctgccgtc aattcaggga ggggcaaacc       8580
tggtgtctgt gttcacaggg agggatccat ccatctgtga ttctcccttc ttatcaggta       8640
gcatgggaaa gctacactgt tgcggggagg agggtcacac gcaggctact tagtaccagg       8700
caccctggac ttggattcag gttgccagtt gtgtgagaaa ctgcccagca cctgaaggcc       8760
ctgaacccat gagaagttgt acctacctcc catgaggagg aatcctgtca tcccatggga       8820
gctgagcttg ggtgcagtcc ctcttgctgg cttgtccagg agtgagctcc agggttgttt       8880
gggacagttc tgctcattgc tttacactgt gtatacatta tctgtagagt tccatgaaga       8940
gaacttcagc actgtaactg caagttttaa catggaacag aattttctc acctgtatta       9000 attcttaaga tttgaagttc tatcaacaag catttagatt gtgtgagat tttttattt       9060 ttatttttgg agacagagtc ttgctctgtt acccagactg gagtggcagt ggcatggtct       9120
```

```
tggctcactg caggctctac ttcctgggtt caagcgattc tcatgcctca gtgtcctgat    9180
tagctaggac tacaggtaca caccaccatg ctggctaatt tttgtatttt tagtagagac    9240
gaggtttcac cgtattggtc aggctggtct cgaactccca gcctcaagca gtccacccac    9300
ctcggcctcc caaactgctg ggattacagg tgtgagccac catgcttgac tgacatcatc    9360
atgttaaaag aataaatgtt ctagggagct gggcacagtg tcatgtttct gtagttctag    9420
ctgctcggga ggctgaggca ggaagatccc ttgagccctg gagttcaagt ccagcctggg    9480
caacatagtg agatctcttt ttttaaataa ataataact gttctaggga ctaaaatttc     9540
cttttcaccat tagtaattta ctgtagaatc tccaagaatg aacttatttt aggtactgaa   9600
aatgagggag actaaatgtt ttatacagta gtttttagta aaatatgaga tttgatgcat    9660
ttgatagatg atgtttgttt aaaataattc ttaaattttt gatcatgtaa ttatagtttc    9720
attaatggta gatttgtaaa ataaatgtta ccaaatgaaa atgcatgtac ctatgttaat    9780
tatccttatc taaagctgaa agttcagttc aactatgtta aaacatagta ggggcctggc    9840
agggtggctc ttgcctgtaa tcccagaact tagggaggcc aaggtgggca gatcacgagg    9900
tcaggagatc gagaccatcc tggctaacat tgtgaaaccg tatcgctact aaaaatacaa    9960
aaaattagcc gggcatggcg gtgggcacct gtagtcgcag ctacttggta ggctgaggca   10020
ggagaatggc gtgaactcag gaggcagagc ttacagtgag ccgagatcat gccactgcac   10080
tccaggctgg gtgacagagc aagactccat ctcaaaaaaa aaaaaaaagt tggccaggtg   10140
tggcggctca cacctgtaat cccagcactt tggaggccg aggcaggcgg atcacaagat    10200
caggagtttg agaccagcct ggctaacaga gtgaaaccct gtatatacta aaaatacaaa   10260
aattagccag gcatggtggt gcatgcctgt agtcccagct acttgagagg ctgaggcagg   10320
agaatcactt gaacccggga ggcggaggtt gtggtaagct gagattgctc cactgcactc   10380
cagcctggac aacagagcaa gactctgtct caaaaaaaaa aaaaattaat gattaaatta   10440
tttaggggag ccgggcgcag tggctcacgc ctgtaatccc agcactttgg gaggccaagg   10500
cgggcggatc acgaggtcag gagatcaaga ccatcctggc taacacagga tgaaaccccg   10560
tctctactaa aaatacaaaa atttagccgg gcgtggtggc gggtgcctgt agtaccagct   10620
actcgggagg ctgaggcagg agaatggcat gaacccgggt ggcggagctt gcagtgagcc   10680
aagatagcgc cactgcactc cggcctgggt gaaagagtga gactccgtct caaaaaaaaa   10740
aaaaaattat ttaggggaag atactataca attctgttta acaagtcaca tttttaatttt   10800
ttcttttgga aatattagca agaaggctca ctttgtgctc aacattgcct gaataactta   10860
ttgcaaggag aatattttag ccctgtggaa ttatcctcaa ttgcacatca gctggatgag   10920
gaggagagga tgagaatggc agaaggagga gttactagtg aagattatcg cacgttttta   10980
caggtactga ttttaaactc actaagtcac atttcttttt ttttttttttt tttgagacgg   11040
agtctcgccc tgttgcccat gctggagtgc aatggcgcga tctcggctca ctgcaacctc   11100
tgcctcccgg gttcaagcga ttctcctgcc tcagcctccc aagtagctgg gattacaggc   11160
acacggcact atgcccggct aattttttgt atctttgtta gagatggggt ttcaccatgt   11220
tggtcaggtt ggtctcaaac tcctgacctt atgatccacc tgtcttggcc tcccaaagtg   11280
ctgggattat aggtgtgagc caccacaccc ggcttacatt tcttttaaaa atgtggatac   11340
catttagaaa aggatgggcc attcttccta tagggatctg actggtgaat tataactgtg   11400
ctgttaactt tggaaatggg aatgcacaag atattgtttt aaatatgcac gctaatgaca   11460
```

```
gtttgtatcc ttctttcccc acccccaccc ttgcttcaac tacctgtcaa aattaacagc   11520
agccttctgg aaatatggat gacagtggtt ttttctctat tcaggtaagt agtcacaagc   11580
atgtactatg tgttgcttac atcccaggca ccgtttcaca gcctttcaat agtcactgta   11640
acaaggcgac cttcggaagt tcttctgtct acagagtata gattatactc tagagtacta   11700
gatttttttt ttcttgagac agagtctcgt tctgtcacct aggctggagt gcagtggcgt   11760
gatcttggct cactgtagcc tctgcctccc gggttcaagc gatcctcctg cctcagcctc   11820
ccaagtagct gggattacag gcacccgcca ccacaccagt taatatttgt attttttagta  11880 gagatagtgg ggtttcaccg tgttggccag tctggtctcc aactcctgac ctcagcctcc   11940
caaagtgctg ggattacagg tgtgagccac tgcacctggc caactagagt actagatttt   12000
tatatagata aacatgaaag gattgtagaa tcttcatatt agagtggggc atttaaaaat   12060
tccttcttga gaaagattaa tttgcatctg gatgctaata ataaccttaa ttctggccgg   12120
gcgcggtggc tcacacctgt aatcccagca ctttggggag gccgaggtgg gcggatcacg   12180
aggtcaggag attgagacca tcctggctaa catggtgaaa ccccgtctct actaaaaata   12240
caaaaattag ctggacgtgg tgacacgtgc ctgtaatccc agctactcgg gaggctgagg   12300
caggagaatc gcttgaacca gggagtcgta ggttgcagtg agccaagatc gcgccactgc   12360
actctagcct ggtgacagag cgagactcca tctcaaagaa aaaagaaat ccttaattct    12420 aataagtcac aatgtctcaa acttaccatc tgttgggtaa atttgagaaa atgcaatacc   12480
ttgctaccat cctttttaaat cagcctacca gactggatttt ccttattatg gtttgtggct 12540
tttgattttt tttttttaat gtatagctct ctttgaattc tttggtggtt atatatatat   12600
gtactcgcaa gattcttttta tctgtgggtc tttcattctt tttctaacac tgtgagttgt  12660
atccagagta ctttcggaac ctctcctgag cgacctatct ctgcagatat ctttgtttat   12720
gtttcccttg tactgccctc ctggactctt cctcatccac cagcatttcc atctagtgct   12780
ttaccgtgcc actgctaaca ggtaatggct actgcagggc tgaaatcaga ggccagagta   12840
ggcccagcac ttggcgtttc ctatttgtgc cttgctgctc ttggtgcctg ttcatgtgtg   12900
cccactacct tgcactcaat ttctgtcttt gctggtacct ggctcacttg cttctttgtt   12960
ggctaccttg gagggcagat agtgaatttt cagaaatttc ccttttttg tcagacagat    13020 tgaaataaac aggtttgcat tttgttttttt ctacaagcgg caagcccatg acctagaag   13080 tctgacatct atggaacctt cagtttaaat gcccagggag aacttatttt ggtagatatg   13140
atttctgaca ttgcaggtag caagttgaat ataattttc taaagtagca cccacagcag    13200
ccaaattatc agatgtatat agtagactag ttttaagaaa agcacttatg ggtagaatat   13260
acatctggat ttttgaggca gttttattta ggaattgtgt ggttttctgg aacatctcag   13320
agacctggta tgaaaagcac tcttctaata tatatgtgtt tttttttatg gatttagtga   13380
tatatctata cacacacact ttttaaaacc tatagccggc tgggcgtggt ggctcatgcc   13440
tgtaatccca gtactttggg aggcccaggc gggtggatca aaggtcagg agattgagac    13500 cagcctggcc aacaaggtga aaccctgtct ctactaaaaa tacaaaaata gctgggtgtg   13560
gtggcgtgtg cttgtaatcc cagctactcg ggagcctcag gaggagaatc gcttgaacct   13620
gggaggcgga ggttgcagcg agccgagatc gtgccactat actccagcct gggcgacaga   13680
gcaagactct gtcacaaaaa aaaaaaaaa aacctatagc cttctagaga aatttatata    13740
tgaagtacac aactaacata gctacacttc ctaaatttgg aatggagtgg tttagcttat   13800
gaaaagttgc tattttctctt aacaggttat aagcaatgcc ttgaaagttt ggggtttaga  13860
```

```
actaatcctg ttcaacagtc cagagtatca gaggctcagg atcgatccta tgtaagattc   13920
tgttttgcat ttcatacatt tcttttccca aatttgattt ttaaagttgt aatttcttaa   13980
agaagagaaa tacattttga atactttttgt tttgatgttc cctgtttcat tcactcagac   14040
tttcctattt cacctttgtg atgtccatga gcatctgccc tgtagccttc ctggcacccc   14100
agtgtctgtg gcagcacaga gctgaccccca taagtggtgc atgaggccat cttgtggcac   14160
agcatcacta agctgctgca gagacgttca tatggttgtg tgatctttta aaaacatcag   14220
tgacacttaa ctataaatat aatcttaaat tatcacaaat tttatataat atttgccagt   14280
agacaacata aatatgaatt caatatttca agttaatatt gtctgttttc ttttttagaa   14340
atgaaagatc atttatatgc aattataagg aacactggtt tacagttaga aaattaggaa   14400
aacaggtaac atttcttacc cttccttgtc ttttttttctt atattgtacc ccatttaaaa   14460
ctaaaatgtg ggccaggtgt ggtggctcat gccaacagtt tgggaggctg aggtgggggg   14520
atcacttgaa gccaggagtt tgagaccagc ctgggcaaca aagggaggtc ctgtctctta   14580
aaaaaaaaat aaaaataaaa ataaaaataa ataaaaaaaa aaacaaagag ccaggcatgg   14640
tggctcacat ctgtaattcc agcttacttg gaaggctgag tcagaaggat cacttgagct   14700
caggagtttg aggctgcagt gaactatgat tttgtcactg taccccagcc tgggtgacag   14760
agtaagactg ttctataaaa cataaaaata aaaaaaatat atttaaaaat taaaaaaaaa   14820
aaaggattgc tgactttaaa attaggaaac tgaccagtaa tgtgtgtgtg tgtagcatgg   14880
tttatccttc ttgatagata gaaattgtca ttttaaaaga taatatcagt tttcctttata   14940 aatttatttg tgacaagtat atgcaattta actatatcat aagaaaaatt ctatattaaa   15000
gataatacaa atgtggttac ttttaagtgg gttttttatgt gatgactatg ttctgtcagt   15060
taattattac atttatagat ttgtatttag catagtgctg tcacaaagcc tgaaatagtg   15120
tcaagcatga ataaagcatt caattatgtt tgctttagtg taagattatt cattatgatt   15180
ccaaaagcca tgtaatacgt acgtctacag aaaatcactt ctattttttta aataaaacat   15240 gaaatatgtc ttgagcaagc tatttttaaga aacaatcatt taacgtcctt gttattagaa   15300
ttttgaatct ttgaaagagg gttattgaaa accagctagg acagtaaaaa agaataaaact   15360 agtgatacat gcagcaatat ggatgaatct caaataatt atgctgaaag aataacccac   15420
aaacaaaata ctacctgctg tatggtatca tttattaaaa gtctagaaaa gtgcagattc   15480
atctgtagtg atggaaagca gattgaccag cggttgcctg gggacgagaa ggctatggag   15540
gagtgagagg ggagggttac agagaggcac gggaaacatg gcaatgagga atgtgttcac   15600
tatcttggtt gtagtaatgg tttcatggga gtacagtata caaatgtgaa aacatttcag   15660
aggccagatg cagtggctca tgcctgtaat cccagcactt tgggaggcca aggcaggagg   15720
attgcttgag ctcaaggagt tcaggaccag cctgggcaat ggcacaagac cccatctcta   15780
aaaaaaaaat gaaagaaaaa aaaattggct aggcgtggtg atgcatggcc gtagtcccag   15840
gtgctaggga ggctgaggag ggagcacaga ggtcaagcct gcagtgaatc atgatcgtgc   15900
tactgcactc cagcttgggt gacagaagga gatcctgtct caaaaaaaaa gtttcaaatt   15960
atacacttta aatatgtgca gtttattata tgtcacttat accccaataa atctgttttt   16020
tttaaaatgt aaatacaagc caaaaaggt ataagtcaag aaaatatatt gaattaaatc   16080
tgtaagagat aattcaaaaa caaaaaccct attgttatct tttaagtcac ccaaatcaaa   16140
tttgggaaaa gtcacctact tagcttcatc ctaagttggt tctttctttc tttctttcct   16200
```

```
tcttttgaga cggattcttg ctctatcgcc caggctggat tgcagtggcg ggatcttggc    16260
tccctgcaac ctccgccacc tgggttcaag caattctctt gtctcagcct cccaaatagc    16320
tgtgtctaca gccacgcacc accacaccca gctaattttt gtattttag tagagacggg     16380 gtttcgccat gttggtcagg ctggtcttga actcctgacc tcaggtgatc cgtccgtctc    16440
tgcctctcaa agtgctgggg ttacaggcgt gagccaccat gccgagccct aagttggttc    16500
tttcttaaag ttcttcctga ggagccaaga gcaagttaag gagatgtaac ctagaagctt    16560
acagtggagg ctagctgggt gcagtggttc acgcctgtaa tcccagcact ttaggaggct    16620
gaggcaggga gatcactgag gccaggagct tgagagcagc ttggcccaac acagtgacac    16680
cttgtctcta caaaaaaaaa aaaaaaaaaa ggcagcttac agcagtagag gctgatgcga    16740
gtgggaatca cctctaggta aaaccagtg tagcgtactg ctgagattat ttaacctctg     16800
ggttttattt atgtgttttt aaaaattatg atccagtatt ttttactttt ttttgtataa    16860
agtaagcact gaattttaa ggttgtatta atttgcaaat aaatgtctat cttattattt     16920
tgagagattt aaaaaattt agttcttcaa aattgcattt tcacattttg aattacgtta     16980
tctttgacaa atacagaaga tgtcaaattt tggtttattt tctttggttc taatttatat    17040
ttttgtttaa aactatattt ttcactatag actcttctg tctctcgagg tccctgtata     17100
atgaaaaaga aggctggaaa aagtattaac attgtcaaaa tccaggaaaa gtagttggtc    17160
atgatattga tcgttaactt tagaaacttt ttgtatcttg tgggttaaat taggattact    17220
atgtggtagt gataaatgat gttaattagg gccgagtgca gtggctaaca cctgtaattc    17280
cagcatgtag ggaggctgag gtgggaggat gtcttgaatc caggagtttg agaccagcct    17340
gtacaacata gtgtaagacc ccttctccac acaaaaaaat tagaaaattt gtcaagcatc    17400
ttggtgcaca cctgtagtcc cagctgcttg ggaggatgaa gcgagagaat cacttaagcc    17460
caggtgttcg aggctgcagt gagctatgat tgcaccactg cactccagac tagatgacca    17520 tctctttaa aaaaatgtgt ttatatgtta tatgtgatag tgcttttaa aaacattttt      17580 aaattataga gacagggtct cactatgtta cagcccaggc tggtctcaaa ttcctgggct    17640
caagcaatcc tcccaccta gctaacctcc caaagtgctc ggattatagg catgagctgc     17700
atgcccagct aatttagtga ttttaaaaa ctgagctggt aattataaat tctcttcctg     17760
gaacttctga ctttctcaca attggaatct tttgacaaaa attatcagta atgggaaaac    17820
tttgtgtagt tgtcattttt cctcccatca gtgtgataga tatgattgga gttatgttgg    17880
actgatattt tgaaaaaaga tttaattata gctattaata aagacattta aactactgac    17940
tatgcatttt tattcttttg ggagggttta atgtttatag tttaaagcaa actgttgttt    18000
ttaaaaaagt atctaacagg gccgggcgcg gtggctcaca cctgtaatcc cagcactttg    18060
ggaggcctag gcgggcggat cacaaggtca agagatcaag accatcctgg ctaacatggt    18120
gaaaccctgt ctctactaaa aatacaaaaa aatagctggg tgtggcggcg tgcgcctgta    18180
gtcccagcta ctcgggaggc tgaggcagga ggatggcatg aacccgggag gcggagcttg    18240
cagtgagccg agatcgcgcc actgcactcc agcctgggcg acagagcaat actctgtcta    18300 aaaaaaaaa aaaaaaaaa aaaagagtat ttagcagagg ccaggtgcag tggctcatgt     18360
ttgtaatccc agaactttgg gaggctgagg cgggcggatc atttgaggtc aggagtttga    18420
gaccagcctg gccaatgtgg caaatgtgct gtctctaact aaaaatacaa aaattagctg    18480
ggtgtggtgg tgcagacctg tagtcccagc tacttgggag gctgaggcag gagaatcact    18540
tgaacctggg aggcagaggt tgcagtgatc cgagatcatg ccactgcact ccagcctggg    18600
```

```
ttacagagtg agactcttct caaaaaaaaa aaaaagtatt taatagtgat aaatctgcag   18660
tattctcttg tagtttttaa gatcatatta ttcagtcaaa gaaagagct caacttgaaa    18720 tatttccaga gtttaaacaa tcttactaag ctttgatggg ttgtatctat tcttaacatg   18780
tgaaacttcc ttattaccta taatatacac taacttaaat attgacaatt tttttccagt   18840
ggtttaactt gaattctctc ttgacgggtc cagaattaat atcagataca tatcttgcac    18900 tttcttggc tcaattacaa caggaaggta agtaacggct gaacattttg taatgttacc    18960
tttcgaagta gttaaataac caggcacatt agatgacagt gtgataaaac tgttttttctg   19020 gcagtggcag tgaaacaatc tttagttttg acgtggtgat aggctgtgat ttgggtgacg   19080
ctgttcagtt agagttctca ctgacacctg gcccttcctc ttctgaggat gctgctttct    19140
ttgcagccct tctaagtaat ggcttttttct tttatacatc acatatcaca cggctgagag    19200
gagggataga tgttttttctt ctttgcctct tctaggccac tgttcttcct tataaactcc    19260
agtttctttg aaatacatgc ccctaacggc tgggcacggt ggctcacgcc tgtaatccca    19320
gcactttggg aggctgaggc aggcggatca cgatgtcagg agatcgagac catcctggct    19380
aacacggtga atcctgtctc tactaaaaaa taacaaaaaa ttagccgggg tgtggtggcg    19440
gacgcctgta gtccgagcta ctcgggaggc tgaggcagga gaatggcgtg aacccaggag    19500
gcggagcttg cagtgagctg agatcgcgcc actgccctcc agcctgggcg acagagcgag    19560
actccgtctc aaaaaaaaaa agaaaagaaa aaaaaagaa atacatgccc ctagattaaa    19620
ctatcccttg tccttttgca ctcatccaca agtctctttt catcagtgat tttaggatct    19680
gactcgttgt cttttttctct acttcaacta ctttttatcat tcttaattat ttctgtatcg    19740
tcaatcaatc cagtacctgc ctcttagttt caaaatcact tactcttgct tagctattac    19800
cagtaatcat aaccactgtc aaatctcaat tgcaagcata ttactctttta actaccacct    19860 cctatctttta aaccatgttt tgtctgtttt tttattccag ccattcttta aaccctactg    19920
tggggcccaa gcatttcctt tatacgcatt cttccttttct tctactgctt attttctgta    19980
atccgtcatc ataatcactc cattgcattc ttcaacgtgt ttccctctc tcctccatc    20040 atacttgaat gacaaaaatc tcaaccctgg ttaaaccaca tcttggcctt gtccattcct    20100
gtaccagagt agctggacgt ggctaaaaaa taacataaaa catgatgatt ggttttactt    20160
ttttcttaaa tgatctatcc atccattcac ccatccatct atcaaagtga ctaggcctat    20220
ttctgaagcc caggctggag tgcagcagca taatcacagc tcattgcagc tccaaactcc    20280
tgggctcaag tgattctctt gccttagcct gttgagtagc tgggactaca ggcttgtgct    20340
accacaccta gctaaggttt tactttaaat ttattataat cacaaaattc agatgagcct    20400
ttagtgctgt ctgatatttc tactatgttt tcttagtgat gtaccaccct ccaaggtgtt   20460
tataaaaaat tatgtaccac tctccaagaa gtttataaaa aataatgtgc caccctccaa    20520
ggtgactaat ttcacagctt atgtctttaa acctttaagc actttcctct cccttacaca    20580
ccttccttgt ggctttccgt tacattctgc tgagaacata gaagcaatta aaattatgtt    20640
ctttctacca gcaaatttat caatttgctt atatcttcac ctgtgctttg agcctattta    20700
aatagatgaa tggtcccta cctctaacca aaaccagtcc ctcacttgtg ggctggatcc    20760
cagctcttct cacctactca agatgttcct gctttcatct ctccactctc ttatataatc    20820
agttcccccc ccctttttttt gtaatattcc tataagcagt aaaataagct ttttatttcc    20880
attgattaaa aataaaaatc ctctcttaat tccatgaaac tccagctgcc tccccatttt    20940
```

-continued

```
tattttttcc ttaggattgt ctctagtgtg ccttctcctt ttcttgaact ctgcctcctg   21000
ggttcaagcg attctcctgc ctcaacctcc cgagtagctg ggattacagg cgtgcaccac   21060
catgaccggc taatttttt tttttttttt tgagatggag tttccctctt gttgctccgg   21120
ctggagtgca atggcgtgat ctcggctcac cgtaacttct gcctcctggg ttcaagcgat   21180
tttcttgcct cagcctcccg agtagctgga tttacaggca tgtgccacca tgcctggcta   21240
attttgtatt ttagtagaga tggaaggggt ttctccatgt tgttaggct ggtctccaac    21300 tcctgacctc aggtgagccg cccacctcgg cccCctaaag tgctgggatt acaggcatga   21360
gccactgcgc ctggccccgg ctaaatttt tttttttttt tttgtatttt tagtagagac    21420
agggtttcac catattggcc aggttggtct cgaattcctg gcctcgagtg atccacctgc   21480
ctcagcctcc caaagtgctg ggattacagg cgtgagtcac cttgcctagc catcttttag   21540
taatggtatt tggagatcac aatttgagtg ctggcatgct tattgctgct gggtttgtta   21600
tgtagttatt gtgaattcac atttaggaat atagggtttt taattctttg attttagata   21660
cttgtatctt ttttctttta tatttaaaac cttggttcct gatgatatcc cttcttagaa   21720
accctgtcta cctttggcct tcagcccacc atgctgtggt tttcctaact tgctgcctgc   21780
acttttcaga ttccttttcat ggatcttaaa tatcatctgt aaataagatc tatgtgtcaa   21840
taattaccaa acttttatct ttagtcttga catctaccct gaacacctag ctttgactaa   21900
ctcctagctt tggcatctcc acttggaaat ccaaaaagtg tttcaaactg aacatgtcta   21960
tgaaagactt atttttttct ctctatccat gctatccatc aggttttcca tttccataag   22020
ggtgactctt gtactctggt tcctatatat tataccgaca gagcagccca gagtgcttct   22080
taaccagtgt aaggcctgtt atgtcccacc ctcactcttt gtccttcagt ggcttcccag   22140
cacacttaga ataaaatctg aagtcttagg ccgggcttgg tggctcatgc ctgcaatccc   22200
agcactttgg gaggatgagg gggcagatca cttgaggtca ggagttgatg agaccagcct   22260
ggccaacatg gtgaaaccct gtctctacca aaaaatacaa aaattaactg ggtgtggtgt   22320
tgtgcacctg tagtcccagc tactcgggag gctgagatag gagaatcact tgaacccggg   22380
aggcagaggt tacagcgagc caagatcata ccactgcact ccagcctggg tgacagaacg   22440
agactctcaa aaaaaaatta aaaaaaaaa atatgtgaag tcttgaataa acccaagat    22500 ctttaccatg gccccctgaac agggcagagt atccattctt cagacactct tcatagaata   22560
ccatggtgag ctggcatatt tattatacaa tacagaaaca attttactgg cagaaaacac   22620
attaaaccgt ctaaactctg aatacagttg tcctcataaa aaatgttcaa catactattt   22680
tgaggttttc cattaatagt tcttataatc tttgtcccat tatgtgttaa tccaacaaag   22740
gatatccaat aacaaacacc aaagtttaag aaaaatgtgc taggcgcggt ggctcacacc   22800
tgtaatccca gcactttggg aggccgaggt gggcagatca cctgaggtca ggagttcgag   22860
accagcccag ccaacatggt gaaaccctgc ctctcctaaa aatacaaaca ttaactgggt   22920
gtggtggtgg gtgcctgtaa tcccagctac tcaggaggct gaggcaggag aatcgcttga   22980
acctcctggg aggcagaggt tgcagtgagc taatattgca ccactgcact ccagcctggg   23040
tgacagagtg agactccatc tcaaattaaa aaaaaaaaa aattaatgat agagaaactt   23100
aaatcagtta gattgtttta ggtatagccc atccttggtt tttgtgtgta gcatctagct   23160
tggggaaacc ctggatttct ggaatcatat ttagacacag tcacactaga ctaatgtaat   23220
tcttttggga tgcaaaccac acgtttgaca ccttaaatag cttttaggta tttggcttcc   23280
cagcccctat ttttagttac aaggggtgta catgtgtggg tcagggtggg ggtagctctt   23340
```

```
tccgcagatg attagtttta gccatgttac tagttattgc acacattatc tgtgtcctca   23400
cagcagccct gtgagtaagt gtattagggt tctctagagg gacagaacta ataaggtaga   23460
tgtatatatg aagggtaatg tattaaggag tatcgactcg tatgatcaca aggtgaagtc   23520
ccacaatagg ctctctgcag gctgaggaac caggaagcca gtccaagtcc caaaacctca   23580
aaagtaggga agctgacagt gcagccttca gtctgtggca aaaggcctga gagccctgg    23640 caaaccactg tgtaagttc aagagtccaa aagatgaaga acttggagtc tgatgtttga    23700
gggcaggaag catccagcat gggagaaaga tgaaggctca gcaagtctag tacttccaca   23760
ctcttatttc tgcctgcttt attctagctg agctggcagc tgattagatg gtgaccaccc   23820
agtttgaggg tgggtctacc tctcccagtt cactggctta aatgttaatc tcctttggca   23880
acaccctcgc agacacaccc agaaacaata atttgtagcc ttcaatccaa tcaagttgat   23940
aatattaacc atcacaggaa ggtactagta tcatatgttt aacagtagaa accaagacaa   24000
atgcagctag gaagtgggag aactgggatc agatgcaggc agtctgattc taaatcagtt   24060
gctgttaccc actctgacaa cagtaagtga gtagcctgct cagtcaagta ctatattagt   24120
agggcccttt acagacatat ttatttctca cagtcactca atgagacggc tcttccagtc   24180
ttacaatgga gaaagtgagg ctcagagact ttaagtaact taccttagac gactttacta   24240
gtaagtataa gaatcattat ttggactaaa gtctttctga atcctcagct tgtatttttt   24300
tccagtgttc tgtgctgcct ttttatctac tagtgtttta catcaatttt gaatctcttt   24360
actaactggt taggttgatt tttgcctttt tttttaggt tattctatat ttgtcgttaa    24420
gggtgatctg ccagattgcg aagctgacca actcctgcag atgattaggg tccaacagat   24480
gcatcgacca aaacttattg gagaagaatt agcacaacta aaagagcaaa ggtaaaaatg   24540
aggcctgcag tatggaatat atggtagtat ttcattatga gaattaaatt ttcatgctta   24600
gattgaatat gtggtccttg tgttgttggc gactctattt tggaccttat attttagtga   24660
agtttattag tttaaacttg aatcaactct ttgaaatact taaatatatt aacttagtta   24720
gctggtatgg tatattccta gcacttcggg aggctgaggc aggctgattg cttcaaccca   24780
ggagttcgag accagcctgg gcaacatggc aaaacctcat ctctacaaat agtacaaaaa   24840
ttagccagat gtggtggtgt atgcctatag tcccagctac ttgggaggca gaggaagaag   24900
gatcacctga aactggggag gtagagacta cagtgagcca taatcacact accgcactcc   24960
agcctggtcg agagagtcag accctgtctc aaaaaaaaaa aaaaaagaa acggaaaaaa    25020 aaaacttagt tggattcaaa ttgcaacaca atcattatat tactagagct tatttgccag   25080
aaaacatttt aagttttgac ttacttaaag cctttacatt acaaatgcct ttatgttatg   25140
tctaaaatag aagattggtt gcagttatta ccagtgcttt tgttctttag agtccataaa   25200
acagacctgg aacgagtgtt agaagcaaat gatggctcag gaatgttaga cgaagatgag   25260
gaggatttgc agagggctct ggcactaagt cgccaagaaa ttgacatgga agatgaggaa   25320
gcagatctcc gcagggctat tcagctaagt atgcaaggta aagacattct gatgtgtgtt   25380
gtattcattg ctgaagaatt gattccaatt attcttagat ttcatggaag ttaatgtact   25440
cttagaggtg ttttgacaat tactgcagaa gcaaagctca tatagtgggc tttccctta    25500 gatttcttat aatggaaatc acttttaca acctatattt tattaggagt agttatattt    25560
ttactcctgg ttatttatt tggtttcaac actgtactaa cacaatagta aattgtggtt    25620
ttaatctttg tgggtatcag ttgacccttta tccaaatcag ctgttacata aatatgtgcc   25680
```

```
attagacact atggaagggc ctggacaggg aatataaact gattttacaa aacccaaca    25740 tttattggct atgcaactta aaccgtaagc ccactttggt gggcccagtt ttttagtgat   25800
ataaactatc aatagagaaa agcgaaaaca tatcccctag acaatctagg caaagaaaaa   25860
tgttaagaca tagctcaaag tagcttaatt aaaagtttga agtgggtttt ttgttttatt   25920
tttttctaac tcatatgtat ttgcttctac tttctaatga aattatttat cagttgattt   25980
ccttagatat ctaaataaaa ttgaaatttc attaatggga agattatttt tatcctgaac   26040
ttttcttgcc tctatgcatg cctctgagta ctccatatgg tgtgcaatcc cattttgat    26100 taatagagtc ctgctggatt agcagggaca gaaatcagct ttagatttct ttcttttttt   26160
tttttctttc tttttttttt tttttttttt tgagtcagag tctcactgtc gcccagcctg   26220
gagtgcagtg atcttggctc actgcaaccc ctgcctccga ggttcaagcg attctcctgc   26280
ctcagcctcc tgagtagctg ggactacagg cgcctaccac cacgcccagc taattttttg   26340 tactttagt agagataggg ttttgcccctt ttggccaggc tggtcttgaa ctcctgacct    26400
caggtgatcc acctgccttg gcctcccaaa gtgctgggat tacatgtgtg agccaccacg   26460
cccagccaga agagtagaat attcttaaag agaaaacgtt ttaaaggctt actcaaatga   26520
gtataaacaa acatattgtt gcttgaattg gtaaatacag tgattggttt ttgttgtgtt    26580
gtgttttgtt ttcaggtagt tccagaaaca tatctcaaga tatgacacag acatcaggta   26640
caaatcttac ttcagaagag cttcggaaga acgagaagc ctactttgaa aagtaaagta    26700
gttggtacaa gttaaagtag catgtttaat atttgctttg gctattttgt ctatttgtaa   26760
atggttactg cctgaatcct gtgaatattt gaatgtattt tttaaaaatt tacagcaaat   26820
aggacgggca cggtggctta cgcctgtgat gctagcagtt tgggaggcca aggcgggcag   26880
attgcctgag gtcaggagtt cgagaccagc ctgggcaaca cagtgaaacc ccatctctac   26940
taaaaataca aagaatcag ctgggcatgg aagcgtgcgc ctgtagtccc agctgcttgg    27000
gaggctgagc caggagaatt gcttgaaccc gggacgtgga ggttgcagtg agccgagatc   27060
gcaccactgc cctccagact gggtgacaga gtgagactcc gtctccaaaa atatatgtat   27120
atatatataa ataaaaataa aaatttacgg caaataacat gaaacaaaaa aaccttgccc   27180
caatactgga taaattttt aaactgagtg aaggaaacct tataaaattt catttattaa    27240
aagaaaaatg aaattaggac aagacaagaa gaatgccaat tgatcctttg gatgtacttc   27300
ttgcttacct gattaaccct gcaaaattcc tctaccaatc agtacgaaaa acagctttgg   27360
aggtatggga gcgcattccc aaatagacgt ggtagttcat ttagctgctc atggccgctt   27420
caggcagtcc tgtaagcctg ttagcatcag gggaatggat gcaaaccata aatctggatc   27480
aactcctaaa accttacctt gtgcccagcc ttgtaagtgc ttgctaaata ggaattccac   27540
catatgaaaa tacattcttt tcaagtaact atcattcaga cttttgtccc ccactttttt   27600
tttttaaaga aaaataaaag gctgggcacg gtggcttacg tctgtaatcc caccatttta   27660
ggaggccaag gcaggtggat cacctgaggt caggaattca agaccagcct gaccaacatg   27720 gtgaaaccctc atctctacta aaaatacaaa aattagccgg gcatggtggt gggtgcctgt   27780
aatcccagct acttgggagg ctcagacagg agaatcgctt gaatctggga ggcagaagtt   27840
gcagtgagct gagataacgc cattgcactc cagcctgggg acaagagcg agacttcgtc    27900 tcaaaaaaaa agagaaagaa aacttcatgt taaagattac aagataaaata atcagaccca   27960 ctgatcctag gtcagaaaac agagtcatag ctcaatctga cttactattt gctgtattc     28020 atccattctg agatgcacat agtttcacat ttcaatgtct ctgaaattga gaagcatctt   28080
```

```
acagtcataa ttgacagtat attagcagca cctataaata ttggctcatt ttacatttga   28140
tggtataatg aagaaaatat ttacctttt ttctgttttg tttttaagtc acaactcaga    28200
agtagatgaa ggaaaattct gatcagctga catcctctta atgtgagata tttctagtct   28260
ttattcagta tagattaatg gctaattata tgttaaattt caaagtagtg cttattagtg   28320 cttttactt ttaagtttca aaattaactt ttttattata ataaactcca aatttataca    28380
aaagtagaaa aactagcata ctcctgttta tgacccagat tcaacaaata ctagcacacg   28440
gccaatcttg cttttttttt tttttttttt tgagatggag tcttgctctg ttgcccaggc   28500
tggagtgcaa tggcacaatt tctgctcact gcaacctctg cctcctgagt tcaagcgatt   28560
ctcccacttc agcctcccaa gtagctggga ttacaggtac acaccaccat gcctggctaa   28620
ttcttgtatt tttagtagac acgggatttc accatgtcgt ccaggctggc cttaaactcc   28680
tgacctcaag tgatccacct gcctcggcct cccagagtgc tgggattaca ggcatgagcc   28740
actgagcccg gcccaatctc gttttataat actcccatct cccattcttt ccactgtccc   28800
acctgcaagt ttggattatt ttgtaacaaa tctcaatcat catattattc tataaccatt   28860
ttaatatgtg tctctaaaat atattagctt tattttaac atagttaaat gctattgtca    28920
taaaataata atcataataa ttaattgtaa ttctatatca tcaattatct agttaatgta   28980
aaaaataaat ctaaggccag gcgcggtggc tcacacctgt aatcccagca ctttgggagg   29040
ctgaggtggg cagatcacct gagatcagga gttcaagacc agcctgacca acatggagaa   29100
accccatctc tactaaaaat acaaaaaatt agccaggcgt ggtggcgcat gcttgtaatc   29160
ccagctactt gagaggctga ggcaggagaa tcacttgaac ccgggaggcg aggttgcggt   29220
gagccgagat cgtgccattg cactctagcc tgggcaaaaa gagtgaaact ccatctcaaa   29280
taaataaata ataaataat aaaaaataac ttaaatctac ttaattagaa aaactaacat    29340
tctaaaaatt ttatttaag aaatatcaaa attggctggg cacggtggct cacgcctcta   29400
atccctgcac tttggaaggc tgaggtgggc ggatcacctg aggtcaggag ggtcaggagt   29460
acaagaccag cctggccaac atggcgaaac cctgtctcca ctaaaaatac aaaaattagc   29520
caggcatgat gatgggcacc tgtaatccca gctactcagg aggctgagac agaagaatcg   29580
cttgaaccca ggaggtagag gttgcagtga gctgagatca ccccactgca ctccagcctg   29640
ggtgacagag tgaaactccg cctcaaaaaa aaaaaaaga gaaagaaat atagaaatta    29700 aagcatacat ggccaggcgt agtggctcat gtctgtaatc ccagcacttt gggaggctga   29760
ggcaggcaga tcacttgagg ccatgagttc aagaccaacc tggccaacat ggcgaaagcc   29820
tgtctctact aaaaatacaa aaaattagt tgggcatggt ggtgcacacc tgtaatcaca    29880
gctactttgg aggctgaggc aggagaatcg tttgaaccca gaggtggagg ttgcagtgag   29940
ccgagattgt gccactgcac tctatcctgg gtgacagagc gagatactgt ctcaaaaga    30000 aaaaaaaag ctgggcgcg gtagttcatg cctgcaatcc cagcactttg ggaggccgag     30060
gcaggcagat tacgaagtca ggagatggag accatcctgg ctaatacagt gaaacccgt    30120 ctctactaaa aaatacacaa aaattagctg ggtgtggtgg caggcacctg tagtcccagc   30180
tactctggag gctgaggcag gagaatggca tgaacccggg aggtggagct tgcagtgagc   30240
agagatcaca ccactgcact ccagtctggg cgacagagcg aggctctgtc tcaaaaaaaa   30300 aaagaaagc atactctcac ctccttcagt gactgatgtt agtattttgg cacattcttt    30360
ttctgtgaca tatacacact taccttgtaa gtgttgtact catttcctat gacagtaaat   30420
```

-continued

```
agtctttgta acaggctgca tgatatttca taaaatgaat ggatgtggca taatttatat    30480
gtgagccttt tgaattctgc tattataatt aatattgcaa tgaacaattc ttatattgcc    30540
tctacacctc aaatgtctta tcatttcttc tagttttcct gaggatgtca gattattggg    30600
ttaaaggata tgaacatttt taaggccttg aacagattt ctaaattgct ttccagaata     30660
attcccatgt gatactttca ccatgtttat ttcagacttt tttttttttt ttttttgag     30720 acgaaatctc actctgtcac ccaggctgga gtgtagtggc atgatctcgg ctcactgcaa    30780
cctccgcctc ctgagtttaa gcgattattc tgcctcagcc tcccaagtag ctgcggttac    30840
aggcaagtgc ctccatgcct ggctaatttt tgtgtctttt gtagacatgg ggtttcacca    30900
tgttgcccag gctggtttcg aactcctgag ctcaggcaat ctgcctacct cggcctccca    30960
aagttctggg attacaggcg tgcaccaccg cgcccagcca tcagagtctt ttttgtcaaa    31020
ataaaatggt ctaaagacat acatcataga gaaactataa tacaaaattt acaggtatat    31080
ctaagaaaag aaaagtatat ttaaagcata aaaataaact gctcttttac ttaaaatttt    31140
ttaaaaactg gattaaaaat atgaaacttc caacaaattg agcttttttt tttttttttt    31200
tcttttttga gacgaggtct cgcttttgtc acccagtctg gagtgcagtg gcgcgatctc    31260
ggctcactgc aacctccacc tccctggttc aagcaattcc cctgcctcag cctcccaagt    31320
agctgggatt acaggcgcat gccaccacgt cgggctaatt ttttttgtatt tttagtagag    31380 agggggtttc accatgttgg ccagactggt ctcgaactcc tgatctcagg caatctgcca    31440
gcctgggtct cccaacatgc tgggattaca ggcatgagcc actgcactcg gcctgaactt    31500
tttatagtag taacgataat tcagtaatgt ccaataatga ctaagtaagt tataacaagt    31560
acaatgtcag caataactag tgcttttttag taaacagggt caggcaacct tgtacccttt    31620
taaaaatgtt cgaatatcga tatacctcct tcctacttgg tggaggattg attgaggagg    31680
aaagtgtgca gtgatggtta ccagcttcag cctcttggct tgactttgca aatactggtg    31740
agaatttgga aagagcttga gaatatctta catagtcaca tgttgctgag aagagttaag    31800
aactaacttc ttgatgttca ttttaacaa tggcttgcat tcaaaacctt gtagagctca    31860
ttagtaggag ctaagaagct aatatttgcc tttcactaaa attcctgatt acttagccta    31920
ggtagttcgt tgtctctcta ggttctgtct ttgggagctt gggtctaagg ttatcaagct    31980
aactctttct tccctctcac ccttcccaaa ttgaccctgg tgctgatttg ttattcatac    32040
gattttctag ttttttcttt cccttttgga gtatttgaag cttcatactg aatatagtaa    32100
tcatagtatt catgcataaa gaaaatcata aagtaattgc ataaatgcat aaagtaatca    32160
tagttttcat gcattaaaaa aactagtttt ggctgggcgc tatggctcac gcttgtaatc    32220
ccagcacttt cggaggccaa ggcaggcgaa tcatctgagg tcaggagttc gagactagcc    32280
tggccaacat ggcgaaacct cttctctact aaaaatacaa aaaaattagc cgagtatggt    32340
ggcgggcgcc tgtaatccta gctatttggc aggctgaggc aggagaatca cttgaacctg    32400
ggaggcagag gttgcagtga gccgaggttg tgccattgca ctacagccta ggcgacaaga    32460
gcaagactcc atctcaaaaa aaaaaaaaa aaaaaaaaa ctccctatta cagattcata    32520
atttatgagt cattaaataa tattttcaag ccatgacatt ttttccagca gtagtctcta    32580
aatctgtttt accatcataa aaccccaagc aaaactctac tacatcagct gtgtcactgt    32640
aaaacctgcc ttaactcaca gaagcatgaa attaagcaat gtgtgtgaaa ctattttata    32700
aactgtaaag tattccatac atacatgttg gcagttatta atgtcttctc taggtgtggc    32760
tttgaaatgg atgcagatgc tttctgttac aaaaaacata agttgcaaat gttctataac    32820
```

```
aaggagagac acaaatatct tcatggacat ggattgctat gagtgtttga ttgcctaata    32880
cttgagccac cacttcagtg atatggtata atttatcaaa cagtgttgag aaacagaaac    32940
tactggggat gttttaaaga ggaaaatact taatatagaa attaggggtt tacataatct    33000
taagaaagga tgaaggtgca gctcttagcc aggcctccac agtaccacaa accaacttgc    33060
aggaagagct gtaaccactg ccccagttgg gacaatgggt aatgaggata ttaaatttaa    33120
gaacatactg ctatagcaat gatccttggc atagaaagct gccaccacaa ttgcctagag    33180
atgggaacat gaagtctggc ccccattgca acagcagtga agcagaattt tgggactggc    33240
atctcccaaa tggctttgct tgccaccaga gaacaaccaa agtggaggga gatggctagg    33300
cctcatttct gcctatttta ttttattttt tgagacggag tcttgtctgt cgcccaggct    33360
ggagtgcagt agtgtgatct cggctcactg cagcctccgc ctcccagctt caaacaattc    33420
tcctgcctca gcctcctgag tagctgggat tacaggcacc cgccactgtg cccagccaat    33480
tttcttattt ttagtagagg tggggttttg ccacgttggc caggctggtc ttgaactcct    33540
gacctcaggt gatctgcccg cctcagcctc ccaaagtgtt gtgattacag gtatgagcca    33600
ccatgcctgg cccattttctc cctttttttt tttttttttt ttttgaggtg gagtctcact    33660
ctgttgccca gactggagtg cagtggtgca atcttggcgc attgcaacct ctgcctccca    33720
gtttcaagca attcttctgc ttcagcctcc tgagtagctg ggactacagg tgtgtagcac    33780
cacacctggc taattttttgt ttttgttttg tttttttttga dacagagtct cactctgtca    33840
cccaggctgg agtgtagtgg catgatctgg gctcactaca acctccgcct cccgggttca    33900
agcaattctc ctgcctcagc tccagagta gctgggatta caggtgtgcg ccaacacacc    33960
tggctaattt ttttgtattt ttaatagaga tggggtttca ccatgttggc caggctggtc    34020
tcgaactcct gacctcgtga tccgcccgcc tcggcctccc aaagtgctgg gattacaggc    34080
atgagccacc gtgcccagac aaggtttgta tttttagtag agacagtttt gccatgttgg    34140
ccaggctggt cttgaactcc tcacctcagg tgatccgcct gccttggcct cccaaagtgc    34200
tgggattaca ggcgcaagcc actgtgcctg acccgtttct gcttttttaaa gctcatgtga    34260
gcacttaatt tgtaaccaga atcctacttg taaaataatc taagacatgt agcttttagc    34320
tttgtaaccct ctataatatt gatggcacag tgggagtgga tgctgagtac cacttgaaca    34380
tgttccacct cagtgtcttc acagctggaa ggtgtctaca ttgtttcaag gtggacaatt    34440
gatttacttc tcatttttca taaactaaaa gtagaataaa ggctattcct ctaaaattgc    34500
tatctcacct gtcactccct tgcattctca catacctttct tgagtggagg ggcagagggc    34560
atggagtgat agcagatgtg ccaggaattc tccataactc agtccgtccc tcttgtgcta    34620
tgttgcagca tcaggatttg ctaatgggag gatactgccc ttacgtgcat cattagccat    34680
gcacactaag gtcttacacc tacacacagg tcagtattct ggctcagaga ccaacaggga    34740
gaaattgcag ttctcattag ttgaactttc ttattgttc acagttttaa aacacaaaat    34800
tgagaggaac tctataaaaa atgtgccatt ctattaataa ttgttgctgg taatttaaaa    34860
atccttgttc cttttcaaat tcttatatac ctttttttttt taaacacttg atcttagcca    34920
aaagaccgag aagcaatctt tttttttttt tttttttttt ttaacctata gcttctcact    34980
gagattgtca gctgtttgta agttttggtt tttggttttc tgtgtttgta tttacatata    35040
tgaaatacag attgagtatc ccttatccaa aatgcttaag actggaagtg ttttagtttt    35100
ggggttttttt aggatttgtg aatatttgca ctatacttac cagttaagca ttccaaatcc    35160
```

```
aaaatttcaa atctgaagtg ttccactgag cacctctttt gagtatcatg ttggtgctca    35220
aaaagtttct gattttggag catttggatt tctgattctc ggatttagga tgcttgacct    35280
gtaatttcag atttacataa aagcagaaat agtacacaga gctccttata tccttcaccc    35340
agattcccca attattggcc tttctgaacc atttgggaat aatatgcaga tatgattttc    35400
cattatgtct cagttgttca gtgtatattt tctaagtaca agaatatatt cctacatatt    35460
tacatgataa ccgtcatgtt taaacatttt aaaatgggga tttgtattac attgtttctc    35520 ttttttgaaaa aattacagag gagcttaatg caatcagtat tacttaaaat ctgataatgt    35580
gtgttaaata gtagttttca tttatttcat ttatcaggtg ttcagtgaat gcttactatg    35640
taacagcaca gttatcagca ctggggaaat agatgagtaa gataagattt gcactttcat    35700
tagcttacat gccataaaga gggaaataaa gagaacacca gatgatgata agtttatgct    35760
gagaattaaa atgaagtgat gaaataatgg gaatgtcagg tggctacttt tggtgggatg    35820
gtcaggaaag gcatctctgg ggagataaat tttaagctca gacctgagtg aaaagaatga    35880
gccagccatg gaaacattat gttaactcac atggtagttt gaaatgcttt atctgatcaa    35940
aggtacttat ttttggtgac tttcaacaat attaagggtc tataaaccaa cactcatttg    36000
cataagaata actaccagtg aatcttttg tatgataggt tttttgtttg ttgtttttttt    36060 gagacagagt ctcgctctgt cgcccaggct ggagtgcagt ggcgcgatct tggctcactg    36120
caacctctac ctcccggtt caagtgattc tcctgcctca gcctcccaaa gtagctggga    36180
ttacaggtgc ctgccaccac gcctggctaa ttttttgtatt tttagtagag atggggtttc    36240
accgtgttgt ccaggctcgt gtcaaacttc tgacctcaag ccatccaccc gcctcggcct    36300
cccaaagtgc tgggattaca ggtgtgagcc accactcctg gccatgatag gttattttgt    36360
gatgaaaata cctacctctt aatttgtctg ataaatttaa attttatgtc tagatttcct    36420
aagatcagca cttccatatt ttaaagtaat ctgtatcaga ctaactgctc ttgcattctt    36480
ttaataccag tgactacttt gattcgtgaa acaatgtatt ttccttatga atagtttttc    36540
tcatggtgta tttattcttt taagttttgt ttttttaaata tacttcactt ttgaatgttt    36600
cagacagcag caaaagcagc aacagcagca gcagcagcag cagcagggg acctatcagg    36660 acagagttca catccatgtg aaaggccagc caccagttca ggagcacttg ggagtgatct    36720
aggtaaggcc tgctcaccat tcatcatgtt cgctaccttc acactttatc tgacatacga    36780
gctccatgtg attttgctt tacattattc ttcattccct ctttaatcat attaagaatc    36840
ttaagtaaat ttgtaatcta ctaaatttcc ctggattaag gagcagttac caaaagaaaa    36900
aaaaaaaaaa aagctagatg tggtggctca catctgtaat cccagcactt tgggaaacca    36960
aggcaggaga ggattgctag aacatttaat gaatacttta acataataat ttaaacttca    37020
cagtaatttg tacagtctcc aaaaattcct tagacatcat ggatatttt cttttttga    37080 gatggagtct tgctctgtca cccaggctgg agtgcagtgt cgcgatctcg gctcactgca    37140
agctctgctt cctgggttca tggcattctc ctgcctcagc ctcctgagta gctgggacta    37200
caggcgcccg ccacatcgcc tggctaattt tttgtatttt tagtagagac agggtttcac    37260
catgttagcc aggatggtct caatctcctg acctcatgat ccgcccgcct cggcctccca    37320
aagtgctggg attacaggcg tgagccatca cgtccggcca gaaatcatga atattagtag    37380
gtgaaaaata aacacatttt accacctgga aaatgaaaaa tacttgagta taatctaaat    37440
aacaatggga agtgcagagt tactttccag gtctcggttt aaatatgtct taaactttgg    37500
ccaattagta gtagaagttg agagaaaaag taactatctg acaaagaaat tataagcaga    37560
```

```
atatataaag aactcttaaa actgaataat cagaaaacaa ctcaataaaa aggtgaagga   37620
tttgaaaaga tatttcacca aataagacat agggatgaca aataagcaca tgaaaagact   37680
ctcagcatca ctagtcacag ggaaatgcac gataaaacca cagtgagaca ccatggcacc   37740
cctgtaggta tggctttaat gaagaaataa aactgacaat accaagtgtt ggcaaggatc   37800
caagcagctg agactcatat actgttaatg ggaatgtaaa agtgtacagc tttggaaaac   37860
agtttggcat ttttttgata aatgtatact tagccatgtg atccagcagt cccaatcatg   37920
tatatataac caaaagaaaa gaaaacttag gttcacataa aaacttatat caaatgctta   37980
tagctgacca ggcatggtgg cccatgccta taatcccagc actttgggag gccgaggttg   38040
gcagatacct gaagtcaagt gttcgagacc agcctggcca acatggcaaa accctgtctc   38100
tacttaaaat acaaaaatta gccaggcgtg atggcaggca cctgtagtcc agctattcag   38160
gaggctgagg caggagaatc acgtgaaccc gggaggcaga ggttgcagtg agccgagatc   38220
gtgccactat actccagcct gggtgacaga gcaaaactct gtctcaaaaa aaaaaaaaaa   38280
aaaaagggct ggacacggtg gcttacgcct gttatcccgg cactttggga ggccaaggct   38340
gatggatcac ctgaggtcag gagttcaaga ccagcctggc caacatggtg aaacccccatc  38400 tctactaaaa atacaaaaat ttgctgggca tggtggtggg cacctgtaat cccaggaggc   38460
tgaggcagga gaatcacttg aacccgggag gcggagattg cagtgagcca agattgtgcc   38520
attgaactcc agcctgggtg acaagaccaa aactccttct caaaaaaaaa aaagattata   38580
gcatctttat tcatcattgc ccaaaattac aaactgccta aatgtagacc ttcatttagt   38640
taatgaatgc acaaactgtg gtatatccaa acaattgaat aaaaaaagga atgaactggt   38700
acttttttct attcctcctg tttaagtaca gccaaaacac ctcaacattt gtataaaaca   38760
tgagctgggc tgggtgcggt ggctcacacg tgtaatccca gcactttggg aggctgaggc   38820
gggtggatca cctaaggttg ggagttcaag accggtctga ccaacatgga gaaaccctgt   38880
ctcaactaaa aatacaagat tagtcgggca tggtggcgca tgcctgtaat cccagcttct   38940
tgggaggctg aggcaggaga attgcttgat cccgggaagc gaaggttgca gtaagctgag   39000
attgcaccat tgcactccag cctgggcaac aagagcaaaa ctctgtctca aaagaaaaa   39060 aaaaaccatt cagctgaatc tcaaaggcag agagaagaca gactggctag ggaccttgga   39120
accagaggag cagtgtggtg gggagtggac tggattttct ttttgcctca tttatcctgg   39180
acttggtgct ggagaagcta tgggttcaga ccaagagaaa accccatgaa aagcctgctc   39240
tctctagcca aaagaggcaa cctagcaaga taaaaacctt tagataataa gcacttgact   39300
ccagtcaaac aaaacagaat aaactggccc cattcacccc tgtcagcaaa ggccaagtgg   39360
gagccaagat atgtacccca acctggaagt cataaggtac acttctcccc tttcccagcc   39420
aaggtggtgt tagagaaggc tgactgggga gctgggattc tcattccctc caggaggtga   39480
taacactcct ttcacatggt gtcagtggtc acagggaggc tgaacttcca cccagtaata   39540
cataggcatc tctctggctc ctatatgggt gatgttggag aagaggccga gtagagaatc   39600
cagactgttg ctgacaccca gcagtaacaa ggacacctcc acaatgtccg tggaggccat   39660
gtggagatca gtaacaaggc actgctctcc ctcccagtca gagagatgtc agtggaggac   39720
tagggggcta gaactcccat gtgcgttcag cagtaatccc catgaccgcc actccttgac   39780
atcacaggcc ttgaagaaac ctggactttc actcccctct ggttgtagcg aggtggcact   39840
ccctttcccc tgttgccagt gctgtgtcag tggaggcttg ctaaattgga agatgtaaat   39900
```

```
aagattcaca ttctcataac ataatacccc aaattttcag gatttaattg aaaatcacta    39960
agctgggcat ggtggctcac acctgtaatc ccagcacttt gggaggccaa ggtgggccaa    40020
acacttaagg tcaggaattc aagaccagcc tggccagcat ggtgaaaccc tgtctctact    40080
aaaaatacaa aaattagctg gcgtggtgg cacatgcctg taatcccagc tactgggaag    40140
gctaaggcag gaaaatcact ggaacctggg agacggaggt tgcagtgatc caagatcgca    40200
ctagtgtact gcagcctggg caacagagca agactccatc taaatttgtg tcaggattcc    40260
cagaaggaga tgagaaaggg tggggctgaa aaaaattgag gaagaagtca tggctgaaaa    40320
tttcccaaat ttggcaaaag tcagaaacct acagattgaa aaagctgaat gaagctcaaa    40380
tatgataaac tcaaagaagt tcacacagag acacatcaca gtcagatttc tgaacactgc    40440
agacaaaaaa tgaagatctc gaaattagca agaaatgacc ttacctaagc aatttgaatg    40500
acagcagatt tcccatcaga gatcataaag gccagaagga aggggtacat acaacatttt    40560
ttctagtgct gaaagacaaa aactctaggc tgggcacggt ggcacacacc tgtaatccca    40620
gcacttttgg aggctgaggc aggcagatca cctgaagtca ggagttcgag accagcctgg    40680
ccaacatggg gaaaccctgt ctctactaaa aatacaaaaa ttagccaggt gtggtggcac    40740
gcacctataa tcctagctac ttgggaggct gaggcagggg aatcgcttga acctgggagg    40800
cgacggttgc agtgagccaa ggtcgcgcca ctgcactcca gcctgggcag ttgagcgaga    40860
ctccatctca aaaaaaaaa aattatccag gcttggtggt gggcgcctat agtcccagct    40920
acttgggagg ctgaggcaag agaattggtt gaacccagga ggtggaggtt gcagtgagcc    40980
aagctcatgc cactgtactc cagcctgggt gacagagcga gaccttgtct caaaaaaaaa    41040
aaaaaaaaaa aaaaacaaga aaaaaactct aaacccagag ttacatatcc agtgaaatat    41100
ccttcaggag tgaagggaaa attaacgatt tgtcttcagg agacctaccc taaaagaatg    41160
gctaaaggaa tttctctaaa cagaaagaa atgataaaag aagtaatttt ggaacatcag    41220
gaaggaagaa agaacaataa aaagagtaaa atatgggtaa acacaataga ctttccctc    41280 cttttgaatt ttctaaattg tatgatggtt gaagcaagaa ttatagcact gatttggttt    41340
tcagtatata tattgaaat atttaaggca ttatgttaca gatgaaggag ggtcaaagga    41400
tataaaggga ggtaaccttt ctatatttct tttgtactga tgcaggcact ttggaaaata    41460
atttcactat ttgtttaaaa actgaacata ccctgaccat atgacatagc atctatactc    41520
ctgggcattt atcccagaga aacagaaatt tatttatttt ttttttagta ttacactccg    41580
taagtgctgt aatactagca cttagggagg ctgaggcaag cagattgctt gagcccagga    41640
gttcaagacc agcctgggca atgctgcaca gtcaaaaaag aaaaacaaac atttagaaaa    41700
ctattttaaa agtctttaat tgctgaatgc ctctttggct aatatttgga agatcattat    41760
tattattttt cttttttagg cagagtcttg ctctgtcact gaggctggag tgcagtggcg    41820
ccatctcggc ttactgcaac ctctgcctcc cgggttcacg ccattctcct gcctcagcct    41880
cccgagtagc tgggactaca ggcgtgtgcc accatgcccg gctaattttt tgtgttttta    41940
gtagagatgg ggtttcacta tgttagtcag gatggtctcc atctcctaac ctcgtgatcc    42000
gcccacctcg gcttcccaaa atgctgggat tacaggcgtg agccactgtg cccagcctgg    42060
aagatcatta tttagtccta caactgacac attgttccac tgacgcaatt gcccaggctg    42120
gtcttgaact cctgggctca agcaatctgc ctgcctcggc ctccctaagt gctagtatta    42180
caggcttgag ccactgtgcc cagccaaaaa tagaaattta tattctcaca aaacatgta    42240 catgaatgtt tatagcagct ttacttgtca taatcaaaaa ctggaaacaa ccaaaatgtc    42300
```

```
ctacagtgaa acaaactgta gtacatccat agcatgtaat actctactgt caggattaaa    42360
aagaaaccca ctgttggcac aggcagcacc gtggctggat ctcagggca ttatgctgag    42420 tgcaaaaaag cctcaaaggg tcttacactg tatgattcca cttgttcaac taaaaatgac    42480
agctgtatag agatagagaa catattagtg gtttccacta gttagagaaa gtgggtaaaa    42540
gataggtggg tgggaatata aatcgatagc agggagatct tgtggtatt ataacacttc    42600 tatgtcttga ttgtagtggt ggtggttaca tgaatacacg tgtgataaaa tgccatgtag    42660
aactacatat aacgttgtgc caatgtcaat atctaggttt tagtttgatc tttagttaca    42720
taagatgtaa ctattgggtg aaattgggca aaagagtaca cgaaacctct cttaaatatc    42780
tttacaactt cctttgaatt gacagttttt caaaatagaa agttgggttt ttgtaaatac    42840
atgaattgtt gatatacaca acaaatctca aatgcattat gctacgtgaa agaagccata    42900
ttcaaaaggc tacataccta ctgatgcctt ttatatgacg tgcaggaaaa gataaaactg    42960
taggacagag aatatactgg tggctatctg ggattaggaa atggggatcg accacaaagg    43020
ggcagcatgg gggaattttc tggggcaatg gaatggttgt gtatcttgat ggtgtatttg    43080
tcaaaatata tagaactata aaagtaaatt ttgctttata tgtattaaat caaaaaaga    43140 aactcgtgct caaatagaaa tacatttct gagaacttgc ttttgatga ctttgagaat    43200 tttctggaaa tttaaagaa atgtggtttt gtttcccaac aggtgatgct atgagtgaag    43260
aagacatgct tcaggcagct gtgaccatgt ctttagaaac tgtcagaaat gatttgaaaa    43320
cagaaggaaa aaaataatac ctttaaaaaa taatttagat attcatactt tccaacatta    43380
tcctgtgtga ttacagcata gggtccactt tggtaatgtg tcaaagagat gaggaaataa    43440
gacttttagc ggtttgcaaa caaaatgatg ggaaagtgga acaatgcgtc ggttgtagga    43500
ctaaataatg atcttccaaa tattagccaa agaggcattc agcaattaaa gacatttaaa    43560
atagttttct aaatgtttct tttctttt tgagtgtgca atatgtaaca tgtctaaagt    43620
tagggcattt ttcttggatc tttttgcaga ctagctaatt agctctcgcc tcaggctttt    43680
tccatatagt ttgttttctt tttctgtctt gtaggtaagt tggctcacat catgtaatag    43740
tggctttcat ttcttattaa ccaaattaac ctttcaggaa agtatctcta ctttcctgat    43800
gttgataata gtaatggttc tagaaggat aacagttctc ccttcaactg tataccgtgt    43860
gctccagtgt tttcttgtgt tgttttctct gatcacaact tttctgctac ctggttttca    43920 ttatttccc acaattcttt tgaaagatgg taatctttc tgaggtttag cgttttaagc    43980
cctacgatgg gatcattatt tcatgactgg tgcgttccta aactctgaaa tcagccttgc    44040
acaagtactt gagaataaat gagcattttt taaaatgtgt gagcatgtgc tttcccagat    44100
gctttatgaa tgtctttca cttatatcaa aaccttacag ctttgttgca acccttcct    44160 cctgcgcctt atttttttcct ttcttctcca attgagaaaa ctaggagaag catagtatgc    44220
aggcaagtct ccttctgtta gaagactaaa catacgtacc caccatgaat gtatgataca    44280
tgaaatttgg ccttcaattt taatagcagt tttatttat tttttctcct atgactggag    44340
ctttgtgttc tctttacagt tgagtcatgg aatgtaggtg tctgcttcac atctttttagt    44400 aggtatagct tgtcaaagat ggtgatctgg aacatgaaaa taatttacta atgaaaatat    44460
gtttaaattt atactgtgat ttgacacttg catcatgttt agatagctta agaacaatgg    44520
aagtcacagt acttagtgga tctataaata agaaagtcca tagttttgat aaatattctc    44580
tttaattgag atgtacagag agtttcttgc tgggtcaata ggatagtatc attttggtga    44640
```

```
aaaccatgtc tctgaaattg atgttttagt ttcagtgttc cctatccctc attctccatc    44700
tccttttgaa gctcttttga atgttgaatt gttcataagc taaaatccaa gaaatttcag    44760
ctgacaactt cgaaaattat aatatggtat attgccctcc tggtgtgtgg ctgcacacat    44820
tttatcaggg aaagttttt gatctaggat ttattgctaa ctaactgaaa agagaagaaa     44880
aaatatcttt tatttatgat tataaaatag cttttcttc gatataacag atttttttaag    44940 tcattatttt gtgccaatca gttttctgaa gtttcccta cacaaaagga tagctttatt    45000
ttaaaatcta aagtttcttt taatagttaa aaatgtttca gaagaattat aaaactttaa    45060
aactgcaagg gatgttggag tttagtacta ctccctcaag atttaaaaag ctaaatattt    45120
taagactgaa catttatgtt aattattacc agtgtgtttg tcatattttc catggatatt    45180
tgttcattac ctttttccat tgaaaagtta cattaaactt ttcatacact tgaattgatg    45240
agctacctaa tataaaaatg agaaaaccaa tatgcatttt aaagttttaa ctttagagtt    45300
tataaagttc atatataccc tagttaaagc acttaagaaa atatggcatg tttgactttt    45360
agttcctaga gagttttttgt ttttgttttt gttttttttt gagacggagt cttgctatgt    45420
ctcccaggct ggagggcagt ggcatgatct cggctcacta caacttccac ctcccgggtt    45480
caagcaattc tcctgcctca gcctccagag tagctgggat tacaggcgcc caccaccaca    45540
cccggcagat ttttgtattt ttggtagaga cgcggtttca tcatgtttgg ccaggctggt    45600
ctcgaactcc tgacctcagg tgatccgcct gccttggcct cccaaagtgt tgggattaca    45660
ggcatgagcc actgcgcctg ccagctaga gagttttta agcagagctg agcacacact      45720
ggatgcgttt gaatgtgttt gtgtagtttg ttgtgaaatt gttacattta gcaggcagat    45780
ccagaagcac tagtgaactg tcatcttggt ggggttggct taaatttaat tgactgttta    45840
gattccattt cttaattgat tggccagtat gaaaagatgc cagtgcaagt aaccatagta    45900
tcaaaaaagt taaaaattat tcaaagctat agtttataca tcaggtactg ccatttactg    45960
taaaccacct gcaagaaagt caggaacaac taaattcaca agaactgtcc tgctaagaag    46020
tgtattaaag atttccattt tgttttacta attgggaaca tcttaatgtt taatatttaa    46080
actattggta tcattttct aatgtataat ttgtattact gggatcaagt atgtacagtg     46140
gtgatgctag tagaagttta agccttggaa ataccacttt catattttca gatgtcatgg    46200
atttaatgag taatttatgt ttttaaaatt cagaatagtt aatctctgat ctaaaaccat    46260
caatctatgt tttttacggt aatcatgtaa atatttcagt aatataaact gtttgaaaag    46320
gctgctgcag gtaaactcta tactaggatc ttggccaaat aatttacaat tcacagaata    46380
ttttatttaa ggtggtgctt tttttttttg tccttaaaac ttgattttc ttaactttat     46440 tcatgatgcc aaagtaaatg aggaaaaaaa ctcaaaacca gttgagtatc attgcagaca    46500
aaactaccag tagtccatat tgtttaatat taagttgaat aaaataaatt ttatttcagt    46560
cagagcctaa atcacatttt gattgtctga attttgata ctattttaa aatcatgcta      46620 gtggcggctg ggcgtggtag ctcacgcctg taatcccagc attttgggag ccgaagtgg     46680 gtggatcacg aggtcgggag ttcgagacca gcttggccaa aatggtgaaa ccccatctgt    46740
actaaaaact acaaaaatta gctgggcgcg gtggcaggtg cctgtaatcc cagctacctg    46800
ggagtctgag gcaggagaat tgcttgaacc ctggcgacag aggatgcagt gagccaagat    46860
ggtgccactg tactccagac tgggcgacag agtgagactc tgtctcaaaa aaaaaaaaa    46920 aatcatgcta gtgccaagag ctactaaatt cttaaaccg gcccattgga cctgtacaga     46980
taaaaaatag attcagtgca taatcaaaat atgataattt taaaatctta agtagaaaaa    47040
```

```
taaatcttga tgttttaaat tcttacgagg attcaatagt taatattgat gatctcccgg      47100
ctgggtgcag tggctcacgc ctgtaatccc agcagttctg gaggctgagg tgggcgaatc      47160
acttcaggcc aggagttcaa gaccagtctg gcaacatgg tgaaacctcg tttctactaa       47220
aaatacaaaa attagccggg cgtggttgca cacacttgta atcccagcta ctcaggaggc      47280
taagaatcgc atgagcctag gaggcagagg ttgcagagtg ccaagggctc accactgcat      47340
tccagcctgc ccaacagagt gagacactgt ttctgaaaaa aaaaaatata tatatatata      47400
tatatatgtg tgtatatata tatgtatata tatgactt cctattaaaa actttatccc        47460 agtcggggc agtggctcac gcctgtaatc ccaacacttt gggaggctga ggcaggtgga       47520
tcacctgaag tccggagttt gagaccagcc tggccaacat ggtgaaaccc catctctact      47580
aaaaatacaa aacttaagcc aggtatggtg gcgggcacct gtaatcccag ttacttggga     47640
ggctgaggca ggagaatcgt ttaaacccag gaggtggagg ttgcagtgag ctgagatcgt      47700
gccattgcac tctagcctgg gcaacaagag taaaactcca tcttaaaggt ttgtttgttt      47760 tttttaatc cggaaacgaa gaggcgttgg gccgctattt tcttttctt tctttctttc        47820 tttctttttt tttttttctg agacggagtc tagctctgct gcccaggctg gagtacaatg      47880
acacgatgtt ggctcactgc aacctccacc tcctgggttc aagcgattct cctgcctcag      47940
cctcccaagt acctgggatt acaggcacct gccactacac ctggcgaata tttgtttttt     48000
ttagtagaga cgggcttta ccatgttagg ctggtctcaa actcctgacc tcaggtgatc       48060
tgcctgcctt ggcctcccaa agtgctggga ttacaggtgc aggccaccac acccggcctt     48120
gggccactgt tttcaaagtg aattgtttgt tgtatcgagt ccttaagtat ggatatatat      48180
gtgaccctaa ttaagaacta ccagattgga tcaactaatc atgtcagcaa tgtaaataac     48240 tttattttc atattcaaaa taaaaactt cttttatttc tggccccttt ataaccagca         48300 tcttttgct ttaaaaatg acctggcttt gtattttttt agtcttaaac ataataaaaa        48360 tattttgtt ctaatttgct ttcatgagtg aagattattg acatcgttgg taaattctag       48420
aattttgatt ttgttttta atttgaagaa atctttgct attattattt tttccaagtg        48480
gtctggcatt ttaagaatta gtgctaataa cgtaacttct aaatttgtcg taattggcat     48540
gtttaatagc atatcaaaaa acatttttaag cctgtggatt catagacaaa gcaatgagaa    48600
acattagtaa aatataaatg gatattcctg atgcatttag gaagctctca attgtctctt      48660
gcatagttca aggaatgttt tctgaatttt tttaatgctt ttttttttt tgaaagagga       48720 aaacatacat ttttaaatgt gattatctaa ttttacaac actgggctat taggaataac       48780 ttttaaaaa ttactgttct gtataaatat ttgaaattca agtacagaaa atatctgaaa       48840
caaaaagcat tgttgtttgg ccatgataca agtgcactgt ggcagtgccg cttgctcagg     48900
acccagccct gcagcccttc tgtgtgtgct ccctcgttaa gttcatttgc tgttattaca     48960
cacacaggcc ttcctgtctg gtcgttagaa aagcccgggct tccaaagcac tgttgaacac    49020
aggattctgt tgttagtgtg gatgttcaat gagttgtatt ttaaatatca aagattatta     49080
aataaagata atgtttgctt ttctatttcc ttttgaattt gtgtttattg ttaattcata     49140
gctattcaaa gtgtgattag agctgggctt ggtggcttgc atctacagtt ccagctaccc     49200
aggaggcaga agcaggagga ttgcttgagc ctaggagttc gaggctgcag tgagctatga     49260
tcctgccact gaattctagc ctgggcgaca aacaggaaaa aaagtatgga tggaggacca    49320
gcagcatctg tatcacctgt gagtctttca gaaatgcaga gtttcaggct acactcggac     49380
```

```
ctactgaatc agaacttgca cttttttacaa gatccccagg acactaaagt atagagtgaa     49440
gcttgagaag cgctgttgtg tggattgttc ttaaccagct gcagtgatga atatgaataa     49500
cgcaggccag cacagtccat tgatattcta ttccagctta ctgcctgcca aaaggtccat     49560
tattactgga tcctcagtct tttccaagag aagctaagaa ttccaaattt ttatttgaaa     49620
tatattttt aaatgtttgt tcaactggcc cagtgccagt ggctcatgcc tttaatccta     49680
gcactttgag aggccgaggt ggaaggatca cttgacccca ggagtttgag accagcctgg     49740
gcaacataaa gagacccat ctctattaaa aaaaatag acaatgctg ccttaaaaaa       49800
gtcaaataaa tgtttgctca actgattttt aatactgagg gccaaacaaa gcacatcaaa     49860
tttttaagtg ctgcttttcc tcattttatc caactctgga caccagaatc caaatgtagt     49920
gattggaatc cacctagact gattgaggaa tatattgtcc tcaaatttta tgagggttga     49980
ctattcattt taactttaat t                                               50001

<210> SEQ ID NO 3
<211> LENGTH: 6438
<212> TYPE: DNA
<213> ORGANISM: Homo sapiens

<400> SEQUENCE: 3
gagaggggca gggggcggag ctggaggggg tggttcggcg tgggggccgt tggctccaga       60
caaataaaca tggagtccat cttccacgag aaacaagaag gctcactttg tgctcaacat      120
tgcctgaata acttattgca aggagaatat tttagccctg tggaattatc ctcaattgca      180
catcagctgg atgaggagga gaggatgaga atggcagaag gaggagttac tagtgaagat      240
tatcgcacgt ttttacagca gccttctgga aatatggatg acagtggttt tttctctatt      300
caggttataa gcaatgcctt gaaagtttgg ggtttagaac taatcctgtt caacagtcca      360
gagtatcaga ggctcaggat cgatcctata aatgaaagat catttatatg caattataag      420
gaacactggt ttacagttag aaaattagga aaacagacag cagcaaaagc agcaacagca      480
gcagcagcag cagcagcagg gggacctatc aggacagagt tcacatccat gtgaaaggcc      540
agccaccagt tcaggagcac ttgggagtga tctaggtgat gctatgagtg aagaagacat      600
gcttcaggca gctgtgacca tgtctttaga aactgtcaga aatgatttga aacagaagg      660
aaaaaaataa tacctttaaa aataatttta gatattcata cttttccaaca ttatcctgtg      720
tgattacagc atagggtcca ctttggtaat gtgtcaaaga gatgaggaaa taagactttt      780
agcggtttgc aaacaaaatg atgggaaagt ggaacaatgc gtcggttgta ggactaaata      840
atgatcttcc aaatattagc caaagaggca ttcagcaatt aaagacattt aaaatagttt      900
tctaaatgtt tctttttctt ttttgagtgt gcaatatgta acatgtctaa agttagggca      960
tttttcttgg atcttttgc agactagcta attagctctc gcctcaggct ttttccatat     1020
agtttgttt cttttctgt cttgtaggta agttggctca catcatgtaa tagtggcttt     1080
catttcttat taaccaaatt aaccttttcag gaaagtatct ctactttcct gatgttgata     1140
atagtaatgg ttctagaagg atgaacagtt ctcccttcaa ctgtataccg tgtgctccag     1200
tgtttttcttg tgttgttttc tctgatcaca acttttctgc tacctggttt tcattatttt     1260
cccacaattc ttttgaaaga tggtaatctt ttctgaggtt tagcgtttta agccctacga     1320
tgggatcatt atttcatgac tggtgcgttc ctaaactctg aaatcagcct tgcacaagta     1380
cttgagaata aatgagcatt ttttaaaatg tgtgagcatg tgctttccca gatgcttat     1440
gaatgtcttt tcacttatat caaaacctta cagctttgtt gcaaccccctt cttcctgcgc     1500
```

```
cttattttttt cctttcttct ccaattgaga aaactaggag aagcatagta tgcaggcaag    1560
tctccttctg ttagaagact aaacatacgt acccaccatg aatgtatgat acatgaaatt    1620
tggccttcaa ttttaatagc agttttattt tatttttcct cctatgactg gagctttgtg    1680
ttctctttac agttgagtca tggaatgtag gtgtctgctt cacatctttt agtaggtata    1740
gcttgtcaaa gatggtgatc tggaacatga aaataattta ctaatgaaaa tatgtttaaa    1800
tttatactgt gatttgacac ttgcatcatg tttagatagc ttaagaacaa tggaagtcac    1860
agtacttagt ggatctataa ataagaaagt ccatagtttt gataaatatt ctctttaatt    1920
gagatgtaca gagagtttct tgctgggtca ataggatagt atcattttgg tgaaaaccat    1980
gtctctgaaa ttgatgtttt agtttcagtg ttccctatcc ctcattctcc atctccttt    2040 gaagctcttt tgaatgttga attgttcata agctaaaatc caagaaattt cagctgacaa    2100
cttcgaaaat tataatatgg tatattgccc tcctggtgtg tggctgcaca cattttatca    2160
gggaaagttt tttgatctag gatttattgc taactaactg aaaagagaag aaaaaatatc    2220
ttttatttat gattataaaa tagctttttc ttcgatataa cagattttttt aagtcattat    2280 tttgtgccaa tcagtttcct gaagtttccc ttacacaaaa ggatagcttt atttaaaat    2340 ctaaagtttc ttttaatagt taaaaatgtt tcagaagaat tataaaactt taaaactgca    2400
agggatgttg gagtttagta ctactccctc aagatttaaa aagctaaata ttttaagact    2460
gaacatttat gttaattatt accagtgtgt ttgtcatatt ttccatggat atttgttcat    2520 taccttttc cattgaaaag ttacattaaa cttttcatac acttgaattg atgagctacc    2580
taatataaaa atgagaaaac caatatgcat tttaaagttt taactttaga gtttataaag    2640
ttcatatata ccctagttaa agcacttaag aaaaatatggc atgttgact tttagttcct    2700 agagagtttt tgtttttgtt tttgttttt tttgagacgg agtcttgcta tgtctcccag    2760
gctggagggc agtggcatga tctcggctca ctacaacttc cacctcccgg gttcaagcaa    2820
ttctcctgcc tcagcctcca gagtagctgg gattacaggc gcccaccacc acacccggca    2880 gattttgta ttttggtag agacgcggtt tcatcatgtt tggccaggct ggtctcgaac    2940
tcctgacctc aggtgatccg cctgccttgg cctcccaaag tgttgggatt acaggcatga    3000
gccactgcgc ctggccagct agagagtttt taaagcagag ctgagcacac actggatgcg    3060
tttgaatgtg tttgtgtagt tgttgtgaa attgttacat ttagcaggca gatccagaag    3120
cactagtgaa ctgtcatctt ggtggggttg gcttaaattt aattgactgt ttagattcca    3180
tttcttaatt gattggccag tatgaaaaga tgccagtgca agtaaccata gtatcaaaaa    3240
agttaaaaat tattcaaagc tatagtttat acatcaggta ctgccattta ctgtaaacca    3300
cctgcaagaa agtcaggaac aactaaattc acaagaactg tcctgctaag aagtgtatta    3360
aagatttcca ttttgtttta ctaattggga acatcttaat gtttaatatt taaactattg    3420
gtatcatttt tctaatgtat aatttgtatt actgggatca agtatgtaca gtggtgatgc    3480
tagtagaagt ttaagccttg gaaataccac tttcatattt tcagatgtca tggatttaat    3540
gagtaattta tgtttttaaa attcagaata gttaatctct gatctaaaac catcaatcta    3600
tgttttttac ggtaatcatg taaatatttc agtaatataa actgtttgaa aaggctgctg    3660
caggtaaact ctatactagg atcttggcca ataatttac aattcacaga atattttatt    3720
taaggtggtg cttttttttt ttgtccttaa aacttgattt tcttaacttt tattcatgat    3780
gccaaagtaa atgaggaaaa aaactcaaaa ccagttgagt atcattgcag acaaaactac    3840
```

```
cagtagtcca tattgtttaa tattaagttg aataaaataa attttatttc agtcagagcc    3900
taaatcacat tttgattgtc tgaattttg atactatttt taaaatcatg ctagtggcgg     3960
ctgggcgtgg tagctcacgc ctgtaatccc agcattttgg gaggccgaag tgggtggatc    4020
acgaggtcgg gagttcgaga ccagcttggc caaaatggtg aaaccccatc tgtactaaaa    4080
actacaaaaa ttagctgggc gcggtggcag gtgcctgtaa tcccagctac ctgggagtct    4140
gaggcaggag aattgcttga accctggcga cagaggatgc agtgagccaa gatggtgcca    4200
ctgtactcca gactgggcga cagagtgaga ctctgtctca aaaaaaaaa aaaaatcatg     4260
ctagtgccaa gagctactaa attcttaaaa ccggcccatt ggacctgtac agataaaaaa    4320
tagattcagt gcataatcaa aatatgataa ttttaaaatc ttaagtagaa aaataaatct    4380
tgatgtttta aattcttacg aggattcaat agttaatatt gatgatctcc cggctgggtg    4440
cagtggctca cgcctgtaat cccagcagtt ctggaggctg aggtgggcga atcacttcag    4500
gccaggagtt caagaccagt ctgggcaaca tggtgaaacc tcgtttctac taaaaataca    4560
aaaattagcc gggcgtggtt gcacacactt gtaatcccag ctactcagga ggctaagaat    4620
cgcatgagcc taggaggcag aggttgcaga gtgccaaggg ctcaccactg cattccagcc    4680
tgcccaacag agtgagacac tgtttctgaa aaaaaaaat atatatatat atatatatat    4740
gtgtgtatat atatatgtat atatatatga cttcctatta aaactttat cccagtcggg     4800
ggcagtggct cacgcctgta atcccaacac tttgggaggc tgaggcaggt ggatcacctg    4860
aagtccggag tttgagacca gcctggccaa catggtgaaa ccccatctct actaaaaata    4920
caaaacttaa gccaggtatg gtggcgggca cctgtaatcc cagttacttg ggaggctgag    4980
gcaggagaat cgtttaaacc caggaggtgg aggttgcagt gagctgagat cgtgccattg    5040
cactctagcc tgggcaacaa gagtaaaact ccatcttaaa ggtttgtttg ttttttttta    5100
atccggaaac gaagaggcgt tgggccgcta ttttcttttt ctttctttct ttctttcttt    5160
ttttttttt ctgagacgga gtctagctct gctgcccagg ctggagtaca atgacacgat     5220
gttggctcac tgcaacctcc acctcctggg ttcaagcgat tctcctgcct cagcctccca    5280
agtacctggg attacaggca cctgccacta cacctggcga atatttgttt ttttttagtag    5340
agacgggctt ttaccatgtt aggctggtct caaactcctg acctcaggtg atctgcctgc    5400
cttggcctcc caaagtgctg ggattacagg tgcaggccac cacacccggc cttgggccac    5460
tgttttcaaa gtgaattgtt tgttgtatcg agtccttaag tatggatata tatgtgaccc    5520
taattaagaa ctaccagatt ggatcaacta atcatgtcag caatgtaaat aactttattt    5580
ttcatattca aaataaaaac tttctttat ttctggcccc tttataacca gcatcttttt     5640
gctttaaaaa atgacctggc tttgtatttt tttagtctta aacataataa aaatatttt     5700
gttctaattt gctttcatga gtgaagatta ttgacatcgt tggtaaattc tagaattttg    5760
atttttgtttt ttaatttgaa gaaaatcttt gctattatta ttttttccaa gtggtctggc    5820
attttaagaa ttagtgctaa taacgtaact tctaaattg tcgtaattgg catgtttaat     5880
agcatatcaa aaaacatttt aagcctgtgg attcatagac aaagcaatga gaaacattag    5940
taaaatataa atggatattc ctgatgcatt taggaagctc tcaattgtct cttgcatagt    6000
tcaaggaatg ttttctgaat ttttttaatg cttttttttt ttttgaaaga ggaaaacata    6060
catttttaaa tgtgattatc taatttttac aacactgggc tattaggaat aacttttaa     6120
aaattactgt tctgtataaa tatttgaaat tcaagtacag aaaatatctg aaacaaaaag    6180
cattgttgtt tggccatgat acaagtgcac tgtggcagtg ccgcttgctc aggacccagc    6240
```

```
cctgcagccc ttctgtgtgt gctccctcgt taagttcatt tgctgttatt acacacacag    6300
gccttcctgt ctggtcgtta gaaaagccgg gcttccaaag cactgttgaa cacaggattc    6360
tgttgttagt gtggatgttc aatgagttgt attttaaata tcaaagatta ttaaataaag    6420
ataatgtttg cttttcta                                                  6438

<210> SEQ ID NO 4
<211> LENGTH: 6878
<212> TYPE: DNA
<213> ORGANISM: Homo sapiens

<400> SEQUENCE: 4
gagaggggca gggggcggag ctggaggggg tggttcggcg tgggggccgt tggctccaga      60
caaataaaca tggagtccat cttccacgag aaacaagaag gctcactttg tgctcaacat     120
tgcctgaata acttattgca aggagaatat tttagccctg tggaattatc ctcaattgca     180
catcagctgg atgaggagga gaggatgaga atggcagaag gaggagttac tagtgaagat     240
tatcgcacgt ttttacaggt tataagcaat gccttgaaag tttggggttt agaactaatc     300
ctgttcaaca gtccagagta tcagaggctc aggatcgatc ctataaatga agatcatttt     360
atatgcaatt ataaggaaca ctggtttaca gttagaaaat taggaaaaca gtggtttaac     420
ttgaattctc tcttgacggg tccagaatta atatcagata catatcttgc acttttcttg     480
gctcaattac aacaggaagg ttattctata tttgtcgtta agggtgatct gccagattgc     540
gaagctgacc aactcctgca gatgattagg gtccaacaga tgcatcgacc aaaacttatt     600
ggagaagaat tagcacaact aaaagagcaa agagtccata aaacagacct ggaacgagtg     660
ttagaagcaa atgatggctc aggaatgtta gacgaagatg aggaggattt gcagagggct     720
ctggcactaa gtcgccaaga aattgacatg gaagatgagg aagcagatct ccgcagggct     780
attcagctaa gtatgcaagg tagttccaga aacatatctc aagatatgac acagacatca     840
ggtacaaatc ttacttcaga agagcttcgg aagagacgag aagcctactt tgaaaaacag     900
cagcaaaagc agcaacagca gcagcagcag cagcagcagg gggacctatc aggacagagt     960
tcacatccat gtgaaaggcc agccaccagt tcaggagcac ttgggagtga tctaggtgat    1020
gctatgagtg aagaagacat gcttcaggca gctgtgacca tgtctttaga aactgtcaga    1080
aatgatttga aaacagaagg aaaaaaataa tacctttaaa aataatttta gatattcata    1140
ctttccaaca ttatcctgtg tgattacagc atagggtcca ctttggtaat gtgtcaaaga    1200
gatgaggaaa taagactttt agcggttttgc aaacaaaatg atgggaaagt ggaacaatgc    1260
```

```
tgctttccca gatgctttat gaatgtctttt tcacttatat caaaaccctta cagctttgtt   1920 gcaaccccctt cttcctgcgc cttatttttt cctttcttct ccaattgaga aaactaggag   1980
aagcatagta tgcaggcaag tctccttctg ttagaagact aaacatacgt acccaccatg   2040
aatgtatgat acatgaaatt tggccttcaa ttttaatagc agttttattt tatttttttct  2100 cctatgactg gagctttgtg ttctctttac agttgagtca tggaatgtag gtgtctgctt   2160 cacatcttt agtaggtata gcttgtcaaa gatggtgatc tggaacatga aaataattta    2220
ctaatgaaaa tatgttttaaa tttatactgt gatttgacac ttgcatcatg tttagatagc  2280
ttaagaacaa tggaagtcac agtacttagt ggatctataa ataagaaagt ccatagtttt   2340
gataaatatt ctctttaatt gagatgtaca gagagtttct tgctgggtca ataggatagt   2400
atcattttgg tgaaaaccat gtctctgaaa ttgatgtttt agtttcagtg ttccctatcc   2460
ctcattctcc atctccttt gaagctcttt tgaatgttga attgttcata agctaaaatc    2520
caagaaattt cagctgacaa cttcgaaaat tataatatgg tatattgccc tcctggtgtg   2580
tggctgcaca cattttatca gggaaagttt tttgatctag gatttattgc taactaactg   2640
aaaagagaag aaaaaatatc ttttattttat gattataaaa tagcttttttc ttcgatataa  2700 cagatttttt aagtcattat tttgtgccaa tcagttttct gaagtttccc ttacacaaaa   2760
ggatagcttt atttttaaaat ctaaagtttc ttttaatagt taaaaatgtt tcagaagaat  2820 tataaaacttt taaaactgca agggatgttg gagtttagta ctactccctc aagatttaaa  2880 aagctaaaata ttttaagact gaacatttat gttaattatt accagtgtgt ttgtcatatt  2940
ttccatggat atttgttcat taccttttttc cattgaaaag ttacattaaa cttttcatac  3000
acttgaattg atgagctacc taatataaaa atgagaaaac caatatgcat tttaaagttt   3060 taacttaga gttataaaag ttcatatata ccctagttaa agcacttaag aaaatatggc    3120
atgtttgact tttagttcct agagagtttt tgttttgtt tttgttttt tttgagacgg     3180 agtcttgcta tgtctcccag gctggagggc agtggcatga tctcggctca ctacaacttc   3240
cacctcccgg gttcaagcaa ttctcctgcc tcagcctcca gagtagctgg gattacaggc   3300
gcccaccacc acacccggca gattttgta tttttggtag agacgcggtt tcatcatgtt    3360
tggccaggct ggtctcgaac tcctgacctc aggtgatccg cctgccttgg cctcccaaag   3420
tgttgggatt acaggcatga gccactgcgc ctggccagct agagagtttt taaagcagag   3480
ctgagcacac actggatgcg tttgaatgtg tttgtgtagt ttgttgtgaa attgttacat   3540
ttagcaggca gatccagaag cactagtgaa ctgtcatctt ggtggggttg gcttaaattt   3600
aattgactgt ttagattcca tttcttaatt gattggccag tatgaaaaga tgccagtgca   3660
agtaaccata gtatcaaaaa agttaaaaat tattcaaagc tatagtttat acatcaggta   3720
ctgccattta ctgtaaacca cctgcaagaa agtcaggaac aactaaattc acaagaactg   3780
tcctgctaag aagtgtatta aagatttcca ttttgtttta ctaattggga acatcttaat   3840
gtttaatatt taaactattg gtatcatttt tctaatgtat aatttgtatt actgggatca   3900
agtatgtaca gtggtgatgc tagtagaagt ttaagccttg gaaataccac tttcatattt   3960
tcagatgtca tggatttaat gagtaattta tgttttaaa attcagaata gttaatctct   4020
gatctaaaac catcaatcta tgtttttttac ggtaatcatg taaatatttc agtaatataa  4080
actgtttgaa aaggctgctg caggtaaact ctatactagg atcttggcca ataattttac   4140
aattcacaga atatttttatt taaggtggtg cttttttttt ttgtccttaa aacttgatttt 4200 ttcttaactt tattcatgat gccaaagtaa atgaggaaaa aaactcaaaa ccagttgagt   4260
```

```
atcattgcag acaaaactac cagtagtcca tattgtttaa tattaagttg aataaaataa    4320
attttatttc agtcagagcc taaatcacat tttgattgtc tgaattttg atactatttt     4380 taaaatcatg ctagtggcgg ctgggcgtgg tagctcacgc ctgtaatccc agcattttgg    4440
gaggccgaag tgggtggatc acgaggtcgg gagttcgaga ccagcttggc caaaatggtg    4500 aaacccatc tgtactaaaa actacaaaaa ttagctgggc gcggtggcag gtgcctgtaa     4560
tcccagctac ctgggagtct gaggcaggag aattgcttga accctggcga cagaggatgc    4620
agtgagccaa gatggtgcca ctgtactcca gactgggcga cagagtgaga ctctgtctca    4680
aaaaaaaaaa aaaaatcatg ctagtgccaa gagctactaa attcttaaaa ccggcccatt    4740
ggacctgtac agataaaaaa tagattcagt gcataatcaa aatatgataa ttttaaaatc    4800
ttaagtagaa aaataaatct tgatgtttta aattcttacg aggattcaat agttaatatt    4860
gatgatctcc cggctgggtg cagtggctca cgcctgtaat cccagcagtt ctggaggctg    4920
aggtgggcga atcacttcag gccaggagtt caagaccagt ctgggcaaca tggtgaaacc    4980
tcgtttctac taaaaataca aaaattagcc gggcgtggtt gcacacactt gtaatcccag    5040
ctactcagga ggctaagaat cgcatgagcc taggaggcag aggttgcaga gtgccaaggg    5100
ctcaccactg cattccagcc tgcccaacag agtgagacac tgtttctgaa aaaaaaaaat    5160
atatatatat atatatatat gtgtgtatat atatatgtat atatatatga cttcctatta    5220
aaaactttat cccagtcggg ggcagtggct cacgcctgta atcccaacac tttgggaggc    5280
tgaggcaggt ggatcacctg aagtccggag tttgagacca gcctggccaa catggtgaaa    5340
ccccatctct actaaaaata caaaacttaa gccaggtatg gtggcgggca cctgtaatcc    5400
cagttacttg ggaggctgag gcaggagaat cgtttaaacc caggaggtgg aggttgcagt    5460
gagctgagat cgtgccattg cactctagcc tgggcaacaa gagtaaaact ccatcttaaa    5520
ggtttgtttg ttttttttta atccggaaac gaagaggcgt tgggccgcta ttttcttttt    5580 cttctttct ttctttcttt tttttttttt ctgagacgga gtctagctct gctgcccagg     5640
ctggagtaca atgacacgat gttggctcac tgcaacctcc acctcctggg ttcaagcgat    5700
tctcctgcct cagcctccca agtacctggg attacaggca cctgccacta cacctggcga    5760
atatttgttt tttttagtag agacgggctt ttaccatgtt aggctggtct caaactcctg    5820
acctcaggtg atctgcctgc cttggcctcc caaagtgctg ggattacagg tgcaggccac    5880
cacacccggc cttgggccac tgttttcaaa gtgaattgtt tgttgtatcg agtccttaag    5940
tatggatata tatgtgaccc taattaagaa ctaccagatt ggatcaacta atcatgtcag    6000
caatgtaaat aactttattt ttcatattca aaataaaaac tttcttttat ttctggcccc    6060
tttataacca gcatcttttt gctttaaaaa atgacctggc tttgtatttt tttagtctta    6120
aacataataa aaatattttt gttctaattt gctttcatga gtgaagatta ttgacatcgt    6180
tggtaaattc tagaattttg attttgtttt ttaatttgaa gaaatctttt gctattatta    6240
ttttttccaa gtggtctggc attttaagaa ttagtgctaa taacgtaact tctaaatttg    6300
tcgtaattgg catgtttaat agcatatcaa aaaacatttt aagcctgtgg attcatagac    6360
aaagcaatga gaaacattag taaaatataa atggatattc ctgatgcatt taggaagctc    6420
tcaattgtct cttgcatagt tcaaggaatg ttttctgaat ttttttaatg ctttttttt     6480 ttttgaaaga ggaaaacata cattttttaaa tgtgattatc taatttttac aacactgggc    6540
tattaggaat aacttttaa aaattactgt tctgtataaa tatttgaaat tcaagtacag     6600
```

| | |
|---|---:|
| aaaatatctg aaacaaaaag cattgttgtt tggccatgat acaagtgcac tgtggcagtg | 6660 |
| ccgcttgctc aggacccagc cctgcagccc ttctgtgtgt gctccctcgt taagttcatt | 6720 |
| tgctgttatt acacacacag gccttcctgt ctggtcgtta gaaaagccgg gcttccaaag | 6780 |
| cactgttgaa cacaggattc tgttgttagt gtggatgttc aatgagttgt attttaaata | 6840 |
| tcaaagatta ttaaataaag ataatgtttg cttttcta | 6878 |

<210> SEQ ID NO 5
<211> LENGTH: 6713
<212> TYPE: DNA
<213> ORGANISM: Homo sapiens

<400> SEQUENCE: 5

| | |
|---|---:|
| gagaggggca gggggcggag ctggaggggg tggttcggcg tggggccgt tggctccaga | 60 |
| caaataaaca tggagtccat cttccacgag aaagttataa gcaatgcctt gaaagtttgg | 120 |
| ggtttagaac taatcctgtt caacagtcca gagtatcaga ggctcaggat cgatcctata | 180 |
| aatgaaagat catttatatg caattataag gaacactggt ttacagttag aaaattagga | 240 |
| aaacagtggt ttaacttgaa ttctctcttg acgggtccag aattaatatc agatacatat | 300 |
| cttgcacttt tcttggctca attaacacag gaaggttatt ctatatttgt cgttaagggt | 360 |
| gatctgccag attgcgaagc tgaccaactc ctgcagatga ttagggtcca acagatgcat | 420 |
| cgaccaaaac ttattggaga agaattagca caactaaaag agcaaagagt ccataaaaca | 480 |
| gacctggaac gagtgttaga agcaaatgat ggctcaggaa tgttagacga agatgaggag | 540 |
| gatttgcaga gggctctggc actaagtcgc caagaaattg acatggaaga tgaggaagca | 600 |
| gatctccgca gggctattca gctaagtatg caaggtagtt ccagaaacat atctcaagat | 660 |
| atgacacaga catcaggtac aaatcttact tcagaagagc ttcggaagag cgagaagcc | 720 |
| tactttgaaa acagcagca aaagcagcaa cagcagcagc agcagcagca gcaggggac | 780 |
| ctatcaggac agagttcaca tccatgtgaa aggccagcca ccagttcagg agcacttggg | 840 |
| agtgatctag gtgatgctat gagtgaagaa acatgcttc aggcagctgt gaccatgtct | 900 |
| ttagaaactg tcagaaatga tttgaaaaca gaaggaaaaa aataatacct taaaaaata | 960 |
| atttagatat tcatactttc caacattatc ctgtgtgatt acagcatagg gtccactttg | 1020 |
| gtaatgtgtc aaagagatga ggaaataaga cttttagcgg tttgcaaaca aaatgatggg | 1080 |
| aaagtggaac aatgcgtcgg ttgtaggact aaataatgat cttccaaata ttagccaaag | 1140 |
| aggcattcag caattaaaga catttaaaat agttttctaa atgtttcttt ttctttttg | 1200 |
| agtgtgcaat atgtaacatg tctaaagtta gggcattttt cttggatctt tttgcagact | 1260 |
| agctaattag ctctcgcctc aggctttttc catatagttt gttttctttt tctgtcttgt | 1320 |
| aggtaagttg gctcacatca tgtaatagtg gctttcattt cttattaacc aaattaacct | 1380 |
| ttcaggaaag tatctctact ttcctgatgt tgataatagt aatggttcta gaaggatgaa | 1440 |
| cagttctccc ttcaactgta taccgtgtgc tccagtgttt tcttgtgttg ttttctctga | 1500 |
| tcacaacttt tctgctacct ggttttcatt attttcccac aattcttttg aaagatggta | 1560 |
| atcttttctg aggtttagcg ttttaagccc tacgatggga tcattatttc atgactggtg | 1620 |
| cgttcctaaa ctctgaaatc agccttgcac aagtacttga gaataaatga gcatttttta | 1680 |
| aaatgtgtga gcatgtgctt tcccagatgc tttatgaatg tcttttcact tatatcaaaa | 1740 |
| ccttacagct ttgttgcaac ccttcttcc tgcgcctat ttttccttt cttctccaat | 1800 |
| tgagaaaact aggagaagca tagtatgcag gcaagtctcc ttctgttaga agactaaaca | 1860 |

```
tacgtaccca ccatgaatgt atgatacatg aaatttggcc ttcaatttta atagcagttt   1920
tattttattt tttctcctat gactggagct ttgtgttctc tttacagttg agtcatggaa   1980
tgtaggtgtc tgcttcacat cttttagtag gtatagcttg tcaaagatgg tgatctggaa   2040
catgaaaata atttactaat gaaaatatgt ttaaatttat actgtgattt gacacttgca   2100
tcatgtttag atagcttaag aacaatggaa gtcacagtac ttagtggatc tataaataag   2160
aaagtccata gttttgataa atattctctt taattgagat gtacagagag tttcttgctg   2220
ggtcaatagg atagtatcat tttggtgaaa accatgtctc tgaaattgat gttttagttt   2280
cagtgttccc tatccctcat tctccatctc cttttgaagc tcttttgaat gttgaattgt   2340
tcataagcta aaatccaaga aatttcagct gacaacttcg aaaattataa tatggtatat   2400
tgccctcctg gtgtgtggct gcacacattt tatcagggaa agttttttga tctaggattt   2460
attgctaact aactgaaaag agaagaaaaa atatctttta tttatgatta taaaatagct   2520
ttttcttcga tataacagat tttttaagtc attattttgt gccaatcagt tttctgaagt   2580
ttcccttaca caaaggata gctttatttt aaaatctaaa gtttctttta atagttaaaa    2640
atgtttcaga agaattataa aactttaaaa ctgcaaggga tgttggagtt tagtactact   2700
ccctcaagat ttaaaagct aaatatttta agactgaaca tttatgttaa ttattaccag    2760
tgtgtttgtc atattttcca tggatatttg ttcattacct ttttccattg aaagttaca    2820 ttaaactttt catacacttg aattgatgag ctacctaata taaaaatgag aaaaccaata   2880
tgcattttaa agttttaact ttagagttta taaagttcat atatacccta gttaaagcac   2940
ttaagaaaat atggcatgtt tgactttag ttcctagaga gttttgttt ttgttttgt      3000 ttttttttga cggagtct tgctatgtct cccaggctgg agggcagtgg catgatctcg      3060
gctcactaca acttccacct cccgggttca agcaattctc ctgcctcagc ctccagagta   3120
gctgggatta caggcgccca ccaccacacc cggcagattt ttgtatttt ggtagagacg     3180 cggtttcatc atgtttggcc aggctggtct cgaactcctg acctcaggtg atccgcctgc   3240
cttggcctcc caaagtgttg ggattacagg catgagccac tgcgcctggc cagctagaga   3300
gtttttaaag cagagctgag cacacactgg atgcgtttga atgtgtttgt gtagtttgtt   3360
gtgaaattgt tacatttagc aggcagatcc agaagcacta gtgaactgtc atcttggtgg   3420
ggttggctta aatttaattg actgtttaga ttccatttct taattgattg ccagtatga    3480 aaagatgcca gtgcaagtaa ccatagtatc aaaaagtta aaaattattc aaagctatag    3540
tttatacatc aggtactgcc atttactgta aaccacctgc aagaaagtca ggaacaacta   3600
aattcacaag aactgtcctg ctaagaagtg tattaaagat ttccattttg ttttactaat   3660
tgggaacatc ttaatgttta atatttaaac tattggtatc atttttctaa tgtataattt   3720
gtattactgg gatcaagtat gtacagtggt gatgctagta gaagtttaag ccttggaaat   3780
accactttca tattttcaga tgtcatggat ttaatgagta atttatgttt ttaaaattca   3840
gaatagttaa tctctgatct aaaaccatca atctatgttt tttacggtaa tcatgtaaat   3900
atttcagtaa tataaactgt ttgaaaaggc tgctgcaggt aaactctata ctaggatctt   3960
ggccaaataa tttacaattc acagaatatt ttatttaagg tggtgctttt ttttttgtc    4020 cttaaaactt gattttctt aactttattc atgatgccaa agtaaatgag gaaaaaaact    4080
caaaaccagt tgagtatcat tgcagacaaa actaccagta gtccatattg tttaatatta   4140
agttgaataa aataaatttt atttcagtca gagcctaaat cacattttga ttgtctgaat   4200
```

```
ttttgatact attttaaaa tcatgctagt ggcggctggg cgtggtagct cacgcctgta    4260
atcccagcat tttgggaggc cgaagtgggt ggatcacgag gtcgggagtt cgagaccagc    4320
ttggccaaaa tggtgaaacc ccatctgtac taaaaactac aaaaattagc tgggcgcggt    4380
ggcaggtgcc tgtaatccca gctacctggg agtctgaggc aggagaattg cttgaaccct    4440
ggcgacagag gatgcagtga gccaagatgg tgccactgta ctccagactg ggcgacagag    4500
tgagactctg tctcaaaaaa aaaaaaaaaa tcatgctagt gccaagagct actaaattct    4560
taaaaccggc ccattggacc tgtacagata aaaatagat tcagtgcata atcaaaatat     4620
gataatttta aaatcttaag tagaaaaata atcttgatg ttttaaattc ttacgaggat     4680
tcaatagtta atattgatga tctcccggct gggtgcagtg gctcacgcct gtaatcccag    4740
cagttctgga ggctgaggtg ggcgaatcac ttcaggccag gagttcaaga ccagtctggg    4800
caacatggtg aaacctcgtt tctactaaaa atacaaaaat tagccgggcg tggttgcaca    4860
cacttgtaat cccagctact caggaggcta agaatcgcat gagcctagga ggcagaggtt    4920
gcagagtgcc aagggctcac cactgcattc cagcctgccc aacagagtga gacactgttt    4980
ctgaaaaaaa aaaatatata tatatatata tatgtgtg tatatatata tgtatatata      5040
tatgacttcc tattaaaaac tttatcccag tcggggcag tggctcacgc ctgtaatccc     5100
aacactttgg gaggctgagg caggtggatc acctgaagtc cggagtttga ccagcctg      5160 gccaacatgg tgaaaccca tctctactaa aaatacaaaa cttaagccag gtatggtggc    5220
gggcacctgt aatcccagtt acttgggagg ctgaggcagg agaatcgttt aaacccagga    5280
ggtggaggtt gcagtgagct gagatcgtgc cattgcactc tagcctgggc aacaagagta    5340
aaactccatc ttaaaggttt gtttgttttt ttttaatccg gaaacgaaga ggcgttgggc    5400 cgctatttc ttttcttc tttctttctt tcttttttt ttttctgag acggagtcta        5460 gctctgctgc ccaggctgga gtacaatgac acgatgttgg ctcactgcaa cctccacctc    5520
ctgggttcaa gcgattctcc tgcctcagcc tcccaagtac ctgggattac aggcacctgc    5580
cactacacct ggcgaatatt tgtttttttt agtagagacg ggcttttacc atgttaggct    5640
ggtctcaaac tcctgacctc aggtgatctg cctgccttgg cctcccaaag tgctgggatt    5700
acaggtgcag gccaccacac ccggccttgg gccactgttt tcaaagtgaa ttgtttgttg    5760
tatcgagtcc ttaagtatgg atatatatgt gaccctaatt aagaactacc agattggatc    5820
aactaatcat gtcagcaatg taaataactt tattttcat attcaaaata aaaactttct     5880 tttattctg gccccttat aaccagcatc ttttgcttt aaaaaatgac ctggctttgt       5940
atttttttag tcttaaacat aataaaaata ttttgttct aatttgcttt catgagtgaa     6000
gattattgac atcgttggta aattctagaa ttttgatttt gttttttaat ttgaagaaaa    6060
tctttgctat tattatttt tccaagtggt ctggcatttt aagaattagt gctaataacg     6120
taacttctaa atttgtcgta attggcatgt ttaatagcat atcaaaaaac attttaagcc    6180
tgtggattca tagacaaagc aatgagaaac attagtaaaa tataaatgga tattcctgat    6240
gcatttagga agctctcaat tgtctcttgc atagttcaag gaatgttttc tgaattttt     6300 taatgctttt tttttttg aaagaggaaa acatacattt ttaaatgtga ttatctaatt      6360
tttacaacac tgggctatta ggaataactt tttaaaaatt actgttctgt ataaatattt    6420
gaaattcaag tacagaaaat atctgaaaca aaaagcattg ttgtttggcc atgatacaag    6480
tgcactgtgg cagtgccgct tgctcaggac ccagccctgc agcccttctg tgtgtgctcc    6540
ctcgttaagt tcatttgctg ttattacaca cacaggcctt cctgtctggt cgttagaaaa    6600
```

```
gccgggcttc caaagcactg ttgaacacag gattctgttg ttagtgtgga tgttcaatga      6660
gttgtatttt aaatatcaaa gattattaaa taaagataat gtttgctttt cta            6713

<210> SEQ ID NO 6
<211> LENGTH: 6672
<212> TYPE: DNA
<213> ORGANISM: Homo sapiens

<400> SEQUENCE: 6
gagaggggca gggggcggag ctggaggggg tggttcggcg tggggccgt tggctccaga        60 caaataaaca tggagtccat cttccacgag aaacagcctt ctggaaatat ggatgacagt      120
ggttttttct ctattcagaa atgaaagatc atttatatgc aattataagg aacactggtt      180
tacagttaga aaattaggaa acagtggtt taacttgaat tctctcttga cgggtccaga      240
attaatatca gatacatatc ttgcactttt cttggctcaa ttacaacagg aaggttattc      300
tatatttgtc gttaagggtg atctgccaga ttgcgaagct gaccaactcc tgcagatgat      360
tagggtccaa cagatgcatc gaccaaaact tattggagaa gaattagcac aactaaaaga      420
gcaaagagtc cataaaacag acctggaacg agtgttagaa gcaaatgatg gctcaggaat      480
gttagacgaa gatgaggagg atttgcagag ggctctggca ctaagtcgcc aagaaattga      540
catgaaagat gaggaagcag atctccgcag ggctattcag ctaagtatgc aaggtagttc      600
cagaaacata tctcaagata tgacacagac atcaggtaca aatcttactt cagaagagct      660
tcggaagaga cgagaagcct actttgaaaa acagcagcaa aagcagcaac agcagcagca      720
gcagcagcag caggggggacc tatcaggaca gagttcacat ccatgtgaaa ggccagccac      780
cagttcagga gcacttggga gtgatctagg tgatgctatg agtgaagaag acatgcttca      840
ggcagctgtg accatgtctt tagaaactgt cagaaatgat ttgaaaacag aaggaaaaaa      900
ataatacctt taaaaaataa tttagatatt catactttcc aacattatcc tgtgtgatta      960
cagcataggg tccactttgg taatgtgtca aagagatgag gaaataagac ttttagcggt     1020
ttgcaaacaa aatgatggga agtggaaca atgcgtcggt tgtaggacta ataatgatc       1080 ttccaaatat tagccaaaga ggcattcagc aattaaagac atttaaaata gttttctaaa     1140
tgtttctttt tcttttttga gtgtgcaata tgtaacatgt ctaaagttag ggcatttttc     1200
ttggatcttt ttgcagacta gctaattagc tctcgcctca ggcttttttcc atatagtttg     1260 ttttcttttt ctgtcttgta ggtaagttgg ctcacatcat gtaatagtgg ctttcatttc     1320
ttattaacca aattaacctt tcaggaaagt atctctactt tcctgatgtt gataatagta     1380
atggttctag aaggatgaac agttctccct tcaactgtat accgtgtgct ccagtgtttt     1440
cttgtgttgt tttctctgat cacaactttt ctgctacctg gttttcatta tttttcccaca     1500 attcttttga aagatggtaa tcttttctga ggtttagcgt tttaagccct acgatgggat     1560
cattatttca tgactggtgc gttcctaaac tctgaaatca gccttgcaca agtacttgag     1620
aataaatgag cattttttaa aatgtgtgag catgtgcttt cccagatgct ttatgaatgt     1680
cttttcactt atatcaaaac cttacagctt tgttgcaacc ccttcttcct gcgccttatt     1740
ttttcctttc ttctccaatt gagaaaacta ggagaagcat agtatgcagg caagtctcct     1800
tctgttagaa gactaaacat acgtacccac catgaatgta tgatacatga aatttggcct     1860
tcaattttaa tagcagtttt atttattttt ttctcctatg actggagctt tgtgttctct     1920
ttacagttga gtcatggaat gtaggtgtct gcttcacatc ttttagtagg tatagcttgt     1980
```

```
caaagatggt gatctggaac atgaaaataa tttactaatg aaaatatgtt taaatttata    2040
ctgtgatttg acacttgcat catgtttaga tagcttaaga acaatggaag tcacagtact    2100
tagtggatct ataaataaga aagtccatag ttttgataaa tattctcttt aattgagatg    2160
tacagagagt tcttgctgg gtcaatagga tagtatcatt ttggtgaaaa ccatgtctct     2220
gaaattgatg ttttagtttc agtgttccct atccctcatt ctccatctcc ttttgaagct    2280
cttttgaatg ttgaattgtt cataagctaa atccaagaa atttcagctg acaacttcga     2340
aaattataat atggtatatt gccctcctgg tgtgtggctg cacacatttt atcagggaaa    2400
gttttttgat ctaggattta ttgctaacta actgaaaaga gaagaaaaaa tatcttttat    2460
ttatgattat aaaatagctt tttcttcgat ataacagatt ttttaagtca ttattttgtg    2520
ccaatcagtt ttctgaagtt tcccttacac aaaaggatag ctttatttta aaatctaaag    2580
tttctttttaa tagttaaaaa tgtttcagaa gaattataaa actttaaaac tgcaagggat   2640
gttggagttt agtactactc cctcaagatt taaaaagcta aatattttaa gactgaacat    2700
ttatgttaat tattaccagt gtgtttgtca tattttccat ggatatttgt tcattacctt    2760
tttccattga aaagttacat taaacttttc atacacttga attgatgagc tacctaatat    2820
aaaaatgaga aaaccaatat gcattttaaa gttttaactt tagagtttat aaagttcata    2880
tatacccctag ttaaagcact taagaaaata tggcatgttt gacttttagt tcctagagag   2940
ttttttgtttt tgtttttgtt tttttttgag acggagtctt gctatgtctc ccaggctgga   3000
gggcagtggc atgatctcgg ctcactacaa cttccacctc ccgggttcaa gcaattctcc    3060
tgcctcagcc tccagagtag ctgggattac aggcgcccac caccacccc ggcagatttt     3120
tgtattttg gtagagacgc ggtttcatca tgtttggcca ggctggtctc gaactcctga     3180
cctcaggtga tccgcctgcc ttggcctccc aaagtgttgg gattacaggc atgagccact    3240
gcgcctggcc agctagagag ttttaaagc agagctgagc acacactgga tgcgtttgaa     3300
tgtgtttgtg tagtttgttg tgaaattgtt acatttagca ggcagatcca gaagcactag    3360
tgaactgtca tcttggtggg gttggcttaa atttaattga ctgtttagat tccatttctt    3420
aattgattgg ccagtatgaa aagatgccag tgcaagtaac catagtatca aaaaagttaa    3480
aaattattca aagctatagt ttatacatca ggtactgcca tttactgtaa accacctgca    3540
agaaagtcag gaacaactaa attcacaaga actgtcctgc taagaagtgt attaaagatt    3600
tccattttgt tttactaatt gggaacatct taatgtttaa tatttaaact attggtatca    3660
tttttctaat gtataatttg tattactggg atcaagtatg tacagtggtg atgctagtag    3720
aagtttaagc cttggaaata ccactttcat attttcagat gtcatggatt taatgagtaa    3780
tttatgtttt taaaattcag aatagttaat ctctgatcta aaaccatcaa tctatgtttt    3840
ttacggtaat catgtaaata tttcagtaat ataaactgtt tgaaaaggct gctgcaggta    3900
aactctatac taggatcttg gccaaataat ttacaattca cagaatattt tatttaaggt    3960
ggtgcttttt ttttttgtcc ttaaaacttg attttcctta actttattca tgatgccaaa    4020
gtaaatgagg aaaaaaactc aaaccagtt gagtatcatt gcagacaaaa ctaccagtag     4080
tccatattgt ttaatattaa gttgaataaa ataattttta tttcagtcag agcctaaatc    4140
acattttgat tgtctgaatt tttgatacta ttttttaaaat catgctagtg gcggctgggc   4200
gtggtagctc acgcctgtaa tcccagcatt ttgggaggcc gaagtgggtg gatcacgagg    4260
tcgggagttc gagaccagct tggccaaaat ggtgaaaccc catctgtact aaaaactaca    4320
aaaattagct gggcgcggtg gcaggtgcct gtaatcccag ctacctggga gtctgaggca    4380
```

```
ggagaattgc ttgaaccctg gcgacagagg atgcagtgag ccaagatggt gccactgtac    4440
tccagactgg gcgacagagt gagactctgt ctcaaaaaaa aaaaaaaaat catgctagtg    4500
ccaagagcta ctaaattctt aaaaccggcc cattggacct gtacagataa aaaatagatt    4560
cagtgcataa tcaaaatatg ataattttaa aatcttaagt agaaaataaa atcttgatgt    4620
tttaaattct tacgaggatt caatagttaa tattgatgat ctcccggctg ggtgcagtgg    4680
ctcacgcctg taatcccagc agttctggag gctgaggtgg gcgaatcact tcaggccagg    4740
agttcaagac cagtctgggc aacatggtga aacctcgttt ctactaaaaa tacaaaaatt    4800
agccgggcgt ggttgcacac acttgtaatc ccagctactc aggaggctaa gaatcgcatg    4860
agcctaggag gcagaggttg cagagtgcca agggctcacc actgcattcc agcctgccca    4920
acagagtgag acactgtttc tgaaaaaaaa aaatatatat atatatatat atatgtgtgt    4980
atatatatat gtatatatat atgacttcct attaaaaact ttatcccagt cggggcagt     5040 ggctcacgcc tgtaatccca cactttggg aggctgaggc aggtggatca cctgaagtcc     5100
ggagtttgag accagcctgg ccaacatggt gaaaccccat ctctactaaa aatacaaaac    5160
ttaagccagg tatggtggcg ggcacctgta atcccagtta cttgggaggc tgaggcagga    5220
gaatcgttta aacccaggag gtggaggttg cagtgagctg agatcgtgcc attgcactct    5280
agcctgggca acaagagtaa aactccatct taaaggtttg tttgttttt tttaatccgg     5340 aaacgaagag gcgttgggcc gctatttct ttttctttct ttctttcttt cttttttttt     5400
ttttctgaga cggagtctag ctctgctgcc caggctggag tacaatgaca cgatgttggc    5460
tcactgcaac ctccacctcc tgggttcaag cgattctcct gcctcagcct cccaagtacc    5520
tgggattaca ggcacctgcc actacacctg gcgaatattt gtttttttta gtagagacgg    5580
gcttttacca tgttaggctg gtctcaaact cctgacctca ggtgatctgc ctgccttggc    5640
ctcccaaagt gctgggatta caggtgcagg ccaccacacc cggccttggg ccactgtttt    5700
caaagtgaat tgtttgttgt atcgagtcct taagtatgga tatatatgtg accctaatta    5760
agaactacca gattggatca actaatcatg tcagcaatgt aaataacttt atttttcata    5820
ttcaaaataa aaactttctt ttatttctgg cccctttata accagcatct ttttgcttta    5880
aaaaatgacc tggctttgta ttttttttagt cttaaacata ataaaaatat ttttgttcta   5940
atttgctttc atgagtgaag attattgaca tcgttggtaa attctagaat tttgattttg    6000 tttttttaatt tgaagaaaat ctttgctatt attattttt ccaagtggtc tggcatttta    6060
agaattagtg ctaataacgt aacttctaaa tttgtcgtaa ttggcatgtt taatagcata    6120
tcaaaaaaca ttttaagcct gtggattcat agacaaagca atgagaaaca ttagtaaaat    6180
ataaatggat attcctgatg catttaggaa gctctcaatt gtctcttgca tagttcaagg    6240
aatgttttct gaattttttt aatgctttt tttttttga aagaggaaaa catacatttt      6300
taaatgtgat tatctaattt ttacaacact gggctattag gaataacttt ttaaaaatta    6360
ctgttctgta taaatatttg aaattcaagt acagaaaata tctgaaacaa aaagcattgt    6420
tgtttggcca tgatacaagt gcactgtggc agtgccgctt gctcaggacc cagccctgca    6480
gcccttctgt gtgtgctccc tcgttaagtt catttgctgt tattacacac acaggccttc    6540
ctgtctggtc gttagaaaag ccgggcttcc aaagcactgt tgaacacagg attctgttgt    6600
tagtgtggat gttcaatgag ttgtatttta aatatcaaag attattaaat aaagataatg    6660
tttgcttttc ta                                                        6672
```

<210> SEQ ID NO 7
<211> LENGTH: 6627
<212> TYPE: DNA
<213> ORGANISM: Homo sapiens

<400> SEQUENCE: 7

| | | | | | | |
|---|---|---|---|---|---|---|
| gagaggggca | gggggcggag | ctggaggggg | tggttcggcg | tggggccgt | tggctccaga | 60 |
| caaataaaca | tggagtccat | cttccacgag | aaaaaatgaa | agatcattta | tatgcaatta | 120 |
| taaggaacac | tggtttacag | ttagaaaatt | aggaaaacag | tggtttaact | tgaattctct | 180 |
| cttgacgggt | ccagaattaa | tatcagatac | atatcttgca | cttttcttgg | ctcaattaca | 240 |
| acaggaaggt | tattctatat | ttgtcgttaa | gggtgatctg | ccagattgcg | aagctgacca | 300 |
| actcctgcag | atgattaggg | tccaacagat | gcatcgacca | aaacttattg | gagaagaatt | 360 |
| agcacaacta | aaagagcaaa | gagtccataa | aacagacctg | gaacgagtgt | tagaagcaaa | 420 |
| tgatggctca | ggaatgttag | acgaagatga | ggaggatttg | cagagggctc | tggcactaag | 480 |
| tcgccaagaa | attgacatgg | aagatgagga | agcagatctc | cgcagggcta | ttcagctaag | 540 |
| tatgcaaggt | agttccagaa | acatatctca | agatatgaca | cagacatcag | gtacaaatct | 600 |
| tacttcagaa | gagcttcgga | agagacgaga | agcctacttt | gaaaaacagc | agcaaaagca | 660 |
| gcaacagcag | cagcagcagc | agcagcaggg | ggacctatca | ggacagagtt | cacatccatg | 720 |
| tgaaaggcca | gccaccagtt | caggagcact | gggagtgat | ctaggtgatg | ctatgagtga | 780 |
| agaagacatg | cttcaggcag | ctgtgaccat | gtctttagaa | actgtcagaa | atgatttgaa | 840 |
| aacagaagga | aaaaataat | acctttaaaa | aataatttag | atattcatac | tttccaacat | 900 |
| tatcctgtgt | gattacagca | tagggtccac | tttggtaatg | tgtcaaagag | atgaggaaat | 960 |
| aagactttta | gcggtttgca | acaaaatga | tgggaaagtg | gaacaatgcg | tcggttgtag | 1020 |
| gactaaataa | tgatcttcca | aatattagcc | aaagaggcat | tcagcaatta | aagacattta | 1080 |
| aaatagtttt | ctaaatgttt | cttttttctt | tttgagtgtg | caatatgtaa | catgtctaaa | 1140 |
| gttagggcat | ttttcttgga | tcttttttgca | gactagctaa | ttagctctcg | cctcaggctt | 1200 |
| tttccatata | gtttgttttc | ttttttctgtc | ttgtaggtaa | gttggctcac | atcatgtaat | 1260 |
| agtggctttc | atttcttatt | aaccaaatta | acctttcagg | aaagtatctc | tactttcctg | 1320 |
| atgttgataa | tagtaatggt | tctagaagga | tgaacagttc | tcccttcaac | tgtataccgt | 1380 |
| gtgctccagt | gttttcttgt | gttgtttttct | ctgatcacaa | cttttctgct | acctggtttt | 1440 |
| cattatttc | ccacaattct | tttgaaagat | ggtaatcttt | tctgaggttt | agcgttttaa | 1500 |
| gccctacgat | gggatcatta | tttcatgact | ggtgcgttcc | taaactctga | aatcagcctt | 1560 |
| gcacaagtac | ttgagaataa | atgagcattt | tttaaaatgt | gtgagcatgt | gctttcccag | 1620 |
| atgctttatg | aatgtctttt | cacttatatc | aaaaccttac | agctttgttg | caacccttc | 1680 |
| ttcctgcgcc | ttattttttc | cttcttctc | caattgagaa | aactaggaga | agcatagtat | 1740 |
| gcaggcaagt | ctccttctgt | tagaagacta | aacatacgta | cccaccatga | atgtatgata | 1800 |
| catgaaattt | ggccttcaat | tttaatagca | gttttatttt | attttttctc | ctatgactgg | 1860 |
| agctttgtgt | tctctttaca | gttgagtcat | ggaatgtagg | tgtctgcttc | acatcttta | 1920 |
| gtaggtatag | cttgtcaaag | atggtgatct | ggaacatgaa | aataatttac | taatgaaaat | 1980 |
| atgtttaaat | ttatactgtg | atttgacact | tgcatcatgt | ttagatagct | taagaacaat | 2040 |
| ggaagtcaca | gtactagtg | gatctataaa | taagaaagtc | catagttttg | ataaatattc | 2100 |
| tcttttaattg | agatgtacag | agagtttctt | gctgggtcaa | taggatagta | tcattttggt | 2160 |

```
gaaaaccatg tctctgaaat tgatgtttta gtttcagtgt tccctatccc tcattctcca    2220
tctccttttg aagctctttt gaatgttgaa ttgttcataa gctaaaatcc aagaaatttc    2280
agctgacaac ttcgaaaatt ataatatggt atattgccct cctggtgtgt ggctgcacac    2340
attttatcag ggaaagtttt ttgatctagg atttattgct aactaactga aaagagaaga    2400
aaaaatatct tttatttatg attataaaat agcttttct  tcgatataac agattttta    2460 agtcattatt ttgtgccaat cagttttctg aagtttccct tacacaaaag gatagcttta    2520
ttttaaaatc taaagtttct tttaatagtt aaaaatgttt cagaagaatt ataaaacttt    2580
aaaactgcaa gggatgttgg agtttagtac tactccctca agatttaaaa agctaaatat    2640
tttaagactg aacatttatg ttaattatta ccagtgtgtt tgtcatattt tccatggata    2700
tttgttcatt acctttttcc attgaaaagt tacattaaac ttttcataca cttgaattga    2760
tgagctacct aatataaaaa tgagaaaacc aatatgcatt ttaaagtttt aactttagag    2820
tttataaagt tcatatatac cctagttaaa gcacttaaga aaatatggca tgtttgactt    2880
ttagttccta gagagttttt gttttttgttt ttgtttttttt ttgagacgga gtcttgctat    2940
gtctcccagg ctggagggca gtggcatgat ctcggctcac tacaacttcc acctcccggg    3000
ttcaagcaat tctcctgcct cagcctccag agtagctggg attacaggcg cccaccacca    3060
cacccggcag attttgtat  ttttggtaga gacgcggttt catcatgttt ggccaggctg    3120
gtctcgaact cctgacctca ggtgatccgc ctgccttggc ctcccaaagt gttgggatta    3180
caggcatgag ccactgcgcc tggccagcta gagagttttt aaagcagagc tgagcacaca    3240
ctggatgcgt ttgaatgtgt ttgtgtagtt tgttgtgaaa ttgttacatt tagcaggcag    3300
atccagaagc actagtgaac tgtcatcttg gtggggttgg cttaaattta attgactgtt    3360
tagattccat ttcttaattg attggccagt atgaaaagat gccagtgcaa gtaaccatag    3420
tatcaaaaaa gttaaaaatt attcaaagct atagtttata catcaggtac tgccatttac    3480
tgtaaaccac ctgcaagaaa gtcaggaaca actaaattca caagaactgt cctgctaaga    3540
agtgtattaa agatttccat tttgttttac taattgggaa catcttaatg tttaatattt    3600
aaactattgg tatcattttt ctaatgtata atttgtatta ctgggatcaa gtatgtacag    3660
tggtgatgct agtagaagtt taagccttgg aaataccact ttcatatttt cagatgtcat    3720
ggatttaatg agtaatttat gttttttaaaa ttcagaatag ttaatctctg atctaaaacc    3780
atcaatctat gttttttacg gtaatcatgt aaatatttca gtaatataaa ctgtttgaaa    3840
aggctgctgc aggtaaactc tatactagga tcttggccaa ataatttaca attcacagaa    3900
tattttattt aaggtggtgc ttttttttttt tgtccttaaa acttgatttt tcttaacttt    3960
attcatgatg ccaaagtaaa tgaggaaaaa aactcaaaac cagttgagta tcattgcaga    4020
caaaactacc agtagtccat attgtttaat attaagttga ataaaataaa ttttatttca    4080
gtcagagcct aaatcacatt ttgattgtct gaattttga  tactattttt aaaatcatgc    4140
tagtggcggc tgggcgtggt agctcacgcc tgtaatccca gcattttggg aggccgaagt    4200
gggtggatca cgaggtcggg agttcgagac cagcttggcc aaaatggtga acccccatct    4260
gtactaaaaa ctacaaaaat tagctgggcg cggtggcagg tgcctgtaat cccagctacc    4320
tgggagtctg aggcaggaga attgcttgaa ccctggcgac agaggatgca gtgagccaag    4380
atggtgccac tgtactccag actgggcgac agagtgagac tctgtctcaa aaaaaaaaaa    4440
aaaatcatgc tagtgccaag agctactaaa ttcttaaaac cggcccattg gacctgtaca    4500
```

```
gataaaaaat agattcagtg cataatcaaa atatgataat tttaaaatct taagtagaaa   4560
aataaatctt gatgttttaa attcttacga ggattcaata gttaatattg atgatctccc   4620
ggctgggtgc agtggctcac gcctgtaatc ccagcagttc tggaggctga ggtgggcgaa   4680
tcacttcagg ccaggagttc aagaccagtc tgggcaacat ggtgaaacct cgtttctact   4740
aaaaatacaa aaattagccg ggcgtggttg cacacacttg taatcccagc tactcaggag   4800
gctaagaatc gcatgagcct aggaggcaga ggttgcagag tgccaagggc tcaccactgc   4860
attccagcct gcccaacaga gtgagacact gtttctgaaa aaaaaaaata tatatatata   4920
tatatatatg tgtgtatata tatatgtata tatatatgac ttcctattaa aactttatc    4980
ccagtcgggg gcagtggctc acgcctgtaa tcccaacact tgggaggct gaggcaggtg    5040
gatcacctga gtccggagt ttgagaccag cctggccaac atggtgaaac cccatctcta    5100
ctaaaaatac aaaacttaag ccaggtatgg tggcgggcac ctgtaatccc agttacttgg   5160
gaggctgagg caggagaatc gtttaaaccc aggaggtgga ggttgcagtg agctgagatc   5220
gtgccattgc actctagcct gggcaacaag agtaaaactc catcttaaag gtttgtttgt   5280
ttttttttaa tccggaaacg aagaggcgtt gggccgctat tttcttttc tttctttctt    5340
tctttcttt ttttttttc tgagacgag tctagctctg ctgcccaggc tggagtacaa      5400
tgacacgatg ttggctcact gcaacctcca cctcctgggt tcaagcgatt ctcctgcctc   5460
agcctcccaa gtacctggga ttacaggcac ctgccactac acctggcgaa tatttgtttt   5520
ttttagtaga cgggctttt taccatgtta ggctggtctc aaactcctga cctcaggtga    5580
tctgcctgcc ttggcctccc aaagtgctgg gattacaggt gcaggccacc acacccggcc   5640
ttgggccact gttttcaaag tgaattgttt gttgtatcga gtccttaagt atggatatat   5700
atgtgaccct aattaagaac taccagattg gatcaactaa tcatgtcagc aatgtaaata   5760
actttatttt tcatattcaa aataaaaact ttctttatt tctggcccct ttataaccag    5820
catcttttg cttaaaaaaa tgacctggct ttgtatttt ttagtcttaa acataataaa     5880
aatattttg ttctaatttg ctttcatgag tgaagattat tgacatcgtt ggtaaattct    5940
agaattttga ttttgttttt taatttgaag aaaatctttg ctattattat tttttccaag   6000
tggtctggca ttttaagaat tagtgctaat aacgtaactt ctaaatttgt cgtaattggc   6060
atgtttaata gcatatcaaa aaacatttta agcctgtgga ttcatagaca aagcaatgag   6120
aaacattagt aaaatataaa tggatattcc tgatgcattt aggaagctct caattgtctc   6180
ttgcatagtt caaggaatgt tttctgaatt tttttaatgc tttttttttt tttgaaagag   6240
gaaaacatac atttttaaat gtgattatct aattttaca acactgggct attaggaata   6300
acttttaaa aattactgtt ctgtataaat atttgaaatt caagtacaga aaatatctga    6360
aacaaaaagc attgttgttt ggccatgata caagtgcact gtggcagtgc cgcttgctca   6420
ggacccagcc ctgcagccct tctgtgtgtg ctccctcgtt aagttcattt gctgttatta   6480
cacacacagg ccttcctgtc tggtcgttag aaaagccggg cttccaaagc actgttgaac   6540
acaggattct gttgttagtg tggatgttca atgagttgta ttttaaatat caaagattat   6600
taaataaaga taatgtttgc ttttcta                                       6627
```

<210> SEQ ID NO 8
<211> LENGTH: 6684
<212> TYPE: DNA
<213> ORGANISM: Homo sapiens

<400> SEQUENCE: 8

```
gagaggggca gggggcggag ctggaggggg tggttcggcg tggggccgt tggctccaga      60 caaataaaca tggagtccat cttccacgag aaacagcctt ctggaaatat ggatgacagt    120
ggttttttct ctattcagaa atgaaagatc atttatatgc aattataagg aacactggtt    180
tacagttaga aaattaggaa aacagtggtt taacttgaat tctctcttga cgggtccaga    240
attaatatca gatacatatc ttgcactttt cttggctcaa ttacaacagg aaggttattc    300
tatatttgtc gttaagggtg atctgccaga ttgcgaagct gaccaactcc tgcagatgat    360
tagggtccaa cagatgcatc gaccaaaact tattggagaa gaattagcac aactaaaaga    420
gcaaagagtc cataaaacag acctggaacg agtgttagaa gcaaatgatg gctcaggaat    480
gttagacgaa gatgaggagg atttgcagag ggctctggca ctaagtcgcc aagaaattga    540
catggaagat gaggaagcag atctccgcag ggctattcag ctaagtatgc aaggtagttc    600
cagaaacata tctcaagata tgacacagac atcaggtaca aatcttactt cagaagagct    660
tcggaagaga cgagaagcct actttgaaaa gtaaagtagt tgacagcagc aaaagcagca    720
acagcagcag cagcagcagc agcaggggga cctatcagga cagagttcac atccatgtga    780
aaggccagcc accagttcag gagcacttgg gagtgatcta ggtgatgcta tgagtgaaga    840
agacatgctt caggcagctg tgaccatgtc tttagaaact gtcagaaatg atttgaaaac    900
agaaggaaaa aaataatacc tttaaaaaat aatttagata ttcatacttt ccaacattat    960
cctgtgtgat tacagcatag ggtccacttt ggtaatgtgt caaagagatg aggaaataag   1020
acttttagcg gtttgcaaac aaaatgatgg gaaagtggaa caatgcgtcg gttgtaggac   1080
taaataatga tcttccaaat attagccaaa gaggcattca gcaattaaag acatttaaaa   1140
tagttttcta aatgtttctt tttcttttt gagtgtgcaa tatgtaacat gtctaaagtt   1200
agggcatttt tcttggatct ttttgcagac tagctaatta gctctcgcct caggcttttt   1260
ccatatagtt tgttttcttt ttctgtcttg taggtaagtt ggctcacatc atgtaatagt   1320
ggctttcatt tcttattaac caaattaacc tttcaggaaa gtatctctac tttcctgatg   1380
ttgataatag taatggttct agaaggatga acagttctcc cttcaactgt ataccgtgtg   1440
ctccagtgtt ttcttgtgtt gttttctctg atcacaactt ttctgctacc tggttttcat   1500
tattttccca caattctttt gaaagatggt aatctttttct gaggtttagc gttttaagcc   1560
ctacgatggg atcattattt catgactggt gcgttcctaa actctgaaat cagccttgca   1620
caagtacttg agaataaatg agcattttt aaaatgtgtg agcatgtgct ttcccagatg   1680
ctttatgaat gtcttttcac ttatatcaaa accttacagc tttgttgcaa ccccttcttc   1740
ctgcgcctta ttttttcctt tcttctccaa ttgagaaaac taggagaagc atagtatgca   1800
ggcaagtctc cttctgttag aagactaaac atacgtaccc accatgaatg tatgatacat   1860
gaaatttggc cttcaatttt aatagcagtt ttattttatt ttttctccta tgactggagc   1920
tttgtgttct ctttacagtt gagtcatgga atgtaggtgt ctgcttcaca tcttttagta   1980
ggtatagctt gtcaaagatg gtgatctgga acatgaaaat aatttactaa tgaaaatatg   2040
tttaaattta tactgtgatt tgacacttgc atcatgttta gatagcttaa gaacaatgga   2100
agtcacagta cttagtggat ctataaataa gaaagtccat agttttgata aatattctct   2160
ttaattgaga tgtacagaga gtttcttgct gggtcaatag gatagtatca ttttggtgaa   2220
aaccatgtct ctgaaattga tgttttagtt tcagtgttcc ctatccctca ttctccatct   2280 cctttttgaag ctcttttgaa tgttgaattg ttcataagct aaaatccaag aaatttcagc   2340
```

```
tgacaacttc gaaaattata atatggtata ttgccctcct ggtgtgtggc tgcacacatt    2400
ttatcaggga agttttttg atctaggatt tattgctaac taactgaaaa gagaagaaaa     2460
aatatctttt atttatgatt ataaaatagc ttttcttcg atataacaga ttttttaagt    2520
cattattttg tgccaatcag ttttctgaag tttcccttac acaaaaggat agctttattt    2580
taaaatctaa agtttctttt aatagttaaa aatgtttcag aagaattata aaactttaaa    2640
actgcaaggg atgttggagt ttagtactac tccctcaaga tttaaaaagc taaatatttt    2700
aagactgaac atttatgtta attattacca gtgtgtttgt catattttcc atggatattt    2760
gttcattacc tttttccatt gaaaagttac attaaacttt tcatacactt gaattgatga    2820
gctacctaat ataaaaatga gaaaaccaat atgcatttta aagttttaac tttagagttt    2880
ataaagttca tatatacccct agttaaagca cttaagaaaa tatggcatgt ttgactttta    2940
gttcctagag agttttttgtt tttgttttg ttttttttg agacggagtc ttgctatgtc      3000
tcccaggctg agggcagtg gcatgatctc ggctcactac aacttccacc tcccgggttc     3060
aagcaattct cctgcctcag cctccagagt agctgggatt acaggcgccc accaccacac    3120
ccggcagatt tttgtatttt tggtagagac gcggtttcat catgtttggc caggctggtc    3180
tcgaactcct gacctcaggt gatccgcctg ccttggcctc ccaaagtgtt gggattacag    3240
gcatgagcca ctgcgcctgg ccagctagag agttttttaaa gcagagctga gcacacactg    3300
gatgcgtttg aatgtgtttg tgtagtttgt tgtgaaattg ttacatttag caggcagatc    3360
cagaagcact agtgaactgt catcttggtg gggttggctt aaatttaatt gactgtttag    3420
attccatttc ttaattgatt ggccagtatg aaaagatgcc agtgcaagta accatagtat    3480
caaaaaagtt aaaaattatt caaagctata gtttatacat caggtactgc catttactgt    3540
aaaccacctg caagaaagtc aggaacaact aaattcacaa gaactgtcct gctaagaagt    3600
gtattaaaga tttccatttt gttttactaa ttgggaacat cttaatgttt aatatttaaa    3660
ctattggtat catttttcta atgtataatt tgtattactg ggatcaagta tgtacagtgg    3720
tgatgctagt agaagtttaa gccttggaaa taccactttc atattttcag atgtcatgga    3780
tttaatgagt aatttatgtt tttaaaattc agaatagtta atctctgatc taaaaccatc    3840
aatctatgtt ttttacggta atcatgtaaa tatttcagta atataaactg tttgaaaagg    3900
ctgctgcagg taaactctat actaggatct tggccaaata atttacaatt cacagaatat    3960
tttatttaag gtggtgcttt ttttttttgt ccttaaaact tgattttct taactttatt     4020 catgatgcca agtaaatga ggaaaaaaac tcaaaaccag ttgagtatca ttgcagacaa     4080
aactaccagt agtccatatt gtttaatatt aagttgaata aaataaattt tatttcagtc    4140
agagcctaaa tcacattttg attgtctgaa tttttgatac tatttttaaa atcatgctag    4200
tggcggctgg gcgtggtagc tcacgcctgt aatcccagca ttttgggagg ccgaagtggg    4260
tggatcacga ggtcgggagt tcgagaccag cttggccaaa atggtgaaac cccatctgta    4320
ctaaaaacta caaaaattag ctgggcgcgg tggcaggtgc ctgtaatccc agctacctgg    4380
gagtctgagg caggagaatt gcttgaaccc tggcgacaga ggatgcagtg agccaagatg    4440
gtgccactgt actccagact gggcgacaga gtgagactct gtctcaaaaa aaaaaaaaaa    4500
atcatgctag tgccaagagc tactaaattc ttaaaaccgg cccattggac ctgtacagat    4560
aaaaaataga ttcagtgcat aatcaaaata tgataatttt aaaatcttaa gtagaaaaat    4620
aaatcttgat gttttaaatt cttacgagga ttcaatagtt aatattgatg atctcccggc    4680
tgggtgcagt ggctcacgcc tgtaatccca gcagttctgg aggctgaggt gggcgaatca    4740
```

```
cttcaggcca ggagttcaag accagtctgg gcaacatggt gaaacctcgt ttctactaaa    4800
aatacaaaaa ttagccgggc gtggttgcac acacttgtaa tcccagctac tcaggaggct    4860
aagaatcgca tgagcctagg aggcagaggt tgcagagtgc caaggctca ccactgcatt    4920 ccagcctgcc aacagagtg agacactgtt tctgaaaaaa aaaatatat atatatat        4980 atatatgtgt gtatatat atgtatat atgacttc ctattaaaaa ctttatccca           5040
gtcgggggca gtggctcacg cctgtaatcc caacactttg ggaggctgag gcaggtggat    5100
cacctgaagt ccggagtttg agaccagcct ggccaacatg gtgaaacccc atctctacta    5160
aaaatacaaa acttaagcca ggtatggtgg cgggcacctg taatcccagt tacttgggag    5220
gctgaggcag gagaatcgtt taaacccagg aggtggaggt tgcagtgagc tgagatcgtg    5280
ccattgcact ctagcctggg caacaagagt aaaactccat cttaaaggtt tgtttgtttt    5340
tttttaatcc ggaaacgaag aggcgttggg ccgctatttt ctttttcttt ctttctttct    5400
ttcttttttt ttttttctga cggagtct agctctgctg cccaggctgg agtacaatga       5460
cacgatgttg gctcactgca acctccacct cctgggttca agcgattctc ctgcctcagc    5520
ctcccaagta cctgggatta caggcacctg ccactcacc tggcgaatat tgttttttt      5580 tagtagagac gggcttttac catgttaggc tggtctcaaa ctcctgacct caggtgatct    5640
gcctgccttg gcctcccaaa gtgctgggat tacaggtgca ggccaccaca cccggccttg    5700
ggccactgtt ttcaaagtga attgtttgtt gtatcgagtc cttaagtatg gatatatatg    5760
tgaccctaat taagaactac cagattggat caactaatca tgtcagcaat gtaaataact    5820
ttatttttca tattcaaaat aaaaactttc ttttatttct ggccccttta taaccagcat    5880 cttttttgctt taaaaatga cctggctttg tattttttta gtcttaaaca taataaaaat    5940 attttttgttc taatttgctt tcatgagtga agattattga catcgttggt aaattctaga   6000
attttgattt tgttttttaa tttgaagaaa atctttgcta ttattatttt ttccaagtgg    6060
tctggcattt taagaattag tgctaataac gtaacttcta aatttgtcgt aattggcatg    6120
tttaatagca tatcaaaaaa cattttaagc ctgtggattc atagacaaag caatgagaaa    6180
cattagtaaa atataaatgg atattcctga tgcatttagg aagctctcaa ttgtctcttg    6240
catagttcaa ggaatgtttt ctgaatttt ttaatgcttt ttttttttt gaaagaggaa      6300 aacatacatt tttaaatgtg attatctaat ttttacaaca ctgggctatt aggaataact    6360
ttttaaaaat tactgttctg tataaatatt tgaaattcaa gtacagaaaa tatctgaaac    6420
aaaaagcatt gttgtttggc catgatacaa gtgcactgtg gcagtgccgc ttgctcagga    6480
cccagccctg cagcccttct gtgtgtgctc cctcgttaag ttcatttgct gttattacac    6540
acacaggcct tcctgtctgg tcgttagaaa agccgggctt ccaaagcact gttgaacaca    6600
ggattctgtt gttagtgtgg atgttcaatg agttgtattt taaatatcaa agattattaa    6660
ataaagataa tgtttgcttt tcta                                            6684
```

<210> SEQ ID NO 9
<211> LENGTH: 6560
<212> TYPE: DNA
<213> ORGANISM: Homo sapiens

<400> SEQUENCE: 9

```
gagaggggca gggggcggag ctggaggggg tggttcggcg tgggggccgt tggctccaga      60
caaataaaca tggagtccat cttccacgag aaatggttta acttgaattc tctcttgacg     120
```

```
ggtccagaat taatatcaga tacatatctt gcacttttct tggctcaatt acaacaggaa    180
ggttattcta tatttgtcgt taagggtgat ctgccagatt gcgaagctga ccaactcctg    240
cagatgatta gggtccaaca gatgcatcga ccaaaactta ttggagaaga attagcacaa    300
ctaaaagagc aaagagtcca taaaacagac ctggaacgag tgttagaagc aaatgatggc    360
tcaggaatgt tagacgaaga tgaggaggat ttgcagaggg ctctggcact aagtcgccaa    420
gaaattgaca tggaagatga ggaagcagat ctccgcaggg ctattcagct aagtatgcaa    480
ggtagttcca gaaacatatc tcaagatatg acacagacat caggtacaaa tcttacttca    540
gaagagcttc ggaagagacg agaagcctac tttgaaaaac agcagcaaaa gcagcaacag    600
cagcagcagc agcagcagca gggggaccta tcaggacaga gttcacatcc atgtgaaagg    660
ccagccacca gttcaggagc acttgggagt gatctaggtg atgctatgag tgaagaagac    720
atgcttcagg cagctgtgac catgtcttta gaaactgtca gaaatgattt gaaaacagaa    780
ggaaaaaaat aataccttta aaaataatt tagatattca tactttccaa cattatcctg    840
tgtgattaca gcatagggtc cactttggta atgtgtcaaa gagatgagga aataagactt    900
ttagcggttt gcaaacaaaa tgatgggaaa gtggaacaat gcgtcggttg taggactaaa    960
taatgatctt ccaaatatta gccaaagagg cattcagcaa ttaaagacat ttaaaatagt   1020
tttctaaatg tttcttttc ttttttgagt gtgcaatatg taacatgtct aaagttaggg   1080
catttttctt ggatctttt gcagactagc taattagctc tcgcctcagg cttttttccat  1140
atagtttgtt ttctttttct gtcttgtagg taagttggct cacatcatgt aatagtggct   1200
ttcatttctt attaaccaaa ttaacctttc aggaaagtat ctctactttc ctgatgttga   1260
taatagtaat ggttctagaa ggatgaacag ttctcccttc aactgtatac cgtgtgctcc   1320
agtgttttct tgtgttgttt tctctgatca caacttttct gctacctggt tttcattatt   1380
ttcccacaat tcttttgaaa gatggtaatc ttttctgagg tttagcgttt taagccctac   1440
gatgggatca ttatttcatg actggtgcgt tcctaaactc tgaaatcagc cttgcacaag   1500
tacttgagaa taaatgagca ttttttaaaa tgtgtgagca tgtgctttcc cagatgcttt   1560
atgaatgtct tttcacttat atcaaaaacct tacagctttg ttgcaacccc ttcttcctgc   1620
gccttatttt ttcctttctt ctccaattga gaaaactagg agaagcatag tatgcaggca   1680
agtctccttc tgttagaaga ctaaacatac gtacccacca tgaatgtatg atacatgaaa   1740
tttggccttc aatttaata gcagttttat tttattttt ctcctatgac tggagctttg    1800
tgttctcttt acagttgagt catggaatgt aggtgtctgc ttcacatctt ttagtaggta   1860
tagcttgtca aagatggtga tctggaacat gaaaataatt tactaatgaa aatatgttta   1920
aatttatact gtgatttgac acttgcatca tgtttagata gcttaagaac aatggaagtc   1980
acagtactta gtggatctat aaataagaaa gtccatagtt ttgataaata ttctctttaa   2040
ttgagatgta cagagagttt cttgctgggt caataggata gtatcatttt ggtgaaaacc   2100
atgtctctga aattgatgtt ttagtttcag tgttccctat ccctcattct ccatctcctt   2160
ttgaagctct tttgaatgtt gaattgttca taagctaaaa tccaagaaat ttcagctgac   2220
aacttcgaaa attataatat ggtatattgc cctcctggtg tgtggctgca cacattttat   2280
cagggaaagt ttttttgatct aggatttatt gctaactaac tgaaaagaga agaaaaaata  2340
tcttttattt atgattataa aatagctttt tcttcgatat aacagatttt ttaagtcatt   2400
attttgtgcc aatcagtttt ctgaagtttc ccttacacaa aaggatagct ttattttaaa   2460
atctaaagtt tcttttaata gttaaaaatg tttcagaaga attataaaac tttaaaactg   2520
```

```
caagggatgt tggagtttag tactactccc tcaagattta aaaagctaaa tattttaaga    2580
ctgaacattt atgttaatta ttaccagtgt gtttgtcata ttttccatgg atatttgttc    2640 attaccttt tccattgaaa agttacatta aactttcat acacttgaat tgatgagcta     2700
cctaatataa aaatgagaaa accaatatgc attttaaagt tttaacttta gagtttataa    2760
agttcatata taccctagtt aaagcactta agaaaatatg gcatgtttga cttttagttc    2820
ctagagagtt tttgttttg ttttgtttt tttgagac ggagtcttgc tatgtctccc      2880
aggctggagg gcagtggcat gatctcggct cactacaact tccacctccc gggttcaagc    2940
aattctcctg cctcagcctc cagagtagct gggattacag gcgcccacca ccacacccgg    3000 cagattttg tattttggt agagacgcgg tttcatcatg tttggccagg ctggtctcga     3060
actcctgacc tcaggtgatc cgcctgcctt ggcctcccaa agtgttggga ttacaggcat    3120
gagccactgc gcctggccag ctagagagtt tttaaagcag agctgagcac acactggatg    3180
cgtttgaatg tgtttgtgta gtttgttgtg aaattgttac atttagcagg cagatccaga    3240
agcactagtg aactgtcatc ttggtggggt tggcttaaat ttaattgact gtttagattc    3300
catttcttaa ttgattggcc agtatgaaaa gatgccagtg caagtaacca tagtatcaaa    3360
aaagttaaaa attattcaaa gctatagttt atacatcagg tactgccatt tactgtaaac    3420
cacctgcaag aaagtcagga acaactaaat tcacaagaac tgtcctgcta agaagtgtat    3480
taaagatttc cattttgttt tactaattgg gaacatctta atgtttaata tttaaactat    3540
tggtatcatt tttctaatgt ataatttgta ttactgggat caagtatgta cagtggtgat    3600
gctagtagaa gtttaagcct tggaaatacc acttttcatat tttcagatgt catggattta    3660
atgagtaatt tatgttttta aaattcagaa tagttaatct ctgatctaaa accatcaatc    3720 tatgttttt acggtaatca tgtaaatatt tcagtaatat aaactgtttg aaaaggctgc    3780
tgcaggtaaa ctctatacta ggatcttggc caaataattt acaattcaca gaatatttta    3840
tttaaggtgg tgcttttttt ttttgtcctt aaaacttgat ttttcttaac tttattcatg    3900
atgccaaagt aaatgaggaa aaaaactcaa aaccagttga gtatcattgc agacaaaact    3960
accagtagtc catattgttt aatattaagt tgaataaaat aaattttatt tcagtcagag    4020
cctaaatcac attttgattg tctgaatttt tgatactatt tttaaaatca tgctagtggc    4080
ggctgggcgt ggtagctcac gcctgtaatc ccagcatttt gggaggccga agtgggtgga    4140
tcacgaggtc gggagttcga accagcttg gccaaaatgg tgaaacccca tctgtactaa    4200
aaactacaaa aattagctgg gcgcggtggc aggtgcctgt aatcccagct acctgggagt    4260
ctgaggcagg agaattgctt gaaccctggc gacagaggat gcagtgagcc aagatggtgc    4320
cactgtactc cagactgggc gacagagtga gactctgtct caaaaaaaaa aaaaaaatca    4380
tgctagtgcc aagagctact aaattcttaa aaccggccca ttggacctgt acagataaaa    4440
aatagattca gtgcataatc aaaatatgat aattttaaaa tcttaagtag aaaaataaat    4500
cttgatgttt taaattctta cgaggattca atagttaata ttgatgatct cccggctggg    4560
tgcagtggct cacgcctgta atcccagcag ttctggaggc tgaggtgggc gaatcacttc    4620
aggccaggag ttcaagacca gtctgggcaa catggtgaaa cctcgtttct actaaaaata    4680
caaaaattag ccgggcgtgg ttgcacacac ttgtaatccc agctactcag gaggctaaga    4740
atcgcatgag cctaggaggc agaggttgca gagtgccaag ggctcaccac tgcattccag    4800
cctgcccaac agagtgagac actgtttctg aaaaaaaaaa atatatatat atatatatat    4860
```

-continued

| | |
|---|---|
| atgtgtgtat atatatatgt atatatatat gacttcctat taaaaacttt atcccagtcg | 4920 |
| ggggcagtgg ctcacgcctg taatcccaac actttgggag gctgaggcag gtggatcacc | 4980 |
| tgaagtccgg agtttgagac cagcctggcc aacatggtga aaccccatct ctactaaaaa | 5040 |
| tacaaaactt aagccaggta tggtggcggg cacctgtaat cccagttact tgggaggctg | 5100 |
| aggcaggaga atcgtttaaa cccaggaggt ggaggttgca gtgagctgag atcgtgccat | 5160 |
| tgcactctag cctgggcaac aagagtaaaa ctccatctta aaggtttgtt tgttttttt | 5220 |
| taatccggaa acgaagaggc gttgggccgc tattttcttt ttctttcttt ctttctttct | 5280 |
| ttttttttt ttctgagacg gagtctagct ctgctgccca ggctggagta caatgacacg | 5340 |
| atgttggctc actgcaacct ccacctcctg ggttcaagcg attctcctgc ctcagcctcc | 5400 |
| caagtacctg ggattacagg cacctgccac tacacctggc gaatatttgt ttttttagt | 5460 |
| agagacgggc ttttaccatg ttaggctggt ctcaaactcc tgacctcagg tgatctgcct | 5520 |
| gccttggcct cccaaagtgc tgggattaca ggtgcaggcc accacacccg gccttgggcc | 5580 |
| actgttttca aagtgaattg tttgttgtat cgagtcctta agtatggata tatatgtgac | 5640 |
| cctaattaag aactaccaga ttggatcaac taatcatgtc agcaatgtaa ataactttat | 5700 |
| ttttcatatt caaaataaaa actttctttt atttctggcc cctttataac cagcatcttc | 5760 |
| ttgctttaaa aaatgacctg gctttgtatt ttttagtct taaacataat aaaaatattt | 5820 |
| ttgttctaat ttgctttcat gagtgaagat tattgacatc gttggtaaat tctagaattt | 5880 |
| tgattttgtt ttttaatttg aagaaaatct ttgctattat tattttttcc aagtggtctg | 5940 |
| gcattttaag aattagtgct aataacgtaa cttctaaatt tgtcgtaatt ggcatgttta | 6000 |
| atagcatatc aaaaaacatt ttaagcctgt ggattcatag acaaagcaat gagaaacatt | 6060 |
| agtaaaatat aaatggatat tcctgatgca tttaggaagc tctcaattgt ctcttgcata | 6120 |
| gttcaaggaa tgttttctga atttttttaa tgctttttt tttttttgaaa gaggaaaaca | 6180 |
| tacatttta aatgtgatta tctaatttt acaacactgg gctattagga ataacttttt | 6240 |
| aaaaattact gttctgtata aatatttgaa attcaagtac agaaaatatc tgaaacaaaa | 6300 |
| agcattgttg tttggccatg atacaagtgc actgtggcag tgccgcttgc tcaggaccca | 6360 |
| gccctgcagc ccttctgtgt gtgctccctc gttaagttca tttgctgtta ttacacacac | 6420 |
| aggccttcct gtctggtcgt tagaaaagcc gggcttccaa agcactgttg aacacaggat | 6480 |
| tctgttgtta gtgtggatgt tcaatgagtt gtatttaaaa tatcaaagat tattaaataa | 6540 |
| agataatgtt tgcttttcta | 6560 |

<210> SEQ ID NO 10
<211> LENGTH: 6835
<212> TYPE: DNA
<213> ORGANISM: Homo sapiens

<400> SEQUENCE: 10

| | |
|---|---|
| gagaggggca gggggcggag ctggaggggg tggttcggcg tgggggccgt tggctccaga | 60 |
| caaataaaca tggagtccat cttccacgag aaacaagaag gctcactttg tgctcaacat | 120 |
| tgcctgaata acttattgca aggagaatat tttagccctg tggaattatc ctcaattgca | 180 |
| catcagctgg atgaggagga gaggatgaga atggcagaag gaggagttac tagtgaagat | 240 |
| tatcgcacgt tttacagca gccttctgga aatatggatg acagtggttt tttctctatt | 300 |
| caggttataa gcaatgcctt gaaagtttgg ggtttagaac taatcctgtt caacagtcca | 360 |
| gagtatcaga ggctcaggat cgatcctata aatgaaagat catttatatg caattataag | 420 |

-continued

```
gaacactggt ttacagttag aaaattagga aaacaggtta ttctatattt gtcgttaagg    480
gtgatctgcc agattgcgaa gctgaccaac tcctgcagat gattagggtc aacagatgc     540 atcgaccaaa acttattgga gaagaattag cacaactaaa agagcaaaga gtccataaaa    600
cagacctgga acgagtgtta gaagcaaatg atggctcagg aatgttagac gaagatgagg    660
aggatttgca gagggctctg gcactaagtc gccaagaaat tgacatggaa gatgaggaag    720
cagatctccg cagggctatt cagctaagta tgcaaggtag ttccagaaac atatctcaag    780
atatgacaca gacatcaggt acaaatctta cttcagaaga gcttcggaag agacgagaag    840
cctactttga aaaacagcag caaaagcagc aacagcagca gcagcagcag cagcagggg     900 acctatcagg acagagttca catccatgtg aaaggccagc caccagttca ggagcacttg    960
ggagtgatct aggtgatgct atgagtgaag aagacatgct tcaggcagct gtgaccatgt   1020
ctttagaaac tgtcagaaat gatttgaaaa cagaaggaaa aaaataatac ctttaaaaaa   1080
taatttagat attcatactt tccaacatta tcctgtgtga ttacagcata gggtccactt   1140
tggtaatgtg tcaaagagat gaggaaataa gacttttagc ggtttgcaaa caaaatgatg   1200
ggaaagtgga acaatgcgtc ggttgtagga ctaaataatg atcttccaaa tattagccaa   1260
agaggcattc agcaattaaa gacatttaaa atagttttct aaatgtttct ttttcttttt   1320
tgagtgtgca atatgtaaca tgtctaaagt tagggcattt tcttggatc ttttgcaga     1380 ctagctaatt agctctcgcc tcaggctttt tccatatagt ttgttttctt tttctgtctt   1440
gtaggtaagt tggctcacat catgtaatag tggctttcat ttcttattaa ccaaattaac   1500
ctttcaggaa agtatctcta cttctgat gttgataata gtaatggttc tagaaggatg     1560
aacagttctc ccttcaactg tataccgtgt gctccagtgt tttcttgtgt tgttttctct   1620
gatcacaact tttctgctac ctggttttca ttattttccc acaattcttt tgaaagatgg   1680 taatctttc tgaggtttag cgttttaagc cctacgatgg gatcattatt tcatgactgg    1740
tgcgttccta aactctgaaa tcagccttgc acaagtactt gagaataaat gagcattttt   1800
taaaatgtgt gagcatgtgc tttcccagat gctttatgaa tgtcttttca cttatatcaa   1860
aaccttacag ctttgttgca accccttctt cctgcgcctt attttttcct ttcttctcca   1920
attgagaaaa ctaggagaag catagtatgc aggcaagtct ccttctgtta gaagactaaa   1980
catacgtacc caccatgaat gtatgataca tgaaatttgg ccttcaattt taatagcagt   2040 tttatttttat tttttctcct atgactggag ctttgtgttc tctttacagt tgagtcatgg   2100
aatgtaggtg tctgcttcac atcttttagt aggtatagct tgtcaaagat ggtgatctgg   2160
aacatgaaaa taatttacta atgaaaatat gtttaaattt atactgtgat ttgacacttg   2220
catcatgttt agatagctta agaacaatgg aagtcacagt acttagtgga tctataaata   2280
agaaagtcca tagtttttgat aaatattctc tttaattgag atgtacagag agtttcttgc   2340
tgggtcaata ggatagtatc attttggtga aaaccatgtc tctgaaattg atgttttagt   2400
ttcagtgttc cctatccctc attctccatc tccttttgaa gctcttttga atgttgaatt   2460
gttcataagc taaaatccaa gaaatttcag ctgacaactt cgaaaattat aatatggtat   2520
attgccctcc tggtgtgtgg ctgcacacat tttatcaggg aaagtttttt gatctaggat   2580
ttattgctaa ctaactgaaa agagaagaaa aaatatcttt tatttatgat tataaaatag   2640 cttttttcttc gatataacag attttttaag tcattatttt gtgccaatca gttttctgaa   2700 gtttcccttta cacaaaagga tagctttatt ttaaaatcta aagtttcttt taatagttaa   2760
```

```
aaatgtttca gaagaattat aaaactttaa aactgcaagg gatgttggag tttagtacta    2820
ctccctcaag atttaaaaag ctaaatattt taagactgaa catttatgtt aattattacc    2880
agtgtgtttg tcatattttc catggatatt tgttcattac cttttccat tgaaaagtta     2940 cattaaactt ttcatacact tgaattgatg agctaccta tataaaatg agaaaaccaa      3000 tatgcatttt aaagttttaa ctttagagtt tataaagttc atatataccc tagttaaagc    3060
acttaagaaa atatggcatg tttgactttt agttcctaga gagttttgt ttttgttttt     3120 gttttttttt gagacggagt cttgctatgt ctcccaggct ggagggcagt ggcatgatct    3180
cggctcacta caacttccac ctcccgggtt caagcaattc tcctgcctca gcctccagag    3240
tagctgggat tacaggcgcc caccaccaca cccggcagat ttttgtattt ttggtagaga    3300
cgcggtttca tcatgtttgg ccaggctggt ctcgaactcc tgacctcagg tgatccgcct    3360
gccttggcct cccaaagtgt tgggattaca ggcatgagcc actgcgcctg ccagctaga    3420 gagtttttaa agcagagctg agcacacact ggatgcgttt gaatgtgttt gtgtagtttg    3480
ttgtgaaatt gttacattta gcaggcagat ccagaagcac tagtgaactg tcatcttggt    3540
ggggttggct taaatttaat tgactgttta gattccattt cttaattgat tggccagtat    3600
gaaaagatgc cagtgcaagt aaccatagta tcaaaaagt taaaaattat tcaaagctat     3660
agtttataca tcaggtactg ccatttactg taaaccacct gcaagaaagt caggaacaac    3720
taaattcaca agaactgtcc tgctaagaag tgtattaaag atttccattt tgttttacta    3780
attgggaaca tcttaatgtt taatatttaa actattggta tcattttct aatgtataat     3840 ttgtattact gggatcaagt atgtacagtg gtgatgctag tagaagttta agccttggaa    3900
ataccacttt catattttca gatgtcatgg atttaatgag taatttatgt ttttaaaatt    3960
cagaatagtt aatctctgat ctaaaaccat caatctatgt ttttacggt aatcatgtaa     4020 atatttcagt aatataaact gtttgaaaag gctgctgcag gtaaactcta tactaggatc    4080
ttggccaaat aatttacaat tcacagaata ttttatttaa ggtggtgctt tttttttttg    4140
tccttaaaac ttgatttttc ttaactttat tcatgatgcc aaagtaaatg aggaaaaaaa    4200
ctcaaaacca gttgagtatc attgcagaca aaactaccag tagtccatat tgtttaatat    4260
taagttgaat aaaataaatt ttatttcagt cagagcctaa atcacatttt gattgtctga    4320 attttgata ctattttaa aatcatgcta gtggcggctg ggcgtggtag ctcacgcctg      4380
taatcccagc attttgggag gccgaagtgg gtggatcacg aggtcgggag ttcgagacca    4440
gcttggccaa aatggtgaaa ccccatctgt actaaaaact acaaaaatta gctgggcgcg    4500
gtggcaggtg cctgtaatcc cagctacctg ggagtctgag gcaggagaat tgcttgaacc    4560
ctggcgacag aggatgcagt gagccaagat ggtgccactg tactccagac tgggcgacag    4620
agtgagactc tgtctcaaaa aaaaaaaaa aatcatgcta gtgccaagag ctactaaatt     4680
cttaaaaccg gcccattgga cctgtacaga taaaaatag attcagtgca taatcaaaat     4740
atgataattt taaaatctta agtagaaaaa taaatcttga tgttttaaat tcttacgagg    4800
attcaatagt taatattgat gatctcccgg ctgggtgcag tggctcacgc ctgtaatccc    4860
agcagttctg gaggctgagg tgggcgaatc acttcaggcc aggagttcaa gaccagtctg    4920
ggcaacatgg tgaaacctcg tttctactaa aaatacaaaa attagccggg cgtggttgca    4980
cacacttgta atcccagcta ctcaggaggc taagaatcgc atgagcctag gaggcagagg    5040
ttgcagagtg ccagggctc accactgcat tccagcctgc ccaacagagt gagacactgt     5100
ttctgaaaaa aaaaaatata tatatatata tatatatgtg tgtatatata tatgtatata    5160
```

```
tatatgactt cctattaaaa actttatccc agtcggggc agtggctcac gcctgtaatc      5220
ccaacacttt gggaggctga ggcaggtgga tcacctgaag tccggagttt gagaccagcc      5280
tggccaacat ggtgaaaccc catctctact aaaaatacaa aacttaagcc aggtatggtg      5340
gcgggcacct gtaatcccag ttacttggga ggctgaggca ggagaatcgt ttaaacccag      5400
gaggtggagg ttgcagtgag ctgagatcgt gccattgcac tctagcctgg caacaagag       5460 taaaactcca tcttaaaggt ttgtttgttt tttttaatc cggaaacgaa gaggcgttgg       5520
gccgctattt tcttttttctt tctttctttc tttcttttttt ttttttttctg agacggagtc   5580 tagctctgct gcccaggctg gagtacaatg acacgatgtt ggctcactgc aacctccacc      5640
tcctgggttc aagcgattct cctgcctcag cctcccaagt acctgggatt acaggcacct      5700
gccactacac ctggcgaata tttgtttttt ttagtagaga cgggcttttta ccatgttagg     5760 ctggtctcaa actcctgacc tcaggtgatc tgcctgcctt ggcctcccaa agtgctggga     5820
ttacaggtgc aggccaccac acccggcctt gggccactgt tttcaaagtg aattgtttgt     5880
tgtatcgagt ccttaagtat ggatatatat gtgaccctaa ttaagaacta ccagattgga     5940
tcaactaatc atgtcagcaa tgtaaataac tttattttc atattcaaaa taaaaacttt      6000
cttttatttc tggccccttt ataaccagca tcttttgct ttaaaaatg acctggcttt       6060 gtatttttt agtcttaaac ataataaaaa tatttgtt ctaatttgct ttcatgagtg         6120
aagattattg acatcgttgg taaattctag aattttgatt ttgttttta atttgaagaa      6180 aatctttgct attattattt tttccaagtg gtctggcatt ttaagaatta gtgctaataa     6240
cgtaacttct aaatttgtcg taattggcat gtttaatagc atatcaaaaa acattttaag     6300
cctgtggatt catagacaaa gcaatgagaa acattagtaa aatataaatg gatattcctg     6360
atgcatttag gaagctctca attgtctctt gcatagttca aggaatgttt tctgaatttt      6420
tttaatgctt ttttttttt tgaaagagga aaacatacat tttaaatgt gattatctaa       6480 tttttacaac actgggctat taggaataac ttttaaaaa ttactgttct gtataaatat      6540
ttgaaattca agtacagaaa atatctgaaa caaaaagcat tgttgtttgg ccatgataca     6600
agtgcactgt ggcagtgccg cttgctcagg acccagccct gcagccttc tgtgtgtgct     6660 ccctcgttaa gttcatttgc tgttattaca cacacaggcc ttcctgtctg gtcgttagaa     6720
aagccgggct tccaaagcac tgttgaacac aggattctgt tgttagtgtg gatgttcaat     6780
gagttgtatt ttaaatatca agattatta ataaagata atgtttgctt ttcta            6835

<210> SEQ ID NO 11
<211> LENGTH: 6472
<212> TYPE: DNA
<213> ORGANISM: Homo sapiens

<400> SEQUENCE: 11
gagaggggca gggggcggag ctggaggggg tggttcggcg tgggggccgt tggctccaga       60
caaataaaca tggagtccat cttccacgag aaagttattc tatatttgtc gttaagggtg      120
atctgccaga ttgcgaagct gaccaactcc tgcagatgat tagggtccaa cagatgcatc      180
gaccaaaact tattggagaa gaattagcac aactaaaaga gcaaagagtc cataaaacag      240
acctggaacg agtgttagaa gcaaatgatg gctcaggaat gttagacgaa gatgaggagg      300
atttgcagag ggctctggca ctaagtcgcc aagaaattga catggaagat gaggaagcag      360
atctccgcag ggctattcag ctaagtatgc aaggtagttc cagaaacata tctcaagata      420
```

```
tgacacagac atcaggtaca aatcttactt cagaagagct tcggaagaga cgagaagcct    480
actttgaaaa acagcagcaa aagcagcaac agcagcagca gcagcagcag cagggggacc    540
tatcaggaca gagttcacat ccatgtgaaa ggccagccac cagttcagga gcacttggga    600
gtgatctagg tgatgctatg agtgaagaag acatgcttca ggcagctgtg accatgtctt    660
tagaaactgt cagaaatgat ttgaaaacag aaggaaaaaa ataatacctt taaaaaataa    720
tttagatatt catactttcc aacattatcc tgtgtgatta cagcataggg tccactttgg    780
taatgtgtca aagagatgag gaaataagac ttttagcggt ttgcaaacaa aatgatggga    840
aagtggaaca atgcgtcggt tgtaggacta aataatgatc ttccaaatat tagccaaaga    900
ggcattcagc aattaaagac atttaaaata gttttctaaa tgtttctttt tctttttga    960
gtgtgcaata tgtaacatgt ctaaagttag ggcatttttc ttggatcttt ttgcagacta   1020
gctaattagc tctcgcctca ggcttttttcc atatagtttg ttttcttttt ctgtcttgta   1080
ggtaagttgg ctcacatcat gtaatagtgg ctttcatttc ttattaacca aattaacctt   1140
tcaggaaagt atctctactt tcctgatgtt gataatagta atggttctag aaggatgaac   1200
agttctccct tcaactgtat accgtgtgct ccagtgtttt cttgtgttgt tttctctgat   1260
cacaactttt ctgctacctg gttttcatta ttttcccaca attcttttga aagatggtaa   1320
tcttttctga ggtttagcgt tttaagccct acgatgggat cattatttca tgactggtgc   1380
gttcctaaac tctgaaatca gccttgcaca agtacttgag aataaatgag catttttaa   1440
aatgtgtgag catgtgcttt cccagatgct ttatgaatgt cttttcactt atatcaaaac   1500
cttacagctt tgttgcaacc ccttcttcct gcgccttatt ttttcctttc ttctccaatt   1560
gagaaaacta ggagaagcat agtatgcagg caagtctcct tctgttagaa gactaaacat   1620
acgtacccac catgaatgta tgatacatga aatttggcct tcaattttaa tagcagtttt   1680
attttatttt ttctcctatg actggagctt tgtgttctct ttacagttga gtcatggaat   1740
gtaggtgtct gcttcacatc ttttagtagg tatagcttgt caaagatggt gatctggaac   1800
atgaaaataa tttactaatg aaaatatgtt taaatttata ctgtgatttg acacttgcat   1860
catgtttaga tagcttaaga acaatggaag tcacagtact tagtggatct ataaataaga   1920
aagtccatag ttttgataaa tattctcttt aattgagatg tacagagagt ttcttgctgg   1980
gtcaatagga tagtatcatt ttggtgaaaa ccatgtctct gaaattgatg tttttagtttc   2040
agtgttccct atccctcatt ctccatctcc ttttgaagct cttttgaatg ttgaattgtt   2100
cataagctaa aatccaagaa atttcagctg acaacttcga aaattataat atggtatatt   2160
gccctcctgg tgtgtggctg cacacatttt atcagggaaa gttttttgat ctaggattta   2220
ttgctaacta actgaaaaga gaagaaaaaa tatcttttat ttatgattat aaaatagctt   2280
tttcttcgat ataacagatt ttttaagtca ttattttgtg ccaatcagtt ttctgaagtt   2340
tcccttacac aaaaggatag ctttatttta aaatctaaag tttcttttaa tagttaaaaa   2400
tgtttcagaa gaattataaa actttaaaac tgcaagggat gttggagttt agtactactc   2460
cctcaagatt taaaaagcta aatattttaa gactgaacat ttatgttaat tattaccagt   2520
gtgtttgtca tattttccat ggatatttgt tcattacctt tttccattga aaagttacat   2580
taaactttc atacacttga attgatgagc tacctaatat aaaaatgaga aaaccaatat   2640
gcattttaaa gttttaactt tagagtttat aaagttcata tatccctag ttaaagcact   2700
taagaaaata tggcatgttt gacttttagt tcctagagag ttttgttttt tgttttgtt   2760
tttttttgag acggagtctt gctatgtctc ccaggctgga gggcagtggc atgatctcgg   2820
```

```
ctcactacaa cttccacctc ccggcttcaa gcaattctcc tgcctcagcc tccagagtag    2880
ctgggattac aggcgcccac caccacaccc ggcagatttt tgtattttg gtagagacgc     2940 ggtttcatca tgtttggcca ggctggtctc gaactcctga cctcaggtga tccgcctgcc    3000
ttggcctccc aaagtgttgg gattacaggc atgagccact gcgcctggcc agctagagag    3060
tttttaaagc agagctgagc acacactgga tgcgtttgaa tgtgtttgtg tagtttgttg    3120
tgaaattgtt acatttagca ggcagatcca gaagcactag tgaactgtca tcttggtggg    3180
gttggcttaa atttaattga ctgtttagat tccatttctt aattgattgg ccagtatgaa    3240
aagatgccag tgcaagtaac catagtatca aaaagttaa aaattattca aagctatagt     3300
ttatacatca ggtactgcca tttactgtaa accacctgca agaaagtcag gaacaactaa    3360
attcacaaga actgtcctgc taagaagtgt attaaagatt tccattttgt tttactaatt    3420
gggaacatct taatgtttaa tatttaaact attggtatca tttttctaat gtataatttg    3480
tattactggg atcaagtatg tacagtggtg atgctagtag aagtttaagc cttggaaata    3540
ccactttcat attttcagat gtcatggatt taatgagtaa tttatgtttt taaaattcag    3600
aatagttaat ctctgatcta aaaccatcaa tctatgtttt ttacggtaat catgtaaata    3660
tttcagtaat ataaactgtt tgaaaaggct gctgcaggta aactctatac taggatcttg    3720
gccaaataat ttacaattca cagaatattt tatttaaggt ggtgcttttt ttttttgtcc    3780
ttaaaacttg attttctta actttattca tgatgccaaa gtaaatgagg aaaaaaactc     3840
aaaaccagtt gagtatcatt gcagacaaaa ctaccagtag tccatattgt ttaatattaa    3900
gttgaataaa ataaatttta tttcagtcag agcctaaatc acattttgat tgtctgaatt    3960
tttgatacta ttttaaaat catgctagtg gcggctgggc gtggtagctc acgcctgtaa    4020
tcccagcatt ttgggaggcc gaagtgggtg gatcacgagg tcgggagttc gagaccagct    4080
tggccaaaat ggtgaaaccc catctgtact aaaaactaca aaaattagct gggcgcggtg    4140
gcaggtgcct gtaatcccag ctacctggga gtctgaggca ggagaattgc ttgaaccctg    4200
gcgacagagg atgcagtgag ccaagatggt gccactgtac tccagactgg gcgacagagt    4260
gagactctgt ctcaaaaaaa aaaaaaaat catgctagtg ccaagagcta ctaaattctt     4320
aaaaccggcc cattggacct gtacagataa aaaatagatt cagtgcataa tcaaaatatg    4380 ataatttaa aatcttaagt agaaaataa atcttgatgt tttaaattct tacgaggatt      4440
caatagttaa tattgatgat ctcccggctg ggtgcagtgg ctcacgcctg taatcccagc    4500
agttctggag gctgaggtgg gcgaatcact tcaggccagg agttcaagac cagtctgggc    4560
aacatggtga aacctcgttt ctactaaaaa tacaaaaatt agccgggcgt ggttgcacac    4620
acttgtaatc ccagctactc aggaggctaa gaatcgcatg agcctaggag gcagaggttg    4680
cagagtgcca agggctcacc actgcattcc agcctgccca acagagtgag acactgtttc    4740 tgaaaaaaa aaatatatat atatatatat atatgtgtgt atatatatat gtatatatat     4800
atgacttcct attaaaaact ttatcccagt cgggggcagt ggctcacgcc tgtaatccca    4860
acactttggg aggctgaggc aggtggatca cctgaagtcc ggagtttgag accagcctgg    4920
ccaacatggt gaaaccccat ctctactaaa aatacaaaac ttaagccagg tatggtggcg    4980
ggcacctgta atcccagtta cttgggaggc tgaggcagga gaatcgttta aacccaggag    5040
gtggaggttg cagtgagctg agatcgtgcc attgcactct agcctgggca acaagagtaa    5100
aactccatct taaaggtttg tttgtttttt tttaatccgg aaacgaagag gcgttgggcc    5160
```

```
gctattttct ttttctttct ttctttcttt ctttttttttt ttttctgaga cggagtctag    5220
ctctgctgcc caggctggag tacaatgaca cgatgttggc tcactgcaac ctccacctcc    5280
tgggttcaag cgattctcct gcctcagcct cccaagtacc tgggattaca ggcacctgcc    5340
actacacctg gcgaatattt gttttttta gtagagacgg gcttttacca tgttaggctg    5400
gtctcaaact cctgacctca ggtgatctgc ctgccttggc ctcccaaagt gctgggatta    5460
caggtgcagg ccaccacacc cggccttggg ccactgtttt caaagtgaat tgtttgttgt    5520
atcgagtcct taagtatgga tatatatgtg accctaatta agaactacca gattggatca    5580
actaatcatg tcagcaatgt aaataacttt atttttcata ttcaaaataa aactttctt     5640 ttatttctgg cccctttata accagcatct ttttgcttta aaaaatgacc tggctttgta    5700 ttttttagt cttaaacata ataaaaatat ttttgttcta atttgctttc atgagtgaag     5760
attattgaca tcgttggtaa attctagaat tttgattttg ttttttaatt tgaagaaaat    5820
ctttgctatt attattttt ccaagtggtc tggcatttta agaattagtg ctaataacgt     5880
aacttctaaa tttgtcgtaa ttggcatgtt taatagcata tcaaaaaaca ttttaagcct    5940
gtggattcat agacaaagca atgagaaaca ttagtaaaat ataaatggat attcctgatg    6000
catttaggaa gctctcaatt gtctcttgca tagttcaagg aatgttttct gaattttttt    6060
aatgcttttt ttttttttga aagaggaaaa catacatttt taaatgtgat tatctaattt    6120
ttacaacact gggctattag gaataacttt ttaaaaatta ctgttctgta taaatatttg    6180
aaattcaagt acagaaaata tctgaaacaa aaagcattgt tgtttggcca tgatacaagt    6240
gcactgtggc agtgccgctt gctcaggacc cagccctgca gcccttctgt gtgtgctccc    6300
tcgttaagtt catttgctgt tattacacac acaggccttc ctgtctggtc gttagaaaag    6360
ccgggcttcc aaagcactgt tgaacacagg attctgttgt tagtgtggat gttcaatgag    6420
ttgtatttta aatatcaaag attattaaat aaagataatg tttgcttttc ta            6472
```

<210> SEQ ID NO 12
<211> LENGTH: 6814
<212> TYPE: DNA
<213> ORGANISM: Homo sapiens

<400> SEQUENCE: 12

```
gagaggggca gggggcggag ctggaggggg tggttcggcg tgggggccgt tggctccaga      60
caaataaaca tggagtccat cttccacgag aaacaagaag gctcactttg tgctcaacat     120
tgcctgaata acttattgca aggagaatat tttagccctg tggaattatc ctcaattgca     180
catcagctgg atgaggagga gaggatgaga atggcagaag gaggagttac tagtgaagat     240
tatcgcacgt ttttacagca gccttctgga aatatggatg acagtggttt tttctctatt     300
cagaaatgaa agatcattta tatgcaatta taaggaacac tggtttacag ttagaaaatt     360
aggaaaacag tggtttaact tgaattctct cttgacgggt ccagaattaa tatcagatac     420
atatcttgca ctttcttgg ctcaattaca acaggaaggg tgatctgcca gattgcgaag      480
ctgaccaact cctgcagatg attagggtcc aacagatgca tcgaccaaaa cttattggag    540
aagaattagc acaactaaaa gagcaaagag tccataaaac agacctggaa cgagtgttag    600
aagcaaatga tggctcagga atgttagacg aagatgagga ggatttgcag agggctctgg    660
cactaagtcg ccaagaaatt gacatggaag atgaggaagc agatctccgc agggctattc    720
agctaagtat gcaaggtagt tccagaaaca tatctcaaga tatgacacag acatcaggta    780
caaatcttac ttcagaagag cttcggaaga gacgagaagc ctactttgaa aaacagcagc    840
```

```
aaaagcagca acagcagcag cagcagcagc agcaggggga cctatcagga cagagttcac    900
atccatgtga aaggccagcc accagttcag gagcacttgg gagtgatcta ggtgatgcta    960
tgagtgaaga agacatgctt caggcagctg tgaccatgtc tttagaaact gtcagaaatg   1020
atttgaaaac agaaggaaaa aaataatacc tttaaaaaat aatttagata ttcatacttt   1080
ccaacattat cctgtgtgat tacagcatag ggtccacttt ggtaatgtgt caaagagatg   1140
aggaaataag acttttagcg gtttgcaaac aaaatgatgg gaaagtggaa caatgcgtcg   1200
gttgtaggac taaataatga tcttccaaat attagccaaa gaggcattca gcaattaaag   1260
acatttaaaa tagttttcta aatgtttctt tttcttttt gagtgtgcaa tatgtaacat    1320
gtctaaagtt agggcatttt tcttggatct ttttgcagac tagctaatta gctctcgcct   1380
caggcttttt ccatatagtt tgttttcttt ttctgtcttg taggtaagtt ggctcacatc   1440
atgtaatagt ggctttcatt tcttattaac caaattaacc tttcaggaaa gtatctctac   1500
tttcctgatg ttgataatag taatggttct agaaggatga acagttctcc cttcaactgt   1560
ataccgtgtg ctccagtgtt ttcttgtgtt gttttctctg atcacaactt ttctgctacc   1620
tggttttcat tattttccca caattctttt gaaagatggt aatcttttct gaggtttagc   1680
gttttaagcc ctacgatggg atcattattt catgactggt gcgttcctaa actctgaaat   1740
cagccttgca caagtacttg agaataaatg agcattttt aaaatgtgtg agcatgtgct    1800
ttcccagatg ctttatgaat gtcttttcac ttatatcaaa accttacagc tttgttgcaa   1860
ccccttcttc ctgcgcctta tttttttcctt tcttctccaa ttgagaaaac taggagaagc  1920
atagtatgca ggcaagtctc cttctgttag aagactaaac atacgtaccc accatgaatg   1980
tatgatacat gaaatttggc cttcaatttt aatagcagtt ttattttatt ttttctccta   2040
tgactggagc tttgtgttct ctttacagtt gagtcatgga atgtaggtgt ctgcttcaca   2100
tcttttagta ggtatagctt gtcaaagatg gtgatctgga acatgaaaat aatttactaa   2160
tgaaaatatg tttaaattta tactgtgatt tgacacttgc atcatgttta gatagcttaa   2220
gaacaatgga agtcacagta cttagtggat ctataaataa gaaagtccat agttttgata   2280
aatattctct ttaattgaga tgtacagaga gtttcttgct gggtcaatag gatagtatca   2340
ttttggtgaa aaccatgtct ctgaaattga tgttttagtt tcagtgttcc ctatccctca   2400
ttctccatct ccttttgaag ctcttttgaa tgttgaattg ttcataagct aaaatccaag   2460
aaatttcagc tgacaacttc gaaaattata atatggtata ttgccctcct ggtgtgtggc   2520
tgcacacatt ttatcaggga aagttttttg atctaggatt tattgctaac taactgaaaa   2580
gagaagaaaa aatatctttt atttatgatt ataaaatagc ttttcttcg atataacaga    2640
tttttaagt cattattttg tgccaatcag ttttctgaag tttcccttac acaaaaggat    2700
agctttattt taaaatctaa agttctttt aatagttaaa aatgtttcag aagaattata    2760
aaactttaaa actgcaaggg atgttggagt ttagtactac tccctcaaga tttaaaaagc   2820
taaatatttt aagactgaac atttatgtta attattacca gtgtgtttgt cataattccc   2880
atggatattt gttcattacc ttttttccatt gaaaagttac attaaacttt tcatacactt   2940
gaattgatga gctacctaat ataaaaatga gaaaaccaat atgcatttta aagttttaac   3000
tttagagttt ataaagttca tatatacccct agttaaagca cttaagaaaa tatggcatgt   3060
ttgactttta gttcctagag agttttttgtt tttgttttg tttttttttg agacggagtc   3120
ttgctatgtc tcccaggctg gagggcagtg gcatgatctc ggctcactac aacttccacc   3180
```

-continued

| | |
|---|---|
| tcccgggttc aagcaattct cctgcctcag cctccagagt agctgggatt acaggcgccc | 3240 |
| accaccacac ccggcagatt tttgtatttt tggtagagac gcggtttcat catgtttggc | 3300 |
| caggctggtc tcgaactcct gacctcaggt gatccgcctg ccttggcctc ccaaagtgtt | 3360 |
| gggattacag gcatgagcca ctgcgcctgg ccagctagag agttttttaaa gcagagctga | 3420 |
| gcacacactg gatgcgtttg aatgtgtttg tgtagtttgt tgtgaaattg ttacatttag | 3480 |
| caggcagatc cagaagcact agtgaactgt catcttggtg gggttggctt aaatttaatt | 3540 |
| gactgtttag attccatttc ttaattgatt ggccagtatg aaaagatgcc agtgcaagta | 3600 |
| accatagtat caaaaaagtt aaaaattatt caaagctata gtttatacat caggtactgc | 3660 |
| catttactgt aaaccacctg caagaaagtc aggaacaact aaattcacaa gaactgtcct | 3720 |
| gctaagaagt gtattaaaga tttccatttt gttttactaa ttgggaacat cttaatgttt | 3780 |
| aatatttaaa ctattggtat cattttttcta atgtataatt tgtattactg ggatcaagta | 3840 |
| tgtacagtgg tgatgctagt agaagtttaa gccttggaaa taccactttc atattttcag | 3900 |
| atgtcatgga tttaatgagt aatttatgtt tttaaaattc agaatagtta atctctgatc | 3960 |
| taaaaccatc aatctatgtt ttttacggta atcatgtaaa tatttcagta atataaactg | 4020 |
| tttgaaaagg ctgctgcagg taaactctat actaggatct tggccaaata atttacaatt | 4080 |
| cacagaatat tttatttaag gtggtgcttt ttttttttgt ccttaaaact tgattttct | 4140 |
| taactttatt catgatgcca aagtaaatga ggaaaaaaac tcaaaaccag ttgagtatca | 4200 |
| ttgcagacaa aactaccagt agtccatatt gtttaatatt aagttgaata aaataaattt | 4260 |
| tatttcagtc agagcctaaa tcacatttg attgtctgaa tttttgatac tattttttaaa | 4320 |
| atcatgctag tggcggctgg gcgtggtagc tcacgcctgt aatcccagca ttttgggagg | 4380 |
| ccgaagtggg tggatcacga ggtcgggagt tcgagaccag cttggccaaa atggtgaaac | 4440 |
| cccatctgta ctaaaaacta caaaaattag ctgggcgcgg tggcaggtgc ctgtaatccc | 4500 |
| agctacctgg gagtctgagg caggagaatt gcttgaaccc tggcgacaga ggatgcagtg | 4560 |
| agccaagatg gtgccactgt actccagact gggcgacaga gtgagactct gtctcaaaaa | 4620 |
| aaaaaaaaaa atcatgctag tgccaagagc tactaaattc ttaaaaccgg cccattggac | 4680 |
| ctgtacagat aaaaaataga ttcagtgcat aatcaaaata tgataatttt aaaatcttaa | 4740 |
| gtagaaaaat aaatcttgat gttttaaatt cttacgagga ttcaatagtt aatattgatg | 4800 |
| atctcccggc tgggtgcagt ggctcacgcc tgtaatccca gcagttctgg aggctgaggt | 4860 |
| gggcgaatca cttcaggcca ggagttcaag accagtctgg gcaacatggt gaaacctcgt | 4920 |
| ttctactaaa aatacaaaaa ttagccgggc gtggttgcac acacttgtaa tcccagctac | 4980 |
| tcaggaggct aagaatcgca tgagcctagg aggcagaggt tgcagagtgc aagggctca | 5040 |
| ccactgcatt ccagcctgcc caacagagtg agacactgtt tctgaaaaaa aaaatatat | 5100 |
| atatatatat atatatgtgt gtatatatat atgtatatat atgacttc ctattaaaaa | 5160 |
| ctttatccca gtcgggggca gtggctcacg cctgtaatcc caacactttg ggaggctgag | 5220 |
| gcaggtggat cacctgaagt ccggagtttg agaccagcct ggccaacatg gtgaaacccc | 5280 |
| atctctacta aaaatacaaa acttaagcca ggtatggtgg cgggcacctg taatcccagt | 5340 |
| tacttgggag gctgaggcag gagaatcgtt taaacccagg aggtggaggt tgcagtgagc | 5400 |
| tgagatcgtg ccattgcact ctagcctggg caacaagagt aaaactccat cttaaaggtt | 5460 |
| tgtttgtttt ttttaatcc ggaaacgaag aggcgttggg ccgctatttt cttttctcttt | 5520 |
| ctttctttct ttcttttttt ttttttctga gacggagtct agctctgctg cccaggctgg | 5580 |

```
agtacaatga cacgatgttg gctcactgca acctccacct cctgggttca agcgattctc    5640
ctgcctcagc ctcccaagta cctgggatta caggcacctg ccactacacc tggcgaatat    5700 ttgtttttt  tagtagagac gggcttttac catgttaggc tggtctcaaa ctcctgacct    5760
caggtgatct gcctgccttg gcctcccaaa gtgctgggat tacaggtgca ggccaccaca    5820
cccggccttg ggcactgtt  ttcaaagtga attgtttgtt gtatcgagtc cttaagtatg    5880
gatatatatg tgaccctaat taagaactac cagattggac caactaatca tgtcagcaat    5940
gtaaataact ttattttca  tattcaaaat aaaactttc  ttttatttct ggccccttta    6000
taaccagcat cttttgctt  taaaaaatga cctggctttg tatttttta  gtcttaaaca    6060 taataaaaat attttgttc  taatttgctt tcatgagtga agattattga catcgttggt    6120
aaattctaga atttttgatt tgttttttaa tttgaagaaa atctttgcta ttattatttt    6180
ttccaagtgg tctggcattt taagaattag tgctaataac gtaacttcta aatttgtcgt    6240
aattggcatg tttaatagca tatcaaaaaa cattttaagc ctgtggattc atagacaaag    6300
caatgagaaa cattagtaaa atataaatgg atattcctga tgcatttagg aagctctcaa    6360
ttgtctcttg catagttcaa ggaatgtttt ctgaattttt ttaatgcttt ttttttttt     6420 gaaagaggaa aacatacatt tttaaatgtg attatctaat ttttacaaca ctgggctatt    6480
aggaataact ttttaaaaat tactgttctg tataaatatt tgaaattcaa gtacagaaaa    6540
tatctgaaac aaaaagcatt gttgtttggc catgatacaa gtgcactgtg gcagtgccgc    6600
ttgctcagga cccagccctg cagcccttct gtgtgtgctc cctcgttaag ttcatttgct    6660
gttattacac acacaggcct tcctgtctgg tcgttagaaa agccgggctt ccaaagcact    6720
gttgaacaca ggattctgtt gttagtgtgg atgttcaatg agttgtattt taaatatcaa    6780
agattattaa ataaagataa tgtttgcttt tcta                                6814
```

```
<210> SEQ ID NO 13
<211> LENGTH: 6838
<212> TYPE: DNA
<213> ORGANISM: Homo sapiens

<400> SEQUENCE: 13
```

```
gagaggggca gggggcggag ctggagggg  tggttcggcg tggggccgt  tggctccaga      60 caaataaaca tggagtccat cttccacgag aaacaagaag gctcactttg tgctcaacat     120
tgcctgaata acttattgca aggagaatat tttagccctg tggaattatc ctcaattgca     180
catcagctgg atgaggagga gaggatgaga atggcagaag gaggagttac tagtgaagat     240
tatcgcacgt ttttacagca gccttctgga aatatggatg acagtggttt tttctctatt     300
cagtggttta acttgaattc tctcttgacg ggtccagaat taatatcaga tacatatctt     360
gcacttttct tggctcaatt acaacaggaa gtcactcaat gagacggctc ttccagtctt     420
acaatggaga aagtgaggct cagagacttt aagtaactta ccttagacga ctttactagt     480
aaggtgatct gccagattgc gaagctgacc aactcctgca gatgattagg gtccaacaga     540
tgcatcgacc aaaacttatt ggagaagaat tagcacaact aaaagagcaa agagtccata     600
aaacagacct ggaacgagtg ttagaagcaa atgatggctc aggaatgtta gacgaagatg     660
aggaggattt gcagagggct ctggcactaa gtcgccaaga aattgacatg aagatgaggg     720
aagcagatct ccgcagggct attcagctaa gtatgcaagg tagttccaga aacatatctc     780
aagatatgac acagacatca ggtacaaatc ttacttcaga agagcttcgg aagagacgag     840
```

```
aagcctactt tgaaaaacag cagcaaaagc agcaacagca gcagcagcag cagcagcagg        900
gggacctatc aggacagagt tcacatccat gtgaaaggcc agccaccagt tcaggagcac        960
ttgggagtga tctaggtgat gctatgagtg aagaagacat gcttcaggca gctgtgacca       1020
tgtctttaga aactgtcaga atgatttga aaacagaagg aaaaaaataa taccttaaaa        1080
aaataattta gatattcata ctttccaaca ttatcctgtg tgattacagc atagggtcca       1140
ctttggtaat gtgtcaaaga gatgaggaaa taagacttt agcggtttgc aaacaaaatg        1200
atgggaaagt ggaacaatgc gtcggttgta ggactaaata atgatcttcc aaatattagc       1260
caaagaggca ttcagcaatt aaagacattt aaaatagttt tctaaatgtt tcttttctt        1320
ttttgagtgt gcaatatgta acatgtctaa agttagggca ttttcttgg atctttttgc        1380
agactagcta attagctctc gcctcaggct ttttccatat agtttgttt cttttctgt         1440
cttgtaggta agttggctca catcatgtaa tagtggcttt catttcttat taaccaaatt       1500
aaccttcag gaaagtatct ctactttcct gatgttgata atagtaatgg ttctagaagg        1560
atgaacagtt ctccctctcaa ctgtataccg tgtgctccag tgttttcttg tgttgttttc      1620
tctgatcaca acttttctgc tacctggttt tcattatttt cccacaattc ttttgaaaga       1680
tggtaatctt ttctgaggtt tagcgttta agccctacga tgggatcatt atttcatgac       1740
tggtgcgttc ctaaactctg aaatcagcct tgcacaagta cttgagaata atgagcatt        1800
ttttaaaatg tgtgagcatg tgctttccca gatgctttat gaatgtcttt tcacttatat      1860
caaaacctta cagctttgtt gcaaccctt cttcctgcgc cttattttt cctttcttct       1920
ccaattgaga aaactaggag aagcatagta tgcaggcaag tctccttctg ttagaagact     1980
aaacatacgt acccaccatg aatgtatgat acatgaaatt tggccttcaa tttaatagc       2040
agttttattt tattttttct cctatgactg gagctttgtg ttctcttttac agttgagtca     2100
tggaatgtag gtgtctgctt cacatctttt agtaggtata gcttgtcaaa gatggtgatc      2160
tggaacatga aaataattta ctaatgaaaa tatgttaaa tttatactgt gatttgacac       2220
ttgcatcatg tttagatagc ttaagaacaa tggaagtcac agtacttagt ggatctataa      2280
ataagaaagt ccatagtttt gataaatatt ctctttaatt gagatgtaca gagagtttct     2340
tgctgggtca ataggatagt atcatttgg tgaaaaccat gtctctgaaa ttgatgtttt       2400
agtttcagtg ttccctatcc ctcattctcc atctcctttt gaagctcttt tgaatgttga      2460
attgttcata agctaaaatc caagaaattt cagctgacaa cttcgaaaat tataatatgg      2520
tatattgccc tcctggtgtg tggctgcaca catttatca gggaaagttt tttgatctag       2580
gatttattgc taactaactg aaaagagaag aaaaaatatc ttttatttat gattataaaa      2640
tagcttttc ttcgatataa cagattttt aagtcattat tttgtgccaa tcagtttct         2700
gaagtttccc ttacacaaaa ggatagcttt attttaaaat ctaaagttc ttttaatagt       2760
taaaaatgtt tcagaagaat tataaaactt taaaactgca agggatgttg gagtttagta      2820
ctactcctc aagatttaaa aagctaaata ttttaagact gaacatttat gttaattatt        2880
accagtgtgt ttgtcatatt ttccatggat atttgttcat tacctttttc cattgaaaag      2940
ttacattaaa ctttcatac acttgaattg atgagctacc taatataaaa atgagaaaac       3000
caatatgcat tttaaagttt taactttaga gtttataaag ttcatatata ccctagttaa      3060
agcacttaag aaaatatggc atgtttgact tttagttcct agagagtttt tgttttttgtt      3120
tttgttttt tttgagacgg agtcttgcta tgtctcccag gctggagggc agtggcatga       3180
tctcggctca ctacaacttc cacctcccgg gttcaagcaa ttctcctgcc tcagcctcca      3240
```

```
gagtagctgg gattacaggc gcccaccacc acacccggca gattttttgta tttttggtag   3300
agacgcggtt tcatcatgtt tggccaggct ggtctcgaac tcctgacctc aggtgatccg   3360
cctgccttgg cctcccaaag tgttgggatt acaggcatga gccactgcgc ctggccagct   3420
agagagtttt taaagcagag ctgagcacac actggatgcg tttgaatgtg tttgtgtagt   3480
ttgttgtgaa attgttacat ttagcaggca gatccagaag cactagtgaa ctgtcatctt   3540
ggtggggttg gcttaaattt aattgactgt ttagattcca tttcttaatt gattggccag   3600
tatgaaaaga tgccagtgca agtaaccata gtatcaaaaa agttaaaaat tattcaaagc   3660
tatagtttat acatcaggta ctgccattta ctgtaaacca cctgcaagaa agtcaggaac   3720
aactaaattc acaagaactg tcctgctaag aagtgtatta agatttccat ttttgttttat   3780
ctaattggga acatcttaat gtttaatatt taaactattg gtatcatttt tctaatgtat   3840
aatttgtatt actgggatca agtatgtaca gtggtgatgc tagtagaagt ttaagccttg   3900
gaaataccac tttcatattt tcagatgtca tggatttaat gagtaattta tgttttaaa    3960
attcagaata gttaatctct gatctaaaac catcaatcta tgttttttac ggtaatcatg   4020
taaatatttc agtaatataa actgtttgaa aaggctgctg caggtaaact ctatactagg   4080
atcttggcca ataatttac aattcacaga atattttatt taaggtggtg ctttttttttt   4140
ttgtccttaa aacttgattt ttcttaactt tattcatgat gccaaagtaa atgaggaaaa   4200
aaactcaaaa ccagttgagt atcattgcag acaaaactac cagtagtcca tattgtttaa   4260
tattaagttg aataaaataa attttatttc agtcagagcc taaatcacat tttgattgtc   4320
tgaattttg atactatttt taaaatcatg ctagtggcgg ctgggcgtgg tagctcacgc    4380
ctgtaatccc agcattttgg gaggccgaag tgggtggatc acgaggtcgg gagttcgaga   4440
ccagcttggc caaaatggtg aaacccccatc tgtactaaaa actacaaaaa ttagctgggc   4500
gcggtggcag gtgcctgtaa tcccagctac ctgggagtct gaggcaggag aattgcttga   4560
accctggcga cagaggatgc agtgagccaa gatggtgcca ctgtactcca gactgggcga   4620
cagagtgaga ctctgtctca aaaaaaaaaa aaaaatcatg ctagtgccaa gagctactaa   4680
attcttaaaa ccggcccatt ggacctgtac agataaaaaa tagattcagt gcataatcaa   4740
aatatgataa ttttaaaatc ttaagtagaa aaataaatct tgatgtttta aattcttacg   4800
aggattcaat agttaatatt gatgatctcc cggctgggtg cagtggctca cgcctgtaat   4860
cccagcagtt ctggaggctg aggtgggcga atcacttcag gccaggagtt caagaccagt   4920
ctgggcaaca tggtgaaacc tcgtttctac taaaaataca aaaattagcc gggcgtggtt   4980
gcacacactt gtaatcccag ctactcagga ggctaagaat cgcatgagcc taggaggcag   5040
aggttgcaga gtgccaaggg ctcaccactg cattccagcc tgcccaacag agtgagacac   5100
tgtttctgaa aaaaaaaaat atatatatat atatatatat gtgtgtatat atatatgtat   5160
atatatatga cttcctatta aaactttat cccagtcggg ggcagtggct cacgcctgta   5220
atcccaacac tttgggaggc tgaggcaggt ggatcacctg aagtccggag tttgagacca   5280
gcctggccaa catggtgaaa ccccatctct actaaaaata caaaacttaa gccaggtatg   5340
gtggcgggca cctgtaatcc cagttacttg ggaggctgag gcaggagaat cgtttaaacc   5400
caggaggtgg aggttgcagt gagctgagat cgtgccattg cactctagcc tgggcaacaa   5460
gagtaaaact ccatccttaaa ggtttgtttg tttttttttta atccggaaac gaagaggcgt   5520
tgggccgcta ttttcttttt ctttctttct ttctttcttt tttttttttt ctgagacgga   5580
```

-continued

| | |
|---|---|
| gtctagctct gctgcccagg ctggagtaca atgacacgat gttggctcac tgcaacctcc | 5640 |
| acctcctggg ttcaagcgat tctcctgcct cagcctccca agtacctggg attacaggca | 5700 |
| cctgccacta cacctggcga atatttgttt tttttagtag agacgggctt ttaccatgtt | 5760 |
| aggctggtct caaactcctg acctcaggtg atctgcctgc cttggcctcc caaagtgctg | 5820 |
| ggattacagg tgcaggccac cacacccggc cttgggccac tgttttcaaa gtgaattgtt | 5880 |
| tgttgtatcg agtccttaag tatggatata tatgtgaccc taattaagaa ctaccagatt | 5940 |
| ggatcaacta atcatgtcag caatgtaaat aactttattt ttcatattca aaataaaaac | 6000 |
| tttcttttat ttctggcccc tttataacca gcatcttttt gctttaaaaa atgacctggc | 6060 |
| tttgtatttt tttagtctta aacataataa aaatattttt gttctaattt gctttcatga | 6120 |
| gtgaagatta ttgacatcgt tggtaaattc tagaattttg attttgtttt ttaatttgaa | 6180 |
| gaaaatcttt gctattatta ttttttccaa gtggtctggc attttaagaa ttagtgctaa | 6240 |
| taacgtaact tctaaatttg tcgtaattgg catgtttaat agcatatcaa aaacattttt | 6300 |
| aagcctgtgg attcatagac aaagcaatga gaaacattag taaaatataa atggatattc | 6360 |
| ctgatgcatt taggaagctc tcaattgtct cttgcatagt tcaaggaatg ttttctgaat | 6420 |
| tttttaatg ctttttttttt ttttgaaaga ggaaaacata cattttttaaa tgtgattatc | 6480 |
| taattttttac aacactgggc tattaggaat aacttttttaa aaattactgt tctgtataaa | 6540 |
| tatttgaaat tcaagtacag aaaatatctg aaacaaaaag cattgttgtt tggccatgat | 6600 |
| acaagtgcac tgtggcagtg ccgcttgctc aggacccagc cctgcagccc ttctgtgtgt | 6660 |
| gctccctcgt taagttcatt tgctgttatt acacacacag gccttcctgt ctggtcgtta | 6720 |
| gaaaagccgg gcttccaaag cactgttgaa cacaggattc tgttgttagt gtggatgttc | 6780 |
| aatgagttgt attttaaata tcaaagatta ttaaataaag ataatgtttg cttttcta | 6838 |

<210> SEQ ID NO 14
<211> LENGTH: 6339
<212> TYPE: DNA
<213> ORGANISM: Homo sapiens

<400> SEQUENCE: 14

| | |
|---|---|
| gagaggggca gggggcggag ctggaggggg tggttcggcg tggggccgt tggctccaga | 60 |
| caaataaaca tggagtccat cttccacgag aaaagtccat aaaacagacc tggaacgagt | 120 |
| gttagaagca aatgatggct caggaatgtt agacgaagat gaggaggatt tgcagagggc | 180 |
| tctggcacta agtcgccaag aaattgacat ggaagatgag gaagcagatc tccgcagggc | 240 |
| tattcagcta agtatgcaag gtagttccag aaacatatct caagatatga cacagacatc | 300 |
| aggtacaaat cttacttcag aagagcttcg gaagagacga gaagcctact ttgaaaaaca | 360 |
| gcagcaaaag cagcaacagc agcagcagca gcagcagcag ggggacctat caggacagag | 420 |
| ttcacatcca tgtgaaaggc cagccaccag ttcaggagca cttgggagtg atctaggtga | 480 |
| tgctatgagt gaagaagaca tgcttcaggc agctgtgacc atgtctttag aaactgtcag | 540 |
| aaatgatttg aaaacagaag gaaaaaaata taccctttaa aaaataattt agatattcat | 600 |
| actttccaac attatcctgt gtgattacag catagggtcc actttggtaa tgtgtcaaag | 660 |
| agatgaggaa ataagacttt tagcggtttg caaacaaaat gatgggaaag tggaacaatg | 720 |
| cgtcggttgt aggactaaat aatgatcttc caaatattag ccaaagaggc attcagcaat | 780 |
| taaagacatt taaaatagtt ttctaaatgt ttcttttttct tttttgagtg tgcaatatgt | 840 |
| aacatgtcta agttagggc attttttcttg gatcttttttg cagactagct aattagctct | 900 |

```
cgcctcaggc ttttttccata tagtttgttt tcttttttctg tcttgtaggt aagttggctc    960
acatcatgta atagtggctt tcatttctta ttaaccaaat taacctttca ggaaagtatc   1020
tctactttcc tgatgttgat aatagtaatg gttctagaag gatgaacagt tctcccttca   1080
actgtatacc gtgtgctcca gtgttttctt gtgttgtttt ctctgatcac aacttttctg   1140
ctacctggtt ttcattattt tcccacaatt cttttgaaag atggtaatct tttctgaggt   1200
ttagcgtttt aagccctacg atgggatcat tatttcatga ctggtgcgtt cctaaactct   1260
gaaatcagcc ttgcacaagt acttgagaat aaatgagcat ttttttaaaat gtgtgagcat   1320
gtgctttccc agatgcttta tgaatgtctt ttcacttata tcaaaacctt acagctttgt   1380
tgcaaccccct tcttcctgcg ccttattttt tcctttcttc tccaattgag aaaactagga   1440
gaagcatagt atgcaggcaa gtctccttct gttagaagac taaacatacg tacccaccat   1500
gaatgtatga tacatgaaat ttggccttca attttaatag cagttttatt ttattttttc   1560
tcctatgact ggagctttgt gttctcttta cagttgagtc atggaatgta ggtgtctgct   1620
tcacatcttt tagtaggtat agcttgtcaa agatggtgat ctggaacatg aaaataattt   1680
actaatgaaa atatgtttaa atttatactg tgatttgaca cttgcatcat gtttagatag   1740
cttaagaaca atggaagtca cagtacttag tggatctata aataagaaag tccatagttt   1800
tgataaatat tctctttaat tgagatgtac agagagtttc ttgctgggtc aataggatag   1860
tatcattttg gtgaaaacca tgtctctgaa attgatgttt tagtttcagt gttccctatc   1920
cctcattctc catctccttt tgaagctctt ttgaatgttg aattgttcat aagctaaaat   1980
ccaagaaatt tcagctgaca acttcgaaaa ttataatatg gtatattgcc ctcctggtgt   2040
gtggctgcac acattttatc agggaaagtt ttttgatcta ggattattg ctaactaact   2100
gaaaagagaa gaaaaaatat cttttattta tgattataaa atagcttttt cttcgatata   2160
acagattttt taagtcatta ttttgtgcca atcagttttc tgaagtttcc cttacacaaa   2220
aggatagctt tatttttaaaa tctaaagttt cttttaatag ttaaaaatgt ttcagaagaa   2280
ttataaaact ttaaaactgc aagggatgtt ggagtttagt actactccct caagatttaa   2340
aaagctaaat atttttaagac tgaacattta tgttaattat taccagtgtg tttgtcatat   2400
tttccatgga tatttgttca ttacctttttt ccattgaaaa gttacattaa acttttcata   2460
cacttgaatt gatgagctac ctaatataaa aatgagaaaa ccaatatgca ttttaaagtt   2520
ttaactttag agtttataaa gttcatatat accctagtta aagcacttaa gaaaatatgg   2580
catgtttgac ttttagttcc tagagagttt ttgtttttgt ttttgttttt ttttgagacg   2640
gagtcttgct atgtctccca ggctggaggg cagtggcatg atctcggctc actacaactt   2700
ccacctcccg ggttcaagca attctcctgc ctcagcctcc agagtagctg ggattacagg   2760
cgcccaccac cacacccggc agattttttgt attttttggta gagacgcggt ttcatcatgt   2820
ttggccaggc tggtctcgaa ctcctgacct caggtgatcc gcctgccttg gcctcccaaa   2880
gtgttgggat tacaggcatg agccactgcg cctggccagc tagagagttt ttaaagcaga   2940
gctgagcaca cactggatgc gtttgaatgt gtttgtgtag tttgttgtga aattgttaca   3000
tttagcaggc agatccagaa gcactagtga actgtcatct tggtggggtt ggcttaaatt   3060
taattgactg tttagattcc atttcttaat tgattggcca gtatgaaaag atgccagtgc   3120
aagtaaccat agtatcaaaa aagttaaaaa ttattcaaag ctatagttta tacatcaggt   3180
actgccattt actgtaaacc acctgcaaga aagtcaggaa caactaaatt cacaagaact   3240
```

```
gtcctgctaa gaagtgtatt aaagatttcc attttgtttt actaattggg aacatcttaa    3300
tgtttaatat ttaaactatt ggtatcattt ttctaatgta taatttgtat tactgggatc    3360
aagtatgtac agtggtgatg ctagtagaag tttaagcctt ggaaatacca ctttcatatt    3420
ttcagatgtc atggatttaa tgagtaattt atgttttttaa aattcagaat agttaatctc    3480
tgatctaaaa ccatcaatct atgtttttta cggtaatcat gtaaatattt cagtaatata    3540
aactgtttga aaaggctgct gcaggtaaac tctatactag gatcttggcc aaataattta    3600
caattcacag aatattttat ttaaggtggt gctttttttt tttgtcctta aaacttgatt    3660
tttcttaact ttattcatga tgccaaagta aatgaggaaa aaaactcaaa accagttgag    3720
tatcattgca gacaaaacta ccagtagtcc atattgttta atattaagtt gaataaaata    3780
aattttattt cagtcagagc ctaaatcaca ttttgattgt ctgaattttt gatactattt    3840
ttaaaatcat gctagtggcg gctgggcgtg gtagctcacg cctgtaatcc cagcattttg    3900
ggaggccgaa gtgggtggat cacgaggtcg ggagttcgag accagcttgg ccaaaatggt    3960
gaaaccccat ctgtactaaa aactacaaaa attagctggg cgcggtggca ggtgcctgta    4020
atcccagcta cctgggagtc tgaggcagga gaattgcttg aacctggcg acagaggatg     4080 cagtgagcca agatggtgcc actgtactcc agactgggcg acagagtgag actctgtctc    4140
aaaaaaaaaa aaaaaatcat gctagtgcca agagctacta aattcttaaa accggcccat    4200
tggacctgta cagataaaaa atagattcag tgcataatca aaatatgata atttttaaaat   4260 cttaagtaga aaataaaatc ttgatgtttt aaattcttac gaggattcaa tagttaatat    4320
tgatgatctc ccggctgggt gcagtggctc acgcctgtaa tcccagcagt tctgaggct     4380 gaggtgggcg aatcacttca ggccaggagt tcaagaccag tctgggcaac atggtgaaac    4440 ctcgttttcta ctaaaaatac aaaaattagc cgggcgtggt gcacacact tgtaatccca    4500 gctactcagg aggctaagaa tcgcatgagc ctaggaggca gaggttgcag agtgccaagg    4560
gctcaccact gcattccagc ctgcccaaca gagtgagaca ctgtttctga aaaaaaaaa    4620 tatatatata tatatatata tgtgtgtata tatatatgta tatatatatg acttcctatt    4680
aaaaacttta tcccagtcgg gggcagtggc tcacgcctgt aatcccaaca ctttgggagg    4740
ctgaggcagg tggatcacct gaagtccgga gtttgagacc agcctggcca acatggtgaa    4800
accccatctc tactaaaaat acaaaactta agccaggtat ggtggcgggc acctgtaatc    4860
ccagttactt gggaggctga ggcaggagaa tcgtttaaac ccaggaggtg gaggttgcag    4920
tgagctgaga tcgtgccatt gcactctagc ctgggcaaca agagtaaaac tccatcttaa    4980
aggtttgttt gttttttttt aatccggaaa cgaagaggcg ttgggccgct attttctttt    5040
tctttctttc tttctttctt ttttttttt tctgagacgg agtctagctc tgctgcccag    5100
gctggagtac aatgacacga tgttggctca ctgcaaccct cacctcctgg gttcaagcga    5160
ttctcctgcc tcagcctccc aagtacctgg gattacaggc acctgccact acacctggcg    5220
aatatttgtt ttttttagta gagacgggct tttaccatgt taggctggtc tcaaactcct    5280
gacctcaggt gatctgcctg ccttggcctc ccaaagtgct gggattacag gtgcaggcca    5340
ccacacccgg cctgggcca ctgttttcaa agtgaattgt tgttgtatc gagtccttaa      5400 gtatggatat atatgtgacc ctaattaaga actaccagat tggatcaact aatcatgtca    5460
gcaatgtaaa taactttatt tttcatattc aaaataaaaa cttctcttta tttctggccc    5520
ctttataacc agcatctttt tgcttttaaaa aatgacctgg ctttgtattt ttttagtctt   5580
aaacataata aaaatatttt tgttctaatt tgctttcatg agtgaagatt attgacatcg    5640
```

```
ttggtaaatt ctagaatttt gattttgttt tttaatttga agaaaatctt tgctattatt     5700 atttttcca agtggtctgg cattttaaga attagtgcta ataacgtaac ttctaaattt     5760
gtcgtaattg gcatgtttaa tagcatatca aaaacatttt aagcctgtg gattcataga     5820 caaagcaatg agaaacatta gtaaaatata aatggatatt cctgatgcat ttaggaagct     5880
ctcaattgtc tcttgcatag ttcaaggaat gttttctgaa ttttttttaat gcttttttt     5940 tttttgaaag aggaaaacat acattttaa atgtgattat ctaatttta caacactggg     6000 ctattaggaa taacttttta aaaattactg ttctgtataa atatttgaaa ttcaagtaca     6060
gaaaatatct gaaacaaaaa gcattgttgt ttggccatga tacaagtgca ctgtggcagt     6120
gccgcttgct caggacccag ccctgcagcc cttctgtgtg tgctccctcg ttaagttcat     6180
ttgctgttat tacacacaca ggccttcctg tctggtcgtt agaaaagccg ggcttccaaa     6240
gcactgttga acacaggatt ctgttgttag tgtggatgtt caatgagttg tattttaaat     6300
atcaaagatt attaaataaa gataatgttt gcttttcta                          6339
```

<210> SEQ ID NO 15
<211> LENGTH: 6075
<212> TYPE: DNA
<213> ORGANISM: Homo sapiens

<400> SEQUENCE: 15

```
gagaggggca gggggcggag ctggaggggg tggttcggcg tggggccgt tggctccaga       60 caaataaaca tggagtccat cttccacgag aaaacagcag caaagcagc aacagcagca     120 gcagcagcag cagcagggg acctatcagg acagagttca catccatgtg aaaggccagc     180
caccagttca ggagcacttg ggagtgatct aggtgatgct atgagtgaag aagacatgct     240
tcaggcagct gtgaccatgt ctttagaaac tgtcagaaat gatttgaaaa cagaaggaaa     300
aaaataatac ctttaaaaaa taatttagat attcatactt ccaacatta tcctgtgtga     360 ttacagcata gggtccactt tggtaatgtg tcaaagagat gaggaaataa gacttttagc     420
ggtttgcaaa caaaatgatg ggaaagtgga acaatgcgtc ggttgtagga ctaaataatg     480
atcttccaaa tattagccaa agaggcattc agcaattaaa gacatttaaa atagttttct     540
aaatgtttct ttttcttttt tgagtgtgca atatgtaaca tgtctaaagt tagggcattt     600
ttcttggatc ttttttgcaga ctagctaatt agctctcgcc tcaggctttt tccatatagt     660
ttgttttctt tttctgtctt gtaggtaagt tggctcacat catgtaatag tggctttcat     720
ttcttattaa ccaaattaac cttttcaggaa agtatctcta cttttcctgat gttgataata     780 gtaatggttc tagaaggatg aacagttctc ccttcaactg tataccgtgt gctccagtgt     840
tttcttgtgt tgttttctct gatcacaact tttctgctac ctggttttca ttattttccc     900
acaattcttt tgaaagatgg taatcttttc tgaggtttag cgttttaagc cctacgatgg     960
gatcattatt tcatgactgg tgcgttccta aactctgaaa tcagccttgc acaagtactt    1020
gagaataaat gagcattttt taaaatgtgt gagcatgtgc tttcccagat gctttatgaa    1080
tgtcttttca cttatatcaa aaccttacag ctttgttgca acccttctt cctgcgcctt    1140 attttttcct ttcttctcca attgagaaaa ctaggagaag catagtatgc aggcaagtct    1200
ccttctgtta gaagactaaa catacgtacc caccatgaat gtatgataca tgaaatttgg    1260
ccttcaattt taatagcagt tttattttat tttttctcct atgactggag ctttgtgttc    1320
tctttacagt tgagtcatgg aatgtaggtg tctgcttcac atcttttagt aggtatagct    1380
```

-continued

```
tgtcaaagat ggtgatctgg aacatgaaaa taatttacta atgaaaatat gtttaaattt    1440
atactgtgat ttgacacttg catcatgttt agatagctta agaacaatgg aagtcacagt    1500
acttagtgga tctataaata agaaagtcca tagttttgat aaatattctc tttaattgag    1560
atgtacagag agtttcttgc tgggtcaata ggatagtatc attttggtga aaaccatgtc    1620
tctgaaattg atgttttagt ttcagtgttc cctatccctc attctccatc tccttttgaa    1680
gctcttttga atgttgaatt gttcataagc taaaatccaa gaaatttcag ctgacaactt    1740
cgaaaattat aatatggtat attgccctcc tggtgtgtgg ctgcacacat tttatcaggg    1800
aaagtttttt gatctaggat ttattgctaa ctaactgaaa agagaagaaa aaatatcttt    1860
tatttatgat tataaaatag cttttttcttc gatataacag attttttaag tcattatttt    1920
gtgccaatca gttttctgaa gtttccctta cacaaaagga tagctttatt ttaaaatcta    1980
aagtttcttt taatagttaa aaatgtttca gaagaattat aaaactttaa aactgcaagg    2040
gatgttggag tttagtacta ctccctcaag atttaaaaag ctaaatattt taagactgaa    2100
catttatgtt aattattacc agtgtgtttg tcatattttc catggatatt tgttcattac    2160 cttttttccat tgaaaagtta cattaaactt ttcatacact tgaattgatg agctacctaa    2220
tataaaaatg agaaaaccaa tatgcatttt aaagttttaa ctttagagtt tataaagttc    2280
atatataccc tagttaaagc acttaagaaa atatggcatg tttgactttt agttcctaga    2340 gagttttttgt ttttgttttt gttttttttt gagacggagt cttgctatgt ctcccaggct    2400
ggagggcagt ggcatgatct cggctcacta caacttccac ctcccgggtt caagcaattc    2460
tcctgcctca gcctccagag tagctgggat tacaggcgcc caccaccaca cccggcagat    2520 ttttgtatt ttggtagaga cgcggtttca tcatgtttgg ccaggctggt ctcgaactcc    2580
tgacctcagg tgatccgcct gccttggcct cccaaagtgt tgggattaca ggcatgagcc    2640
actgcgcctg gccagctaga gagttttaa agcagagctg agcacacact ggatgcgttt    2700
gaatgtgttt gtgtagtttg ttgtgaaatt gttacattta gcaggcagat ccagaagcac    2760
tagtgaactg tcatcttggt ggggttggct taaatttaat tgactgttta gattccattt    2820
cttaattgat tggccagtat gaaaagatgc cagtgcaagt aaccatagta tcaaaaaagt    2880
taaaaattat tcaaagctat agtttataca tcaggtactg ccatttactg taaaccacct    2940
gcaagaaagt caggaacaac taaattcaca agaactgtcc tgctaagaag tgtattaaag    3000
atttccattt tgttttacta attgggaaca tcttaatgtt taatatttaa actattggta    3060
tcatttttct aatgtataat ttgtattact gggatcaagt atgtacagtg gtgatgctag    3120
tagaagttta agccttggaa ataccacttt catattttca gatgtcatgg atttaatgag    3180
taatttatgt ttttaaaatt cagaatagtt aatctctgat ctaaaaccat caatctatgt    3240
tttttacggt aatcatgtaa atatttcagt aatataaact gtttgaaaag gctgctgcag    3300
gtaaactcta tactaggatc ttggccaaat aatttacaat tcacagaata tttatttaa    3360 ggtggtgctt ttttttttg tccttaaaac ttgatttttc ttaactttat tcatgatgcc    3420
aaagtaaatg aggaaaaaaa ctcaaaacca gttgagtatc attgcagaca aaactaccag    3480
tagtccatat tgtttaatat taagttgaat aaaataaatt ttatttcagt cagagcctaa    3540
atcacatttt gattgtctga attttgata ctattttaa aatcatgcta gtggcggctg    3600
ggcgtggtag ctcacgcctg taatcccagc attttgggag gccgaagtgg gtggatcacg    3660 aggtcggag ttcgagacca gcttggccaa aatggtgaaa ccccatctgt actaaaaact    3720
acaaaaatta gctgggcgcg gtggcaggtg cctgtaatcc cagctacctg ggagtctgag    3780
```

```
gcaggagaat tgcttgaacc ctggcgacag aggatgcagt gagccaagat ggtgccactg    3840
tactccagac tgggcgacag agtgagactc tgtctcaaaa aaaaaaaaaa aatcatgcta    3900
gtgccaagag ctactaaatt cttaaaaccg gcccattgga cctgtacaga taaaaaatag    3960
attcagtgca taatcaaaat atgataattt taaaatctta agtagaaaaa taaatcttga    4020
tgttttaaat tcttacgagg attcaatagt taatattgat gatctcccgg ctgggtgcag    4080
tggctcacgc ctgtaatccc agcagttctg gaggctgagg tgggcgaatc acttcaggcc    4140
aggagttcaa gaccagtctg gcaacatgg tgaaacctcg tttctactaa aaatacaaaa    4200
attagccggg cgtggttgca cacacttgta atcccagcta ctcaggaggc taagaatcgc    4260
atgagcctag gaggcagagg ttgcagagtg ccaagggctc accactgcat tccagcctgc    4320
ccaacagagt gagacactgt ttctgaaaaa aaaaaatata tatatatata tatatatgtg    4380
tgtatatata tatgtatata tatgtgactt cctattaaaa actttatccc agtcggggc     4440 agtggctcac gcctgtaatc ccaacacttt gggaggctga ggcaggtgga tcacctgaag    4500
tccggagttt gagaccagcc tggccaacat ggtgaaaccc catctctact aaaaatacaa    4560
aacttaagcc aggtatggtg gcgggcacct gtaatcccag ttacttggga ggctgaggca    4620
ggagaatcgt ttaaacccag gaggtggagg ttgcagtgag ctgagatcgt gccattgcac    4680
tctagcctgg gcaacaagag taaaactcca tcttaaaggt ttgtttgttt ttttttaatc    4740
cggaaacgaa gaggcgttgg gccgctattt tcttttttctt tctttcttc tttcttttt     4800 ttttttttctg agacggagtc tagctctgct gcccaggctg gagtacaatg acacgatgtt    4860
ggctcactgc aacctccacc tcctgggttc aagcgattct cctgcctcag cctcccaagt    4920
acctgggatt acaggcacct gccactacac ctggcgaata tttgtttttt ttagtagaga    4980 cgggcttttta ccatgttagg ctggtctcaa actcctgacc tcaggtgatc tgcctgcctt    5040
ggcctcccaa agtgctggga ttacaggtgc aggccaccac acccggcctt gggccactgt    5100
tttcaaagtg aattgtttgt tgtatcgagt ccttaagtat ggatatatat gtgaccctaa    5160
ttaagaacta ccagattgga tcaactaatc atgtcagcaa tgtaaataac tttattttc     5220 atattcaaaa taaaaacttt cttttatttc tggccccttt ataaccagca tcttttgct     5280 ttaaaaaatg acctggcttt gtatttttt agtcttaaac ataataaaaa tattttgtt      5340 ctaatttgct ttcatgagtg aagattattg acatcgttgg taaattctag aattttgatt    5400 ttgttttta atttgaagaa atctttgct attattattt tttccaagtg gtctggcatt     5460
ttaagaatta gtgctaataa cgtaacttct aaatttgtcg taattggcat gtttaatagc    5520
atatcaaaaa acattttaag cctgtggatt catagacaaa gcaatgagaa acattagtaa    5580
aatataaatg gatattcctg atgcatttag gaagctctca attgtctctt gcatagttca    5640
aggaatgttt tctgaatttt tttaatgctt tttttttttt tgaaagagga aaacatacat    5700
ttttaaatgt gattatctaa tttttacaac actgggctat taggaataac tttttaaaaa    5760
ttactgttct gtataaatat ttgaaattca agtacagaaa atatctgaaa caaaaagcat    5820
tgttgtttgg ccatgataca agtgcactgt ggcagtgccg cttgctcagg acccagccct    5880
gcagcccttc tgtgtgtgct ccctcgttaa gttcatttgc tgttattaca cacacaggcc    5940
ttcctgtctg gtcgttagaa aagccgggct tccaaagcac tgttgaacac aggattctgt    6000
tgttagtgtg gatgttcaat gagttgtatt ttaaatatca aagattatta aataaagata    6060
atgtttgctt ttcta                                                    6075
```

<210> SEQ ID NO 16
<211> LENGTH: 6846
<212> TYPE: DNA
<213> ORGANISM: Homo sapiens

<400> SEQUENCE: 16

| | | | | | | |
|---|---|---|---|---|---|---|
| gagaggggca | gggggcggag | ctggaggggg | tggttcggcg | tggggccgt | tggctccaga | 60 |
| caaataaaca | tggagtccat | cttccacgag | aaacaagaag | gctcactttg | tgctcaacat | 120 |
| tgcctgaata | acttattgca | aggagaatat | tttagccctg | tggaattatc | ctcaattgca | 180 |
| catcagctgg | atgaggagga | gaggatgaga | atggcagaag | gaggagttac | tagtgaagat | 240 |
| tatcgcacgt | ttttacagaa | atgaaagatc | atttatatgc | aattataagg | aacactggtt | 300 |
| tacagttaga | aaattaggaa | acagtggtt | taacttgaat | tctctcttga | cgggtccaga | 360 |
| attaatatca | gatacatatc | ttgcactttt | cttggctcaa | ttacaacagg | aaggttattc | 420 |
| tatatttgtc | gttaagggtg | atctgccaga | ttgcgaagct | gaccaactcc | tgcagatgat | 480 |
| tagggtccaa | cagatgcatc | gaccaaaact | tattggagaa | gaattagcac | aactaaaaga | 540 |
| gcaaagagtc | cataaaacag | acctggaacg | agtgttagaa | gcaaatgatg | gctcaggaat | 600 |
| gttagacgaa | gatgaggagg | atttgcagag | ggctctggca | ctaagtcgcc | aagaaattga | 660 |
| catggaagat | gaggaagcag | atctccgcag | ggctattcag | ctaagtatgc | aaggtagttc | 720 |
| cagaaacata | tctcaagata | tgacacagac | atcaggtaca | aatcttactt | cagaagagct | 780 |
| tcggaagaga | cgagaagcct | actttgaaaa | tcacaactca | gaagtagatg | aaggaaaatt | 840 |
| ctgatcagct | gacatcctct | taatacagca | gcaaagcag | caacagcagc | agcagcagca | 900 |
| gcagcagggg | gacctatcag | gacagagttc | acatccatgt | gaaaggccag | ccaccagttc | 960 |
| aggagcactt | gggagtgatc | taggtgatgc | tatgagtgaa | gaagacatgc | ttcaggcagc | 1020 |
| tgtgaccatg | tctttagaaa | ctgtcagaaa | tgatttgaaa | acagaaggaa | aaaaataata | 1080 |
| cctttaaaaa | ataatttaga | tattcatact | ttccaacatt | atcctgtgtg | attacagcat | 1140 |
| agggtccact | ttggtaatgt | gtcaaagaga | tgaggaaata | agacttttag | cggtttgcaa | 1200 |
| acaaaatgat | gggaaagtgg | aacaatgcgt | cggttgtagg | actaaataat | gatcttccaa | 1260 |
| atattagcca | aagaggcatt | cagcaattaa | agacatttaa | aatagttttc | taaatgtttc | 1320 |
| tttttctttt | ttgagtgtgc | aatatgtaac | atgtctaaag | ttagggcatt | tttcttggat | 1380 |
| cttttttgcag | actagctaat | tagctctcgc | ctcaggcttt | ttccatatag | tttgttttct | 1440 |
| ttttctgtct | tgtaggtaag | ttggctcaca | tcatgtaata | gtggctttca | tttcttatta | 1500 |
| accaaattaa | cctttcagga | aagtatctct | actttcctga | tgttgataat | agtaatggtt | 1560 |
| ctagaaggat | gaacagttct | cccttcaact | gtataccgtg | tgctccagtg | ttttcttgtg | 1620 |
| ttgttttctc | tgatcacaac | ttttctgcta | cctggttttc | attattttcc | cacaattctt | 1680 |
| ttgaaagatg | gtaatctttt | ctgaggttta | gcgtttaag | ccctacgatg | ggatcattat | 1740 |
| ttcatgactg | gtgcgttcct | aaactctgaa | atcagccttg | cacaagtact | tgagaataaa | 1800 |
| tgagcatttt | ttaaaatgtg | tgagcatgtg | ctttcccaga | tgctttatga | atgtcttttc | 1860 |
| acttatatca | aaaccttaca | gctttgttgc | aaccccttct | tcctgcgcct | tattttttcc | 1920 |
| tttcttctcc | aattgagaaa | actaggagaa | gcatagtatg | caggcaagtc | tccttctgtt | 1980 |
| agaagactaa | acatacgtac | ccaccatgaa | tgtatgatac | atgaaatttg | gccttcaatt | 2040 |
| ttaatagcag | ttttatttta | ttttttctcc | tatgactgga | gctttgtgtt | ctctttacag | 2100 |
| ttgagtcatg | gaatgtaggt | gtctgcttca | catctttag | taggtatagc | ttgtcaaaga | 2160 |

```
tggtgatctg gaacatgaaa ataatttact aatgaaaata tgtttaaatt tatactgtga    2220
tttgacactt gcatcatgtt tagatagctt aagaacaatg gaagtcacag tacttagtgg    2280
atctataaat aagaaagtcc atagttttga taaatattct ctttaattga gatgtacaga    2340
gagtttcttg ctgggtcaat aggatagtat cattttggtg aaaaccatgt ctctgaaatt    2400
gatgttttag tttcagtgtt ccctatccct cattctccat ctccttttga agctcttttg    2460
aatgttgaat tgttcataag ctaaaatcca agaaatttca gctgacaact tcgaaaatta    2520
taatatggta tattgccctc ctggtgtgtg gctgcacaca ttttatcagg gaaagttttt    2580
tgatctagga tttattgcta actaactgaa aagagaagaa aaaatatctt ttatttatga    2640
ttataaaata gcttttctt cgatataaca gatttttaa gtcattattt tgtgccaatc      2700
agttttctga gtttcccctt acacaaaagg atagctttat tttaaaatct aaagtttctt    2760
ttaatagtta aaaatgtttc agaagaatta taaaactttta aaactgcaag ggatgttgga   2820
gtttagtact actccctcaa gatttaaaaa gctaaatatt ttaagactga acatttatgt    2880
taattattac cagtgtgttt gtcatatttt ccatggatat ttgttcatta ccttttttcca   2940 ttgaaaagtt acattaaact tttcatacac ttgaattgat gagctaccta atataaaaat    3000
gagaaaacca atatgcattt taaagttttta actttagagt ttataaagtt catatatacc   3060
ctagttaaag cacttaagaa aatatggcat gtttgacttt tagttcctag agagtttttg    3120 ttttgtttt tgttttttt tgagacggag tcttgctatg tctcccaggc tggagggcag      3180
tggcatgatc tcggctcact acaacttcca cctcccgggt tcaagcaatt ctcctgcctc    3240
agcctccaga gtagctggga ttacaggcgc ccaccaccac acccggcaga ttttttgtatt   3300 tttggtagag acgcggtttc atcatgtttg gccaggctgg tctcgaactc ctgacctcag    3360
gtgatccgcc tgccttggcc tcccaaagtg ttgggattac aggcatgagc cactgcgcct    3420
ggccagctag agagttttta aagcagagct gagcacacac tggatgcgtt tgaatgtgtt    3480
tgtgtagttt gttgtgaaat tgttacattt agcaggcaga tccagaagca ctagtgaact    3540
gtcatcttgg tggggttggc ttaaatttaa ttgactgttt agattccatt tcttaattga    3600
ttggccagta tgaaagatg ccagtgcaag taaccatagt atcaaaaaag ttaaaaatta     3660
ttcaaagcta tagtttatac atcaggtact gccatttact gtaaaccacc tgcaagaaag    3720
tcaggaacaa ctaaattcac aagaactgtc ctgctaagaa gtgtattaaa gatttccatt    3780
ttgttttact aattgggaac atcttaatgt ttaatattta aactattggt atcattttc     3840 taatgtataa tttgtattac tgggatcaag tatgtacagt ggtgatgcta gtagaagttt    3900
aagccttgga ataccactt tcatattttc agatgtcatg gatttaatga gtaatttatg     3960
tttttaaaat tcagaatagt taatctctga tctaaaacca tcaatctatg tttttacgg     4020 taatcatgta aatatttcag taatataaac tgtttgaaaa ggctgctgca ggtaaactct    4080
atactaggat cttggccaaa taatttacaa ttcacagaat attttattta aggtggtgct    4140 tttttttt gtccttaaaa cttgattttt cttaacttta ttcatgatgc caaagtaaat      4200
gaggaaaaaa actcaaaacc agttgagtat cattgcagac aaaactacca gtagtccata    4260
ttgtttaata ttaagttgaa taaaataaat tttatttcag tcagagccta aatcacattt    4320
tgattgtctg aattttttgat actatttta aaatcatgct agtggcggct gggcgtggta    4380
gctcacgcct gtaatcccag cattttggga ggccgaagtg ggtggatcac gaggtcggga   4440
gttcgagacc agcttggcca aaatggtgaa accccatctg tactaaaaac tacaaaaatt    4500
```

```
agctgggcgc ggtggcaggt gcctgtaatc ccagctacct gggagtctga ggcaggagaa    4560
ttgcttgaac cctggcgaca gaggatgcag tgagccaaga tggtgccact gtactccaga    4620
ctgggcgaca gagtgagact ctgtctcaaa aaaaaaaaa aaatcatgct agtgccaaga    4680
gctactaaat tcttaaaacc ggcccattgg acctgtacag ataaaaaata gattcagtgc    4740
ataatcaaaa tatgataatt ttaaaatctt aagtagaaaa ataaatcttg atgttttaaa    4800
ttcttacgag gattcaatag ttaatattga tgatctcccg gctgggtgca gtggctcacg    4860
cctgtaatcc cagcagttct ggaggctgag gtgggcgaat cacttcaggc caggagttca    4920
agaccagtct gggcaacatg gtgaaacctc gtttctacta aaatacaaaa attagccgg    4980
gcgtggttgc acacacttgt aatcccagct actcaggagg ctaagaatcg catgagccta    5040
ggaggcagag gttgcagagt gccaagggct caccactgca ttccagcctg cccaacagag    5100
tgagacactg tttctgaaaa aaaaaaatat atatatatat atatatatgt gtgtatatat    5160
atatgtatat atatatgact tcctattaaa aactttatcc cagtcggggg cagtggctca    5220
cgcctgtaat cccaacactt tgggaggctg aggcaggtgg atcacctgaa gtccggagtt    5280
tgagaccagc ctggccaaca tggtgaaaacc ccatctctac taaaaataca aaacttaagc    5340
caggtatggt ggcgggcacc tgtaatccca gttacttggg aggctgaggc aggagaatcg    5400
tttaaaccca ggaggtggag gttgcagtga gctgagatcg tgccattgca ctctagcctg    5460
ggcaacaaga gtaaaactcc atcttaaagg tttgtttgtt ttttttttaat ccggaaacga    5520
agaggcgttg ggccgctatt ttcttttttct ttctttcttt ctttcttttt ttttttttct    5580
gagacggagt ctagctctgc tgcccaggct ggagtacaat gacacgatgt ggctcactg    5640
caacctccac ctcctgggtt caagcgattc tcctgcctca gcctcccaag tacctgggat    5700
tacaggcacc tgccactaca cctggcgaat atttgttttt tttagtagag acgggctttt    5760
accatgttag gctggtctca aactcctgac ctcaggtgat ctgcctgcct tggcctccca    5820
aagtgctggg attacaggtg caggccacca caccggcct tgggccactg ttttcaaagt    5880
gaattgtttg ttgtatcgag tccttaagta tggatatata tgtgacccta attaagaact    5940
accagattgg atcaactaat catgtcagca atgtaaataa ctttattttt catattcaaa    6000
ataaaaactt tcttttatt tctggcccctt tataaccagc atcttttttgc tttaaaaaat    6060
gacctggctt tgtatttttt tagtcttaaa cataataaaa atattttttgt tctaaatttgc    6120
tttcatgagt gaagattatt gacatcgttg gtaaattcta gaattttgat tttgttttt    6180
aatttgaaga aaatctttgc tattattatt ttttccaagt ggtctggcat tttaagaatt    6240
agtgctaata acgtaacttc taaatttgtc gtaattggca tgtttaatag catatcaaaa    6300
aacattttaa gcctgtggat tcatagacaa agcaatgaga acattagta aaatataaat    6360
ggatattcct gatgcattta ggaagctctc aattgtctct tgcatagttc aaggaatgtt    6420
ttctgaattt ttttaatgct tttttttttt ttgaaagagg aaaacataca ttttaaatg    6480
tgattatcta atttttacaa cactgggcta ttaggaataa cttttaaaa attactgttc    6540
tgtataaata tttgaaattc aagtacagaa aatatctgaa acaaaaagca ttgttgtttg    6600
gccatgatac aagtgcactg tggcagtgcc gcttgctcag gacccagccc tgcagccctt    6660
ctgtgtgtgc tccctcgtta agttcatttg ctgttattac acacacaggc cttcctgtct    6720
ggtcgttaga aaagccgggc ttccaaagca ctgttgaaca caggattctg ttgttagtgt    6780
ggatgttcaa tgagttgtat tttaaatatc aaagattatt aaataaagat aatgtttgct    6840
tttcta                                                              6846
```

<210> SEQ ID NO 17
<211> LENGTH: 6982
<212> TYPE: DNA
<213> ORGANISM: Homo sapiens

<400> SEQUENCE: 17

| | | | | | | |
|---|---|---|---|---|---|---|
| gagaggggca | gggggcggag | ctggaggggg | tggttcggcg | tgggggccgt | tggctccaga | 60 |
| caaataaaca | tggagtccat | cttccacgag | aaacaagaag | gctcactttg | tgctcaacat | 120 |
| tgcctgaata | acttattgca | aggagaatat | tttagccctg | tggaattatc | ctcaattgca | 180 |
| catcagctgg | atgaggagga | gaggatgaga | atggcagaag | gaggagttac | tagtgaagat | 240 |
| tatcgcacgt | ttttacagca | gccttctgga | aatatggatg | acagtggttt | tttctctatt | 300 |
| cagaaatgaa | agatcattta | tatgcaatta | taaggaacac | tggtttacag | ttagaaaatt | 360 |
| aggaaaacag | tggtttaact | tgaattctct | cttgacgggt | ccagaattaa | tatcagatac | 420 |
| atatcttgca | cttttcttgg | ctcaattaca | acaggaagtc | actcaatgag | acggctcttc | 480 |
| cagtcttaca | atggagaaag | tgaggctcag | agactttaag | taacttacct | tagacgactt | 540 |
| tactagtaag | ttattctata | tttgtcgtta | agggtgatct | gccagattgc | gaagctgacc | 600 |
| aactcctgca | gatgattagg | gtccaacaga | tgcatcgacc | aaaacttatt | ggagaagaat | 660 |
| tagcacaact | aaaagagcaa | agagtccata | aaacagacct | ggaacgagtg | ttagaagcaa | 720 |
| atgatggctc | aggaatgtta | gacgaagatg | aggaggattt | gcagagggct | ctggcactaa | 780 |
| gtcgccaaga | aattgacatg | gaagatgagg | aagcagatct | ccgcagggct | attcagctaa | 840 |
| gtatgcaagg | tagttccaga | aacatatctc | aagatatgac | acagacatca | ggtacaaatc | 900 |
| ttacttcaga | agagcttcgg | aagagacgag | aagcctactt | tgaaaatcac | aactcagaag | 960 |
| tagatgaagg | aaaattctga | tcagctgaca | tcctcttaat | acagcagcaa | aagcagcaac | 1020 |
| agcagcagca | gcagcagcag | caggggggacc | tatcaggaca | gagttcacat | ccatgtgaaa | 1080 |
| ggccagccac | cagttcagga | gcacttggga | gtgatctagg | tgatgctatg | agtgaagaag | 1140 |
| acatgcttca | ggcagctgtg | accatgtctt | tagaaactgt | cagaaatgat | ttgaaaacag | 1200 |
| aaggaaaaaa | ataataccctt | taaaaaataa | tttagatatt | catactttcc | aacattatcc | 1260 |
| tgtgtgatta | cagcataggg | tccactttgg | taatgtgtca | aagagatgag | gaaataagac | 1320 |
| ttttagcggt | ttgcaaacaa | aatgatggga | aagtggaaca | atgcgtcggt | tgtaggacta | 1380 |
| aataatgatc | ttccaaatat | tagccaaaga | ggcattcagc | aattaaagac | atttaaaata | 1440 |
| gttttctaaa | tgtttctttt | tcttttttga | gtgtgcaata | tgtaacatgt | ctaaagttag | 1500 |
| ggcattttc | ttggatcttt | ttgcagacta | gctaattagc | tctcgcctca | ggcttttttcc | 1560 |
| atatagtttg | ttttctttt | ctgtcttgta | ggtaagttgg | ctcacatcat | gtaatagtgg | 1620 |
| ctttcatttc | ttattaacca | aattaacctt | tcaggaaagt | atctctactt | tcctgatgtt | 1680 |
| gataatagta | atggttctag | aaggatgaac | agttctccct | tcaactgtat | accgtgtgct | 1740 |
| ccagtgtttt | cttgtgttgt | tttctctgat | cacaactttt | ctgctacctg | gttttcatta | 1800 |
| ttttcccaca | attcttttga | agatggtaa | tcttttctga | ggtttagcgt | tttaagccct | 1860 |
| acgatgggat | cattatttca | tgactggtgc | gttcctaaac | tctgaaatca | gccttgcaca | 1920 |
| agtacttgag | aataaatgag | cattttttaa | aatgtgtgag | catgtgcttt | cccagatgct | 1980 |
| ttatgaatgt | cttttcactt | atatcaaaac | cttacagctt | tgttgcaacc | ccttcttcct | 2040 |
| gcgccttatt | ttttcctttc | ttctccaatt | gagaaaacta | ggagaagcat | agtatgcagg | 2100 |

-continued

```
caagtctcct tctgttagaa gactaaacat acgtacccac catgaatgta tgatacatga    2160
aatttggcct tcaattttaa tagcagtttt attttatttt ttctcctatg actggagctt    2220
tgtgttctct ttacagttga gtcatggaat gtaggtgtct gcttcacatc ttttagtagg    2280
tatagcttgt caaagatggt gatctggaac atgaaaataa tttactaatg aaaatatgtt    2340
taaatttata ctgtgatttg acacttgcat catgtttaga tagcttaaga acaatggaag    2400
tcacagtact tagtggatct ataaataaga aagtccatag ttttgataaa tattctcttt    2460
aattgagatg tacagagagt ttcttgctgg gtcaatagga tagtatcatt ttggtgaaaa    2520
ccatgtctct gaaattgatg ttttagtttc agtgttccct atccctcatt ctccatctcc    2580
ttttgaagct cttttgaatg ttgaattgtt cataagctaa aatccaagaa atttcagctg    2640
acaacttcga aaattataat atggtatatt gccctcctgg tgtgtggctg cacacatttt    2700
atcagggaaa gttttttgat ctaggattta ttgctaacta actgaaaaga gaagaaaaaa    2760
tatcttttat ttatgattat aaaatagctt tttcttcgat ataacagatt ttttaagtca    2820
ttattttgtg ccaatcagtt ttctgaagtt tcccttacac aaaaggatag ctttatttta    2880
aaatctaaag tttcttttaa tagttaaaaa tgtttcagaa gaattataaa actttaaaac    2940
tgcaagggat gttggagttt agtactactc cctcaagatt taaaaagcta aatattttaa    3000
gactgaacat ttatgttaat tattaccagt gtgtttgtca tattttccat ggatatttgt    3060
tcattacctt tttccattga aaagttacat taaactttc atacacttga attgatgagc    3120
tacctaatat aaaaatgaga aaaccaatat gcattttaaa gttttaactt tagagtttat    3180
aaagttcata tatacccctag ttaaagcact taagaaaata tggcatgttt gacttttagt    3240
tcctagagag ttttttgtttt tgtttttgtt tttttttgag acggagtctt gctatgtctc    3300
ccaggctgga gggcagtggc atgatctcgg ctcactacaa cttccacctc ccgggttcaa    3360
gcaattctcc tgcctcagcc tccagagtag ctgggattac aggcgcccac caccacccc    3420 ggcagatttt tgtattttttg gtagagacgc ggtttcatca tgtttggcca ggctggtctc    3480
gaactcctga cctcaggtga tccgcctgcc ttggcctccc aaagtgttgg gattacaggc    3540
atgagccact gcgcctggcc agctagagag tttttaaagc agagctgagc acacactgga    3600
tgcgtttgaa tgtgtttgtg tagtttgttg tgaaattgtt acatttagca ggcagatcca    3660
gaagcactag tgaactgtca tcttggtggg gttggcttaa atttaattga ctgtttagat    3720
tccatttctt aattgattgg ccagtatgaa aagatgccag tgcaagtaac catagtatca    3780
aaaaagttaa aaattattca aagctatagt ttatacatca ggtactgcca tttactgtaa    3840
accacctgca agaaagtcag gaacaactaa attcacaaga actgtcctgc taagaagtgt    3900
attaaagatt tccatttttgt tttactaatt gggaacatct taatgtttaa tatttaaact    3960
attggtatca ttttttctaat gtataatttg tattactggg atcaagtatg tacagtggtg    4020
atgctagtag aagtttaagc cttggaaata ccactttcat attttcagat gtcatggatt    4080
taatgagtaa tttatgtttt taaaattcag aatagttaat ctctgatcta aaaccatcaa    4140
tctatgtttt ttacggtaat catgtaaata tttcagtaat ataaactgtt tgaaaaggct    4200
gctgcaggta aactctatac taggatcttg gccaaataat ttacaattca cagaatattt    4260
tatttaaggt ggtgcttttt tttttttgtcc ttaaaacttg attttctta actttattca    4320 tgatgccaaa gtaaatgagg aaaaaaactc aaaaccagtt gagtatcatt gcagacaaaa    4380
ctaccagtag tccatattgt ttaatattaa gttgaataaa ataaattta tttcagtcag    4440 agcctaaatc acatttttgat tgtctgaatt tttgatacta tttttaaaat catgctagtg    4500
```

```
gcggctgggc gtggtagctc acgcctgtaa tcccagcatt ttgggaggcc gaagtgggtg    4560
gatcacgagg tcgggagttc gagaccagct tggccaaaat ggtgaaaccc catctgtact    4620
aaaaactaca aaaattagct gggcgcggtg gcaggtgcct gtaatcccag ctacctggga    4680
gtctgaggca ggagaattgc ttgaaccctg gcgacagagg atgcagtgag ccaagatggt    4740
gccactgtac tccagactgg gcgacagagt gagactctgt ctcaaaaaaa aaaaaaaaat    4800
catgctagtg ccaagagcta ctaaattctt aaaaccggcc cattggacct gtacagataa    4860
aaaatagatt cagtgcataa tcaaaatatg ataattttaa aatcttaagt agaaaaataa    4920
atcttgatgt tttaaattct tacgaggatt caatagttaa tattgatgat ctcccggctg    4980
ggtgcagtgg ctcacgcctg taatcccagc agttctggag ctgaggtgg gcgaatcact     5040
tcaggccagg agttcaagac cagtctgggc aacatggtga acctcgttt ctactaaaaa     5100
tacaaaaatt agccgggcgt ggttgcacac acttgtaatc ccagctactc aggaggctaa    5160
gaatcgcatg agcctaggag gcagaggttg cagagtgcca agggctcacc actgcattcc    5220
agcctgccca acagagtgag acactgtttc tgaaaaaaaa aaatatatat atatatatat    5280
atatgtgtgt atatatatat gtatatatat atgacttcct attaaaaact ttatcccagt    5340
cgggggcagt ggctcacgcc tgtaatccca acactttggg aggctgaggc aggtggatca    5400
cctgaagtcc ggagtttgag accagcctgg ccaacatggt gaaacccat ctctactaaa     5460
aatacaaaac ttaagccagg tatggtggcg ggcacctgta atcccagtta cttgggaggc    5520
tgaggcagga gaatcgttta aacccaggag gtggaggttg cagtgagctg agatcgtgcc    5580
attgcactct agcctgggca acaagagtaa aactccatct taaaggtttg tttgttttt    5640
tttaatccgg aaacgaagag gcgttgggcc gctattttct ttttcttct ttctttcttt     5700
cttttttttt ttttctgaga cggagtctag ctctgctgcc caggctggag tacaatgaca    5760
cgatgttggc tcactgcaac ctccacctcc tgggttcaag cgattctcct gcctcagcct    5820
cccaagtacc tgggattaca ggcacctgcc actacacctg gcgaatattt gttttttta     5880
gtagagacgg gcttttacca tgttaggctg gtctcaaact cctgacctca ggtgatctgc    5940
ctgccttggc ctcccaaagt gctgggatta caggtgcagg ccaccacacc cggccttggg    6000
ccactgtttt caaagtgaat tgtttgttgt atcgagtcct taagtatgga tatatatgtg    6060
accctaatta agaactacca gattggatca actaatcatg tcagcaatgt aaataacttt    6120
atttttcata ttcaaaataa aaactttctt ttatttctgg ccccttttata accagcatct   6180
ttttgcttta aaaaatgacc tggctttgta ttttttagt cttaaacata ataaaaatat     6240
ttttgttcta atttgctttc atgagtgaag attattgaca tcgttggtaa attctagaat    6300
tttgattttg ttttttaatt tgaagaaaat ctttgctatt attattttt ccaagtggtc     6360
tggcatttta agaattagtg ctaataacgt aacttctaaa tttgtcgtaa ttggcatgtt    6420
taatagcata tcaaaaaaca tttttaagcct gtggattcat agacaaagca atgagaaaca   6480
ttagtaaaat ataaatggat attcctgatg catttaggaa gctctcaatt gtctcttgca    6540
tagttcaagg aatgttttct gaattttttt aatgcttttt ttttttttga aagaggaaaa    6600
catacatttt taaatgtgat tatctaattt ttacaacact gggctattag gaataacttt    6660
ttaaaaatta ctgttctgta taaatatttg aaattcaagt acagaaaata tctgaaacaa    6720
aaagcattgt tgtttggcca tgatacaagt gcactgtggc agtgccgctt gctcaggacc    6780
cagccctgca gcccttctgt gtgtgctccc tcgttaagtt catttgctgt tattacacac    6840
```

```
acaggccttc ctgtctggtc gttagaaaag ccgggcttcc aaagcactgt tgaacacagg    6900
attctgttgt tagtgtggat gttcaatgag ttgtatttta aatatcaaag attattaaat    6960
aaagataatg tttgcttttc ta                                             6982

<210> SEQ ID NO 18
<211> LENGTH: 6120
<212> TYPE: DNA
<213> ORGANISM: Homo sapiens

<400> SEQUENCE: 18
gagaggggca gggggcggag ctggaggggg tggttcggcg tgggggccgt tggctccaga      60
caaataaaca tggagtccat cttccacgag aaacagcctt ctggaaatat ggatgacagt     120
ggttttttct ctattcagac agcagcaaaa gcagcaacag cagcagcagc agcagcagca     180
gggggaccta tcaggacaga gttcacatcc atgtgaaagg ccagccacca gttcaggagc     240
acttgggagt gatctaggtg atgctatgag tgaagaagac atgcttcagg cagctgtgac     300
catgtcttta gaaactgtca gaaatgattt gaaaacagaa ggaaaaaaat aataccttta     360
aaaaataatt tagatattca tactttccaa cattatcctg tgtgattaca gcatagggtc     420
cactttggta atgtgtcaaa gagatgagga ataagactt ttagcggttt gcaaacaaaa     480
tgatgggaaa gtggaacaat gcgtcggttg taggactaaa taatgatctt ccaaatatta     540
gccaaagagg cattcagcaa ttaaagacat ttaaaatagt tttctaaatg tttcttttc     600 ttttttgagt gtgcaatatg taacatgtct aaagttaggg cattttctt ggatctttt     660 gcagactagc taattagctc tcgcctcagg cttttcctcat atagtttgtt ttctttttct     720
gtcttgtagg taagttggct cacatcatgt aatagtggct ttcatttctt attaaccaaa     780
ttaacctttc aggaaagtat ctctactttc ctgatgttga taatagtaat ggttctagaa     840
ggatgaacag ttctcccttc aactgtatac cgtgtgctcc agtgttttct tgtgttgttt     900
tctctgatca caacttttct gctacctggt tttcattatt tcccacaat tcttttgaaa     960 gatggtaatc ttttctgagg tttagcgttt taagccctac gatgggatca ttatttcatg    1020
actggtgcgt tcctaaactc tgaaatcagc cttgcacaag tacttgagaa taaatgagca    1080 tttttaaaa tgtgtgagca tgtgctttcc cagatgcttt atgaatgtct tttcacttat    1140
atcaaaacct tacagctttg ttgcaaccc ttcttcctgc gccttatttt ttcctttctt    1200
ctccaattga gaaaactagg agaagcatag tatgcaggca agtctccttc tgttagaaga    1260
ctaaacatac gtacccacca tgaatgtatg atacatgaaa tttggccttc aatttttaata    1320 gcagttttat tttattttt ctcctatgac tggagctttg tgttctcttt acagttgagt    1380 catgaatgt aggtgtctgc ttcacatctt ttagtaggta tagcttgtca agatggtga    1440 tctggaacat gaaaataatt tactaatgaa aatatgttta aatttatact gtgatttgac    1500
acttgcatca tgtttagata gcttaagaac aatggaagtc acagtactta gtggatctat    1560
aaataagaaa gtccatagtt ttgataaata ttctctttaa ttgagatgta cagagagttt    1620
cttgctgggt caataggata gtatcatttt ggtgaaaacc atgtctctga aattgatgtt    1680
ttagtttcag tgttccctat ccctcattct ccatctcctt tgaagctct tttgaatgtt    1740 gaattgttca taagctaaaa tccaagaaat ttcagctgac aacttcgaaa attataatat    1800
ggtatattgc cctcctggtg tgtggctgca cacattttat cagggaaagt tttttgatct    1860
aggatttatt gctaactaac tgaaaagaga agaaaaaata tctttatttt atgattataa    1920
aatagctttt tcttcgatat aacagatttt ttaagtcatt attttgtgcc aatcagtttt    1980
```

| | |
|---|---|
| ctgaagtttc ccttacacaa aaggatagct ttattttaaa atctaaagtt tcttttaata | 2040 |
| gttaaaaatg tttcagaaga attataaaac tttaaaactg caagggatgt tggagtttag | 2100 |
| tactactccc tcaagattta aaaagctaaa tattttaaga ctgaacattt atgttaatta | 2160 |
| ttaccagtgt gtttgtcata ttttccatgg atatttgttc attacctttt tccattgaaa | 2220 |
| agttacatta aactttttcat acacttgaat tgatgagcta cctaatataa aaatgagaaa | 2280 |
| accaatatgc attttaaagt tttaacttta gagtttataa agttcatata taccctagtt | 2340 |
| aaagcactta agaaaatatg gcatgtttga cttttagttc ctagagagtt tttgtttttg | 2400 |
| tttttgtttt tttttgagac gggagtcttgc tatgtctccc aggctggagg gcagtggcat | 2460 |
| gatctcggct cactacaact tccacctccc gggttcaagc aattctcctg cctcagcctc | 2520 |
| cagagtagct gggattacag gcgcccacca ccacacccgg cagattttttg tattttttggt | 2580 |
| agagacgcgg tttcatcatg tttggccagg ctggtctcga actcctgacc tcaggtgatc | 2640 |
| cgcctgcctt ggcctcccaa agtgttggga ttacaggcat gagccactgc gcctggccag | 2700 |
| ctagagagtt tttaaagcag agctgagcac acactggatg cgtttgaatg tgtttgtgta | 2760 |
| gtttgttgtg aaattgttac atttagcagg cagatccaga agcactagtg aactgtcatc | 2820 |
| ttggtggggt tggcttaaat ttaattgact gtttagattc catttcttaa ttgattggcc | 2880 |
| agtatgaaaa gatgccagtg caagtaacca tagtatcaaa aaagttaaaa attattcaaa | 2940 |
| gctatagttt atacatcagg tactgccatt tactgtaaac cacctgcaag aaagtcagga | 3000 |
| acaactaaat tcacaagaac tgtcctgcta agaagtgtat taaagatttc cattttgttt | 3060 |
| tactaattgg gaacatctta atgtttaata tttaaactat tggtatcatt tttctaatgt | 3120 |
| ataatttgta ttactgggat caagtatgta cagtggtgat gctagtagaa gtttaagcct | 3180 |
| tggaaatacc actttcatat tttcagatgt catggattta atgagtaatt tatgttttta | 3240 |
| aaattcagaa tagttaatct ctgatctaaa accatcaatc tatgtttttt acggtaatca | 3300 |
| tgtaaatatt tcagtaatat aaactgtttg aaaaggctgc tgcaggtaaa ctctatacta | 3360 |
| ggatcttggc caaataattt acaattcaca gaatatttta tttaaggtgg tgcttttttt | 3420 |
| ttttgtcctt aaaacttgat ttttcttaac tttattcatg atgccaaagt aaatgaggaa | 3480 |
| aaaaactcaa aaccagttga gtatcattgc agacaaaact accagtagtc catattgttt | 3540 |
| aatattaagt tgaataaaat aaattttatt tcagtcagag cctaaatcac attttgattg | 3600 |
| tctgaatttt tgatactatt tttaaaatca tgctagtggc ggctgggcgt ggtagctcac | 3660 |
| gcctgtaatc ccagcatttt gggaggccga agtgggtgga tcacgaggtc gggagttcga | 3720 |
| gaccagcttg gccaaaatgg tgaaacccca tctgtactaa aaactacaaa aattagctgg | 3780 |
| gcgcggtggc aggtgcctgt aatcccagct acctgggagt ctgaggcagg agaattgctt | 3840 |
| gaaccctggc gacagaggat gcagtgagcc aagatggtgc cactgtactc cagactgggc | 3900 |
| gacagagtga gactctgtct caaaaaaaaa aaaaaaatca tgctagtgcc aagagctact | 3960 |
| aaattcttaa aaccggccca ttggacctgt acagataaaa aatagattca gtgcataatc | 4020 |
| aaaatatgat aattttaaaa tcttaagtag aaaaataaat cttgatgttt taaattctta | 4080 |
| cgaggattca atagttaata ttgatgatct cccggctggg tgcagtggct cacgcctgta | 4140 |
| atcccagcag ttctggaggc tgaggtgggc gaatcacttc aggccaggag ttcaagacca | 4200 |
| gtctgggcaa catggtgaaa cctcgtttct actaaaaata caaaaattag ccgggcgtgg | 4260 |
| ttgcacacac ttgtaatccc agctactcag gaggctaaga atcgcatgag cctaggaggc | 4320 |

```
agaggttgca gagtgccaag ggctcaccac tgcattccag cctgcccaac agagtgagac    4380
actgtttctg aaaaaaaaaa atatatatat atatatatat atgtgtgtat atatatatgt    4440
atatatatat gacttcctat taaaaacttt atcccagtcg ggggcagtgg ctcacgcctg    4500
taatcccaac actttgggag gctgaggcag gtggatcacc tgaagtccgg agtttgagac    4560
cagcctggcc aacatggtga aaccccatct ctactaaaaa tacaaaactt aagccaggta    4620
tggtggcggg cacctgtaat cccagttact gggaggctg aggcaggaga atcgtttaaa    4680
cccaggaggt ggaggttgca gtgagctgag atcgtgccat tgcactctag cctgggcaac    4740
aagagtaaaa ctccatctta aaggtttgtt tgtttttttt taatccggaa acgaagaggc    4800
gttgggccgc tattttcttt ttctttcttt ctttctttct tttttttttt ttctgagacg    4860
gagtctagct ctgctgccca ggctggagta caatgacacg atgttggctc actgcaacct    4920
ccacctcctg ggttcaagcg attctcctgc ctcagcctcc caagtacctg ggattacagg    4980
cacctgccac tacacctggc gaatatttgt tttttttagt agagacgggc ttttaccatg    5040
ttaggctggt ctcaaactcc tgacctcagg tgatctgcct gccttggcct cccaaagtgc    5100
tgggattaca ggtgcaggcc accacacccg gccttgggcc actgttttca aagtgaattg    5160
tttgttgtat cgagtcctta agtatggata tatatgtgac cctaattaag aactaccaga    5220
ttggatcaac taatcatgtc agcaatgtaa ataactttat ttttcatatt caaaataaaa    5280
actttctttt atttctggcc cctttataac cagcatcttt ttgctttaaa aaatgacctg    5340
gctttgtatt ttttagtct taaacataat aaaaatattt ttgttctaat ttgctttcat     5400
gagtgaagat tattgacatc gttggtaaat tctagaattt tgattttgtt ttttaatttg    5460
aagaaaatct ttgctattat tatttttttcc aagtggtctg gcattttaag aattagtgct    5520
aataacgtaa cttctaaatt tgtcgtaatt ggcatgttta atagcatatc aaaaaacatt    5580
ttaagcctgt ggattcatag acaaagcaat gagaaacatt agtaaaatat aaatggatat    5640
tcctgatgca tttaggaagc tctcaattgt ctcttgcata gttcaaggaa tgttttctga    5700 attttttttaa tgcttttttt tttttgaaa gaggaaaaca tacatttta aatgtgatta     5760 tctaattttt acaacactgg gctattagga ataactttt aaaaattact gttctgtata     5820
aatatttgaa attcaagtac agaaaatatc tgaaacaaaa agcattgttg tttggccatg    5880
atacaagtgc actgtggcag tgccgcttgc tcaggaccca gccctgcagc ccttctgtgt    5940
gtgctccctc gttaagttca tttgctgtta ttacacacac aggccttcct gtctggtcgt    6000
tagaaaagcc gggcttccaa agcactgttg aacacaggat tctgttgtta gtgtggatgt    6060
tcaatgagtt gtatttttaaa tatcaaagat tattaaataa agataatgtt tgcttttcta   6120
```

<210> SEQ ID NO 19
<211> LENGTH: 6240
<212> TYPE: DNA
<213> ORGANISM: Homo sapiens

<400> SEQUENCE: 19

```
gagaggggca gggggcggag ctggaggggg tggttcggcg tgggggccgt tggctccaga      60
caaataaaca tggagtccat cttccacgag aaacaagaag gctcactttg tgctcaacat     120
tgcctgaata acttattgca aggagaatat tttagccctg tggaattatc ctcaattgca     180
catcagctgg atgaggagga gaggatgaga atggcagaag gaggagttac tagtgaagat     240
tatcgcacgt ttttacagac agcagcaaaa gcagcaacag cagcagcagc agcagcagca     300
gggggaccta tcaggacaga gttcacatcc atgtgaaagg ccagccacca gttcaggagc     360
```

```
acttgggagt gatctaggtg atgctatgag tgaagaagac atgcttcagg cagctgtgac    420
catgtcttta gaaactgtca gaaatgattt gaaaacagaa ggaaaaaaat aatacccttta   480
aaaaataatt tagatattca tactttccaa cattatcctg tgtgattaca gcatagggtc    540
cactttggta atgtgtcaaa gagatgagga ataagactt ttagcggttt gcaaacaaaa     600
tgatgggaaa gtggaacaat gcgtcggttg taggactaaa taatgatctt ccaaatatta    660
gccaaagagg cattcagcaa ttaaagacat ttaaaatagt tttctaaatg tttcttttc     720
tttttttgagt gtgcaatatg taacatgtct aaagttaggg cattttctt ggatctttt     780
gcagactagc taattagctc tcgcctcagg cttttccat atagttgtt ttcttttct       840
gtcttgtagg taagttggct cacatcatgt aatagtggct ttcatttctt attaaccaaa    900
ttaaccttc aggaaagtat ctctactttc ctgatgttga taatagtaat ggttctagaa     960
ggatgaacag ttctccttc aactgtatac cgtgtgctcc agtgttttct tgtgttgttt    1020
tctctgatca caacttttct gctacctggt tttcattatt ttcccacaat tctttgaaa   1080
gatggtaatc ttttctgagg tttagcgttt taagccctac gatgggatca ttatttcatg   1140
actggtgcgt tcctaaactc tgaaatcagc cttgcacaag tacttgagaa taatgagca    1200
ttttttaaaa tgtgtgagca tgtgctttcc cagatgcttt atgaatgtct tttcacttat   1260
atcaaaacct tacagctttg ttgcaaccc ttcttcctgc gccttatttt ttcctttctt    1320
ctccaattga gaaaactagg agaagcatag tatgcaggca agtctccttc tgttagaaga   1380
ctaaacatac gtacccacca tgaatgtatg atacatgaaa tttggccttc aatttaata    1440
gcagttttat tttatttttt ctcctatgac tggagctttg tgttctcttt acagttgagt   1500
catgaatgt aggtgtctgc ttcacatctt ttagtaggta tagcttgtca agatggtga     1560
tctgaacat gaaaataatt tactaatgaa aatatgtta aatttatact gtgatttgac     1620
acttgcatca tgtttagata gcttaagaac aatggaagtc acagtactta gtggatctat   1680
aaataagaaa gtccatagtt tgataaata ttctctttaa ttgagatgta cagagagttt    1740
cttgctgggt caataggata gtatcatttt ggtgaaaacc atgtctctga aattgatgtt   1800
ttagtttcag tgttccctat ccctcattct ccatctcctt tgaagctct tttgaatgtt    1860
gaattgttca taagctaaaa tccaagaaat ttcagctgac aacttcgaaa attataatat   1920
ggtatattgc cctcctggtg tgtggctgca cactttat cagggaaagt tttttgatct     1980
aggatttatt gctaactaac tgaaagaga agaaaaaata tcttttattt atgattataa    2040
aatagctttt tcttcgatat aacagattt ttaagtcatt attttgtgcc aatcagtttt    2100
ctgaagtttc ccttacacaa aaggatagct ttattttaaa atctaaagtt tctttaata    2160
gttaaaaatg tttcagaaga attataaaac tttaaaactg caagggatgt ggagtttag    2220
tactactccc tcaagattta aaaagctaaa tattttaaga ctgaacattt atgttaatta   2280
ttaccagtgt gtttgtcata ttttccatgg atatttgttc attaccttt tccattgaaa    2340
agttacatta aacttttcat acacttgaat tgatgagcta cctaatataa aaatgagaaa   2400
accaatatgc attttaaagt tttaacttta gagtttataa agttcatata tacccctagt   2460
aaagcactta agaaaatatg gcatgtttga ctttagttc ctagagagtt tttgttttg     2520
ttttgttttt ttttgagac ggagtcttgc tatgtctccc aggctggagg gcagtggcat    2580
gatctcggct cactacaact tccacctccc gggttcaagc aattctcctg cctcagcctc   2640
cagagtagct gggattacag gcgcccacca ccacacccgg cagattttg tatttttggt    2700
```

```
agagacgcgg tttcatcatg tttggccagg ctggtctcga actcctgacc tcaggtgatc   2760
cgcctgcctt ggcctcccaa agtgttggga ttacaggcat gagccactgc gcctggccag   2820
ctagagagtt tttaaagcag agctgagcac acactggatg cgtttgaatg tgtttgtgta   2880
gtttgttgtg aaattgttac atttagcagg cagatccaga agcactagtg aactgtcatc   2940
ttggtggggt tggcttaaat ttaattgact gtttagattc catttcttaa ttgattggcc   3000
agtatgaaaa gatgccagtg caagtaacca tagtatcaaa aaagttaaaa attattcaaa   3060
gctatagttt atacatcagg tactgccatt tactgtaaac cacctgcaag aaagtcagga   3120
acaactaaat tcacaagaac tgtcctgcta agaagtgtat taaagatttc cattttgttt   3180
tactaattgg gaacatctta atgtttaata tttaaactat tggtatcatt tttctaatgt   3240
ataatttgta ttactgggat caagtatgta cagtggtgat gctagtagaa gtttaagcct   3300
tggaaatacc actttcatat tttcagatgt catggattta atgagtaatt tatgttttta   3360
aaattcagaa tagttaatct ctgatctaaa accatcaatc tatgtttttt acggtaatca   3420
tgtaaatatt tcagtaatat aaactgtttg aaaaggctgc tgcaggtaaa ctctatacta   3480
ggatcttggc caaataattt acaattcaca gaatatttta tttaaggtgg tgcttttttt   3540
ttttgtcctt aaaacttgat ttttcttaac tttattcatg atgccaaagt aaatgaggaa   3600
aaaaactcaa aaccagttga gtatcattgc agacaaaact accagtagtc catattgttt   3660
aatattaagt tgaataaaat aaattttatt tcagtcagag cctaaatcac attttgattg   3720
tctgaatttt tgatactatt tttaaaatca tgctagtggc ggctgggcgt ggtagctcac   3780
gcctgtaatc ccagcatttt gggaggccga agtgggtgga tcacgaggtc gggagttcga   3840
gaccagcttg gccaaaatgg tgaaaccccca tctgtactaa aaactacaaa aattagctgg   3900
gcgcggtggc aggtgcctgt aatcccagct acctgggagt ctgaggcagg agaattgctt   3960
gaaccctggc gacagaggat gcagtgagcc aagatggtgc cactgtactc cagactgggc   4020
gacagagtga gactctgtct caaaaaaaaa aaaaaaatca tgctagtgcc aagagctact   4080
aaattcttaa aaccggccca ttggacctgt acagataaaa aatagattca gtgcataatc   4140
aaaatatgat aattttaaaa tcttaagtag aaaaataaat cttgatgttt taaattctta   4200
cgaggattca atagttaata ttgatgatct cccggctggg tgcagtggct cacgcctgta   4260
atcccagcag ttctggaggc tgaggtgggc gaatacttc aggccaggag ttcaagacca   4320
gtctgggcaa catggtgaaa cctcgtttct actaaaaata caaaaattag ccgggcgtgg   4380
ttgcacacac ttgtaatccc agctactcag gaggctaaga atcgcatgag cctaggaggc   4440
agaggttgca gagtgccaag gctcaccac tgcattccag cctgcccaac agagtgagac   4500
actgtttctg aaaaaaaaaa atatatatat atatatatat atgtgtgtat atatatatgt   4560
atatatatat gacttcctat taaaaacttt atcccagtcg ggggcagtgg ctcacgcctg   4620
taatcccaac actttgggag gctgaggcag gtggatcacc tgaagtccgg agtttgagac   4680
cagcctggcc aacatggtga acccccatct ctactaaaaa tacaaaactt aagccaggta   4740
tggtggcggg cacctgtaat cccagttact tgggaggctg aggcaggaga atcgtttaaa   4800
cccaggaggt ggaggttgca gtgagctgag atcgtgccat gcactctag cctgggcaac   4860 aagagtaaaa ctccatctta aaggtttgtt tgttttttttt taatccggaa acgaagaggc   4920
gttgggccgc tattttcttt ttctttcttt ctttctttct tttttttttt ttctgagacg   4980
gagtctagct ctgctgccca ggctggagta caatgacacg atgttggctc actgcaacct   5040
ccacctcctg ggttcaagcg attctcctgc ctcagcctcc caagtacctg ggattacagg   5100
```

```
cacctgccac tacacctggc gaatatttgt ttttttagt agagacgggc ttttaccatg    5160
ttaggctggt ctcaaactcc tgacctcagg tgatctgcct gccttggcct cccaaagtgc    5220
tgggattaca ggtgcaggcc accacacccg gccttgggcc actgttttca aagtgaattg    5280
tttgttgtat cgagtcctta agtatggata tatatgtgac cctaattaag aactaccaga    5340
ttggatcaac taatcatgtc agcaatgtaa ataactttat ttttcatatt caaaataaaa    5400
actttctttt atttctggcc cctttataac cagcatcttt ttgctttaaa aaatgacctg    5460
gctttgtatt tttttagtct taaacataat aaaaatattt tgttctaat ttgctttcat    5520 gagtgaagat tattgacatc gttggtaaat tctagaattt tgattttgtt ttttaatttg    5580
aagaaaatct ttgctattat tatttttttcc aagtggtctg gcattttaag aattagtgct    5640
aataacgtaa cttctaaatt tgtcgtaatt ggcatgttta atagcatatc aaaaaacatt    5700
ttaagcctgt ggattcatag acaaagcaat gagaaacatt agtaaaatat aaatggatat    5760
tcctgatgca tttaggaagc tctcaattgt ctcttgcata gttcaaggaa tgttttctga    5820
atttttttaa tgctttttttt tttttgaaa gaggaaaaca tacatttttta aatgtgatta    5880 tctaattttt acaacactgg gctattagga ataactttt aaaaattact gttctgtata    5940
aatatttgaa attcaagtac agaaaatatc tgaaacaaaa agcattgttg tttggccatg    6000
atacaagtgc actgtggcag tgccgcttgc tcaggaccca gccctgcagc ccttctgtgt    6060
gtgctccctc gttaagttca tttgctgtta ttacacacac aggccttcct gtctggtcgt    6120
tagaaaagcc gggcttccaa agcactgttg aacacaggat tctgttgtta gtgtggatgt    6180
tcaatgagtt gtattttaaa tatcaaagat tattaaataa agataatgtt tgcttttcta    6240
```

<210> SEQ ID NO 20
<211> LENGTH: 24
<212> TYPE: DNA
<213> ORGANISM: Artificial sequence
<220> FEATURE:
<223> OTHER INFORMATION: Primer
<400> SEQUENCE: 20
tcaggacaga gttcacatcc atgt                                             24

<210> SEQ ID NO 21
<211> LENGTH: 27
<212> TYPE: DNA
<213> ORGANISM: Artificial sequence
<220> FEATURE:
<223> OTHER INFORMATION: Primer
<400> SEQUENCE: 21
ttcactcata gcatcaccta gatcact                                          27

<210> SEQ ID NO 22
<211> LENGTH: 24
<212> TYPE: DNA
<213> ORGANISM: Artificial sequence
<220> FEATURE:
<223> OTHER INFORMATION: Probe
<400> SEQUENCE: 22
aaggccagcc accagttcag gagc                                             24

<210> SEQ ID NO 23
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 23
accccctcca gctccgcc                                                18

<210> SEQ ID NO 24
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 24
gccaacggcc cccacgcc                                                18

<210> SEQ ID NO 25
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 25
tctggagcca acggcccc                                                18

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
atttgtctgg agccaacg                                                18

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
tgtttatttg tctggagc                                                18

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
actccatgtt tatttgtc                                                18

<210> SEQ ID NO 29
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 29
gatggactcc atgtttat                                                18
```

-continued

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
tggaagatgg actccatg                                                 18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
gagccttctt gtttctcg                                                 18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
aaagtgagcc ttcttgtt                                                 18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
agcacaaagt gagccttc                                                 18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
ttgagcacaa agtgagcc                                                 18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
tgcaataagt tattcagg                                                 18

<210> SEQ ID NO 36
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 36
tccacagggc taaaatat					18

<210> SEQ ID NO 37
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 37
gctgatgtgc aattgagg					18

<210> SEQ ID NO 38
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 38
attctcatcc tctcctcc					18

<210> SEQ ID NO 39
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 39
cactagtaac tcctcctt					18

<210> SEQ ID NO 40
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 40
aaggctgctg taaaaacg					18

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
cagaaggctg ctgtaaaa					18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
atttccagaa ggctgctg					18

```
<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
tccatatttc cagaaggc                                                 18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
tgtcatccat atttccag                                                 18

<210> SEQ ID NO 45
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 45
accactgtca tccatatt                                                 18

<210> SEQ ID NO 46
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 46
cttataacct gaatagag                                                 18

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
ctaaacccca aactttca                                                 18

<210> SEQ ID NO 48
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
tagttctaaa ccccaaac                                                 18

<210> SEQ ID NO 49
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 49
aggattagtt ctaaaccc                                                        18

<210> SEQ ID NO 50
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 50
tgaacaggat tagttcta                                                        18

<210> SEQ ID NO 51
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 51
actgttgaac aggattag                                                        18

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
tctggactgt tgaacagg                                                        18

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
atactctgga ctgttgaa                                                        18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
ataggatcga tcctgagc                                                        18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
ccttataatt gcatataa                                                        18

<210> SEQ ID NO 56
<211> LENGTH: 18

```
<212> TYPE: DNA
<213> ORGANISM: Artificial sequence
<220> FEATURE:
<223> OTHER INFORMATION: Synthetic oligonucleotide

<400> SEQUENCE: 56
taactgtaaa ccagtgtt                                                 18

<210> SEQ ID NO 57
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 57
cctaattttc taactgta                                                 18

<210> SEQ ID NO 58
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 58
tcctaatttt ctaactgt                                                 18

<210> SEQ ID NO 59
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 59
attcaagtta aaccactg                                                 18

<210> SEQ ID NO 60
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 60
agagaattca agttaaac                                                 18

<210> SEQ ID NO 61
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 61
aagagagaat tcaagtta                                                 18

<210> SEQ ID NO 62
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 62
```

```
taattctgga cccgtcaa                                                    18

<210> SEQ ID NO 63
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 63
gatattaatt ctggaccc                                                    18

<210> SEQ ID NO 64
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 64
gtatctgata ttaattct                                                    18

<210> SEQ ID NO 65
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 65
gatatgtatc tgatatta                                                    18

<210> SEQ ID NO 66
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 66
taattgagcc aagaaaag                                                    18

<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 67
aatatagaat aaccttcc                                                    18

<210> SEQ ID NO 68
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 68
caaatataga ataacctt                                                    18

<210> SEQ ID NO 69
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 69
tggcagatca cccttaac                                                 18

<210> SEQ ID NO 70
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 70
caatctggca gatcaccc                                                 18

<210> SEQ ID NO 71
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 71
gcaatctggc agatcacc                                                 18

<210> SEQ ID NO 72
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 72
atctgcagga gttggtca                                                 18

<210> SEQ ID NO 73
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 73
gatgcatctg ttggaccc                                                 18

<210> SEQ ID NO 74
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 74
cgatgcatct gttggacc                                                 18

<210> SEQ ID NO 75
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 75
ttggtcgatg catctgtt                                                 18
```

<210> SEQ ID NO 76
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 76
aagttttggt cgatgcat                                                 18

<210> SEQ ID NO 77
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 77
ccaataagtt ttggtcga                                                 18

<210> SEQ ID NO 78
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 78
attcttctcc aataagtt                                                 18

<210> SEQ ID NO 79
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 79
tctttgctct tttagttg                                                 18

<210> SEQ ID NO 80
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 80
cgttccaggt ctgtttta                                                 18

<210> SEQ ID NO 81
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 81
gagccatcat ttgcttct                                                 18

<210> SEQ ID NO 82
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 82
aaatcctcct catcttcg                                                     18

<210> SEQ ID NO 83
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 83
gacttagtgc cagagccc                                                     18

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 84
ctcatcttcc atgtcaat                                                     18

<210> SEQ ID NO 85
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 85
atagccctgc ggagatct                                                     18

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 86
aactaccttg catactta                                                     18

<210> SEQ ID NO 87
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 87
ggaactacct tgcatact                                                     18

<210> SEQ ID NO 88
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 88
catatcttga gatatgtt                                                     18

<210> SEQ ID NO 89

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 89
agatttgtac ctgatgtc                                                    18

<210> SEQ ID NO 90
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 90
tcttccgaag ctcttctg                                                    18

<210> SEQ ID NO 91
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 91
ttcaaagtag gcttctcg                                                    18

<210> SEQ ID NO 92
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 92
tttttcaaag taggcttc                                                    18

<210> SEQ ID NO 93
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 93
taggtccccc tgctgctg                                                    18

<210> SEQ ID NO 94
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 94
catggatgtg aactctgt                                                    18

<210> SEQ ID NO 95
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 95
```

```
ctgaactggt ggctggcc                                                 18

<210> SEQ ID NO 96
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 96
acctagatca ctcccaag                                                 18

<210> SEQ ID NO 97
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 97
atgtcttctt cactcata                                                 18

<210> SEQ ID NO 98
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 98
acatggtcac agctgcct                                                 18

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 99
gacatggtca cagctgcc                                                 18

<210> SEQ ID NO 100
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 100
ctaaagacat ggtcacag                                                 18

<210> SEQ ID NO 101
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 101
agtttctaaa gacatggt                                                 18

<210> SEQ ID NO 102
<211> LENGTH: 18
<212> TYPE: DNA
```

```
<213> ORGANISM: Artificial sequence
<220> FEATURE:
<223> OTHER INFORMATION: Synthetic oligonucleotide

<400> SEQUENCE: 102
atcatttctg acagtttc                                                  18

<210> SEQ ID NO 103
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 103
gaaagtatga atatctaa                                                  18

<210> SEQ ID NO 104
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 104
tgtaatcaca caggataa                                                  18

<210> SEQ ID NO 105
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 105
cattaccaaa gtggaccc                                                  18

<210> SEQ ID NO 106
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 106
ctaaaagtct tatttcct                                                  18

<210> SEQ ID NO 107
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 107
cactttccca tcattttg                                                  18

<210> SEQ ID NO 108
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 108
gtcctacaac cgacgcat                                                  18
```

<210> SEQ ID NO 109
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 109
ctaatatttg gaagatca                                                 18

<210> SEQ ID NO 110
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 110
ttaattgctg aatgcctc                                                 18

<210> SEQ ID NO 111
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 111
ttgcacactc aaaaaaga                                                 18

<210> SEQ ID NO 112
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 112
cctaacttta gacatgtt                                                 18

<210> SEQ ID NO 113
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 113
ctgcaaaaag atccaaga                                                 18

<210> SEQ ID NO 114
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 114
gaggcgagag ctaattag                                                 18

<210> SEQ ID NO 115
<211> LENGTH: 18
<212> TYPE: DNA
<213> ORGANISM: Artificial sequence
<220> FEATURE:

<223> OTHER INFORMATION: Synthetic oligonucleotide

<400> SEQUENCE: 115
tacctacaag acagaaaa                                                 18

<210> SEQ ID NO 116
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 116
ctattacatg atgtgagc                                                 18

<210> SEQ ID NO 117
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 117
tggttaataa gaaatgaa                                                 18

<210> SEQ ID NO 118
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 118
agatactttc ctgaaagg                                                 18

<210> SEQ ID NO 119
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 119
actattatca acatcagg                                                 18

<210> SEQ ID NO 120
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 120
ctgttcatcc ttctagaa                                                 18

<210> SEQ ID NO 121
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 121
acggtataca gttgaagg                                                 18

```
<210> SEQ ID NO 122
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 122
gatcagagaa aacaacac                                                18

<210> SEQ ID NO 123
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 123
gaaaaccagg tagcagaa                                                18

<210> SEQ ID NO 124
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 124
caaaagaatt gtgggaaa                                                18

<210> SEQ ID NO 125
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 125
cctcagaaaa gattacca                                                18

<210> SEQ ID NO 126
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 126
gaaataatga tcccatcg                                                18

<210> SEQ ID NO 127
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 127
gagtttagga acgcacca                                                18

<210> SEQ ID NO 128
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 128
gtacttgtgc aaggctga                                                 18

<210> SEQ ID NO 129
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 129
gcacatgctc acacattt                                                 18

<210> SEQ ID NO 130
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 130
gacattcata aagcatct                                                 18

<210> SEQ ID NO 131
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 131
taaggttttg atataagt                                                 18

<210> SEQ ID NO 132
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 132
aaggcgcagg aagaaggg                                                 18

<210> SEQ ID NO 133
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 133
tcaattggag aagaaagg                                                 18

<210> SEQ ID NO 134
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 134
atactatgct tctcctag                                                 18

<210> SEQ ID NO 135
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 135
ctaacagaag gagacttg                                                 18

<210> SEQ ID NO 136
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 136
acattcatgg tgggtacg                                                 18

<210> SEQ ID NO 137
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 137
gaaggccaaa tttcatgt                                                 18

<210> SEQ ID NO 138
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 138
ctccagtcat aggagaaa                                                 18

<210> SEQ ID NO 139
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 139
actcaactgt aaagagaa                                                 18

<210> SEQ ID NO 140
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 140
gaagcagaca cctacatt                                                 18

<210> SEQ ID NO 141
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 141
```
caagctatac ctactaaa                                       18

<210> SEQ ID NO 142
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 142
atgttccaga tcaccatc                                       18

<210> SEQ ID NO 143
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 143
cacagtataa atttaaac                                       18

<210> SEQ ID NO 144
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 144
taaacatgat gcaagtgt                                       18

<210> SEQ ID NO 145
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 145
acttccattg ttcttaag                                       18

<210> SEQ ID NO 146
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 146
ttatagatcc actaagta                                       18

<210> SEQ ID NO 147
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 147
atcaaaacta tggacttt                                       18

<210> SEQ ID NO 148
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 148
tacatctcaa ttaaagag                                                   18

<210> SEQ ID NO 149
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 149
ttgacccagc aagaaact                                                   18

<210> SEQ ID NO 150
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 150
ttcaccaaaa tgatacta                                                   18

<210> SEQ ID NO 151
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 151
aacatcaatt tcagagac                                                   18

<210> SEQ ID NO 152
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 152
gatggagaat gagggata                                                   18

<210> SEQ ID NO 153
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 153
caacattcaa aagagctt                                                   18

<210> SEQ ID NO 154
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 154
tggattttag cttatgaa                                                   18
```

<210> SEQ ID NO 155
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 155
cgaagttgtc agctgaaa                                                 18

<210> SEQ ID NO 156
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 156
gcaatatacc atattata                                                 18

<210> SEQ ID NO 157
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 157
gtgtgcagcc acacacca                                                 18

<210> SEQ ID NO 158
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 158
aaaactttcc ctgataaa                                                 18

<210> SEQ ID NO 159
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 159
caaaaaactt tccctgat                                                 18

<210> SEQ ID NO 160
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 160
ttagttagca ataaatcc                                                 18

<210> SEQ ID NO 161
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 161
agctatttta taatcata                                                 18

<210> SEQ ID NO 162
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 162
aaaatctgtt atatcgaa                                                 18

<210> SEQ ID NO 163
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 163
attggcacaa aataatga                                                 18

<210> SEQ ID NO 164
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 164
gtaagggaaa cttcagaa                                                 18

<210> SEQ ID NO 165
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 165
ttataattct tctgaaac                                                 18

<210> SEQ ID NO 166
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 166
acatcccttg cagtttta                                                 18

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167
tgagggagta gtactaaa                                                 18

<210> SEQ ID NO 168
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 168
gtcttaaaat atttagct                                                 18

<210> SEQ ID NO 169
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 169
ggtaataatt aacataaa                                                 18

<210> SEQ ID NO 170
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 170
tccatggaaa atatgaca                                                 18

<210> SEQ ID NO 171
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 171
tggaaaaagg taatgaac                                                 18

<210> SEQ ID NO 172
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 172
tgaaaagttt aatgtaac                                                 18

<210> SEQ ID NO 173
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 173
ggtagctcat caattcaa                                                 18

<210> SEQ ID NO 174
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 174
```
gcatattggt tttctcat                                              18

<210> SEQ ID NO 175
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 175
actctaaagt taaaactt                                              18

<210> SEQ ID NO 176
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 176
tataaactct aaagttaa                                              18

<210> SEQ ID NO 177
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 177
tagggtatat atgaactt                                              18

<210> SEQ ID NO 178
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 178
catattttct taagtgct                                              18

<210> SEQ ID NO 179
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 179
taggaactaa aagtcaaa                                              18

<210> SEQ ID NO 180
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 180
ccaaacatga tgaaaccg                                              18

<210> SEQ ID NO 181
<211> LENGTH: 18
<212> TYPE: DNA

```
<213> ORGANISM: Artificial sequence
<220> FEATURE:
<223> OTHER INFORMATION: Synthetic oligonucleotide

<400> SEQUENCE: 181
tctagctggc caggcgca                                                    18

<210> SEQ ID NO 182
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 182
gctcagctct gctttaaa                                                    18

<210> SEQ ID NO 183
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 183
acattcaaac gcatccag                                                    18

<210> SEQ ID NO 184
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 184
atttcacaac aaactaca                                                    18

<210> SEQ ID NO 185
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 185
ggatctgcct gctaaatg                                                    18

<210> SEQ ID NO 186
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 186
gatgacagtt cactagtg                                                    18

<210> SEQ ID NO 187
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 187
taaatttaag ccaacccc                                                    18
```

```
<210> SEQ ID NO 188
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 188
caattaagaa atggaatc                                                 18

<210> SEQ ID NO 189
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 189 gcatctttc atactggc                                                  18

<210> SEQ ID NO 190
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 190
ctggcatctt ttcatact                                                 18

<210> SEQ ID NO 191
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 191
ttttgatact atggttac                                                 18

<210> SEQ ID NO 192
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 192
atagctttga ataatttt                                                 18

<210> SEQ ID NO 193
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 193
tggcagtacc tgatgtat                                                 18

<210> SEQ ID NO 194
<211> LENGTH: 18
<212> TYPE: DNA
<213> ORGANISM: Artificial sequence
<220> FEATURE:
```

```
<223> OTHER INFORMATION: Synthetic oligonucleotide

<400> SEQUENCE: 194
tcttgcaggt ggtttaca                                              18

<210> SEQ ID NO 195
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 195
gtgaatttag ttgttcct                                              18

<210> SEQ ID NO 196
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 196
cacttcttag caggacag                                              18

<210> SEQ ID NO 197
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 197
ttcccaatta gtaaaaca                                              18

<210> SEQ ID NO 198
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 198
ccaatagttt aaatatta                                              18

<210> SEQ ID NO 199
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 199
tacaaattat acattaga                                              18

<210> SEQ ID NO 200
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 200
ctgtacatac ttgatccc                                              18
```

```
<210> SEQ ID NO 201
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 201
ttaaacttct actagcat                                                 18

<210> SEQ ID NO 202
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 202
tatgaaagtg gtatttcc                                                 18

<210> SEQ ID NO 203
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 203
attaaatcca tgacatct                                                 18

<210> SEQ ID NO 204
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 204
gattaactat tctgaatt                                                 18

<210> SEQ ID NO 205
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 205
tagattgatg gttttaga                                                 18

<210> SEQ ID NO 206
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 206
ttacatgatt accgtaaa                                                 18

<210> SEQ ID NO 207
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 207
aacagtttat attactga                                                 18

<210> SEQ ID NO 208
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 208
gtttacctgc agcagcct                                                 18

<210> SEQ ID NO 209
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 209
tttggccaag atcctagt                                                 18

<210> SEQ ID NO 210
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 210
aatattctgt gaattgta                                                 18

<210> SEQ ID NO 211
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 211
aaaaaaagca ccacctta                                                 18

<210> SEQ ID NO 212
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 212
tcatgaataa agttaaga                                                 18

<210> SEQ ID NO 213
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 213
gtttttttcc tcatttac                                                 18

<210> SEQ ID NO 214
<211> LENGTH: 18
```

```
<212> TYPE: DNA
<213> ORGANISM: Artificial sequence
<220> FEATURE:
<223> OTHER INFORMATION: Synthetic oligonucleotide

<400> SEQUENCE: 214
caatgatact caactggt                                                   18

<210> SEQ ID NO 215
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 215
tggactactg gtagtttt                                                   18

<210> SEQ ID NO 216
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 216
tctgactgaa ataaaatt                                                   18

<210> SEQ ID NO 217
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 217
gacaatcaaa atgtgatt                                                   18

<210> SEQ ID NO 218
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 218
cactagcatg attttaaa                                                   18

<210> SEQ ID NO 219
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 219
tcctctgtcg ccagggtt                                                   18

<210> SEQ ID NO 220
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 220
```

```
cactagcatg atttttt                                            18

<210> SEQ ID NO 221
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 221
ttttaagaat ttagtagc                                           18

<210> SEQ ID NO 222
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 222
tctgtacagg tccaatgg                                           18

<210> SEQ ID NO 223
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 223
ttatgcactg aatctatt                                           18

<210> SEQ ID NO 224
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 224
cgtaagaatt taaaacat                                           18

<210> SEQ ID NO 225
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 225
catcaatatt aactattg                                           18

<210> SEQ ID NO 226
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 226
tgcgattctt agcctcct                                           18

<210> SEQ ID NO 227
<211> LENGTH: 18
<212> TYPE: DNA
<213> ORGANISM: Artificial sequence
```

```
<220> FEATURE:
<223> OTHER INFORMATION: Synthetic oligonucleotide

<400> SEQUENCE: 227
cccttggcac tctgcaac                                                   18

<210> SEQ ID NO 228
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 228
tgtctcactc tgttgggc                                                   18

<210> SEQ ID NO 229
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 229
taggaagtca tatatata                                                   18

<210> SEQ ID NO 230
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 230
cccgactggg ataaagtt                                                   18

<210> SEQ ID NO 231
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 231
tacctggctt aagttttg                                                   18

<210> SEQ ID NO 232
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 232
acctttaaga tggagttt                                                   18

<210> SEQ ID NO 233
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 233
tccggattaa aaaaaaac                                                   18
```

```
<210> SEQ ID NO 234
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 234
aaaatagcgg cccaacgc                                                 18

<210> SEQ ID NO 235
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 235
aacaaatatt cgccaggt                                                 18

<210> SEQ ID NO 236
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 236
tggcccaagg ccgggtgt                                                 18

<210> SEQ ID NO 237
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 237
caacaaacaa ttcacttt                                                 18

<210> SEQ ID NO 238
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 238
tatccatact taaggact                                                 18

<210> SEQ ID NO 239
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 239
gttcttaatt agggtcac                                                 18

<210> SEQ ID NO 240
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 240
tgattagttg atccaatc                                                 18

<210> SEQ ID NO 241
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 241
taaagttatt tacattgc                                                 18

<210> SEQ ID NO 242
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 242
gatgctggtt ataaaggg                                                 18

<210> SEQ ID NO 243
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 243
gccaggtcat tttttaaa                                                 18

<210> SEQ ID NO 244
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 244
ttattatgtt taagacta                                                 18

<210> SEQ ID NO 245
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 245
tcatgaaagc aaattaga                                                 18

<210> SEQ ID NO 246
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 246
ccaacgatgt caataatc                                                 18

<210> SEQ ID NO 247
```

```
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 247
agaccacttg gaaaaaat                                                 18

<210> SEQ ID NO 248
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 248
ttagcactaa ttcttaaa                                                 18

<210> SEQ ID NO 249
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 249
cgacaaattt agaagtta                                                 18

<210> SEQ ID NO 250
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 250
tatgctatta aacatgcc                                                 18

<210> SEQ ID NO 251
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 251
ccacaggctt aaaatgtt                                                 18

<210> SEQ ID NO 252
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 252
ttctcattgc tttgtcta                                                 18

<210> SEQ ID NO 253
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 253
```
aggaatatcc atttatat                                                          18

<210> SEQ ID NO 254
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 254
attgagagct tcctaaat                                                          18

<210> SEQ ID NO 255
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 255
ttccttgaac tatgcaag                                                          18

<210> SEQ ID NO 256
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 256
attagataat cacattta                                                          18

<210> SEQ ID NO 257
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 257
cctaatagcc cagtgttg                                                          18

<210> SEQ ID NO 258
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 258
tatacagaac agtaattt                                                          18

<210> SEQ ID NO 259
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 259
tctgtacttg aatttcaa                                                          18

<210> SEQ ID NO 260
<211> LENGTH: 18
<212> TYPE: DNA

<213> ORGANISM: Artificial sequence
<220> FEATURE:
<223> OTHER INFORMATION: Synthetic oligonucleotide

<400> SEQUENCE: 260
aaacaacaat gcttttg                                                   18

<210> SEQ ID NO 261
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 261
cacagtgcac ttgtatca                                                  18

<210> SEQ ID NO 262
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 262
gggtcctgag caagcggc                                                  18

<210> SEQ ID NO 263
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 263
acacacagaa gggctgca                                                  18

<210> SEQ ID NO 264
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 264
gcaaatgaac ttaacgag                                                  18

<210> SEQ ID NO 265
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 265
gaaggcctgt gtgtgtaa                                                  18

<210> SEQ ID NO 266
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 266
cggcttttct aacgacca                                                  18

```
<210> SEQ ID NO 267
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 267
ctttggaagc ccggcttt                                                   18

<210> SEQ ID NO 268
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 268
tgttcaacag tgctttgg                                                   18

<210> SEQ ID NO 269
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 269
tccacactaa caacagaa                                                   18

<210> SEQ ID NO 270
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 270
aataatcttt gatattta                                                   18

<210> SEQ ID NO 271
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 271
gcattgctta taacctgt                                                   18

<210> SEQ ID NO 272
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 272
acttttcaaa gtaggctt                                                   18

<210> SEQ ID NO 273
<211> LENGTH: 18
<212> TYPE: DNA
<213> ORGANISM: Artificial sequence
<220> FEATURE:
```

<223> OTHER INFORMATION: Synthetic oligonucleotide

<400> SEQUENCE: 273 aactactttta cttttcaa                                                    18

<210> SEQ ID NO 274
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 274
tggaagagcc gtctcatt                                                     18

<210> SEQ ID NO 275
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 275
taaggtaagt tacttaaa                                                     18

<210> SEQ ID NO 276
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 276
cctttgctct tttagttg                                                     18

<210> SEQ ID NO 277
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 277
ccttcatcta cttctgag                                                     18

<210> SEQ ID NO 278
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 278
gatgtcagct gatcagaa                                                     18

<210> SEQ ID NO 279
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 279
aagaggatgt cagctgat                                                     18

-continued

```
<210> SEQ ID NO 280
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 280
cgccgggcga gatcggca                                                 18

<210> SEQ ID NO 281
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 281
cccgtaataa aaactctt                                                 18

<210> SEQ ID NO 282
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 282
ctaaaaacaa agctggcc                                                 18

<210> SEQ ID NO 283
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 283
atagcattac tatttgta                                                 18

<210> SEQ ID NO 284
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 284
cagatgttct acttatat                                                 18

<210> SEQ ID NO 285
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 285
ttaacatagg tacatgca                                                 18

<210> SEQ ID NO 286
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 286
aagtgagcct tcttgcta                                                   18

<210> SEQ ID NO 287
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 287
aatcagtacc tgtaaaaa                                                   18

<210> SEQ ID NO 288
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 288
ttccagaagg ctgctgtt                                                   18

<210> SEQ ID NO 289
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 289
aaaggctgtg aaacggtg                                                   18

<210> SEQ ID NO 290
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 290
aaaaatctag tactctag                                                   18

<210> SEQ ID NO 291
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 291
agctggtttt caataacc                                                   18

<210> SEQ ID NO 292
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 292
agaaagaacc aacttagg                                                   18

<210> SEQ ID NO 293
<211> LENGTH: 18
```

-continued

```
<212> TYPE: DNA
<213> ORGANISM: Artificial sequence
<220> FEATURE:
<223> OTHER INFORMATION: Synthetic oligonucleotide

<400> SEQUENCE: 293
atttaaccca caagatac                                              18

<210> SEQ ID NO 294
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 294
catgcagctc atgcctat                                              18

<210> SEQ ID NO 295
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 295
tcactaaatt agctgggc                                              18

<210> SEQ ID NO 296
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 296
aagttagtgt atattata                                              18

<210> SEQ ID NO 297
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 297
tctcagcaga atgtaacg                                              18

<210> SEQ ID NO 298
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 298
aactagtaac atggctaa                                              18

<210> SEQ ID NO 299
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 299
```
atatagaata acctaaaa                                            18

<210> SEQ ID NO 300
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 300
aaggcatttg taatgtaa                                            18

<210> SEQ ID NO 301
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 301
accaactact ttactttt                                            18

<210> SEQ ID NO 302
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 302
tgcccgtcct atttgctg                                            18

<210> SEQ ID NO 303
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 303
gtcctaattt cattttc                                             18

<210> SEQ ID NO 304
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 304
tgagttgtga cttaaaaa                                            18

<210> SEQ ID NO 305
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 305
cattaagagg atgtcagc                                            18

<210> SEQ ID NO 306
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 306
tctcacatta agaggatg                                                   18

<210> SEQ ID NO 307
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 307
aaatatctca cattaaga                                                   18

<210> SEQ ID NO 308
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 308
agccattaat ctatactg                                                   18

<210> SEQ ID NO 309
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 309
agatttgaaa ttttggat                                                   18

<210> SEQ ID NO 310
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 310
aatgagtgtt ggtttata                                                   18

<210> SEQ ID NO 311
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 311
tagaaaaaag taccagtt                                                   18

<210> SEQ ID NO 312
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 312
gcatcacctg ttgggaaa                                                   18
```

<210> SEQ ID NO 313
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 313
ctgtctgttt tcctaatt                                                 18

<210> SEQ ID NO 314
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 314
ttataacctg taaaaacg                                                 18

<210> SEQ ID NO 315
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 315
ttgcttataa ctttctcg                                                 18

<210> SEQ ID NO 316
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 316
ttcatttctg aatagaga                                                 18

<210> SEQ ID NO 317
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 317
atctttcatt ttttctcg                                                 18

<210> SEQ ID NO 318
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 318
gtcaactact ttactttt                                                 18

<210> SEQ ID NO 319
<211> LENGTH: 18
<212> TYPE: DNA
<213> ORGANISM: Artificial sequence
<220> FEATURE:
<223> OTHER INFORMATION: Synthetic oligonucleotide

```
<400> SEQUENCE: 319
aagttaaacc atttctcg                                                 18

<210> SEQ ID NO 320
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 320
taacctgttt tcctaatt                                                 18

<210> SEQ ID NO 321
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 321
tatagaataa ctttctcg                                                 18

<210> SEQ ID NO 322
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 322
cccttcctgt tgtaattg                                                 18

<210> SEQ ID NO 323
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 323
accactgaat agagaaaa                                                 18

<210> SEQ ID NO 324
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 324
acttcctgtt gtaattga                                                 18

<210> SEQ ID NO 325
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 325
atcaccttac tagtaaag                                                 18
```

```
<210> SEQ ID NO 326
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 326
ttttatggac ttttctcg                                              18

<210> SEQ ID NO 327
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 327
tttgctgctg ttttctcg                                              18

<210> SEQ ID NO 328
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 328
ttcatttctg taaaaacg                                              18

<210> SEQ ID NO 329
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 329
attttcaaag taggcttc                                              18

<210> SEQ ID NO 330
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 330
tattaagagg atgtcagc                                              18

<210> SEQ ID NO 331
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 331
aacttactag taaagtcg                                              18

<210> SEQ ID NO 332
<211> LENGTH: 18
<212> TYPE: DNA
<213> ORGANISM: Artificial sequence
<220> FEATURE:
<223> OTHER INFORMATION: Synthetic oligonucleotide
```

```
<400> SEQUENCE: 332
ccagaaggct gtttctcg                                                     18

<210> SEQ ID NO 333
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 333
ctgtctgaat agagaaaa                                                     18

<210> SEQ ID NO 334
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 334
ctgctgtctg taaaaacg                                                     18
```